US006432404B1

(12) United States Patent
Gallatin et al.

(10) Patent No.: US 6,432,404 B1
(45) Date of Patent: *Aug. 13, 2002

(54) METHODS OF INHIBITING LOCOMOTOR DAMAGE FOLLOWING SPINAL CORD INJURY WITH α D-SPECIFIC ANTIBODIES

(75) Inventors: W. Michael Gallatin, Mercer Island; Monica Van der Vieren, Snohomish, both of WA (US)

(73) Assignee: ICOS Corporation, Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/688,307

(22) Filed: Oct. 13, 2000

Related U.S. Application Data

(63) Continuation-in-part of application No. 09/350,259, filed on Jul. 8, 1999, which is a continuation of application No. 09/193,043, filed on Nov. 16, 1998, now Pat. No. 6,251,395, which is a continuation-in-part of application No. 08/943, 363, filed on Oct. 3, 1997, now Pat. No. 5,837,478, which is a continuation-in-part of application No. 08/605,672, filed on Feb. 22, 1996, now Pat. No. 5,817,515, which is a continuation-in-part of application No. 08/362,652, filed on Dec. 21, 1994, now Pat. No. 5,766,850, which is a continuation-in-part of application No. 08/286,889, filed on Aug. 5, 1994, now Pat. No. 5,470,953, which is a continuation-in-part of application No. 08/173,497, filed on Dec. 23, 1993, now Pat. No. 5,437,958.

(51) Int. Cl.$^7$ .................. A61K 39/395; C07K 16/28

(52) U.S. Cl. .................. 424/144.1; 424/130.1; 424/141.1; 424/143.1; 424/153.1; 424/154.1; 424/173.1; 530/387.1; 530/388.1; 530/388.2; 530/388.22; 530/388.7; 530/388.73; 530/388.75

(58) Field of Search .................. 424/130.1, 141.1, 424/153.1, 143.1, 144.1, 154.1, 173.1; 530/387.1, 388.22, 388.75, 388.1, 388.2, 388.7, 388.73

(56) References Cited

U.S. PATENT DOCUMENTS

| 4,271,139 A | 6/1981 | Hart |
| 4,568,649 A | 2/1986 | Bertoglio-Matte |
| 6,251,395 B1 * | 6/2001 | Gallatin et al. |

OTHER PUBLICATIONS

Adams, et al., "Experimental graft arteriosclerosis: 1. The Lewis–To–F–344 Allograft Model," *Transplantation* 53:1115–1119 (1992).
Adams, et al., "Experimental graft atreriosclerosis: II. Immunocytochemical analysis of lesion development," *Transplantation* 56:794–799 (1993).
Anderson, et al., "Exact definition of species–specific and cross–reactive epitopes of the 65–kilodalton protein of *mycobacterium leprae* using synthetic peptides," *J. Immunol.* 141:607–613 (1988).

Arfors, et al., "A monoclonal antibody to the membrane glycoprotein complex CD18 inhibits polymorphonuclear leukocyte accumulation and plasma leakage in vivo," *Blood* 69:338–340 (1987).
Arnaout, "Structure and function of the leukocyte adhesion molecules CD11/CD18," *Blood* 75:1037–1050 (1990).
Bainton, et al., "Leukocyte Adhesion Receptors are Stored in Peroxidase–Negative Granules of Human Neutrophils ," *J.Exp.Med.* 166:1641 (1987).
Berman, et al., "Biosynthesis and function of membrane bound and secreted forms of recombinant CD11b/CD18 (Mac–1)," *J.Cell, Biochem* 52:183–195 (1993).
Blight, A.R., "Delayed Demyelination and Macrophage Invasion: A Candidate for Secondary Cell Damage in Spinal Cord Injury," *Central Nervous System Trauma*, 1:299–315 (1985).
Blight, A.R., "Effects of Silica on the Outcome from Experimental Spinal Cord Injury: Implication of Macrophages in Secondary Tissue Damage," *Neurosci*, 60:263–273 (1994).
Bochner, et al., "Flow cytometric methods for the analysis of human basophil surface and viability," *J.Immunol.Meth.* 125:265–271 (1989).
Boucher, et al.,, "IL–3 Augments Adhesiveness for Endothelium and CD11b Expression in Human Basophils but not Neutrophils," *J.Immunol.Meth* 145:1832–1837 (1990).
Burnett, et al., "The IgA heavy–chain gene family in rabbit: cloning and sequence analysis of 13 Cα genes," *EMBO J.* 8:4041–4047 (1989).
Capecchi, "Altering the genome by homologous recombination," *Science* 244:1288–1292 (1989).
Carlson, et al., "Acute Inflammatory Response in Spinal Cord Following Impact Injury," *Exp.Neurol.*, 151:71–81 (1998).
Chang, et al., "A general method for facilitating heterodimeric pairing between two proteins: application to expression of α and β T–cell receptor extracellular segments," *Proc.Natl.Acad. Sci.(USA)* 91:11408–11412 (1994).
Chisaka, et al., "Developmental defects of the ear, cranial nerves and hindbrain resulting from targeted disruption of the mouse homeobox gene Hox–1.6," *Nature* 355:516–520 (1992).
Cobbold, et al., "Non–lineage, LFA–1 family, and leukocyte common antigens: new and previously defined clusters," *Leukocyte Typing III*, McMichael (ed), Oxford Press, p. 788 (1987).
Collins, et al., "The HL–60 promyelocytic leukemia cell line: proliferation, differentiation, and cellular oncogene expression," *Blood* 70:1233–1244 (1987).
Corbi, et al., "cDNA cloning and complete primary structure of the α subunit of a leukocyte adhesion glycoprotein, p150,95," *EMBO J.* 6:4023–4028 (1987).
Corbi, et al., "The human leukocyte adhesion glycoprotein Mac–1 (complement receptor type 3, CD116 α subunit," *J.Biol.Chem.* 263:12403–12411 (1988).

(List continued on next page.)

Primary Examiner—Phillip Gambel
(74) Attorney, Agent, or Firm—Marshall, Gerstein & Borun

(57) ABSTRACT

Methods to treat spinal cord injury using $\alpha_d$ monoclonal antibodies are disclosed.

9 Claims, 4 Drawing Sheets

OTHER PUBLICATIONS

Cromartie, et al., "Arthritis in rats after systemic injection of streptococcal cells or cell walls." *J.Exp. Med.* 146:1585–1602 (1977).

Dana, et al., "Deficiency of a surface membrane glycoprotein (Mo1) in man," *J.Clin.Invest.* 73:153–159 (1984).

Danilenko, et al., "Canine leukocyte cell adhesion molecules (LeuCAMS): characterization of the CD11/CD18 family," *Tissue Antigens* 40:13–21 (1992).

Deng, et al., "Location of crossovers during gene targeting with insertion and replacement vectors," *Mol.Cell.Biol.* 13:2134–2140 (1993).

Denholm and Wolber, "A simple method for the purification of human peripheral blood monocytes", *Immunol.Meth.* 144:247–251 (1991).

Diamond, et al., "The I domain is a major recognition site on the leukocyte integrin Mac–1 (CD11b/CD18) for four distinct adhesion ligands," *J.Cell, Biol.* 120:1031–1043 (1993).

Fleming, et al., "Structural Analysis of the CD11b gene and phylogenetic analysis of the α–antegrin gene family demonstrate remarkable conservation of genomic organization and suggest early diversification during evolution," *J. Immunol.* 150:480–490 (1993).

Frohman, "RACE: Rapid amplification of cDNA ends" in *PCR Protocols: A Guide to Methods and Applications*, Innis, et al. (eds.) Academic press:New York (1990) pp. 28–38.

Gavilondo–Cowley, et al., "Specific Amplification of Rearranged Immunoglobulin Variable Region Genes from Mouse Hybridoma Cells," in Hybridoma, vol. 9, No.:5 1990, Mary Anne Leibert Inc., Publishers, Media, PA pp. 407–417.

Greve, et al., "The major human rhinovirus receptor is ICAM–1," *Cell* 56:839 (1989).

Hanenberg, et al., "Macrophage infiltration precedes and is a prerequisite for lymphocytic insulitis in pancreatic islets of prediabetic BB rats," *Diatetologia* 32:126–134 (1989).

Hansel, et al., "Purification of human blood eosinophils by negative selection using immunomagnetic beads," *J.Immunol.Meth.* 122:97–103 (1989).

Hansel, et al., "An improved immunomagnetic procedure for the isolation of highly purified human blood eosinophils," *J.Immunol.Meth.* 145:105 (1991).

Hart and Greenwald, "Scintillation proximity assay (SPA)—a new method of immunoassay," *Mol.Immunol.* 12:265–267 (1979).

Hart and Greenwald, "Scintillation proximity assay of antigen–antibody binding kinetics: concise communication," *J.Nuc.Med* 20:1062–1065 (1979).

Hildreth & Orentas, "Involvement of a leukocyte adhesion receptor (LFA–1) in HIV–induced syncytium formation," *Science* 244:1075–1078 (1989).

Huitinga, et al., "Treatment with anti–CR3 antibodies ED7 and ED8 suppresses experimental allergic encephalomyelitis in Lewis rats," *Eur.J.Immunol* 23:709–715 (1993).

Hynes, et al., Integrins: Versatility, Modulation, and Signaling in Cell Adhesion, *Cell* 69:11–25 (1992).

Ingalls and Golenbock, "CD11c/CD18, A transmembrane signaling receptor for lipopolysaccharide," *J.Exp.Med.*, 181:1473–1479 (1995).

Jutila, et al., "In vivo distribution and characterization of two novel mononuclear phagocyte differentiation antigens in mice," *J.Leukocyte Biol.* 54: 30–39 (1993).

Karin and Richards, "Human metallothionein genes—primary structure of the metallothionein–II gene and a related processed protein," *Nature* 299:797–802 (1982).

Kishimoto, et al., "Heterologous mutations of the β subunit common to the LFA–1, Mac–1 and p1150,95 glycoproteins cause leukocyte adhesion deficiency," *Cell* 50:193–202 (1987).

Kishimoto, et al., "Cloning of the β subunit of the leukocyte adhesion proteins: homology to an extracellular matrix receptor defines a novel supergene family," *Cell* 48:681–690 (1987).

Koo, et al., "Supressive Effects on Monocytic Cells and Transforming Growth Factor–β, on Natural Killer Cell Differentiation in Autoimmune Viable Motheaten Mutant Mice" *J.Immunol.* 147:1194–1200 (1992).

Koo, et al., "Anti–CD11b Antibody Prevents Immunopathologic Changes in Viable Moth–Eaten Bone Marrow Chimeric Mice," *J.Immunol.* 151:6733–6741 (1993).

Krassioukov, et al., "Morphological Changes in Sympathetic Preganglionic Neurons After Spinal Cord Injury in Rats," *Neurosci.* 70:211–226 (1996).

Krassioukov, et al., "Episodic hypertension due to autonomic dysreflexia in acute and chronic spinal cord–injured rats," *Am.J.Physiol.* 268:H2077–H2083 (1995).

Krenz and Weaver, "Sprouting of Primary Afferent Fibers After Spinal Cord Transection in the Rat," *Neurosci* 85:443–458 (1998).

Kroegel, et al., "Cytokine control of eosinophils in pulmonary disease," *J.Clin.Allergy Immunol.* 93725 (1994).

Kroegel, et al., "Segmental Lung Antigen Challenge of Allergic Subjects Induces the Local Activation and Recruitment of Eosinophilic Leukocytes," *Ann.Rev.Respir.Dis.* 143:A45 (1991).

Kroncke, et al., "Activated macrophages kill pancreatic syngeneic islet cells via arginine–dependent nitric oxide generation," *BBRC* 175:752–758 (1991).

Landis, et al., "A novel LFA–1 activation epitope maps to the I domain," *J. Cell.Biol.* 120:1519–1527 (1993).

Larson, et al., "Primary structure of the leukocyte function–associated molecule–1 α subunit: an integrin with an embedded domain defining a protein superfamily," *J.Cell.Biol.* 108:703–712 (1989).

Larson and Springer, "Structure and function of leukocyte integrins," *Immununol.Rev.* 114:181–217 (1990).

Lawrence, et al., "Purification and characterization of human skin mast cells," *J. Immunol.* 139:3062–2069 (1987).

Letvin, et al., "Conservation of myeloid surface antigens on primary granulocytes," *Blood* 61:408–410 (1983).

Luk, et al., "Biotinylated lipopolysaccharide binds to endotoxin receptor in endothelial and monocytic cells," *Alan.Biochem.* 232:217–224 (1995).

MacMicking, et al., "Altered responses to bacterial infection and endotoxic shock in mice lacking inducible nitric oxide synthase," *Cell* 81:641–650 (1995).

Marks, et al., "Human Antibodies from V–gene Libraries Displayed on Phage," *J.Mol. Biol.* 222:581–597 (1991).

Matsumoto, et al., "Induction os Apoptosis in Human Eosinophils by Anti_Fas Antibody Treatment in Vitro," *Blood* 86:1437 (1995).

McCabe, "Production of single–stranded DNA by asymmetric PCR," in *PCR Protocols: A Guide to Methods and Applications*, Innis et al. (ed) Academic Press: New York (1990) pp. 76–83.

Means, et al., "Neuronophagia by Leukocytes in Experimental Spinal Cord Injury," *J. Neurophathol. & Exp.Neurol.* 42:707–719 (1983).

Merrill, et al., "Microglial cell cytotoxicity of oligodendrocytes is mediated through nitric oxide," *Immunol.* 151:2132 (1993).

Metlay, et al., "The distinct leukocyte integrins of mouse spleen dendritic cells as identified with new hamster monoclonal antibodies," *J.Exp.Med.* 171:1753–1771 (1990).

Michishita, et al., "A novel divalent cation–binding site in the A domain of the $\beta 2$ integrin CR3 (CD11b/CD18) is essential for ligand binding," *Cell* 72:857–867 (1993).

Moore, et al., "Canine leukocyte integrins: characterization of a CD18 homologue," *Tissue Antigens* 36:211–220 (1990).

Mulligan, et al., "Tissue injury caused by deposition of immune complexes is L–arginine dependent," *Proc.Natl.Acad.Sci.(USA)* 88:6338–6342 (1991).

Nourshargh, et al., "Accumulation of $^{111}$In–neutrophils in rabbit skin in allergic and non–allergic inflammatory reactions in vivo," *J.Immunol.* 142:3193–3198 (1989).

Parsons, et al., "Directing phage selections towards specific epitopes," *Protein Engineering*, 9:1043–1049 (1996).

Patarroyo, et al., "Leukocyte–cell adhesion: a molecular process fundamental in leukocyte physiology," *Immunol. Rev.* 114:67–108 (1990).

Price, et al., "In vivo inhibition of neutrophil function in the rabbit using monoclonal antibody to CD18," *J.Immunol.* 139:4174–4177 (1987).

Rabb, et al., "Alterations in Soluble and Leukocyte Surface L–Selectin (CD62L) in Hemodialysis Patients$^{1,2}$", *J.Am.Soc.Nephrol.* 6:1445–1450 (1995).

Rabb, et al., "Cell Adhesion Molecules and the Kidney", *Am.J.Kid.Dis.* 23:155–166 (1994).

Randi and Hogg, "I domain of $\beta_2$ integrin lymphocyte function–associated antigen–1 contains a binding site for ligand intercellular adhesion molecule–1," *J.Biol.Chem.* 269:12395–12398 (1994).

Reynolds, et al., "Nature Killer Activity in the Rat", *J.Immunol.* 132:534–540 (1984).

Rojiani et al., "In vitro interaction of a polypeptide homologous to human Ro/SS–A antigen (calreticulin) with a highly conserved amino acid sequence in the cytoplasmic domain of integrin $\alpha$ subunits," *Biochemistry* 30:9859–9866 (1991).

Rosenfeld, et al., "Fatty streak initiation in Watanabe heritable hyperlipemic and comparably hypercholesterolemic fat–fed rabbits" *Arteriosclerosis* 7:9–23 (1987).

Rosenfeld, et al., "Fatty streak expansion and maturation in Watanabe heritable hyperlipemic and comparably hypercholesterolemic fat–fed rabbits" *Arteriosclerosis* 7:24–34 (1987).

Sadhu, et al., "LFA–1 Binding site in ICAM–3 contains a conserved motif and non–contiguous amino acids" *Cell Adhesion and Communication* 2:429–440 (1994).

Sambrook, et al.,(eds), "Immobilization of Bacteriophage $\lambda$ plaques on nitrocellulose filters or nylon membranes" in *Molecular Cloning: a laboratory manual*, Cold Spring Harbor Press:Cold Spring Harbor, NY (1989) p. 2.110.

Sanchez–Madrid, et al., "A human leukocyte differentiation antigen family with distinct $\alpha$–subunits and a common $\beta$–subunit," *J.Exp.Med.* 154:1517 (1981).

Schall, "Biology of the rantes/sis cytokine family" *Cytokine*, 3:165–183 (1991).

Schneiderman, et al., "Expression of 12 rabbit IgA C$\alpha$ genes as chimeric rabbit–mouse IgA antibodies," *Proc.Natl.Acad. Sci. (USA)* 86:7562–7565 (1989).

Schwab, et al., "Pro– and anti–inflammatory roles of interleukin–1 in recurrence of bacterial cell wall–induced arthritis in rats," *Infection and Immunity* 59:4436–4442 (1991).

Searle, et al., "Regulation, linkage, and sequence of mouse metallothionein I and II genes," *Mol.Cell.Biol.* 4:1221–1230 (1984).

Sedgewick, et al., "Comparison of Airway and Blood Eosinophil Function After in Vivo Antigen Challenge," *J.Immunol.* 149:3710 (1992).

Shanley, et al., "Requirements for $\alpha$d in IgG Immune Complex–Induced Rat Lung Injury," *J. Immunol.*, 160:1014 (1998).

Shaw, et al., "Molecular cloning of the human mucosal lymphocyte integrin $\alpha^E$ subunit," *J.Biol.Chem.* 269:6016–6025 (1994).

Smith, et al., "Cooperative interactions of LFA–1 and Mac–1 with intercellular adhesion molecule–1 in facilitating adherence and transendothelial migration of human neutrophils in vitro," *J.Clin.Invest.* 83:2008–2017 (1989).

Springer, "Adhesion molecules of the immune system," *Nature* 346:425–434 (1990).

Stromberg, "Large Granular Lymphocyte Leukemia in F344 Rats", *Am.J.Pathol.* 119:517–519 (1985).

Tamura, et al., "Epithelial integrin$\alpha_6\beta_4$: complete primary structure of $\alpha_6$ and variant forms of $\beta_4$," *J.Cell.Biol.* 111:1593–1604 (1990).

Todd, et al., "Subcellular Localization of the Large Subunit of Mo1 (Mo1$_\alpha$, formerly gp 110), a Surface Glycoprotein Associated with Neutrophil Adhesion" *J.Clin.Invest.*, 74:1280 (1984).

Ueda, et al., "Identification of the complement iC3b binding site in the $\beta 2$ integrin CR3 (CD11b/CD18)," *Proc.Natl.Acad.Sci. (USA)* 91:10680–10684 (1994).

Van der Vieren, et al., "A Novel Leukointegrin $\alpha$d$\beta 2$ Binds Preferentially to ICAM–3," *Immunity* 3:683 (1984).

Varshney, et al., "Structure, organization, and regulation of human metallothionein I$^F$ gene: differential and cell–type–specific expression in response to heavy metals and glucocorticoids," *Mol.Cell.Biol.* 6:26–36 (1986).

Vaughn, et al., "Human Antibodies with Sub–nanomolar Affinities Isolated from a Large Non–immunized Phage Display Library," *Nature Biotechnol.* 14:309–314 (1996).

Ward and Reynolds, "A Heterogeneous Lymphocytic Leukemia in F344 Rats", *Am.J.Pathol.* 110:1–10 (1982).

Warner, et al., "A rapid Percoll technique for the purification of human basophils," *J.Immunol.Meth.* 106:107–110 (1987).

Waterhouse, et al., "Combinatorial infection and in vivo recombination: a strategy for making large phage antibody repertoires," *Nucl.Acids Res.* 21:2265–2266 (1993).

Wright, "Multiple receptors for endotoxin," *Curr.Opin.Immunol.* 3:83–90 (1991).

Yamada, et al.,"Mucosal injury and inflammation in a model of chronic granulomatous colitis in rats," *Gastroenterology* 104:759–771 (1993).

Zhout, et al., "Differential ligand binding specificities of recombinant CD11b/CD8 integrin I–domain" *J.Biol.Chem.* 269:17076–17079 (1994).

Walsh, et al., "IL–5 enhances the in vitro adhesion of human eosinophils, but not neutrophils, in a leucocyte integrin (CD11/18)–dependent manner," *Immunol.* 71:250 (1990).

Basso, et al., "A Sensitive and Reliable Locomotor Rating Scale for Open Field Testing in Rats," *Neurotrauma* 12:1–21 (1995).

Maiorov, et al., "Relationship Between Severity of Spinal Cord Injury and Abnormalities in Neurogenic Cardiovascular Control in Conscious Rats," *J. Neurotrauma* 15:365–74 (1998).

Rivlin, et al., "Effect of Duration of Acute Spinal Cord Compression in a New Acute Cord Injury Model in the Rat," *Surg. Neurol.* 10:38–43 (1978).

* cited by examiner

|       |            |            |            |            |            |     |
|-------|------------|------------|------------|------------|------------|-----|
| αD    | TF-GT--VLL | LSVLASYHGF | NLDVEEPTIF | QEDAGGFGQS | VVQFGGSRLV | 47  |
| CD11B | MA-LR--VLL | LTALTLCHGF | NLDTENAMTF | QENARGFGQS | VVQLQGSRVV | 47  |
| CD11C | MTRTRAALLL | FTALATSLGF | NLDTEELTAF | RVDSAGFGDS | VVQYANSWVV | 50  |
|       |            |            |            |            |            |     |
| αD    | VGAPLEVVAA | NQTGRLYDCA | AATGMCQPIP | LHIRPEAVNM | SLGLTLAAST | 97  |
| CD11B | VGAPQEIVAA | NQRGSLYQCD | YSTGSCEPIR | LQVPVEAVNM | SLGLSLAATT | 97  |
| CD11C | VGAPQKIIAA | NQIGGLYQCG | YSTGACEPIG | LQVPPEAVNM | SLGLSLASTT | 100 |
|       |            |            |            |            |            |     |
| αD    | NGSRLLACGP | TLHRVCGENS | YSKGSCLLLG | SR-WEIIQTV | PDATPECPHQ | 146 |
| CD11B | SPPQLLACGP | TVHQTCSENT | YVKGLCFLFG | SNLRQQPQKF | PEALRGCPQE | 147 |
| CD11C | SPSQLLACGP | TVHHECGRNM | YLTGLCFLLG | PT--QLTQRL | PVSRQECPRQ | 148 |
|       |            |            |            |            |            |     |
| αD    | EMDIVFLIDG | SGSIDQNDFN | QMKGFVQAVM | GQFEGTDTLF | ALMQYSNLLK | 196 |
| CD11B | DSDIAFLIDG | SGSIIPHDFR | RMKEFVSTVM | EQLKKSKTLF | SLMQYSEEFR | 197 |
| CD11C | EQDIVFLIDG | SGSISSRNFA | TMMNFVRAVI | SQFQRPSTQF | SLMQFSNKFQ | 198 |
|       |            |            |            |            |            |     |
| αD    | IHFTFTQFRT | SPSQQSLVDP | IVQLKGLTFT | ATGILTVVTQ | LFHHKNGARK | 246 |
| CD11B | IHFTFKEFQN | NPNPRSLVKP | ITQLLGRTHT | ATGIRKVVRE | LFNITNGARK | 247 |
| CD11C | THFTFEEFRR | TSNPLSLLAS | VHQLQGFTYT | ATAIQNVVHR | LFHASYGARR | 248 |
|       |            |            |            |            |            |     |
| αD    | SAKKILIVIT | DGQKYKDPLE | YSDVIPQAEK | AGIIRYAIGV | GHAFQGPTAR | 296 |
| CD11B | NAFKILVVIT | DGEKFGDPLG | YEDVIPEADR | EGVIRYVIGV | GDAFRSEKSR | 297 |
| CD11C | DAIKILIVIT | DGKKEGDSLD | YKDVIPMADA | AGIIRYAIGV | GLAFQNRNSW | 298 |

FIGURE 1A

| | | | | | |
|---|---|---|---|---|---|
| αD    | QELNTISSAP | PODHVFKVDN | FAALGSIQKQ | LQEKIYAVEG | TQSRASSSFQ | 346 |
| CD11B | QELNTIASKP | PRDHVFQVNN | FEALKTIQNQ | LREKIFAIEG | TQTGSSSSFE | 347 |
| CD11C | KELNDIASKP | SQEHIFKVED | FDALKDIQNQ | LKEKIFAIEG | TETISSSSFE | 348 |
| αD    | HEMSQEGFST | ALTMDGLFLG | AVGSFSWSGG | AFLYPPNMSP | TFINMSQENV | 396 |
| CD11B | HEMSQEGFSA | AITSNGPLLS | TVGSYDWAGG | VFLYTSKEKS | TFINMTRVDS | 397 |
| CD11C | LEMAQEGFSA | VFTPDGPVLG | AVGSFTWSGG | AFLYPPNMSP | TFINMSQENV | 398 |
| αD    | DMRDSYLGYS | TELALWKGVQ | NLVLGAPRYQ | HTGKAVIFTQ | VSRQWRKKAE | 446 |
| CD11B | DMNDAYLGYA | AAIILRNRVQ | SLVLGAPRYQ | HIGLVAMFRQ | NTGMWESNAN | 447 |
| CD11C | DMRDSYLGYS | TELALWKGVQ | SLVLGAPRYQ | HIGKAVIFIQ | VSRQWRMKAE | 448 |
| αD    | VTGTQIGSYF | GASLCSVDVD | SDGSTDLILI | GAPHYYEQTR | GGQVSVCPLP | 496 |
| CD11B | VKGTQIGAYF | GASLCSVDVD | SNGSTDLVLI | GAPHYYEQTR | GGQVSVCPLP | 497 |
| CD11C | VIGTQIGSYF | GASLCSVDVD | TDGSTDLVLI | GAPHYYEQTR | GGQVSVCPLP | 498 |
| αD    | RGQRVQWQCD | AVLRGEQGHP | WGRFGAALTV | LGDVNEDKLI | DVAIGAPGEQ | 546 |
| CD11B | RGQRARWQCD | AVLYGEQGQP | WGRFGAALTV | LGDVNGDKLT | DVAIGAPGEE | 547 |
| CD11C | RGWRRWW-CD | AVLYGEQGHP | WGRFGAALTV | LGDVNGDKLT | DVVIGAPGEE | 547 |
| αD    | ENRGAVYLFH | GASESGISPS | HSQRIASSQL | SPRLQYFGQA | LSGGQDLTQD | 596 |
| CD11B | DNRGAVYLFH | GTSGSGISPS | HSQRIAGSKL | SPRLQYFGQS | LSGGQDLTMD | 597 |
| CD11C | ENRGAVYLFH | GVLGPSISPS | HSQRIAGSQL | SSRLQYFGQA | LSGGQDLTQD | 597 |

FIGURE 1B

```
αD    GLMDLAVGAR GQVLLLRSLP VLKVGVAMRF SPVEVAKAVY RCWEEKPSAL    646
CD11B GLVDLTVGAQ GHVLLLRSQP VLRVKAIMEF NPREVARNVF ECNDQVVKGK    647
CD11C GLVDLAVGAR GQVLLLRTRP VLWVGVSMQF IPAEIPRSAF ECREQVVSEQ    647

αD    EAGDATVCLT IQKSSLDQL- -GDIQSSVRF DLALDPGRLT SRAIFNETKN    694
CD11B EAGEVRVCLH VQKSTRDRLR EGQIQSVVTY DLALDSGRPH SRAVFNETKN    697
CD11C TLVQSNICLY IDKRSKNLLG SRDLQSSVTL DLALAPGRLS PRAIFQETKN    697

αD    PTLTTRKTLG LGIHCETLKL LLPDCVEDVV SPIILHLNFS LVREPIPSPQ    744
CD11B STRRQTQVLG LTQTCETLKL QLPNCIEDPV SPIVLRLNFS LVGTPLSAFG    747
CD11C RSLSRVRVLG LKAHCENFNL LLPSCVEDSV IPIILRLNFT LVGKPLLAFR    747

αD    NLRPVLAVGS QDLFTASLPF EKNCGQDGLC EGDLGVTLSF SGLQTLTVGS    794
CD11B NLRPVLAEDA QRLFTALFPF EKNCGNDNIC QDDLSITFSF MSLDCLVVGG    797
CD11C NLRPMLAALA QRYFTASLPF EKNCGADHIC QDNLGISFSF PGLKSLLVGS    797

αD    SLELNVIVTV WNAGEDSYGT VVSLYYPAGL SHRRVSGAQK QPHQSALRLA    844
CD11B PREFNVTVTV RNDGEDSYRT QVTFFFPLDL SYRKVSTLQN QRSQRSWRLA    847
CD11C NLELNAEVHV WNDGEDSYGT TITFSHPAGL SYRYVAEGQK QGQLRSLHLT    847

αD    CETVPTED-- EGLRSSRCSV NHPIFHEGSN GTFIVTFDVS Y---KATLG     888
CD11B CESASSTEVS GALKSTSCSI NHPIFPENSE ----VTFNIT FDVDSKASLG    893
CD11C CCSA-PVGSQ GTW-STSCRI NHLIFRGGAQ ----ITFLAT FDVSPKAVGL    891
```

FIGURE 1C

```
αD     DRMLMRASAS  SENNKASSSK  ATFQLELPVK  YAVYTMISRQ  EESTKYFNFA   938
CD11B  NKLLLKANVT  SENNMPRTNK  TEFQLELPVK  YAVYMVVTSH  GVSTKYLNFT   943
CD11C  DRLLLIANVS  SENNIPRTSK  TIFQLELPVK  YAVYIVVSSH  EQFTKYLNFS   941

αD     TS-DEKKMKE  AEHRYRVNNL  SQRDLAISIN  FWVPVLLNGV  AVWDVVMEAP   987
CD11B  AS-ENTS-RV  MQHQYQVSNL  GQRSLPISLV  FLVPVRLNQT  VIWDRPQVTF   991
CD11C  ESEEKES-HV  AMHRYQVNNL  GQRDLPVSIN  FWVPVELNQE  AVWMDVEVSH   990

αD     SQSLP--CVS  ERKPPQHSDF  LTQISRSPML  DCSIADCLQF  RCDVPSFSVQ  1035
CD11B  SENLSSTCHT  KERLPSHSDF  LAELRKAPVV  NCSIAVCQRI  QCDIPFFGIQ  1041
CD11C  PQNPSLRCSS  EKIAPPASDF  LAHIQKNPVL  DCSIAGCLRF  RCDVPSFSVQ  1040

αD     EELDFTLKGN  LSFGWVRETL  QKKVLVVSVA  EITFDTSVYS  QLPGQEAFMR  1085
CD11B  EEFNATLKGN  LSFDWYIKTS  HNHLLIVSTA  EILFNDSVFT  LLPGQGAFVR  1091
CD11C  EELDFTLKGN  LSFGWVRQIL  QKKVSVVSVA  EIIFDTSVYS  QLPGQEAFMR  1090

αD     AQMEMVLEED  EVYNAIPIIM  GSSVGALLLL  ALITATLYKL  GFFKRHYKEM  1135
CD11B  SQTETKVEPF  EVPNPLPLIV  GSSVGGLLLL  ALITAALYKL  GFFKRQYKDM  1141
CD11C  AQTITVLEKY  KVHNPIPLIV  GSSIGGLLLL  ALITAVLYKV  GFFKRQYKEM  1140

αD     LEDKPED---  ----TATFS   GDDFSCVAPN  VPLS                    1161
CD11B  M---SEG---  ----GP--P   GAE-----PQ                          1153
CD11C  M---EEANGQ  IAPENGT--Q  TPS-----PP  SEK                     1163
```

FIGURE 1D

METHODS OF INHIBITING LOCOMOTOR DAMAGE FOLLOWING SPINAL CORD INJURY WITH α D-SPECIFIC ANTIBODIES

This application is a continuation-in-part of U.S. patent application Ser. No. 09/350,259 filed Jul. 8, 1999, which is pending which is a continuation of U.S. patent application Ser. No. 09/193,043 filed Nov. 16, 1998, which issued as U.S. Pat. No. 6,251,395 on Jun. 26, 2001, which is a continuation-in-part of U.S. patent application Ser. No. 08/943,363 filed Oct. 3, 1997, which issued as U.S. Pat. No. 5,837,478 on Oct. 17, 1998, which a continuation-in-part of U.S. patent application Ser. No. 08/605,672, filed Feb. 22, 1996, which issued as U.S. Pat. No. 5,817,515 on Oct. 6, 1998, which is a continuation-in-part of U.S. application Ser. No. 08/362,652, filed Dec. 21, 1994, which issued as U.S. Pat. No. 5,766,850 on Jun. 16, 1998, which is a continuation-in-part of U.S. application Ser. No. 08/286,889, filed Aug. 5, 1994, which issued as U.S. Pat. No. 5,470,953 on Nov. 28, 1995, which in turn is a continuation-in-part of U.S. application Ser. No. 08/173,497, filed Dec. 23, 1993, which issued as U.S. Pat. No. 5,437,958 on Aug. 1, 1995. These applications are incorporated herein by reference in their entirety.

BACKGROUND OF THE INVENTION

The integrins are a class of membrane-associated molecules which actively participate in cellular adhesion. Integrins are transmembrane heterodimers comprising an α subunit in noncovalent association with a β subunit. To date, at least fourteen α subunits and eight β subunits have been identified [reviewed in Springer, Nature 346:425–434 (1990)]. The β subunits are generally capable of association with more than one α subunit and the heterodimers sharing a common β subunit have been classified as subfamilies within the integrin population.

One class of human integrins, restricted to expression in white blood cells, is characterized by a common $\beta_2$ subunit. As a result of this cell-specific expression, these integrins are commonly referred to as the leukocyte integrins, Leu-CAMs or leukointegrins. Because of the common $\beta_2$ subunit, an alternative designation of this class is the $\beta_2$ integrins. The $\beta_2$ subunit (CD18) has previously been isolated in association with one of three distinct α subunits, CD11a, CD11b or CD11c. The isolation of a cDNA encoding human CD18 is described in Kishimoto, et al., Cell 48:681–690 (1987). In official WHO nomenclature, the heterodimeric proteins are referred to as CD11a/CD18, CD11b/CD18, and CD11c/CD18; in common nomenclature they are referred to as LFA-1, Mac-1 or Mol and p150,95 or LeuM5, respectively [Cobbold, et al., in Leukocyte Typing III, McMichael (ed), Oxford Press, p.788 (1987)]. The human $\beta_2$ integrin α subunits CD11a, CD11b and CD11c have been demonstrated to migrate under reducing condition in electrophoresis with apparent molecular weights of approximately 180 kD, 155 kD and 150 kD, respectively, and DNAs encoding these subunits have been cloned [CD11a, Larson, et al., J. Cell Biol. 108:703–712 (1989); CD11b, Corbi, et al., J.Biol.Chem. 263:12403–12411 (1988) and CD11c, Corbi, et al. EMBO J. 6:4023–4028 (1987)]. Putative homologs of the human $\beta_2$ integrin α and β chains, defined by approximate similarity in molecular weight, have been variously identified in other species including monkeys and other primates [Letvin, et al., Blood 61:408–410 (1983)], mice [Sanchez-Madrid, et al., J.Exp.Med. 154:1517 (1981)], and dogs [Moore, et al., Tissue Antigens 36:211–220 (1990)].

The absolute molecular weights of presumed homologs from other species have been shown to vary significantly [see, e.g., Danilenko et al., Tissue Antigens 40:13–21 (1992)], and in the absence of sequence information, a definitive correlation between human integrin subunits and those identified in other species has not been possible. Moreover, variation in the number of members in a protein family has been observed between different species. Consider, for example, that more IgA isotypes have been isolated in rabbits than in humans [Burnett, et al., EMBO J. 8:4041–4047 (1989) and Schneiderman, et al., Proc.Natl.Acad.Sci.(USA) 86:7561–7565 (1989)]. Similarly, in humans, at least six variants of the metallothionine protein have been previously identified [Karin and Richards, Nature 299:797–802 (1982) and Varshney, et al., Mol.Cell.Biol. 6:26–37, (1986)], whereas in the mouse, only two such variants are in evidence [Searle, et al., Mol.Cell.Biol. 4:1221–1230 (1984)]. Therefore, existence of multiple members of a protein family in one species does not necessarily imply that corresponding family members exist in another species.

In the specific context of $\beta_2$ integrins, in dogs it has been observed that the presumed canine $\beta_2$ counterpart to the human CD18 is capable of dimer formation with as many as four potentially distinct α subunits [Danilenko, et al., supra]. Antibodies generated by immunizing mice with canine splenocytes resulted in monoclonal antibodies which immunoprecipitated proteins tentatively designated as canine homologs to human CD18, CD11a, CD11b and CD11c based mainly on similar, but not identical, molecular weights. Another anti-canine splenocyte antibody, Ca11.8H2, recognized and immunoprecipitated a fourth α-like canine subunit also capable of association with the $\beta_2$ subunit, but having a unique molecular weight and restricted in expression to a subset of differentiated tissue macrophages.

Antibodies generated by immunization of hamsters with murine dendritic cells resulted in two anti-integrin antibodies [Metlay, et al., J.Exp.Med. 171:1753–1771 (1990)]. One antibody, 2E6, immunoprecipitated a predominant heterodimer with subunits having approximate molecular weights of 180 kD and 90 kD in addition to minor bands in the molecular weight range of 150–160 kD. The second antibody, N418, precipitated another apparent heterodimer with subunits having approximate molecular weights of 150 kD and 90 Kd. Based on cellular adhesion blocking studies, it was hypothesized that antibody 2E6 recognized a murine counterpart to human CD18. While the molecular weight of the N418 antigen suggested recognition of a murine homolog to human CD11c/CD18, further analysis indicated that the murine antigen exhibited a tissue distribution pattern which was inconsistent with that observed for human CD11c/CD18.

The antigens recognized by the canine Ca11.8H2 antibody and the murine N418 antibody could represent a variant species (e.g., a glycosylation or splice variant) of a previously identified canine or murine α subunit. Alternatively, these antigens may represent unique canine and murine integrin α subunits. In the absence of specific information regarding primary structure, these alternatives cannot be distinguished.

In humans, CD11a/CD18 is expressed on all leukocytes. CD11b/CD18 and CD11c/CD18 are essentially restricted to expression on monocytes, granulocytes, macrophages and natural killer (NK) cells, but CD11c/CD18 is also detected on some B-cell types. In general, CD11a/CD18 predominates on lymphocytes, CD11b/CD18 on granulocytes and CD11c/CD18 on macrophages [see review, Arnaout, Blood 75:1037–1050 (1990)]. Expression of the a chains, however, is variable with regard to the state of activation and differentiation of the individual cell types [See review, Larson and Springer, *Immunol.Rev.* 114:181–217 (1990).]

The involvement of the $\beta_2$ integrins in human immune and inflammatory responses has been demonstrated using monoclonal antibodies which are capable of blocking $\beta_2$ integrin-associated cell adhesion. For example, CD11a/CD18, CD11b/CD18 and CD11c/CD18 actively participate in natural killer (NK) cell binding to lymphoma and adenocarcinoma cells [Patarroyo, et al., *Immunol.Rev.* 114:67–108 (1990)], granulocyte accumulation [Nourshargh, et al., *J.Immunol.* 142:3193–3198 (1989)], granulocyte-independent plasma leakage [Arfors, et al., *Blood* 69:338–340 (1987)], chemotactic response of stimulated leukocytes [Arfors, et al., supra] and leukocyte adhesion to vascular endothelium [Price, et al., *J.Immunol.* 139:4174–4177 (1987) and Smith, et al., *J.Clin.Invest.* 83:2008–2017 (1989)]. The fundamental role of $\beta_2$ integrins in immune and inflammatory responses is made apparent in the clinical syndrome referred to as leukocyte adhesion deficiency (LAD), wherein clinical manifestations include recurrent and often life threatening bacterial infections. LAD results from heterogeneous mutations in the $\beta_2$ subunit [Kishimoto, et al., *Cell* 50:193–202 (1987)] and the severity of the disease state is proportional to the degree of the deficiency in $\beta_2$ subunit expression. Formation of the complete integrin heterodimer is impaired by the $\beta_2$ mutation [Kishimoto, et al., supra]. Interestingly, at least one antibody specific for CD18 has been shown to inhibit human immunodeficiency virus type-1 (HIV-1) syncytia formation in vitro, albeit the exact mechanism of this inhibition is unclear [Hildreth and Orentas, *Science* 244:1075–1078 (1989)]. This observation is consistent with the discovery that a principal counterreceptor of CD11a/CD18, ICAM-1, is also a surface receptor for the major group of rhinovirus serotypes [Greve, et al., *Cell* 56:839 (1989)].

The significance of $\beta_2$ integrin binding activity in human immune and inflammatory responses underscores the necessity to develop a more complete understanding of this class of surface proteins. Identification of yet unknown members of this subfamily, as well as their counterreceptors, and the generation of monoclonal antibodies or other soluble factors which can alter biological activity of the $\beta_2$ integrins will provide practical means for therapeutic intervention in $\beta_2$ integrin-related immune and inflammatory responses.

BRIEF DESCRIPTION OF THE INVENTION

In one aspect, the present invention provides novel purified and isolated polynucleotides (e.g., DNA and RNA transcripts, both sense and anti-sense strands) encoding a novel human $\beta_2$ integrin a subunit, $\alpha_d$, and variants thereof (i.e., deletion, addition or substitution analogs) which possess binding and/or immunological properties inherent to $\alpha_d$. Preferred DNA molecules of the invention include cDNA, genomic DNA and wholly or partially chemically synthesized DNA molecules. A presently preferred polynucleotide is the DNA as set forth in SEQ ID NO: 1, encoding the polypeptide of SEQ ID NO: 2. Also provided are recombinant plasmid and viral DNA constructions (expression constructs) which include $\alpha_d$ encoding sequences, wherein the $\alpha_d$ encoding sequence is operatively linked to a homologous or heterologous transcriptional regulatory element or elements.

Also provided by the present invention are isolated and purified mouse and rat polynucleotides which exhibit homology to polynucleotides encoding human $\alpha_d$. A preferred mouse polynucleotide is set forth in SEQ ID NO: 52; a preferred rat polynucleotide is set forth in SEQ ID NO: 54.

As another aspect of the invention, prokaryotic or eukaryotic host cells transformed or transfected with DNA sequences of the invention are provided which express $\alpha_d$ polypeptide or variants thereof. Host cells of the invention are particularly useful for large scale production of $\alpha_d$ polypeptide, which can be isolated from either the host cell itself or from the medium in which the host cell is grown. Host cells which express $\alpha_d$ polypeptide on their extracellular membrane surface are also useful as immunogens in the production of $\alpha_d$-specific antibodies. Preferably, host cells transfected with $\alpha_d$ will be co-transfected to express a $\beta_2$ integrin subunit in order to allow surface expression of the heterodimer.

Also provided by the present invention are purified and isolated $\alpha_d$ polypeptides, fragments and variants thereof. Preferred $\alpha_d$ polypeptides are as set forth in SEQ ID NO: 2. Novel $\alpha_d$ products of the invention may be obtained as isolates from natural sources, but, along with $\alpha_d$ variant products, are preferably produced by recombinant procedures involving host cells of the invention. Completely glycosylated, partially glycosylated and wholly de-glycosylated forms of the $\alpha_d$ polypeptide may be generated by varying the host cell selected for recombinant production and/or post-isolation processing. Variant $\alpha_d$ polypeptides of the invention may comprise water soluble and insoluble $\alpha_d$ polypeptides including analogs wherein one or more of the amino acids are deleted or replaced: (1) without loss, and preferably with enhancement, of one or more biological activities or immunological characteristics specific for $\alpha_d$; or (2) with specific disablement of a particular ligand/receptor binding or signalling function. Fusion polypeptides are also provided, wherein $\alpha_d$ amino acid sequences are expressed contiguously with amino acid sequences from other polypeptides. Such fusion polypeptides may possess modified biological, biochemical, and/or immunological properties in comparison to wild-type $\alpha_d$. Analog polypeptides including additional amino acid (e.g., lysine or cysteine) residues that facilitate multimer formation are contemplated.

Also comprehended by the present invention are polypeptides and other non-peptide molecules which specifically bind to $\alpha_d$. Preferred binding molecules include antibodies (e.g., monoclonal and polyclonal antibodies), counterreceptors (e.g., membrane-associated and soluble forms) and other ligands (e.g., naturally occurring or synthetic molecules), including those which competitively bind $\alpha_d$ in the presence of $\alpha_d$ monoclonal antibodies and/or specific counterreceptors. Binding molecules are useful for purification of $\alpha_d$ polypeptides and identifying cell types which express $\alpha_d$. Binding molecules are also useful for modulating (i.e., inhibiting, blocking or stimulating) of in vivo binding and/or signal transduction activities of $\alpha_d$.

Assays to identify $\alpha_d$ binding molecules are also provided, including in vitro assays such as immobilized ligand binding assays, solution binding assays, and scintillation proximity assays, as well as cell based assays such as di-hybrid screening assays, split hybrid screening assays, and the like. Cell based assays provide for a phenotypic change in a host cell as a result of specific binding interaction or disruption of a specific binding interaction, thereby permitting indirect quantitation or measurement of some specific binding interaction.

In vitro assays for identifying antibodies or other compounds that modulate the activity of $\alpha_d$ may involve, for example, immobilizing $\alpha_d$ or a natural ligand to which $\alpha_d$ binds, detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of $\alpha_d$ binding.

Another type of in vitro assay for identifying compounds that modulate the interaction between $\alpha_d$ and a ligand involves immobilizing $\alpha_d$ or a fragment thereof on a solid support coated (or impregnated with) a fluorescent agent, labeling the ligand with a compound capable of exciting the fluorescent agent, contacting the immobilized $\alpha_d$ with the labeled ligand in the presence and absence of a putative modulator compound, detecting light emission by the fluorescent agent, and identifying modulating compounds as those compounds that affect the emission of light by the fluorescent agent in comparison to the emission of light by the fluorescent agent in the absence of a modulating compound. Alternatively, the $\alpha_d$ ligand may be immobilized and $\alpha_d$ may be labeled in the assay.

A cell based assay method contemplated by the invention for identifying compounds that modulate the interaction between $\alpha_d$ and a ligand involves transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of $\alpha_d$ and either the DNA binding domain or the activating domain of the transcription factor, expressing in the host cells a second hybrid DNA sequence encoding part or all of the ligand and the DNA binding domain or activating domain of the transcription factor which is not incorporated in the first fusion, evaluating the effect of a putative modulating compound on the interaction between $\alpha_d$ and the ligand by detecting binding of the ligand to $\alpha_d$ in a particular host cell by measuring the production of reporter gene product in the host cell in the presence or absence of the putative modulator, and identifying modulating compounds as those compounds altering production of the reported gene product in comparison to production of the reporter gene product in the absence of the modulating compound. Presently preferred for use in the assay are the lexA promoter, the lexA DNA binding domain, the GAL4 transactivation domain, the lacZ reporter gene, and a yeast host cell.

A modified version of the foregoing assay may be used in isolating a polynucleotide encoding a protein that binds to $\alpha_d$ by transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of $\alpha_d$ and either the DNA binding domain or the activating domain of the transcription factor, expressing in the host cells a library of second hybrid DNA sequences encoding second fusions of part or all of putative $\alpha_d$ binding proteins and the DNA binding domain or activating domain of the transcription factor which is not incorporated in the first fusion, detecting binding of an $\alpha_d$ binding protein to $\alpha_d$ in a particular host cell by detecting the production of reporter gene product in the host cell, and isolating second hybrid DNA sequences encoding $\alpha_d$ binding protein from the particular host cell.

In a preferred embodiment utilizing the split hybrid assay, the invention provides a method to identify an inhibitor of binding between an $\alpha_d$ protein or fragment thereof and an $\alpha_d$ binding protein or binding fragment thereof comprising the steps of: (a) transforming or transfecting a host cell with a first DNA expression construct comprising a first selectable marker gene encoding a first selectable marker protein and a repressor gene encoding a repressor protein, said repressor gene under transcriptional control of a promoter; (b) transforming or transfecting said host cell with a second DNA expression construct comprising a second selectable marker gene encoding a second selectable marker protein and a third selectable marker gene encoding a third selectable marker protein, said third selectable marker gene under transcriptional control of an operator, said operator specifically acted upon by said repressor protein such that interaction of said repressor protein with said operator decreases expression of said third selectable marker protein; (c) transforming or transfecting said host cell with a third DNA expression construct comprising a fourth selectable marker gene encoding a fourth selectable marker protein and an $\alpha_d$ fusion protein gene encoding an $\alpha_d$ protein or fragment thereof in frame with either a DNA binding domain of a transcriptional activation protein or a transactivating domain of said transcriptional activation protein; (d) transforming or transfecting said host cell with a fourth DNA expression construct comprising a fifth selectable marker gene encoding a fifth selectable marker protein and a second fusion protein gene encoding an $\alpha_d$ binding protein or binding fragment thereof in frame with either the DNA binding domain of said transcriptional activation protein or the transactivating domain of said transcriptional activation protein, whichever is not included in first fusion protein gene; (e) growing said host cell under conditions which permit expression of said $\alpha_d$ protein or fragment thereof and said $\alpha_d$ binding protein or fragment thereof such that said $\alpha_d$ protein or fragment thereof and $\alpha_d$ binding protein or binding fragment thereof interact bringing into proximity said DNA binding domain and said transactivating domain reconstituting said transcriptional activating protein; said transcriptional activating protein acting on said promoter to increase expression of said repressor protein; said repressor protein interacting with said operator such that said third selectable marker protein is not expressed; (f) detecting absence of expression of said selectable gene; (g) growing said host cell in the presence of a test inhibitor of binding between said $\alpha_d$ protein or fragment thereof and said $\alpha_d$ binding protein or fragment thereof; and (h) comparing expression of said selectable marker protein in the presence and absence of said test inhibitor wherein decreased expression of said selectable marker protein is indicative of an ability of the test inhibitor to inhibit binding between said $\alpha_d$ protein or fragment thereof and said $\alpha_d$ binding protein or binding fragment thereof such that said transcriptional activating protein is not reconstituted, expression of said repressor protein is not increased, and said operator increases expression of said selectable marker protein.

The invention comprehends host cells wherein the various genes and regulatory sequences are encoded on a single DNA molecule as well as host cells wherein one or more of the repressor gene, the selectable marker gene, the $\alpha_d$ fusion protein gene, and the $\alpha_d$ binding protein gene are encoded on distinct DNA expression constructs. In a preferred embodiment, the host cells are transformed or transfected with DNA encoding the repressor gene, the selectable marker gene, the $\alpha_d$ fusion protein gene, and the $_d$ fusion binding protein gene, each encoded on a distinct expression construct. Regardless of the number of DNA expression constructs introduced, each transformed or transfected DNA expression construct further comprises a selectable marker gene sequence, the expression of which is used to confirm that transfection or transformation was, in fact, accomplished. Selectable marker genes encoded on individually transformed or transfected DNA expression constructs are distinguishable from the selectable marker under transcriptional regulation of the tet operator in that expression of the selectable marker gene regulated by the tet operator is central to the preferred embodiment; i.e., regulated expression of the selectable marker gene by the tet operator provides a measurable phenotypic change in the host cell that is used to identify a binding protein inhibitor. Selectable marker genes encoded on individually transformed or transfected DNA expression constructs are provided as determinants of successful transfection or transformation of the individual DNA expression constructs. Preferred host cells of the invention include transformed S. cerevisiae strains designated YI596 and YI584 which were deposited Aug. 13, 1996 with the American Type Culture Collection (ATCC), 12301 Parklawn Drive, Rockville, Md. 20852, and assigned Accession Numbers ATCC 74384 and ATCC 74385, respectively.

The host cells of the invention include any cell type capable of expressing the $\alpha_d$ and $\alpha_d$ binding proteins required as described above and which are capable of being transformed or transfected with functional promoter and operator sequences which regulate expression of the heterologous proteins also as described. In a preferred embodiment, the host cells are of either mammal, insect or yeast origin. Presently, the most preferred host cell is a yeast cell. The preferred yeast cells of the invention can be selected from various strains, including the S. cerevisiae yeast transfonnants described in Table 1. Alternative yeast specimens include S.pombe, K.lactis, P.pastoris, S.carlsbergensis and C.albicans. Preferred mammalian host cells of the invention include Chinese hamster ovary (CHO), COS, HeLa, 3T3, CV1, LTK, 293T3, Rat1, PC12 or any other transfectable cell line of human or rodent origin. Preferred insect cell lines include SF9 cells.

In a preferred embodiment, the selectable marker gene is regulated by an operator and encodes an enzyme in a pathway for synthesis of a nutritional requirement for said host cell such that expression of said selectable marker protein is required for growth of said host cell on media lacking said nutritional requirement. Thus, as in a preferred embodiment where a repressor protein interacts with the operator, transcription of the selectable marker gene is down-regulated and the host cells are identified by an inability to grow on media lacking the nutritional requirement and an ability to grow on media containing the nutritional requirement. In a most preferred embodiment, the selectable marker gene encodes the HIS3 protein, and host cells transformed or transfected with a HIS3-encoding DNA expression construct are selected following growth on media in the presence and absence of histidine. The invention, however, comprehends any of a number of alternative selectable marker genes regulated by an operator. Gene alternatives include, for example, URA3, LEU2, LYS2 or those encoding any of the multitude of enzymes required in various pathways for production of a nutritional requirement which can be definitively excluded from the media of growth. In addition, conventional reporter genes such as chloramphenicol acetyltransferase (CAT), firefly luciferase, β-galactosidase (β-gal), secreted alkaline phosphatase (SEAP), green fluorescent protein (GFP), human growth hormone (hGH), β-glucuronidase, neomycin, hygromycin, thymidine kinase (TK) and the like may be utilized in the invention.

In the preferred embodiment, the host cells include a repressor protein gene encoding the tetracycline resistance protein which acts on the tet operator to decrease expression of the selectable marker gene. The invention, however, also encompasses alternatives to the tet repressor and operator, for example, E.coli trp repressor and operator, his repressor and operator, and lac operon repressor and operator.

The DNA binding domain and transactivating domain components of the fusion proteins may be derived from the same transcription factor or from different transcription factors as long as bringing the two domains into proximity through binding between $\alpha_d$ and the $\alpha_d$ binding protein permits formation of a functional transcriptional activating protein that increases expression of the repressor protein with high efficiency. A high efficiency transcriptional activating protein is defined as having both a DNA binding domain exhibiting high affinity binding for the recognized promoter sequence and a transactivating domain having high affinity binding for transcriptional machinery proteins required to express repressor gene mRNA. The DNA binding domain component of a fusion protein of the invention can be derived from any of a number of different proteins including, for example, LexA or Gal4. Similarly, the transactivating component of the invention's fusion proteins can be derived from a number of different transcriptional activating proteins, including for example, Gal4 or VP16.

The promoter sequence of the invention which regulates transcription of the repressor protein can be any sequence capable of driving transcription in the chosen host cell. The promoter may be a DNA sequence specifically recognized by the chosen DNA binding domain of the invention, or any other DNA sequence with which the DNA binding domain of the fusion protein is capable of high affinity interaction. In a preferred embodiment of the invention, the promoter sequence of the invention is either a HIS3 or alcohol dehydrogenase (ADH) promoter. In a presently most preferred embodiment, the ADH promotor is employed in the invention. The invention, however, encompasses numerous alternative promoters, including, for example, those derived from genes encoding HIS3, ADH, URA3, LEU2 and the like.

The methods of the invention encompass any and all of the variations in host cells as described above. In particular, the invention encompasses a method wherein: the host cell is a yeast cell; the selectable marker gene encodes HIS3; transcription of the selectable marker gene is regulated by the tet operator; the repressor protein gene encodes the tetracycline resistance protein; transcription of the tetracycline resistance protein is regulated by the HIS3 promoter; the DNA binding domain is derived from LexA; and the transactivating domain is derived from VP16. In another embodiment, the invention encompasses a method wherein: the host cell is a yeast cell; the selectable marker gene encodes HIS3; transcription of the selectable marker gene is regulated by the tet operator; the repressor protein gene encodes the tetracycline resistance protein; transcription of the tetracycline resistance protein is regulated by the alcohol dehydrogenase promoter; the DNA binding domain is derived from LexA; and the transactivating domain is derived from VP16.

In alternative embodiments of the invention wherein the host cell is a mammalian cell, variations include the use of mammalian DNA expression constructs to encode the $\alpha_d$ and $\alpha_d$ binding fusion genes, the repressor gene, and the selectable marker gene, and use of selectable marker genes encoding antibiotic or drug resistance markers (i.e., neomycin, hygromycin, thymidine kinase).

There are at least three different types of libraries used for the identification of small molecule modulators. These include: (1) chemical libraries, (2) natural product libraries, and (3) combinatorial libraries comprised of random peptides, oligonucleotides or organic molecules.

Chemical libraries consist of structural analogs of known compounds or compounds that are identified as "hits" via natural product screening. Natural product libraries are collections of microorganisms, animals, plants, or marine organisms which are used to create mixtures for screening by: (1) fermentation and extraction of broths from soil, plant or marine microorganisms or (2) extraction of plants or marine organisms. Combinatorial libraries are composed of large numbers of peptides, oligonucleotides or organic compounds as a mixture. They are relatively easy to prepare by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries.

Hybridoma cell lines which produce antibodies specific for $\alpha_d$ are also comprehended by the invention. Techniques for producing hybridomas which secrete monoclonal antibodies are well known in the art. Hybridoma cell lines may be generated after immunizing an animal with purified $\alpha_d$, variants of $\alpha_d$ or cells which express $\alpha_d$ or a variant thereof on the extracellular membrane surface. Immunogen cell types include cells which express $\alpha_d$ in vivo, or transfected prokaryotic or eukaryotic cell lines which normally do not normally express $\alpha_d$ in vivo. Presently preferred antibodies of the invention are secreted by hybridomas designated 169A, 169B, 170D, 170F, 170E, 170X, 170H, 188A, 188B, 188C, 188E, 188F, 188G, 188I, 188J, 188K, 188L, 188M, 188N, 188P, 188R, 188T, 195A, 195C, 195D, 195E, 195H, 197A-1, 197A-2, 197A-3, 197A-4, 199A, 199H, 199M, 205A, 205C, 205E, 212A, 212D, 217G, 217H, 217I, 217K, 217L, 217M, 226A, 226B, 226C, 226D, 226E, 226F, 226G, 226H, 2261, 236A, 236B, 236C, 236F, 236G, 236H, 236I, 236K, 237L, 236M, 240F, 240G, 240H, and 236L.

The value of the information contributed through the disclosure of the DNA and amino acid sequences of $\alpha_d$ is manifest. In one series of examples, the disclosed $\alpha_d$ cDNA sequence makes possible the isolation of the human $\alpha_d$ genomic DNA sequence, including transcriptional control elements for the genomic sequence. Identification of $\alpha_d$ allelic variants and heterologous species (e.g., rat or mouse) DNAs is also comprehended. Isolation of the human $\alpha_d$ genomic DNA and heterologous species DNAs can be accomplished by standard DNA/DNA hybridization techniques, under appropriately stringent conditions, using all or part of the $\alpha_d$ cDNA sequence as a probe to screen an appropriate library. Alternatively, polymerase chain reaction (PCR) using oligonucleotide primers that are designed based on the known cDNA sequence can be used to amplify and identify genomic $\alpha_d$ DNA sequences. Synthetic DNAs encoding the $\alpha_d$ polypeptide, including fragments and other variants thereof, may be produced by conventional synthesis methods.

DNA sequence information of the invention also makes possible the development, by homologous recombination or "knockout" strategies [see, e.g., Kapecchi, *Science* 244:1288–1292 (1989)], to produce rodents that fail to express a functional $\alpha_d$ polypeptide or that express a variant $\alpha_d$ polypeptide. Such rodents are useful as models for studying the activities of $\alpha_d$ and $\alpha_d$ modulators in vivo.

DNA and amino acid sequences of the invention also make possible the analysis of $\alpha_d$ epitopes which actively participate in counterreceptor binding as well as epitopes which may regulate, rather than actively participate in, binding. Identification of epitopes which may participate in transmembrane signal transduction is also comprehended by the invention.

DNA of the invention is also useful for the detection of cell types which express $\alpha_d$ polypeptide. Standard DNA/RNA hybridization techniques which utilize $\alpha_d$ DNA to detect $\alpha_d$ RNA may be used to determine the constitutive level of $\alpha_d$ transcription within a cell, as well as changes in the level of transcription in response to internal or external agents. Identification of agents which modify transcription and/or translation of $\alpha_d$ can, in turn, be assessed for potential therapeutic or prophylactic value. DNA of the invention also makes possible in situ hybridization of $\alpha_d$ DNA to cellular RNA to determine the cellular localization of $\alpha_d$ specific messages within complex cell populations and tissues.

DNA of the invention is also useful for identification of non-human polynucleotide sequences which display homology to human $\alpha_d$ sequences. Possession of non-human $\alpha_d$ DNA sequences permits development of animal models (including, for example, transgenic models) of the human system.

As another aspect of the invention, monoclonal or polyclonal antibodies specific for $\alpha_d$ may be employed in immunohistochemical analysis to localize $\alpha_d$ to subcellular compartments or individual cells within tissues. Immunohistochemical analyses of this type are particularly useful when used in combination with in situ hybridization to localize both $\alpha_d$ mRNA and polypeptide products of the $\alpha_d$ gene.

Identification of cell types which express $\alpha_d$ may have significant ramifications for development of therapeutic and prophylactic agents. It is anticipated that the products of the invention related to $\alpha_d$ can be employed in the treatment of diseases wherein macrophages are an essential element of the disease process. Animal models for many pathological conditions associated with macrophage activity have been described in the art. For example, in mice, macrophage recruitment to sites of both chronic and acute inflammation is reported by Jutila, et al., *J.Leukocyte Biol.* 54:30–39 (1993). In rats, Adams, et al., [*Transplantation* 53:1115–1119(1992) and *Transplantation* 56:794–799 (1993)] describe a model for graft arteriosclerosis following heterotropic abdominal cardiac allograft transplantation. Rosenfeld, et al., [*Arteriosclerosis* 7:9–23 (1987) and *Arteriosclerosis* 7:24–34 (1987)] describe induced atherosclerosis in rabbits fed a cholesterol supplemented diet. Hanenberg, et al., [*Diabetologia* 32:126–134 (1989)] report the spontaneous development of insulin-dependent diabetes in BB rats. Yamada et al., [*Gastroenterology* 104:759–771 (1993)] describe an induced inflammatory bowel disease, chronic granulomatous colitis, in rats following injections of streptococcal peptidoglycan-polysaccharide polymers. Cromartie, et al., [*J.Exp.Med.* 146:1585–1602 (1977)] and Schwab, et al., [*Infection and Immunity* 59:4436–4442 (1991)] report that injection of streptococcal cell wall protein into rats results in an arthritic condition characterized by inflammation of peripheral joints and subsequent joint destruction. Finally, Huitinga, et al., [*Eur.J.Immunol* 23:709–715 (1993) describe experimental allergic encephalomyelitis, a model for multiple sclerosis, in Lewis rats. In each of these models, $\alpha_d$ antibodies, other $\alpha_d$ binding proteins, or soluble forms of $\alpha_d$ are utilized to attenuate the disease state, presumably through inactivation of macrophage activity.

Pharmaceutical compositions for treatment of these and other disease states are provided by the invention. Pharmaceutical compositions are designed for the purpose of inhibiting interaction between $\alpha_d$ and its ligand(s) and include various soluble and membrane-associated forms of $\alpha_d$ (comprising the entire $\alpha_d$ polypeptide, or fragments thereof which actively participate in $\alpha_d$ binding), soluble and membrane-associated forms of $\alpha_d$ binding proteins (including antibodies, ligands, and the like), intracellular or extracellular modulators of $\alpha_d$ binding activity, and/or modulators of $\alpha_d$ and/or $\alpha_d$-ligand polypeptide expression, including modulators of transcription, translation, post-translational processing and/or intracellular transport.

The invention also comprehends methods for treatment of disease states in which $\alpha_d$ binding, or localized accumulation of cells which express $\alpha_d$, is implicated, wherein a patient suffering from said disease state is provided an amount of a pharmaceutical composition of the invention sufficient to modulate levels of $\alpha_d$ binding or to modulate accumulation of cell types which express $\alpha_d$. The method of treatment of the invention is applicable to disease states such as, but not limited to, Type I diabetes, atherosclerosis, multiple sclerosis, asthma, psoriasis, lung inflammation, acute respiratory distress syndrome and rheumatoid arthritis.

The invention also provides methods for inhibiting macrophage infiltration at the site of a central nervous system injury comprising the step of administering to an individual an effective amount of an anti-$\alpha_d$ monoclonal antibody. In one aspect, the methods comprise use of an anti-$\alpha_d$ monoclonal antibody that blocks binding between $\alpha_d$ and a binding partner. In one embodiment, the binding partner is VCAM-1. In a preferred embodiment, the anti-$\alpha_d$ monoclonal antibody is selected from the group consisting of the monoclonal antibody secreted by hybridoma 226H and the monoclonal antibody secreted by hybridoma 236L. In a most preferred embodiment, methods of the invention are for a central nervous system injury which is a spinal cord injury.

The invention further provides methods for reducing inflammation at the site of a central nervous system injury comprising the step of administering to an individual an effective amount of an anti-$\alpha_d$ monoclonal antibody. In one aspect, the methods comprise use of an anti-$\alpha_d$ monoclonal antibody that blocks binding between $\alpha_d$ and a binding partner. In one embodiment, the binding partner is VCAM-1. In a preferred embodiment, the anti-$\alpha_d$ monoclonal antibody is selected from the group consisting of the monoclonal antibody secreted by hybridoma 226H and the monoclonal antibody secreted by hybridoma 236L. In a most preferred embodiment, methods of the invention are for a central nervous system injury which is a spinal cord injury.

Hybridomas 226H and 236L were received on Nov. 11, 1998 by the American Type Culture Collection, 10801 University Boulevard, Masassas, Va. 20110-2209 under terms of the Budapest Treaty and assigned Accession Nos: HB-12592 and HB-12593, respectively.

The invention also provides methods for modulating TNFα release from macrophage or splenic phagocytes comprising the step of contacting said phagocytes with an affective amount of an immunospecific $\alpha_d$ monoclonal antibody. In a preferred aspect, the method methods of the invention comprise an anti-monoclonal antibody that inhibits TNFα release. In a preferred embodiment, the methods of the invention comprise use of an immunospecific anti-$\alpha_d$ monoclonal antibody that is selected from the group consisting of the monoclonal antibody secreted by hybridoma 205C and the monoclonal antibody secreted by hybridoma 205E.

Methods of the invention are contemplated wherein useful antibodies include fragments of anti-$\alpha_d$ monoclonal antibodies, including for example, Fab or F(ab')$_2$ fragments. Methods utilizing modified antibodies are also embraced by the invention. Modified antibodies include, for example, single chain antibodies, chimeric antibodies, and CDR-grafted antibodies, including compounds which include CDR sequences which specifically recognize a polypeptide of the invention, as well as humanized antibodies. Methods comprising use of human antibodies are also contemplated. Techniques for identifying and isolating human antibodies are disclosed infra.

The invention also provides methods for inhibiting macrophage infiltration at the site of a central nervous system injury comprising the step of administering to an individual an effective amount of a small molecule that inhibits $\alpha_d$ binding. In particular, the methods of the invention comprising a central nervous system injury which is a spinal cord injury. Small molecules specific for $\alpha_d$ binding are identified and isolated from libraries as discussed above.

The invention further provides methods for reducing inflammation at the site of a central nervous system injury comprising the step of administering to an individual an effective amount of a small molecule that inhibits $\alpha_d$ binding. In particular, the methods of the invention comprising a central nervous system injury which is a spinal cord injury. Small molecules specific for $\alpha_d$ binding are identified and isolated from libraries as discussed above.

The invention further embraces methods to detect and diagnose Crohn's disease comprising the steps of obtaining tissue samples from a patient; staining the sample with anti-$\alpha_d$ monoclonal antibodies, and comparing the staining pattern to that on tissue obtained from a known normal donor. In instances wherein staining differences between the two tissue samples can be detected, the patient can be further tested for possible Crohn's disease.

The invention also contemplates use of $\alpha_d$ as a target for removal of pathogenic cell populations expressing $\alpha_d$ on the cell surface. In one aspect, the hypervariable region of an $\alpha_d$ monoclonal antibody is cloned and expressed in the context of a complement-fixing human isotype. Cloning the hypervariable region in this manner will provide a binding partner for $\alpha_d$, which unpon binding in vivo, will lead to complement binding and subsequent cell death. Alternatively, the anti-$\alpha_d$ monoclonal antibody is conjugated to a cytotoxic compound and binding of the antibody to $\alpha_d$ on the pathogenic cell type leads to cell death.

The invention also provide methods for promoting locomoter recovery or inhibiting locomoter damage or limiting locomoter impairment following spinal cord injury by administering an effective amount of an anti-$\alpha_d$ monoclonal antibody to a spinal cord injury victim. Also contemplated are methods of limiting autonomic and sensory dysfunction following spinal cord injury by administration of an effective amount of an anti-$\alpha_d$ monoclonal antibody to a spinal cord injury victim. In one embodiment, the anti-$\alpha_d$ monoclonal antibody is 217L or 226H antibody. In another embodiment the anti-$\alpha_d$ monoclonal antibody competes with 217L or 226H for binding to $\alpha_d$. In a further embodiment, the anti-$\alpha_d$ monoclonal antibody inhibits $\alpha_d$ binding to an $\alpha_d$ ligand. Contemplated $\alpha_d$ ligands include ICAM-R and VCAM-1. Exemplary spinal cord injuries treated by these methods include those involving compression to the spinal cord.

BRIEF DESCRIPTION OF THE DRAWING

Numerous other aspects and advantages of the present invention will be apparent upon consideration of the following description thereof, reference being made to the drawing wherein:

FIGS. 1A through 1D comprises an alignment of the human amino acid sequences of CD11b (SEQ ID NO: 3), CD11c (SEQ ID NO: 4) and $\alpha_d$ (SEQ ID NO: 2).

DETAILED DESCRIPTION OF THE INVENTION

The present invention is illustrated by the following examples relating to the isolation of a cDNA clone encoding $\alpha_d$ from a human spleen cDNA library. More particularly, Example 1 illustrates the use of anti-canine $\alpha_{TM1}$ antibody in an attempt to detect a homologous human protein. Example 2 details purification of canine $\alpha_{TM1}$ and N-terminal sequencing of the polypeptide to design oligonucleotide primers for PCR amplification of the canine $\alpha_{TM1}$ gene. Example 3 addresses large scale purification of canine $\alpha_{TM1}$ for internal sequencing in order to design additional PCR primers. Example 4 describes use of the PCR and internal sequence primers to amplify a fragment of the canine $\alpha_{TM1}$ gene. Example 5 addresses cloning of the human $\alpha_d$-encoding cDNA sequence. Example 6 describes Northern blot hybridization analysis of human tissues and cells for expression of $\alpha_d$ mRNA. Example 7 details the construction of human $\alpha_d$ expression plasmids and transfection of COS cells with the resulting plasmids. Example 8 addresses ELISA analysis of $\alpha_d$ expression in transfected COS cells. Example 9 describes FACS analysis of COS cells transfected with human $\alpha_d$ expression plasmids. Example 10 addresses immunoprecipitation of CD18 in association with $\alpha_d$ in co-transfected COS cells. Example 11 relates to stable transfection of $\alpha_d$ expression constructs in Chinese hamster ovary cells. Example 12 addresses CD18-dependent binding of $\alpha_d$ to the intercellular adhesion molecule ICAM-R, an ICAM-R mutant protein, and complement fact iC3b. Example 13 describes scintillation proximity screening assays to identify inhibitors or enhancers (i.e., modulators) of $\alpha_d$ ligand/anti-ligand binding interactions. Example 14 addresses construction of expression plasmids which encode soluble forms of $\alpha_d$, and binding analyses of the expression products. Example 15 relates to production of $\alpha_d$-specific polyclonal sera and monoclonal antibodies. Example 16 describes flow cytometry analysis using $\alpha_d$ monoclonal antibodies. Example 17 addresses expression of $\alpha_d$ on human monocytes. Example 18 describes analysis of $\alpha_d$ tissue distribution, expression of $\alpha_d$ on peripheral blood leukocytes, expression in inflammatory and non-inflammatory synovium using anti-$\alpha_d$ polyclonal serum, expression in disease lung and liver, human bone marrow, and PBMC from breast cancer patients. Example 19 addresses upregulation of $\alpha_d$ expression in vitro and in vivo. Example 20 describes isolation of rat cDNA sequences which show homology to human $\alpha_d$ gene sequences. Example 21 addresses tissue specific expression of rat $\alpha_d$ mRNA. Example 22 relates to construction of full length rat $\alpha_d$ expression plasmids, rat $\alpha_d$ I domain expression plasmids, including I domain/IgG fusion proteins, production of monoclonal antibodies to full length and I domain fusion proteins, and production of polyclonal antisera to rat $\alpha_d$ I domain sequences fused to human IgG4. Example 23 describes specificity of monoclonal antibody 199M. Example 24 presents results from a T cell proliferation assay using rat $\alpha_d$ expressing macrophages. Example 25 describes immunoprecipitation of rat $\alpha_d$ from bone marrow. Example 26 describes rat $\alpha_d$ expression in various animal models. Example 27 relates to an assay for inhibition of NK-tumor cell-induced target cell lysis using $\alpha_d$ monoclonal antibodies. Example 28 addresses isolation of mouse cDNA sequences which show homology to human $\alpha_d$ gene sequences. Example 29 describes isolation of additional mouse $\alpha_d$ cDNA clones used to confirm sequence analysis. Example 30 relates to in situ hybridization analysis of various mouse tissues to determine tissue and cell specific expression of the putative mouse homolog to human $\alpha_d$. Example 31 describes generation of expression constructs which encode the putative mouse homolog of human $\alpha_d$. Example 32 addresses design of a "knock-out" mouse wherein the gene encoding the putative mouse homolog of human $\alpha_d$ is disrupted. Example 33 describes isolation of rabbit cDNA clones which show homology to human $\alpha_d$ encoding sequences. Example 34 describes isolation of monkey $\alpha_d$. Example 35 relates to characterization of the antigen recognized by monoclonal antibody 217L. Example 36 describes animal models of human disease states wherein modulation of $\alpha_d$ is assayed for therapeutic capabilities. Example 37 describes expression of $\alpha_d$ in animal model disease states. Example 38 addresses the role of $\alpha_d$ in spinal cord injury. Example 39 describes $\alpha_d$ expression in Crohn's disease. Example 40 relates to TNF$\alpha$ release from rat spleen cells that express $\alpha_d$. Example 41 described methods to modulate TNF$\alpha$ release from spleen cells using $\alpha_d$ monoclonal antibodies. Example 42 characterizes $\alpha_d$ expression on eosinophils. Example 43 relates to further characterization of $\alpha_d$ binding to VCAM-1. Example 44 described use of $\alpha_d$ as a target for removal of pathogenic cell populations.

EXAMPLE 1

Attempt to Detect a Human Homolog of Canine $\alpha_{TM1}$

The monoclonal antibody Ca11.8H2 [Moore, et al., supra] specific for canine $\alpha_{TM1}$ was tested for cross-reactivity on human peripheral blood leukocytes in an attempt to identify a human homolog of canine $\alpha_{TM1}$. Cell preparations (typically 1×10$^6$ cells) were incubated with undiluted hybridoma supernatant or a purified mouse IgG-negative control antibody (10 $\mu$g/ml) on ice in the presence of 0.1% sodium azide. Monoclonal antibody binding was detected by subsequent incubation with FITC-conjugated horse anti-mouse IgG (Vector Laboratories, Burlingame, Calif.) at 6 $\mu$g/ml. Stained cells were fixed with 2% w/v parafornaldehyde in phosphate buffered saline (PBS) and were analyzed with a Facstar Plus fluorescence-activated cell sorter (Becton Dickinson, Mountain View, Calif.). Typically, 10,000 cells were analyzed using logarithmic amplification for fluorescence intensity.

The results indicated that Ca11.8H2 did not cross-react with surface proteins expressed on human peripheral blood leukocytes, while the control cells, neoplastic canine peripheral blood lymphocytes, were essentially all positive for $\alpha_{TM1}$.

Because the monoclonal antibody Ca11.8H2 specific for the canine $\alpha$ subunit did not cross react with a human homolog, isolation of canine $\alpha_{TM1}$ DNA was deemed a necessary prerequisite to isolate a counterpart human gene if one existed.

EXAMPLE 2

Affinity Purification of Canine $\alpha_{TM1}$ for N-Terminal Sequencing

Canine $\alpha_{TM1}$ was affinity purified in order to determine N-terminal amino acid sequences for oligonucleotide probe/ primer design. Briefly, anti-$\alpha_{TM1}$ monoclonal antibody Ca11.8H2 was coupled to Affigel® 10 chromatographic resin (BioRad, Hercules, Calif.) and protein was isolated by specific antibody-protein interaction. Antibody was conjugated to the resin, according to the BioRad suggested protocol, at a concentration of approximately 5 mg antibody per ml of resin. Following the conjugation reaction, excess antibody was removed and the resin blocked with three volumes of 0.1 M ethanolamine. The resin was then washed with thirty column volumes of phosphate buffered saline (PBS).

Twenty-five grams of a single dog spleen were homogenized in 250 ml of buffer containing 0.32 M sucrose in 25 mM Tris-HCl, Ph 8.0, with protease inhibitors. Nuclei and cellular debris were pelleted with centrifugation at 1000 g for 15 minutes. Membranes were pelleted from the supernatant with centrifugation at 100,000 g for 30 minutes. The membrane pellet was resuspended in 200 ml lysis buffer (50 mM NaCl, 50 mM borate, pH 8.0, with 2% NP-40) and incubated for 1 hour on ice. Insoluble material was then pelleted by centrifugation at 100,000 g for 60 minutes. Ten milliliters of the cleared lysate were transferred to a 15 ml polypropylene tube with 0.5 ml Ca11.8H2-conjugated Affigel® 10 resin described above. The tube was incubated overnight at 4° C. with rotation and the resin subsequently washed with 50 column volumes D-PBS. The resin was then transferred to a microfuge tube and boiled for ten minutes in 1 ml Laemmli (non-reducing) sample buffer containing 0.1 M Tris-HCl, pH 6.8, 2% SDS, 20% glycerol and 0.002% bromophenol blue. The resin was pelleted by centrifugation and discarded; the supernatant was treated with 1/15 volume β-mercaptoethanol (Sigma, St. Louis, Mo.) and run on a 7% polyacrylamide gel. The separated proteins were transferred to Immobilon PVDF membrane (Millipore, Bedford, Mass.) as follows.

The gels were washed once in deionized, Millipore®— filtered water and equilibrated for 15–45 minutes in 10 mM 3-[cyclohexylamino]-1-propanesulfonic acid (CAPS) transfer buffer, pH 10.5, with 10% methanol. Immobilon membranes were moistened with methanol, rinsed with filtered water, and equilibrated for 15–30 minutes in CAPS transfer buffer. The initial transfer was carried out using a Biorad transfer apparatus at 70 volts for 3 hours. The Immobilon membrane was removed after transfer and stained in filtered 0.1% R250 Coomassie stain for 10 minutes. Membranes were destained in 50% methanol/10% acetic acid three times, ten minutes each time. After destaining, the membranes were washed in filtered water and air-dried.

Protein bands of approximately 150 kD, 95 kD, 50 kD and 30 kD were detected. Presumably the 50 kD and 30 kD bands resulted from antibody contamination. N-terminal sequencing was then attempted on both the 150 kD and 95 kD bands, but the 95 kD protein was blocked, preventing sequencing. The protein band of 150 kD was excised from the membrane and directly sequenced with an Applied Biosystems (Foster City, Calif.) Model 473A protein sequencer according to the manufacturer's instructions. The resulting amino acid sequence is set in SEQ ID NO: 5 using single letter amino acid designations.

FNLDVEEPMVFQ (SEQ ID NO: 5)

The identified sequence included the FNLD sequence characteristic of α subunits of the integrin family [Tamura, et al., *J.Cell.Biol.* 111:1593–1604 (1990)].

Primer Design and Attempt to Amplify Canine $\alpha_{TM1}$ Sequences

From the N-terminal sequence information, three oligonucleotide probes were designed for hybridization: a) "Tommer," a fully degenerate oligonucleotide; b) "Patmer," a partially degenerate oligonucleotide; and c) "Guessmer," a nondegenerate oligonucleotide based on mammalian codon usage. These probes are set out below as SEQ ID NOS: 6, 7 and 8, respectively. Nucleic acid symbols are in accordance with 37 C.F.R. §1.882 for these and all other nucleotide sequences herein.

5'-TTYAAYYTGGAYGTNGARGARCCNATGGTNTT YCA-3' (SEQ ID NO: 6)

5'-TTCAACCTGGACGTGGAGGAGCCCATGGTG TTCCAA-3' (SEQ ID NO: 7)

5'-TTCAACCTGGACGTNGAASANCCCATGGTC TTCCAA-3' (SEQ ID NO: 8)

Based on sequencing data, no relevant clones were detected using these oligonucleotides in several low stringency hybridizations to a canine spleen/peripheral blood macrophage cDNA library cloned into λZAP® (Stratagene, La Jolla, Calif.).

Four other oligonucleotide primers, designated 5'Deg, 5'Spec, 3'Deg and 3'Spec (as set out in SEQ ID NOS: 9, 10, 11 and 12, respectively, wherein Deg indicates degenerate and Spec indicates non-degenerate) were subsequently designed based on the deduced N-terminal sequence for attempts to amplify canine $\alpha_{TM1}$ sequences by PCR from phage library DNA purified from plate lysates of the Stratagene library described above.

5'-TTYAAYYTNGAYGTNGARGARCC-3' (SEQ ID NO: 9)

5'-TTYAAYYTGGACGTNGAAGA-3' (SEQ ID NO: 10)

5'-TGRAANACCATNGGYTC-3' (SEQ ID NO: 11)

5'-TTGGAAGACCATNGGYTC-3' (SEQ ID NO: 12)

The $\alpha_{TM1}$ oligonucleotide primers were paired with T3 or T7 vector primers, as set out in SEQ ID NOS: 13 and 14, respectively, which hybridize to sequences flanking the polylinker region in the Bluescript® phagemid found in λZAP®.

5'-ATTAACCCTCACTAAAG-3' (SEQ ID NO: 13)

5'-AATACGACTCACTATAG-3' (SEQ ID NO: 14)

The PCR amplification was carried out in Taq buffer (Boehringer Mannheim, Indianapolis, Ind.) containing magnesium with 150 ng of library DNA, 1 µg of each primer, 200 µM dNTPs and 2.5 units Taq polymerase (Boehringer Mannheim) and the products were separated by electrophoresis on a 1% agarose gel in Tris-Acetate-EDTA (TAE) buffer with 0.25 µg/ml ethidium bromide. DNA was transferred to a Hybond® (Amersham, Arlington Heights, Ill.) membrane by wicking overnight in 10×SSPE. After transfer, the immobilized DNA was denatured with 0.5 M NaOH with 0.6 M NaCl, neutralized with 1.0 M Tris-HCl, pH 8.0, in 1.5 M NaCl, and washed with 2×SSPE before UV crosslinking with a Stratalinker (Stratagene) crosslinking apparatus. The membrane was incubated in prehybridization buffer (5×SSPE, 4×Denhardts, 0.8% SDS, 30% formamide) for 2 hr at 50° C. with agitation.

Oligonucleotide probes 5'Deg, 5'Spec, 3'Deg and 3'Spec (SEQ ID NOS: 9, 10, 11 and 12, respectively) were labeled using a Boehringer Mannheim kinase buffer with 100–300 µCi γP$^{32}$-dATP and 1–3 units of polynucleotide kinase for 1–3 hr at 37° C. Unincorporated label was removed with Sephadex® G-25 fine (Pharmacia, Piscataway, N.J.) chromatography using 10 mM Tris-HCl, pH 8.0, 1 mM EDTA (TE) buffer and the flow-through added directly to the prehybridization solution. Membranes were probed for 16 hr at 42° C. with agitation and washed repeatedly, with a final stringency wash of 1×SSPE/0.1% SDS at 50° for 15 min. The blot was then exposed to Kodak X-Omat AR film for 1–4 hours at −80° C.

The oligonucleotides 5'Deg, 5'Spec, 3' Deg and 3' Spec only hybridized to PCR products from the reactions in which they were used as primers and failed to hybridize as expected to PCR products from the reactions in which they were not used as primers. Thus, it was concluded that none of the PCR products were specific for $\alpha_{TM1}$ because no product hybridized with all of the appropriate probes.

EXAMPLE 3

Large Scale Affinity Purification of Canine $\alpha_{TM1}$ for Internal Sequencing In order to provide additional amino acid sequence for primer design, canine $\alpha_{TM1}$ was purified for internal sequencing. Three sections of frozen spleen (approximately 50 g each) and frozen cells from two partial spleens from adult dogs were used to generate protein for internal sequencing. Fifty grams of spleen were homogenized in 200–300 ml borate buffer with a Waring blender. The homogenized material was diluted with 1 volume of buffer containing 4% NP-40, and the mixture then gently agitated for at least one hour. The resulting lysate was cleared of large debris by centrifugation at 2000 g for 20 min, and then filtered through either a Corning (Corning, N.Y.) prefilter or a Corning 0.8 micron filter. The lysate was further clarified by filtration through the Corning 0.4 micron filter system.

Splenic lysate and the antibody-conjugated Affigel® 10 resin described in Example 2 were combined at a 150:1 volume ratio in 100 ml aliquots and incubated overnight at 4° C. with rocking. The lysate was removed after centrifugation at 1000 g for 5 minutes, combined with more antibody-conjugated Affigel® 10 resin and incubated overnight as above. The absorbed resin aliquots were then combined and washed with 50 volumes D-PBS/0.1% Tween® 20 and the resin transferred to a 50 ml Biorad column. Adsorbed protein was eluted from the resin with 3–5 volumes of 0.1 M glycine (pH 2.5); fractions of approximately 900 µl were collected and neutralized with 100 µl 1 M Tris buffer, pH 8.0. Aliquots of 15 µl were removed from each fraction and boiled in an equal volume of 2× Laemmli sample buffer with 1/15 volume 1 M dithiothreitol (DTT). These samples were electrophoresed on 8% Novex (San Diego, Calif.) polyacrylamide gels and visualized either by Coomassie stain or by silver stain using a Daiichi kit (Enprotech, Natick, Mass.) according to the manufacturer's suggested protocol. Fractions which contained the largest amounts of protein were combined and concentrated by vacuum. The remaining solution was diluted by 50% with reducing Laemmli sample buffer and run on 1.5 mm 7% polyacrylamide gels in Tris-glycine/SDS buffer. Protein was transferred from the gels to Immobilon membrane by the procedure described in Example 2 using the Hoefer transfer apparatus.

The protein bands corresponding to canine $\alpha_{TM1}$ were excised from 10 PVDF membranes and resulted in approximately 47 µg total protein. The bands were destained in 4 ml 50% methanol for 5 minutes, air dried and cut into 1×2 mm pieces. The membrane pieces were submerged in 2 ml 95% acetone at 4° C. for 30 minutes with occasional vortexing and then air dried.

Prior to proteolytic cleavage of the membrane bound protein, 3 mg of cyanogen bromide (CNBr) (Pierce, Rockford, Ill.) were dissolved in 1.25 ml 70% formic acid. This solution was then added to a tube containing the PVDF membrane pieces and the tube incubated in the dark at room temperature for 24 hours. The supernatant (S1) was then removed to another tube and the membrane pieces washed with 0.25 ml 70% formic acid. This supernatant (S2) was removed and added to the previous supernatant (S1). Two milliliters of Milli Q water were added to the combined supernatants (S1 and S2) and the solution lyophilized. The PVDF membrane pieces were dried under nitrogen and extracted again with 1.25 ml 60% acetonitrile, 0.1% tetrafluoroacetic acid (TFA) at 42° C. for 17 hours. This supernatant (S3) was removed and the membrane pieces extracted again with 1.0 ml 80% acetonitrile with 0.08% TFA at 42° C. for 1 hour. This supernatant (S4) was combined with the previous supernatants (S1, S2 and S3) and vacuum dried.

The dried CNBr fragments were then dissolved in 63 µl 8 M urea, 0.4 M $NH_4HCO_3$. The fragments were reduced in 5 µl 45 mM dithiothreitol (DTT) and subsequently incubated at 50° C. for 15 minutes. The solution was then cooled to room temperature and the fragments alkylated by adding 5 µl 100 mM iodoacetamide (Sigma, St. Louis, Mo.). Following a 15 minute incubation at room temperature, the sample was diluted with 187 µl Milli Q water to a final urea concentration of 2.0 M. Trypsin (Worthington, Freehold, N.J.) was then added at a ratio of 1:25 (w:w) of enzyme to protein and the protein digested for 24 hours at 37° C. Digestion was terminated with addition of 30 µl TFA.

The protein fragments were then separated with high performance liquid chromatography (HPLC) on a Waters 625 LC system (Millipore, Milford, Mass.) using a 2.1×250 mm, 5 micron Vydac C-18 column (Vydac, Hesperia, Calif.) equilibrated in 0.05% TFA and HPLC water (buffer A). The peptides were eluted with increasing concentration of 80% acetonitrile in 0.04% TFA (buffer B) with a gradient of 38–75% buffer B for 65–95 minutes and 75–98% buffer B for 95–105 minutes. Peptides were fractionated at a flow rate of 0.2 ml/minute and detected at 210 nm.

Following fractionation, the amino acid sequence of the peptides was analyzed by automated Edman degradation performed on an Applied Biosystems Model 437A protein sequencer using the manufacturer's standard cycles and the Model 610A Data Analysis software program, Version 1.2.1. All sequencing reagents were supplied by Applied Biosystems. The amino acid sequences of seven of the eight internal fragments are set out below wherein "X" indicates the identity of the amino acid was not certain.

| | |
|---|---|
| VFQEXGAGFGQ | (SEQ ID NO: 15) |
| LYDXVAATGLXQPI | (SEQ ID NO: 16) |
| PLEYXDVIPQAE | (SEQ ID NO: 17) |
| FQEGFSXVLX | (SEQ ID NO: 18) |
| TSPTFIXMSQENVD | (SEQ ID NO: 19) |
| LVVGAPLEVVAVXQTGR | (SEQ ID NO: 20) |
| LDXKPXDTA | (SEQ ID NO: 21) |

Primer Design

One internal amino acid sequence (set out in SEQ ID NO: 22) obtained was then used to design a fully degenerate oligonucleotide primer, designated p4(R) as set out in SEQ ID NO: 23.

| | |
|---|---|
| FGEQFSE | (SEQ ID NO: 22) |
| 5'-RAANCCYTCYTGRAAACTYTC-3' | (SEQ ID NO: 23) |

EXAMPLE 4

PCR Cloning of a Canine $\alpha_{TM1}$ Fragment

The 5' portion of the canine $\alpha_{TM1}$ gene was amplified from double-stranded canine splenic cDNA by PCR.

Generation of Double Stranded Canine Spleen cDNA

One gram of frozen material from a juvenile dog spleen was ground in liquid nitrogen on dry ice and homogenized in 20 ml RNA-Stat 60 buffer (Tel-Test B, Inc, Friendswood, Tex.). Four ml chloroform were added, and the solution extracted by centrifugation at 12,000 g for 15 minutes. RNA was precipitated from the aqueous layer with 10 ml ethanol. Poly A$^+$ RNA was then selected on Dynal Oligo dT Dynabeads® (Dynal, Oslo, Norway). Five aliquots of 100 μg total RNA were combined and diluted with an equal volume of 2× binding buffer (20 mM Tris-HCl, pH 7.5, 1.0 M LiCl, 1 mM EDTA, 0.1% SDS). RNA was then incubated 5 minutes with the Oligo dT Dynabeads® (1.0 ml or 5 mg beads for all the samples). Beads were washed with buffer containing 10 mM Tris-HCl, pH 7.5, 0.15 M LiCl, 1 mM EDTA and 0.1% SDS, according to the manufacturer's suggested protocol prior to elution of poly A$^+$ mRNA with 2 mM EDTA, pH 7.5. Double-stranded cDNA was then generated using the eluted poly A$^+$ mRNA and the Boehringer Mannheim cDNA Synthesis Kit according to the manufacturer's suggested protocol.

Isolation of a Partial Canine $\alpha_{TM1}$ cDNA

Oligonucleotide primers 5'Deg (SEQ ID NO: 9) and p4(R) (SEQ ID NO: 23) were employed in a standard PCR reaction using 150 ng double-stranded cDNA, 500 ng of each primer, 200 μM dNTPs and 1.5 units Taq polymerase (Boehringer Mannheim) in Taq buffer (Boehringer Mannheim) with magnesium. The resulting products (1 μl of the original reaction) were subjected to a second round of PCR with the same primers to increase product yield. This band was eluted from a 1% agarose gel onto Schleicher & Schuell (Keene, N.H.) NA45 paper in a buffer containing 10 mM Tris-HCl, pH 8, 1 mM EDTA, 1.5 M NaCl at 65° C., precipitated, and ligated into the pCR™II vector (Invitrogen, San Diego, Calif.) using the TA cloning kit (Invitrogen) and the manufacturer's suggested protocol. The ligation mixture was transformed by electroporation into XL-1 Blue bacteria (Stratagene). One clone, 2.7, was determined to contain sequences corresponding to $\alpha_{TM1}$ peptide sequences which were not utilized in design of the primers.

Sequencing was performed with an Applied Biosystems 373A DNA sequencer (Foster City, Calif.) with a Dye-deoxy terminator cycle sequence kit (ABI) in which fluorescent-labeled dNTPs were incorporated in an asymmetric PCR reaction [McCabe, "Production of Single Stranded DNA by Asymmetric PCR," in *PCR Protocols: A Guide to Methods and Applications*, Innis, et al. (eds.) pp. 76–83 Academic Press: New York (1990)] as follows. Samples were held at 96° C. for 4 minutes and subjected to 25 cycles of the step sequence: 96° C., for 15 seconds; 50° C. for 1 second; 60° C. for 4 minutes. Sequence data was automatically downloaded into sample files on the computer that included chromatogram and text files. The sequence of the entire insert of clone 2.7 is set out in SEQ ID NO: 24.

Attempts to isolate the full length canine $\alpha_{TM1}$ cDNA from the Stratagene library (as described in Example 2) were unsuccessful. Approximately 1×10$^6$ phage plaques were screened by hybridization under low stringency conditions using 30% formamide with clone 2.7 as a probe, but no positive clones resulted. Attempts to amplify relevant sequences downstream from those represented in clone 2.7 using specific oligonucleotides derived from clone 2.7 or degenerate primers based on amino acid sequence from other peptide fragments paired with a degenerate oligonucleotide based on the conserved a subunit amino acid motif GFFKR [Tamura, et al., supra] were also unsuccessful.

EXAMPLE 5

Cloning of a Putative Human Homolog of Canine $\alpha_{TM1}$

To attempt the isolation of a human sequence homologous to canine $\alpha_{TM1}$ the approximately 1 kb canine $\alpha_{TM1}$ fragment from clone 2.7 was used as a probe. The probe was generated by PCR under conditions described in Example 2 using NT2 (as set out in SEQ ID NO: 25) and p4(R) (SEQ ID NO: 23) primers.

5'-GTNTTYCARGARGAYGG-3' (SEQ ID NO: 25)

The PCR product was purified using the Qiagen (Chatsworth, Ga.) Quick Spin kit and the manufacturer's suggested protocol. The purified DNA (200 ng) was labeled with 200 μCi α$^{32}$PdCTP using the Boehringer Mannheim Random Prime Labelling kit and the manufacturer's suggested protocol. Unincorporated isotope was removed with Sephadex® G25 (fine) gravity chromatography. The probe was denatured with 0.2 N NaOH and neutralized with 0.4 M Tris-HCl, pH 8.0, before use.

Colony lifts on Hybond® filters (Amersham) of a human spleen cDNA library in pCDNA/Amp (Invitrogen, San Diego, Calif.) were prepared. The filters were initially denatured and neutralized as described in Example 2 and subsequently incubated in a prehybridization solution (8 ml/filter) with 30% formamide at 50° C. with gentle agitation for 2 hours. Labeled probe as described above was added to this solution and incubated with the filters for 14 hours at 42° C. The filters were washed twice in 2×SSC/0.1% SDS at 37° C. and twice in 2×SSC/0.1% SDS at 50° C. Final stringency washes were 1×SSC/0.1% SDS, twice at 65° C. (1×SSC is 150 mM NaCl, 15 mM sodium citrate, pH 7.0). Filters were exposed to Kodak X-Omat AR film for six hours with an intensifying screen. Colonies giving signals on duplicate lifts were streaked on LB medium with magnesium (LBM)/carbenicillin plates and incubated overnight at 37° C. Resulting streaked colonies were lifted with Hybond® filters and these filters were treated as above. The filters were hybridized under more stringent conditions with the 1 kb probe from clone 2.7, labeled as previously described, in a 50% formamide hybridization solution at 50° C. for 3 hours. Probed filters were washed with a final stringency of 0.1×SSC/0.1% SDS at 65° C. and exposed to Kodak X-Omat AR film for 2.5 hours at −80° C. with an intensifying screen. Positive colonies were identified and cultured in LBM/carbenicillin medium overnight. DNA from the cultures was prepared using the Promega Wizard® miniprep kit according to the manufacturer's suggested protocol and the resulting DNA was sequenced.

The initial screening resulted in 18 positive clones, while the secondary screening under more stringent hybridization conditions produced one positive clone which was designated 19A2. The DNA and deduced amino acid sequences of the human $\alpha_d$ clone 19A2 are set out in SEQ ID NOS: 1 and 2, respectively.

Characteristics of the Human $\alpha_d$ cDNA and Predicted Polypeptide

Clone 19A2 encompasses the entire coding region for the mature protein, plus 48 bases (16 amino acid residues) of the 5' upstream signal sequence and 241 bases of 3' untranslated sequence which do not terminate in a polyadenylation sequence. The core molecular weight of the mature protein is predicted to be around 125 kD. The extracellular domain is predicted to encompass approximately amino acid residues 17 through 1108 of SEQ ID NO: 2. This extracellular region is contiguous with about a 20 amino acid region homologous to the human CD11c transmembrane region (residues 1109 through 1128 of SEQ ID NO: 2). The cytoplasmic domain comprises approximately 30 amino acids (about residues 1129 through 1161 of SEQ ID NO: 2). The protein also contains a region (around residues 150 through 352) of approximately 202 amino acids homologous to the I (insertion) domain common to CD11a, CD11b and CD11c [Larson and Springer, supra], [Shaw, et al, *J.Biol.Chem.* 269:6016–6025 (1994)] and in VLA-1 and VLA-2, [Tamura, et al., supra]. The I domain in other integrins has been shown to participate in ICAM binding [Landis, et al., *J.Cell.Biol.* 120:1519–1527 (1993); Diamond, et al., *J.Cell. .Biol.* 120:1031–1043 (1993)], suggesting that $\alpha_d$ may also bind members of the ICAM family of surface molecules. This region has not been demonstrated to exist in any other integrin subunits.

The deduced amino acid sequence of $\alpha_d$ shows approximately 36% identity to that of CD11a, approximately 60% identity to CD11b and approximately 66% identity to CD11c. An alignment of amino acid sequences for (CD11b SEQ ID NO: 3), CD11c (SEQ ID NO: 4) and $\alpha_d$ (SEQ ID NO: 2) is presented in FIG. 1.

The cytoplasmic domains of α subunits in $\beta_2$ integrins are typically distinct from one another within the same species, while individual α subunits show high degrees of homology across species boundaries. Consistent with these observations, the cytoplasmic region of $\alpha_d$ differs markedly from CD11a, CD11b, and CD11c except for a membrane proximal GFFKR amino acid sequence which has been shown to be conserved among all a integrins [Rojiani, et al., *Biochemistry* 30: 9859–9866 (1991)]. Since the cytoplasmic tail region of integrins has been implicated in "inside out" signaling and in avidity regulation [Landis et al., supra], it is possible that $\alpha_d$ interacts with cytosolic molecules distinct from those interacting with CD11a, CD11b, and CD11c, and, as a result, participates in signaling pathways distinct from those involving other $\beta_2$ integrins.

The extracellular domain of $\alpha_d$ contains a conserved DGSGS amino acid sequence adjacent the I-domain; in CD11b, the DGSGS sequence is a metal-binding region required for ligand interaction [Michishita, et al. *Cell* 72:857–867 (1993)]. Three additional putative cation binding sites in CD11b and CD11c are conserved in the $\alpha_d$ sequence at amino acids 465–474, 518–527, and 592–600 in clone 19A2 (SEQ ID NO: 1). The $\alpha_d$ I-domain is 36%, 62%, and 57% identical to the corresponding regions in CD11a, CD11b, and CD11c, respectively, and the relatively low sequence homology in this region suggests that $\alpha_d$ may interact with a set of extracellular proteins distinct from proteins with which other known $\beta_2$ integrins interact. Alternatively, the affinity of $\alpha_d$ for known $\beta_2$ integrin ligands, for example, ICAM-1, ICAM-2 and/or ICAM-R, may be distinct from that demonstrated for the other $\beta_2$ integrin/ICAM interactions. [See Example 12.]

Isolation of Additional Human $\alpha_d$ cDNA Clones for Sequence Verification

In order to confirm the DNA sequence encoding human $\alpha_d$, additional human cDNAs were isolated by hybridization from a human splenic oligo dt-primed cDNA library (Invitrogen) in pcDNA/Amp (described in Example 5) which was size selected by agarose gel electrophoresis for cDNA greater than 3 kb in length. The probe for hybridization was derived from a 5' region of $\alpha_d$ as described below. Hybridization conditions were the same as described above for the isolation of the initial human $\alpha_d$ clone, except that following hybridization, filters were washed twice in 2×SSC/0.1% SDS at room temperature and once in 2×SSC/ 0.1% SDS at 42° C. Filters were exposed to Kodak X-Omat AR film overnight.

The 5' $\alpha_d$ hybridization probe was generated by PCR from the 19A2 clone using primers CD11c 5' For (SEQ ID NO: 94) and CD11c 5' Rev (SEQ ID NO: 95) under the following conditions. Samples were held at 94° C. for four minutes and subjected to 30 cycles of the temperature step sequence i) 94° C., for 15 seconds; ii) 5° C., for 30 seconds; and iii) 72° C., for 1 minute in a Perkin-Elmer 9600 thermocycler.

CD11c 5' For: (5')CTGGTCTGGAGGTGCCTTCCTG (3') (SEQ ID NO: 94)

CD11c 5' Rev: (5')CCTGAGCAGGAGCACCTGGCC (3') (SEQ ID NO: 95)

The amplification product was purified using the BioRad (Hercules, Calif.) Prep-A-Gene kit according to manufacturer's suggested protocol. The resulting 5' $\alpha_d$ probe was approximately 720 bases long, corresponding to the region from nucleotide 1121 to nucleotide 1839 in SEQ ID NO: 1. The purified DNA (approximately 50 ng) was labeled with $^{32}$P-dCTP using a Boehringer Mannheim (Indianapolis, Ind.) Random Prime Labeling kit according to manufacturer's suggested protocol. Unincorporated isotope was removed using Centrisep® Spin Columns (Princeton Separations, Adelphia, N.J.) according to manufacturer's suggested protocol. Labeled probe was added to the filters in a prehybridization solution containing 45% formamide and incubation allowed to proceed overnight at 50° C. Following incubation, the filters were washed as described above.

Thirteen colonies gave signals on duplicate lifts. Positive colonies were picked from master plates, diluted in LBM and carbenicillin (100 μg/ml) and plated at varying dilutions onto Hybond® (Amersham) filters. Duplicate filters were hybridized with the same solution from the primary hybridization and following hybridization, the filters were washed at a final stringency of 2'SSC/0.1% SDS at 42° C. and exposed to film.

Ten of the originally identified thirteen positive colonies were confirmed in the secondary screen. Of these ten clones, two (designated A7.Q and A8.Q) were sequenced and determined to encode human $\alpha_d$. Clone A7.Q was found to be approximately 2.5 kb in length, including a 5' leader, part of a coding region, and an additional 60 bases of 5' untranslated sequence. The incomplete coding region was determined to have resulted from an aberrantly spliced intron region at corresponding nucleotide 2152 of SEQ ID NO: 1. Clone A8.Q was determined to be approximately 4 kb in length, spanning the entire $\alpha_d$ coding region and also including an intron sequence at corresponding base 305 of SEQ ID NO: 1. In comparison to the originally isolated $\alpha_d$ clone (SEQ ID NO: 1), one difference was observed in that both A7.Q and A8.Q clones were determined to have a three base CAG codon insertion occurring at base 1495. Sequences for clones A7.Q AND A8.Q are set out in SEQ ID NOs: 96 and 97, respectively, and a composite human sequence derived from clones A7.Q and A8.Q, and its corresponding deduced amino acid sequence, are set out in SEQ ID NOs: 98 and 99, respectively.

EXAMPLE 6

Northern Analysis of Human $\alpha_d$ Expression in Tissues

In order to determine the relative level of expression and tissue specificity of $\alpha_d$, Northern analysis was performed using fragments from clone 19A2 as probes. Approximately 10 μg of total RNA from each of several human tissues or cultured cell lines were loaded on a formaldehyde agarose gel in the presence of 1 μg of ethidium bromide. After electrophoresis at 100 V for 4 hr, the RNA was transferred to a nitrocellulose membrane (Schleicher & Schuell) by wicking in 10×SSC overnight. The membrane was baked 1.5 hr at 80° C. under vacuum. Prehybridization solution containing 50% formamide in 3-(N-morpholino)propane sulfonic acid (MOPS) buffer was used to block the membrane for 3 hr at 42° C. Fragments of clone 19A2 were labeled with the Boehringer Mannheim Random Prime kit according to the manufacturer's instructions including both $\alpha P^{32}dCTP$ and $\alpha P^{32}dTTP$. Unincorporated label was removed on a Sephadex® G25 column in TE buffer. The membrane was probed with $1.5 \times 10^6$ counts per ml of prehybridization buffer. The blot was then washed successively with 2×SSC/ 0.1% SDS at room temperature, 2×SSC/0.1% SDS at 42° C., 2×SSC/0.1% SDS at 50° C., 1×SSC/0.1% SDS at 50° C., 0.5×SSC/0.1% SDS at 50° C. and 0.1×SSC/0.1% SDS at 50° C. The blot was then exposed to film for 19 hr.

Hybridization using a BstXI fragment from clone 19A2 (corresponding to nucleotides 2011 to 3388 in SEQ ID NO: 1) revealed a weak signal in the approximately 5 kb range in liver, placenta, thymus, and tonsil total RNA. No signal was detected in kidney, brain or heart samples. The amount of RNA present in the kidney lane was minimal, as determined with ethidium bromide staining.

When using a second fragment of clone 19A2 (encompassing the region from bases 500 to 2100 in SEQ ID NO: 1), RNA transcripts of two different sizes were detected in a human multi-tissue Northern (MTN) blot using polyA$^+$ RNA (Clontech). An approximately 6.5 kb band was observed in spleen and skeletal muscle, while a 4.5 kb band was detected in lung and peripheral blood leukocytes.

The variation in sizes observed could be caused by tissue specific polyadenylation, cross reactivity of the probe with other integrin family members, or hybridization with alternatively spliced mRNAs.

Northern analysis using a third fragment from clone 19A2, spanning nucleotides 2000 to 3100 in SEQ ID NO: 1, gave results consistent with those using the other clone 19A2 fragments.

RNA from three myeloid lineage cell lines was also probed using the fragments corresponding to nucleotides 500 to 2100 and 2000 to 3100 in SEQ ID NO:1. A THP-1 cell line, previously stimulated with PMA, gave a diffuse signal in the same size range (approximately 5.0 kb), with a slightly stronger intensity than the tissue signals. RNA from unstimulated and DMSO-stimulated HL-60 cells hybridized with the $\alpha_d$ probe at the same intensity as the tissue samples, however, PMA treatment seemed to increase the signal intensity. Since PMA and DMSO drive HL-60 cell differentiation toward monocyte/macrophage and granulocyte pathways, respectively, this result suggests enhanced $\alpha_d$ expression in monocyte/macrophage cell types. U937 cells expressed the $\alpha_d$ message and this signal did not increase with PMA stimulation. No band was detected in Molt, Daudi, H9, JY, or Jurkat cells.

EXAMPLE 7

Transient Expression of Human $\alpha_d$ Constructs

The human clone 19A2 lacks an initiating methionine codon and possibly some of the 5' signal sequence. Therefore, in order to generate a human expression plasmid containing 19A2 sequences, two different strategies were used. In the first, two plasmids were constructed in which signal peptide sequences derived from genes encoding either CD11b or CD11c were spliced into clone 19A2 to generate a chimeric $\alpha_d$ sequence. In the second approach, a third plasmid was constructed in which an adenosine base was added at position 0 in clone 19A2 to encode an initiating methionine.

The three plasmids contained different regions which encoded the 5' portion of the $\alpha_d$ sequence or the chimeric $\alpha_d$ sequence. The $\alpha_d$ region was PCR amplified (see conditions in Example 2) with a specific 3' primer BamRev (set out below in SEQ ID NO: 26) and one of three 5' primers. The three 5' primers contained in sequence: (1) identical non-specific bases at positions 1–6 allowing for digestion, an EcoRI site from positions 7–12 and a consensus Kozak sequence from positions 13–18; (2) a portion of the CD11b (primer ER1B) or CD11c (primer ER1C) signal sequence, or an adenosine (primer ER1D); and (3) an additional 15–17 bases specifically overlapping 5' sequences from clone 19A2 to allow primer annealing. Primers ER1B, ER1C or ER1D are set out in SEQ ID NOS: 27, 28 or 29, respectively, where the initiating methionine codon is underlined and the EcoRI site is double underlined.

5'-CCACTGTCAGGATGCCCGTG-3' (SEQ ID NO: 26)

5'-AGTTACGAATTCGCCACC

ATGGCTCTACGGGTGCTTCTTCTG-3' (SEQ ID NO: 27)

5'-AGTTACGAATTCGCCACC

ATGACTCGGACTGTGCTTCTTCTG-3' (SEQ ID NO: 28)

5'-AGTTACGAATTCGCCACC

ATGACCTTCGGCACTGTG-3' (SEQ ID NO: 29)

The Resulting PCR Product was Digested with EcoRI and BamHI.

All three plasmids contained a common second $\alpha_d$ region (to be inserted immediately downstream from the 5' region described in the previous paragraph) including the 3' end of the $\alpha_d$ clone. The second $\alpha_d$ region, which extended from nucleotide 625 into the XbaI site in the vector 3' polylinker region of clone 19A2, was isolated by digestion of clone 19A2 with BamHI and XbaI.

Three ligation reactions were prepared in which the 3' $\alpha_d$ BamHI/XbaI fragment was ligated to one of the three 5' $\alpha_d$ EcoRI/BamHI fragments using Boehringer Mannheim ligase buffer and T4 ligase (1 unit per reaction). After a 4 hour incubation at 14° C., an appropriate amount of vector pcDNA.3 (Invitrogen) digested with EcoRI and XbaI was added to each reaction with an additional unit of ligase. Reactions were allowed to continue for another 14 hours. One tenth of the reaction mixture was then transformed into competent XL-1 Blue cells. The resulting colonies were cultured and the DNA isolated as in Example 5. Digestion with EcoRI identified three clones which were positive for that restriction site, and thus, the engineered signal sequences. The clones were designated pATM.B1 (CD11b/$\alpha_d$, from primer ER1B), pATM.C10 (CD11c/$\alpha_d$, from primer ER1C) and pATM.D12 (adenosine/$\alpha_d$ from primer ER1d). The presence of the appropriate signal sequences in each clone was verified by nucleic acid sequencing.

Expression from the $\alpha_d$ plasmids discussed above was effected by cotransfection of COS cells with the individual plasmids and a CD18 expression plasmid, pRC.CD18. As a positive control, COS cells were also co-transfected with the plasmid pRC.CD18 and a CD11a expression plasmid, pDC.CD11A.

Cells were passaged in culture medium (DMEM/10% FBS/pen-strep) into 10 cm Corning tissue culture-treated petri dishes at 50% confluency 16 hours prior to transfection. Cells were removed from the plates with Versene buffer (0.5 mM NaEDTA in PBS) without trypsin for all procedures. Before transfection, the plates were washed once with serum-free DMEM. Fifteen micrograms of each plasmid were added to 5 ml transfection buffer (DMEM with 20 µg/ml DEAE-Dextran and 0.5 mM chloroquine) on each plate. After 1.5 hours incubation at 37° C., the cells were shocked for 1 minute with 5 ml DMEM/10% DMSO. This DMSO solution was then replaced with 10 ml/plate culture medium.

Resulting transfectants were analyzed by ELISA, FACS, and immunoprecipitation as described in Examples 8, 9, and 10.

EXAMPLE 8

ELISA Analysis of COS Transfectants

In order to determine if the COS cells co-transfected with CD18 expression plasmid pRC.CD18 and an $\alpha_d$ plasmid expressed $\alpha_d$ on the cell surface in association with CD18, ELISAs were performed using primary antibodies raised against CD18 (e.g., TS1/18 purified from ATCC HB203). As a positive control, ELISAs were also performed on cells co-transfected with the CD18 expression plasmid and a CD11a expression plasmid, pDC.CD11A. The primary antibodies in this control included CD18 antibodies and anti-CD11a antibodies (e.g., TS1/22 purified from ATCC HB202).

For ELISA, cells from each plate were removed with Versene buffer and transferred to a single 96-well flat-bottomed Corning tissue culture plate. Cells were allowed to incubate in culture media 2 days prior to assay. The plates were then washed twice with 150 µl/well D-PBS/0.5% teleost skin gelatin (Sigma) solution. This buffer was used in all steps except during the development. All washes and incubations were performed at room temperature. The wells were blocked with gelatin solution for 1 hour. Primary antibodies were diluted to 10 µg/ml in gelatin solution and 50 µl were then added to each well. Triplicate wells were set up for each primary antibody. After 1 hour incubation, plates were washed 3× with 150 µl/well gelatin solution. Secondary antibody (goat anti-mouse Ig/HRP-Fc specific [Jackson, West Grove, Pa.]) at a 1:3500 dilution was added at 50 µl/well and plates were incubated for 1 hour. After three washes, plates were developed for 20 minutes with 100 µl/well o-phenyldiamine (OPD) (Sigma) solution (1 mg/ml OPD in citrate buffer) before addition of 50 µl/well 15% sulfuric acid.

Analysis of transfectants in the ELISA format with anti-CD18 specific antibodies revealed no significant expression above background in cells transfected only with the plasmid encoding CD18. Cells co-transfected with plasmid containing CD11a and CD18 showed an increase in expression over background when analyzed with CD18 specific antibodies or with reagents specific for CD11a. Further analysis of cells co-transfected with plasmids encoding CD18 and one of the $\alpha_d$ expression constructs (pATM.C10 or pATM.D12) revealed that cell surface expression of CD18 was rescued by concomitant expression of $\alpha_d$. The increase in detectable CD18 expression in COS cells transfected with pATM.C10 or pATM.D12 was comparable to that observed in co-transfected CD11a/CD18 positive control cells.

EXAMPLE 9

FACS Analysis of COS Transfectants

For FACS analysis, cells in petri dishes were fed with fresh culture medium the day after transfection and allowed to incubate 2 days prior to the assay. Transfectant cells were removed from the plates with 3 ml Versene, washed once with 5 ml FACS buffer (DMEM/2% FBS/0.2% sodium azide) and diluted to 500,000 cells/sample in 0.1 ml FACS buffer. Ten microliters of either 1 mg/ml FITC-conjugated CD18, CD11a, or CD11b specific antibodies (Becton Dickinson) or 800 µg/ml CFSE-conjugated murine 23F2G (anti-CD18) (ATCC HB11081) were added to each sample. Samples were then incubated on ice for 45 minutes, washed 3× with 5 ml/wash FACS buffer and resuspended in 0.2 ml FACS buffer. Samples were processed on a Becton Dickinson FACscan and the data analyzed using Lysys II software (Becton Dickinson).

COS cells transfected with CD18 sequences only did not stain for CD18, CD11a or CD11b. When co-transfected with CD11a/CD18, about 15% of the cells stained with antibodies to CD11a or CD18. All cells transfected with CD18 and any $\alpha_d$ construct resulted in no detectable staining for CD11a and CD11b. The pATM.B1, pATM.C10 and pATM.D12 groups stained 4%, 13% and 8% positive for CD18, respectively. Fluorescence of the positive population in the CD11a/CD18 group was 4-fold higher than background. In comparison, the co-transfection of $\alpha_d$ constructs with the CD18 construct produced a positive population that showed a 4- to 7-fold increase in fluorescence intensity over background.

EXAMPLE 10

Biotin-Labeled Immunoprecipitation of Human $\alpha_d$/CD18 Complexes from Co-transfected COS Cells Immunoprecipitation was attempted on cells co-transfected with CD18 and each of the $\alpha_d$ expression plasmids separately described in Example 7 in order to determine if $\alpha_d$ could be isolated as part of the $\alpha\beta$ heterodimer complex characteristic of integrins.

Transfected cells (1–3×10$^8$ cells/group) were removed from petri dishes with Versene buffer and washed 3 times in 50 ml/group D-PBS. Each sample was labeled with 2 mg Sulpho-NHS Biotin (Pierce, Rockford, Ill.) for 15 minutes at room temperature. The reaction was quenched by washing 3 times in 50 ml/sample cold D-PBS. Washed cells were resuspended in 1 ml lysis buffer (1% NP40, 50 mM Tris-HCl, pH 8.0, 0.2 M NaCl, 2 mM Ca$^{++}$, 2 mM Mg$^{++}$, and protease inhibitors) and incubated 15 minutes on ice. Insoluble material was pelleted by centrifugation at 10,000 g for 5 minutes, and the supernatant removed to fresh tubes. In order to remove material non-specifically reactive with mouse immunoglobulin, a pre-clearance step was initially performed. Twenty-five micrograms of mouse immunoglobulin (Cappel, West Chester, Pa.) was incubated with supernatants at 4° C. After 2.5 hr, 100 µl (25 µg) rabbit anti-mouse Ig conjugated Sepharose® (prepared from Protein A Sepharose® 4B and rabbit anti-mouse IgG, both from Zymed, San Francisco, Calif.) was added to each sample; incubation was continued at 4° C. with rocking for 16 hours. Sepharose® beads were removed from the supernatants by centrifugation. After pre-clearance, the supernatants were then treated with 20 µg anti-CD18 antibody (TS1.18) for 2 hours at 4° C. Antibody/antigen complexes were isolated from supernatants by incubation with 100 µl sample rabbit anti-mouse/Protein A-Sepharose® preparation described above. Beads were washed 4 times with 10 mM HEPES, 0.2 M NaCl, and 1% Triton-X 100®. Washed beads were pelleted and boiled for 10 minutes in 20 µl 2× Laemmli sample buffer with 2% β-mercaptoethanol. Samples were centrifuged and run on an 8% prepoured Novex polyacrylamide gel (Novex) at 100 V for 30 minutes. Protein was transferred to nitrocellulose membranes (Schleicher & Schuell) in TBS-T buffer at 200 mAmps for 1 hour. Membranes were blocked for 2 hr with 3% BSA in TBS-T. Membranes were treated with 1:6000 dilution of Strepavidin horse radish peroxidase (POD) (Boehringer Mannheim) for 1 hour, followed by 3 washes in TBS-T. The Amersham Enhanced Chemiluminescence kit was then used according to the manufacturer's instructions to develop the blot. The membrane was exposed to Hyperfilm® MP (Amersham) for 0.5 to 2 minutes.

Immunoprecipitation of CD18 complexes from cells transfected with pRC.CD18 and either pATM.B1, pATM.C10 or pATM.D12 revealed surface expression of a heterodimeric species consisting of approximately 100 kD β chain, consistent with the predicted size of CD18, and an a chain of approximately 150 kD, corresponding to $\alpha_d$.

EXAMPLE 11

Stable Transfection of Human $\alpha_d$ in Chinese Hamster Ovary Cells

To determine whether $\alpha_d$ is expressed on the cell surface as a heterodimer in association with CD18, cDNAs encoding each chain were both transiently and stably transfected into a cell line lacking both $\alpha_d$ and CD18.

For these experiments, $\alpha_d$ cDNA was augmented with additional leader sequences and a Kozak consensus sequence, as described in Example 7, and subcloned into expression vector pcDNA3. The final construct, designated pATM.D12, was co-transfected with a modified commercial vector, pDC1.CD18 encoding human CD18 into dihydrofolate reductase (DHFR)$^-$ Chinese hamster ovary (CHO) cells. The plasmid pDC1.CD18 encodes a DHFR$^+$ marker and transfectants can be selected using an appropriate nucleoside-deficient medium. The modifications which resulted in pDC1.CD18 are as follows.

The plasmid pRC/CMV (Invitrogen) is a mammalian expression vector with a cytomegalovirus promoter and ampicillin resistance marker gene. A DHFR gene from the plasmid pSC1190-DHFR was inserted into pRC/CMV 5' of the SV40 origin of replication. In addition, a polylinker from the 5' region of the plasmid pHF2G-DHF was ligated into the pRC/CMV/DHFR construct, 3' to the DHFR gene. CD18 encoding sequences are subsequently cloned into the resulting plasmid between the 5' flanking polylinker region and the bovine growth hormone poly A encoding region.

Surface expression of CD18 was analyzed by flow cytometry using the monoclonal antibody TS1/18. Heterodimer formation detected between $\alpha_d$ and CD18 in this cell line was consistent with the immunoprecipitation described in Example 10 with transient expression in COS cells.

EXAMPLE 12

Human $\alpha_d$ Binds ICAM-R in a CD18-dependent Fashion

In view of reports that demonstrate interactions between the leukocyte integrins and intercellular adhesion molecules (ICAMs) which mediate cell—cell contact [Hynes, Cell 69:11–25 (1992)], the ability of CHO cells expressing $\alpha_d$/CD18 to bind ICAM-1, ICAM-R, or VCAM-1 was assessed by two methods.

In replicate assays, soluble ICAM-1, ICAM-R, or VCAM-1 IgG1 fusion proteins were immobilized on plastic and the ability of $\alpha_d$/CD18 CHO transfected cells to bind the immobilized ligand was determined. Transfected cells were labeled internally with calcein, washed in binding buffer (RPMI with 1% BSA), and incubated in either buffer only (with or without 10 ng/ml PMA) or buffer with anti-CD18 monoclonal antibodies at 10 μg/ml. Transfected cells were added to 96-well Immulon® 4 microtiter plates previously coated with soluble ICAM-1/IgG1, ICAM-R/IgG1 or VCAM-1/IgG1 fusion protein, or bovine serum albumin (BSA) as a negative control. Design of the soluble forms of these adhesion molecules is described and fully disclosed in co-pending and co-owned U.S. patent application Ser. No. 08/102,852, filed Aug. 5, 1993. Wells were blocked with 1% BSA in PBS prior to addition of labeled cells. After washing the plates by immersion in PBS with 0.1% BSA for 20 minutes, total fluorescence remaining in each well was measured using a Cytofluor® 2300 (Millipore, Milford, Mass.).

In experiments with immobilized ICAMs, $\alpha_d$/CD18 co-transfectants consistently showed a 3–5 fold increase in binding to ICAM-R/IgG1 wells over BSA coated wells. The specificity and CD18-dependence of this binding was demonstrated by the inhibitory effects ofanti-CD18 antibody TS1/18. The binding of cells transfected with CD11a/CD18 to ICAM-1/IgG1 wells was comparable to the binding observed with BSA coated wells. CD11a/CD18 transfected cells showed a 2–3 fold increase in binding to ICAM-1/IgG1 wells only following pretreatment with PMA. PMA treatment of $\alpha_d$/CD18 transfectants did not affect binding to ICAM-1/IgG1 or ICAM-R/IgG1 wells. No detectable binding of $\alpha_d$/CD18 transfectants to VCAM-1/IgG1 wells was observed.

Binding of $\alpha_d$/CD18-transfected cells to soluble ICAM-1/IgG1, ICAM-R/IgG1, or VCAM-1/IgG1 fusion proteins was determined by flow cytometry. Approximately one million $\alpha_d$/CD18-transfected CHO cells (grown in spinner flasks for higher expression) per measurement were suspended in 100 μl binding buffer (RPMI and 1% BSA) with or without 10 μg/ml anti-CD18 antibody. After a 20 minute incubation at room temperature, the cells were washed in binding buffer and soluble ICAM-1/IgG1 or ICAM-R/IgG1 fusion protein was added to a final concentration of 5 μg/ml. Binding was allowed to proceed for 30 minute at 37° C., after which the cells were washed three times and resuspended in 100 μl binding buffer containing FITC-conjugated sheep anti-human IgG1 at a 1:100 dilution. After a 30 minute incubation, samples were washed three times and suspended in 200 μl binding buffer for analysis with a Becton Dickinson FACScan.

Approximately 40–50% of the $\alpha_d$/CD18 transfectants indicated binding to ICAM-R/IgG1, but no binding to ICAM-1/IgG1 or VCAM-1/IgG1 proteins. Pretreatment of transfected cells with PMA has no effect on $\alpha_d$/CD18 binding to either ICAM-1/IgG1, ICAM-R/IgG1 or VCAM-1/IgG1, which was consistent with the immobilized adhesion assay. Binding by ICAM-R was reduced to background levels after treatment of $\alpha_d$/CD18 transfectants with anti-CD18 antibody TS1/18.

The collective data from these two binding assays illustrate that $\alpha_d$/CD18 binds to ICAM-R and does so preferentially as compared to ICAM-1 and VCAM-1. The $\alpha_d$/CD18 binding preference for ICAM-R over ICAM-1 is opposite that observed with CD11a/CD18 and CD11b/CD18. Thus modulation of $\alpha_d$/CD18 binding may be expected to selectively affect normal and pathologic immune function where ICAM-R plays a prominent role. Moreover, results of similar assays, in which antibodies immunospecific for various extracellular domains of ICAM-R were tested for their ability to inhibit binding of ICAM-R to $\alpha_d$/CD18 transfectants, indicated that $\alpha_d$/CD18 and CD11a/CD18 interact with different domains of ICAM-R.

The failure of CD11a/CD18 to bind ICAM-1/IgG1 or ICAM-R/IgG1 in solution suggests that the affinity of binding between CD11a/CD18 and ICAM-1 or ICAM-R is too low to permit binding in solution. Detection of $\alpha_d$/CD18 binding to ICAM-R/IgG1, however, suggests an unusually high binding affinity.

In the assays described above, the VCAM-1/Ig fusion protein comprised the seven extracellular immunoglobulin-like domains. The fusion protein was produced in transfected CHO cells and protein yield determined by sandwich ELISA. The seven domain VCAM-1 fusion protein from CHO cell supernatant was employed without purification and protein yield was found to be extremely low. Because of the low protein yield in the VCAM-1 preparations, $\alpha_d$/CD18 binding to VCAM-1 was re-examined using a commercial VCAM-1 preparation (R & D Systems, Minneapolis, Minn.) in order to determine if the low VCAM-1 concentration resulted in undetectable $\alpha_d$ binding.

As before, CHO cells expressing $\alpha_d$ and CD18 were utilized in adhesion assays employing immobilized recombinant adhesion molecules. Using flow cytometry, it was shown that $\alpha_d$-transfected CHO cells expressed both $\alpha_d$ and CD18 and none of the other $\beta_2$ integrins. The transfected CHO cells were also shown to express neither of the two known VCAM-1 binding partner proteins, $\alpha_4\beta_1$ and $\alpha_4\beta_7$. The parental CHO cell line was shown to express no $\alpha_4$ or $\beta_2$ integrins. Binding experiments were carried out essentially as described above.

Results indicated that $\alpha_d$-transfected CHO cells bound immobilized VCAM-1 at a rate of approximately 14.2% as compared to binding to immobilized BSA at a rate of 7.5% and to immobilized E-selection at a rate of 2.8%. In addition, binding to immobilized VCAM-1 was essentially blocked (3.0% binding) in the presence of a monoclonal antibody specific for the first domain of VCAM-1. The parental CHO cells did not bind either VCAM-1, E-selection or BSA (all binding rates were less than 2%). Binding of the transfected CHO cells also decreased with serial passage of the cells which was consistent with the observed decrease in $\alpha_d$ surface expression over the same time period.

In order to determine if cells which naturally express $\alpha_d$/CD18 utilize VCAM-1 as a binding partner, peripheral blood eosinophils were isolated and cultured five to seven days in the presence of 10 ng/ml IL-5 in order to increase $\alpha_d$ expression. Flow cytometry indicated that IL-5 incubation increased $\alpha_d$ expression two- to four-fold, but had no effect on $\alpha_4$ expression.

Results indicated that the cultured eosinophils bound immobilized VCAM-1 at a rate of approximately 28.8% and that the binding was partially inhibited by both an anti-CD18 monoclonal antibody (binding rate 17.1%) and a monoclonal antibody against $\alpha_4$ (binding rate 18.1%). Contrary to the preliminary results above with low levels and/or impure VCAM-1, these data suggest that $\alpha_d\beta_2$ is a ligand for VCAM-1.

The FACS adhesion assay described above was used to test the binding of an ICAM-R mutant E37A/Ig to CHO cells expressing $\alpha_d$/CD18. E37A/Ig has been shown to obviate binding to an LFA-1/Ig chimera [Sadhu, et al., *Cell Adhesion and Communication* 2:429–440 (1994)]. The mutant protein was expressed in a soluble form from stably transfected CHO cell line and purified over a Prosep® A column as described by Sadhu, et al., supra.

E37A/Ig binding with the $\alpha_d$/CD18 transfectants was not detected in repeated assays. The mean fluorescence intensity (MFI) of the E37A/Ig chimera detected by FITC-conjugated anti-human antibody was identical to the MFI of the detecting antibody alone, indicating there was no detectable signal above background using the E37A/Ig mutant protein in the assay. Similarly, in an ELISA, carried out as described in Example 14, the E37A/Ig mutant did not appear to bind immobilized $\alpha_d$/CD18.

$\alpha_d$ Binding to iC3b

Complement component C3 can be proteolytically cleaved to form the complex iC3b, which initiates the alternative pathway of complement activation and leads ultimately to cell-mediated destruction of a target. Both CD11b and CD11c have been implicated in iC3b binding and subsequent phagocytosis of iC3b-coated particles. A peptide fragment in the CD11b I domain has recently been identified as the site of iC3b interaction [Ueda, et al., *Proc.Natl.Acad.Sci.* (*USA*) 91:10680–10684 (1994)]. The region of iC3b binding is highly conserved in CD11b, CD11c, and $\alpha_d$, suggesting an $\alpha_d$/iC$^3$b binding interaction.

Binding of $\alpha_d$ to iC3b is performed using transfectants or cell lines naturally expressing $\alpha_d$ (for example, PMA-stimulated HL60 cells) and iC3b-coated sheep red blood cells (sRBC) in a rosette assay [Dana, et al., *J.Clin.Invest.* 73:153–159 (1984)]. The abilities of $\alpha_d$/CD18 CHO transfectants, VLA4-CHO transfectants (negative control) and PMA-stimulated HL60 cells (positive control) to form rosettes are compared in the presence and absence of an anti-CD18 monoclonal antibody (for example TS1/18.1).

EXAMPLE 13

Screening by Scintillation Proximity Assay ID of Modulators of $\alpha_d$ Binding Specific inhibitors of binding between the $\alpha_d$ ligands of the present invention and their binding partners ($\alpha_d$ ligand/anti-ligand pair) may be determined by a variety of means, such as scintillation proximity assay techniques as generally described in U.S. Pat. No. 4,271,139, Hart and Greenwald, *Mol.Immunol.* 12:265–267 (1979), and Hart and Greenwald, *J.Nuc.Med.* 20:1062–1065 (1979), each of which is incorporated herein by reference.

Briefly, one member of the $\alpha_d$ ligand/anti-ligand pair is bound to a solid support either directly or indirectly. Indirect capture would involve a monoclonal antibody, directly bound to the support, which recognizes a specific epitope at the C-terminus of the soluble integrin $\beta$ chain protein. This epitope would be either the hemagglutinin protein or the mycobacterial IIIE9 epitope [Anderson, et al., *J.Immunol.* 141:607–613 (1988). A fluorescent agent is also bound to the support. Alternatively, the fluorescent agent may be integrated into the solid support as described in U.S. Pat. No. 4,568,649, incorporated herein by reference. The non-support bound member of the $\alpha_d$ ligand/anti-ligand pair is labeled with a radioactive compound that emits radiation capable of exciting the fluorescent agent. When the ligand binds the radiolabeled anti-ligand, the label is brought sufficiently close to the support-bound fluorescer to excite the fluorescer and cause emission of light. When not bound, the label is generally too distant from the solid support to excite the fluorescent agent, and light emissions are low. The emitted light is measured and correlated with binding between the ligand and the anti-ligand. Addition of a binding inhibitor to the sample will decrease the fluorescent emission by keeping the radioactive label from being captured in the proximity of the solid support. Therefore, binding inhibitors may be identified by their effect on fluorescent emissions from the samples. Potential anti-ligands to $\alpha_d$ may also be identified by similar means.

The soluble recombinant $\alpha_d$/CD18 leucine zipper construct (see Example 14) is used in a scintillation proximity assay to screen for modulators of CAM binding by the following method. The recombinant integrin is immobilized with a nonblocking anti-α subunit or anti-β subunit antibody previously coated on a scintillant-embedded plate. Chemical library compounds and a specific biotinylated CAM/Ig chimera are added to the plate simultaneously. Binding of the CAM/Ig chimera is detected by labeled strepavidin. In the assay, ICAM-1/Ig and ICAM-R/Ig are biotinylated with NHS-Sulfo-biotin LC (long chain, Pierce) according to manufacturer's suggested protocol. Labeled proteins are still reactive with CAM specific antibodies and can be shown to react with immobilized LFA-1 by ELISA, with detection by Strepavidin-HRP and subsequent development with OPD.

Alternatively, the recombinant leucine zipper protein is purified, or partially purified and coated directly on the scintillant embedded plate. Unlabelled CAM/Ig chimera and chemical library compounds are added simultaneously. Bound CAM/Ig is detected with $^{125}$I-labeled anti-human Ig.

As yet another alternative, purified CAM/Ig protein is immobilized on the scintillant plate. Chemical library compounds and concentrated supernatant from cells expressing recombinant leucine zipper integrin are added to the plate. Binding of the recombinant integrin is detected with a labeled, non-blocking α or β subunit antibody.

Screening for Small Molecule Modulators

As an alternative to scintillation proximity assays, $\alpha_d$ binding partners and inhibitors of the same can be identified using ELISA-like assays as described below.

Soluble $\alpha_d$/CD18 leucine zipper (LZ) construct (see Example 14) was captured from tissue culture supernatants using the anti-$\alpha_d$ antibody 212D (see Example 15). The 212D antibody was immobilized on 96-well Immulon® IV plates (Costar) in bicarbonate coating buffer (pH 9.5) overnight at 4° C. The same protocol was used to immobilize the anti-CD11a antibody TS2/4.1 for immobilization of a LFA-1 leucine zipper (LFA-1LZ) fusion protein; LFA-1 was used as a negative control for VCAM-1 binding and a positive control for ICAM-1 binding. The plates were blocked with 300 μl/well 3% bovine serum albumin for one hour and washed in D-PBS. Tissue culture supernatants from stable CHO transfectants expressing either $\alpha_d$/CD18LZ or LFA-1LZ were added at 100 μl/well and allowed to incubate for 6 to 8 hours at 4° C. The plates were washed twice with Tris-buffered saline with Tween® 20 (TBS-T), followed by one wash with TBS (no Tween®) containing 2 mM each calcium chloride, magnesium chloride, and manganese chloride. The latter served as assay and wash buffer during the remainder of the assay.

After integrin capture, the plates were washed three times with 250 μl/well TBS. Purified CAM/Ig (see Example 12) was added to each well following serial 2:3 dilutions starting at a concentration of 10 to 20 μg/ml. CAM/Igs were allowed to bind for two hours at room temperature before plates were washed as above. Bound fusion protein was detected with horseradish peroxidase-conjugated goat anti-human Ig antibody (Jackson Labs) followed by development with o-phenyldiamine (OPD).

Results indicated that while ICAM-1/Ig caused a 5- to 7-fold increase in signal when bound to LFA-1LZ, it failed to bind $\alpha_d$/CD18LZ. In contrast, VCAM-1/Ig exhibited a 5-fold increase in signal above background in wells containing $\alpha_d$/CD18LZ, but not in wells with LFA-1LZ. An ICAM-R mutant E37A/Ig (see Example 12) did not bind either integrin.

The $\alpha_d$ specific monoclonal antibodies 212D, 217L, 217I, 217H, 217G, 217K, and 217M were tested for the ability to inhibit VCAM-1 binding to immobilized $\alpha_d$/CD18. In addition, anti-VCAM-1 monoclonal antibodies 130K, 130P and IG11B1 (Caltag) were used to determine reaction specificity. The anti-$\alpha_d$ monoclonal antibodies were used at 5 μg/ml and the anti-VCAM-1 antibodies at 25 μg/ml; the higher anti-VCAM-1 antibody concentration was used in view of the fact that VCAM-1 is in solution in the assay system.

Partial blocking (50%) resulted in the wells treated with either 217I or 130K and 130P used together. The combination of 130K/130P also completely inhibits the interaction of VLA-4 and VCAM-1 which suggested that $\alpha_d$ and VLA-4 bind to distinct sites on VCAM-1 and the possibility of developing antagonists which selectively interfere with $\alpha_d$/VCAM-1 binding.

This assay can be adapted as follows to perform high throughput screening assays for inhibitors of $\alpha_d$ binding. VCAM-1/Ig is biotinylated and used as above in the presence of pooled chemical compounds previously solubilized in DMSO; bound VCAM-1/Ig is then detected with a strepavidin-europium (Eu) complex. The strepavidin-Eu complex is activated by chelation resulting in measurable light emission. Changes, or more particularly a decrease, in emission is indicative of inhibition of VCAM-1/$\alpha_d$ binding, presumably as a result of action by one or more compounds in the pool of small molecules, which are then assayed individually or in smaller groupings.

EXAMPLE 14

Soluble Human $\alpha_d$ Expression Constructs

The expression of full-length, soluble human $\alpha_d$/CD18 heterodimeric protein provides easily purified material for immunization and binding assays. The advantage of generating soluble protein is that it can be purified from supernatants rather than from cell lysates (as with full-length membrane-bound $\alpha_d$/CD18); recovery in therefore improved and impurities reduced.

The soluble $\alpha_d$ expression plasmid was constructed as follows. A nucleotide fragment corresponding to the region from bases 0 to 3161 in SEQ ID NO: 1, cloned into plasmid pATM.D12, was isolated by digestion with HindIII and AatII. A PCR fragment corresponding to bases 3130 to 3390 in SEQ ID NO: 1, overlapping the HindIII/AatII fragment and containing an addition MluI restriction site at the 3' terminus, was amplified from pATM.D12 with primers sHAD.5 and sHAD.3 set out in SEQ ID NOS: 30 and 31, respectively.

```
                                        (SEQ ID NO: 30)
5'-TTGCTGACTGCCTGCAGTTC-3'

(SEQ ID NO: 31)
5'-GTTCTGACGCGTAATGGCATTGTAGACCTCGTCTTC-3'
```

The PCR amplification product was digested with AatII and MluI and ligated to the HindIII/AatII fragment. The resulting product was ligated into HindIII/MluI-digested plasmid pDC1.s.

This construct is co-expressed with soluble CD18 in stably transfected CHO cells, and expression is detected by autoradiographic visualization of immunoprecipitated CD18 complexes derived from $^{35}$S-methionine labeled cells. The construct is also co-expressed with CD18 in 293 cells [Berman, et al., *J.Cell.Biochem.* 52:183–195 (1993)].

Soluble Full-length $\alpha_d$ Construct

Alternative $\alpha_d$ expression constructs are also contemplated by the invention. In order to facilitate expression and purification of an intact $\alpha_d$/CD18 heterodimer, soluble $\alpha_d$ and CD18 expression plasmids will be constructed to include a "leucine zipper" fusion sequence which should stabilize the heterodimer during purification [Chang, et al., Proc.Natl.Acad.Sci.(USA), 91: 11408–11412 (1994)]. Briefly, DNA encoding the acidic and basic amino acid strands of the zipper have been generated by primer annealing using oligonucleotides described in Chang, et al. The DNA sequences have been further modified to include additional Mlu1 and Xba1 restriction sites at the 5' and 3' ends, respectively, of the DNA to facilitate subcloning into $\alpha_d$ or CD18 expression constructs previously described. In addition, sequences representing either hemagglutinin protein or a polyhistidine sequence have been added, as well as a stop codon inserted after the Xba1 site. The hemagglutinin or polyhistidine sequences are incorporated to facilitate affinity purification of the expressed protein. Sequences encoding the basic strand of the zipper are incorporated on the plasmid vector expressing CD18; the acidic strand is inserted on the a chain construct. Upon expression of the modified $\alpha_d$ and CD18 proteins in a host cell, it is presumed that interaction between the acidic and basic strands of the zipper structure will stabilize the heterodimer and permit isolation of the intact $\alpha_d$/CD18 molecule by affinity purification as described above.

Plasmids were constructed for expression of soluble $\alpha_d$ and CD18 with acidic and basic "leucine zipper" sequences and transfected into COS cells by the DEAE/Dextran method described in Example 7. The resulting protein was referred to as $\alpha_d$/CD18LZ. Hemagglutinin and polyhistidine tags were not incorporated into $\alpha_d$/CD18LZ. Transfected cells were grown for 14 days in reduced serum (2%) conditions. Supernatants harvested every five days from transfected cells were assayed for protein production by ELISA as described in Example 8. Briefly, the $\alpha_d$/CD18LZ heterodimer was immobilized on plates coated with anti-$\alpha_d$ monoclonal antibody 169B (see Example 15). The $\alpha_d$/CD18LZ complex was detected by addition of a biotinylated anti-CD18 monoclonal antibody, TS1/18.1 (see Example 8), followed by addition of strepavidin/horse radish peroxidase (HRP) conjugate and o-phenyldiamine (OPD). Protein was clearly detectable in the supernatants.

Binding Assays Using Soluble Full Length $\alpha_d$ Expression Products

Functional binding assays using the soluble full length $\alpha_d$/CD18LZ heterodimer described above were performed by immobilizing the heterodimer on plates coated with monoclonal antibody 169B or a non-blocking anti-CD18 monoclonal antibody (see Example 15). Wells were blocked with fish skin gelatin to prevent non-specific binding before addition of CAM/Ig chimeras (see Example 12) at a starting concentration of 10 µg/ml. Binding of the chimeras to $\alpha_d$/CD18 was detected with a goat-anti-human Ig HRP conjugate (Jackson Labs) and subsequent development with OPD.

VCAM-1/Ig was observed to bind to captured $\alpha_d$/CD18LZ at a 3–5 fold higher level than to captured CD11a/CD18. ICAM-1/Ig and ICAM-2/Ig bound soluble CD11a/CD18 heterodimer approximately 15 and 10 fold above background, respectively, but did not bind $\alpha_d$/CD18. VCAM-1 binding was reduced approximately 50% in the presence of the VCAM-1 specific antibodies 130K and 130P used in combination.

The binding assay was also performed with the ICAM/Ig protein immobilized on 96-well plates followed by addition of recombinant soluble integrin in cellular supernatant. Binding of the soluble integrins were detected with an unlabeled non-blocking α or β subunit specific murine antibody, followed by incubation with HRP-conjugated goat anti-mouse antibody and development with OPD.

Results indicated that a non-blocking antibody detected $\alpha_d$/CD18LZ binding to ICAM-R/g 10 fold greater than binding detected in control well containing no antibody. Soluble $\alpha_d$/CD18 binding was not detected with immobilized ICAM-1/Ig, however binding was detected between $\alpha_d$/CD18 and immobilized CD11b/CD18 and CD11a/CD18 15 and 5 fold, respectively, greater than background binding.

Because previous studies have demonstrated that CD11b and CD11c bind lipopolysaccharide (LPS) [Wright, Curr.Opin.Immunol. 3:83–90 (1991); Ingalls and Golenbock, J.Exp.Med. 181:1473–1479 (1995)], LPS binding to $\alpha_d$/CD18 was also assessed using flow cytometry and plate-based assays. Results indicated that FITC-labelled LPS isolated from S.Minnesota and S.typhosa (both obtained from Sigma) at 20 µg/ml were able to weakly bind $\alpha_d$/CD18 transfected CHO cells. No binding was observed with un-transfected control CHO cells. In ELISA format assays, biotinylated LPS [Luk, et al., Alan. Biochem. 232:217–224 (1995)] at 0.5–3.0 µg bound immobilized $\alpha_d$/CD18LZ with a signal four fold greater that the capture antibody and blocking reagent alone. Apparent binding of LPS to CD11a/CD18 was discounted by subtracting from each experimental value background binding to anti-CD11a antibody TS2/4.

In order to identify other ligands for $\alpha_d$/CD18, the recombinant $\alpha_d$/CD18LZ protein is used in a two tier study. Binding of various cell types to immobilized protein is used to determine which cells express $\alpha_d$ ligands on the cell surface. Antibody inhibition is then used to determine if the observed cell binding results from interaction with known surface adhesion molecules. If no inhibition results, co-immunoprecipitation with $\alpha_d$/CD18LZ bound to proteins from lysates of cells which will bind $\alpha_d$ is used to attempt to identify the ligand.

Soluble Human $\alpha_d$ I Domain Expression Constructs

It has previously been reported that the I domain in CD11a can be expressed as an independent structural unit that maintains ligand binding capabilities and antibody recognition [Randi and Hogg, J.Biol.Chem. 269:12395–12398 (1994); Zhout, et al., J.Biol.Chem. 269:17075–17079 (1994); Michishita, et al., Cell 72:857–867 (1993)]. To generate a soluble fusion protein comprising the $\alpha_d$ I domain and human IgG4, the $\alpha_d$ I domain is amplified by PCR using primers designed to add flanking BamHI and XhoI restriction sites to facilitate subcloning. These primers are set out in SEQ ID NOS: 32 and 33 with restriction sites underlined.

5'-ACGTATGCA
GGATCCCATCAAGAGATGGACATCGCT (SEQ ID NO: 32)

5'-ACTGCATGT
CTCGAGGCTGAAGCCTTCTTGGGACATC (SEQ ID NO: 33)

The C nucleotide immediately 3' to the BamHI site in SEQ ID NO: 32 corresponds to nucleotide 435 in SEQ ID NO: 1; the G nucleotide 3' to the XhoI site in SEQ ID NO: 33 is complementary to nucleotide 1067 in SEQ ID NO: 1. The amplified I domain is digested with the appropriate enzymes, the purified fragment ligated into the mammalian expression vector pDCs and the prokaryotic expression vector pGEX-4T-3 (Pharmacia) and the I domain fragment sequenced. The fusion protein is then expressed in COS, CHO or E.coli cells transfected or transformed with an appropriate expression construct.

Given the affinity of $\alpha_d$ for ICAM-R, expression of the $\alpha_d$ I domain may be of sufficient affinity to be a useful inhibitor of cell adhesion in which $\alpha_d$ participates.

Analysis of Human $\alpha_d$ I Domain/IgG4 Fusion Proteins

Protein was resolved by SDS-PAGE under reducing and non-reducing conditions and visualized by either silver staining or Coomassie staining. Protein was then transferred to Immobilon PVDF membranes and subjected to Western blot analysis using anti-human IgG monoclonal antibodies or anti-bovine Ig monoclonal antibodies.

Protein detected was determined to migrate at about 120 kD under non-reducing conditions and at about 45 kD under reducing conditions. Minor bands were also detected on non-reducing gels at approximately 40–50 kD which were reactive with the anti-human, but not anti-bovine, antibodies. A 200 kD minor band was determined to be bovine Ig by Western blot.

Binding Assays Using I Domain Expression Products

The ability of the I domain to specifically recognize ICAM-R/IgG chimeric protein was tested in an ELISA format. Serial dilutions of $\alpha_d$ I domain IgG4 fusion protein (I$\alpha_d$/IgG4) in TBS were incubated with ICAM-1/IgG, ICAM-R/IgG, VCAM-1/IgG, or an irrelevant IgG1 myeloma protein immobilized on Immulon® IV RIA/EIA plates. CD11a I domain/IgG chimeric protein and human IgG4/kappa myeloma protein were used as negative controls. Bound IgG4 was detected with the biotinylated anti-IgG4 monoclonal antibody HP6023 followed by addition of strepavidin-peroxidase conjugate and development with substrate o-phenyldiamine.

In repeated assays, no binding of the CD11a/IgG4 protein or the IgG4 myeloma protein was detected with any of the immobilized proteins. The I$\alpha_d$/IgG4 protein did not bind to fish skin gelatin or bovine serum albumin blocking agents, human IgG1, or ICAM-1/IgG. A two to three fold increase in binding signal over background was detected in ICAM-R/IgG protein coated wells using 1–5 μg/ml concentrations of I$\alpha_d$/IgG4 protein. The signal in VCAM-1/IgG protein coated wells was 7–10 fold higher than background. In previous assays, $\alpha_d$/CD18 transfected CHO cells did not bind VCAM-1/IgG protein, suggesting that VCAM-1 binding may be characteristic of isolated I domain amino acid sequences.

Additional $\alpha_d$ I Domain Constructs

Additional $\alpha_d$ I domain constructs are generated in the same fashion as the previous construct, but incorporating more amino acids around the $\alpha_d$ I domain. Specific constructs include: i) sequences from exon 5 (amino acids 127–353 in SEQ ID NO: 2), preceding the current construct, ii) the EF-hand repeats (amino acids 17–603 in SEQ ID NO: 2) following the I domain, and iii) the alpha chain truncated at the transmembrane region (amino acids 17–1029 in SEQ ID NO: 2), with an IgG4 tail for purification and detection purposes. These constructs are ligated into either the mammalian expression vector pDCS 1 or the prokaryotic expression vector pGEX-4T-3 (Pharmacia) and the I domain sequenced. The fusion proteins are then be expressed in COS, CHO, or E.coli cells transformed or transfected with an appropriate expression construct. Protein are purified on a ProSepA® column (Bioprocessing Limited, Durham, England), tested for reactivity with the anti-IgG4 monoclonal antibody HP6023 and visualized on polyacrylamide gels with Coomassie staining.

In order to construct an expression plasmid for the entire $\alpha_d$ polypeptide, pATM.D12, described supra, is modified to express an $\alpha_d$-IgG4 fusion protein by the following method. IgG4 encoding DNA is isolated from the vector pDCS1 by PCR using primers which individually incorporate a 5' AatII restriction site (SEQ ID NO: 89) and a 3' XbaI restriction site (SEQ ID NO: 90).

(SEQ ID NO: 89)
5'-CGCTGTGACGTCAGAGTTGAGTCCAAATATGG-3'

(SEQ ID NO: 90)
5'-GGTGACACTATAGAATAGGGC-3'

Plasmid pATM.D12 is digested with AatII and XbaI, and the appropriately digested and purified IgG4 PCR product ligated into the linear vector.

EXAMPLE 15

Production of Human $\alpha_d$-Specific Monoclonal Antibodies

1. Transiently transfected cells from Example 7 were washed three times in Dulbecco's phosphate buffered saline (D-PBS) and injected at $5 \times 10^6$ cells/mouse into Balb/c mice with 50 μg/mouse muramyl dipeptidase (Sigma) in PBS. Mice were injected two more times in the same fashion at two week intervals. The pre-bleed and immunized serum from the mice were screened by FACS analysis as outlined in Example 9 and the spleen from the mouse with the highest reactivity to cells transfected with $\alpha_d$/CD18 was fused. Hybridoma culture supernatants were then screened separately for lack of reactivity against COS cells transfected with CD11a/CD18 and for reactivity with cells co-transfected with an $\alpha_d$ expression plasmid and CD18.

This method resulted in no monoclonal antibodies.

2. As an alternative for production of monoclonal antibodies, soluble $\alpha_d$ I domain/IgG4 fusion protein was affinity purified from supernatant of stably transfected CHO cells and used to immunize Balb/c mice as described above. Hybridomas were established and supernatants from these hybridomas were screened by ELISA for reactivity against $\alpha_d$ I domain fusion protein. Positive cultures were then analyzed for reactivity with full length $\alpha_d$/CD18 complexes expressed on CHO transfectants.

Mouse 1908 received three initial immunizations of $\alpha_d$/CD18 transfected CHO cells and two subsequent boosts with soluble $\alpha_d$/CD18 heterodimer. Two final immunizations included 50 μg/mouse $\alpha_d$ I domain/IgG4 fusion protein. The fusion produced 270 IgG-producing wells. Supernatant from 45 wells showed at least 7-fold higher binding to I$\alpha_d$/IgG4 fusion protein than to human IgG4 by ELISA. None of the supernatants reacted to $\alpha_d$/CD18 transfected CHO cells as determined by FACS analysis.

To determine whether the supernatants were able to recognize integrin alpha subunit proteins in another context, fresh frozen splenic sections were stained with supernatants from 24 of the 45 wells. Three supernatants were determined to be positive: one stained large cells in the red pulp, while two others stained scattered cells in the red pulp and also trabeculae.

These supernatants were further analyzed by their ability to immunoprecipitate biotinylated CD18 complexes from either $\alpha_d$/CD18 transfected CHO cells or PMA-stimulated HL60 cells. Fusion wells with supernatants that recognized protein in detergent lysates (which should not be as conformationally constrained as protein expressed as heterodimers) were selected for further subcloning. Monoclonal antibodies which recognize protein in detergent may be more useful in immunoprecipitation of heterodimeric complexes from transfectants, tissues, and cell lines.

3. As another alternative to monoclonal antibody production, CD18 complexes were immunoprecipitated from human spleen lysates with the anti-CD18 monoclonal antibody 23F2G after preclearance of CD11a/CD18 (using monoclonal antibody TS2/4) and CD11b/CD18 (using monoclonal antibody Mo-1). Five Balb/c mice, ten to twelve weeks old, were immunized by subcutaneous injection with approximately 30 µg of resulting protein in complete Freund's adjuvant on day 0, followed by two boosts of 30 ug immunogen/mouse on days 28 and 43 in incomplete Freund's adjuvant. Test sera were drawn ten days following the final boost and reactivity was assessed by using 1:500 dilution of each serum to detect 1 µg/lane immunogen in a Western blot. Sera from three mice detected bands of approximately 95 and 150 kD; no signal was seen in lanes treated with a 1:50 dilution of preimmune sera. The 150 kD band was presumed to represent $\alpha_d$ in an in vivo glycosylation state. In addition, all post immune sera immunoprecipitated protein from lysates of biotinylated $\alpha_d$/CD18 CHO cells that migrated at appropriate molecular weights on SDS-PAGE to represent the heterodimer. From these results, mouse #2212 was selected and was further immunized by intraperitoneal injection on day 64 with 30 µg immunogen in PBS. The mouse was sacrificed four days later, and the spleen was sterilely removed.

A single-cell suspension was formed by grinding the spleen between the frosted ends of two glass microscope slides submerged in serum-free RPMI 1640 supplemented with 2 mM L-glutamine, 1 mM sodium pyruvate, 100 units/ml penicillin, and 100 µg/ml streptomycin (RPMI) (Gibco, Canada). The cell suspension was filtered through a sterile 70-mesh Nitex cell strainer (Becton Dickinson, Parsippany, N.J.), and the filtrate washed twice by centrifugation at 200×g for 5 minutes. The resulting pellet was resuspended in 20 ml serum-free RPMI. Thymocytes taken from three naive Balb/c mice were prepared in a similar manner.

Prior to fusion, NS-1 myeloma cells, kept in log phase in RPMI with 10% Fetalclone serum (FCS) (Hyclone Laboratories, Inc., Logan, Utah) for three days prior to fusion, were pelleted by centrifugation at 200×g for 5 minutes, washed twice as described in the foregoing paragraph, and counted. Approximately 2×10$^8$ spleen cells were combined with 4×10$^7$ NS-1 cells, and the resulting mixture pelleted by centrifugation at 200×g. The supernatant was discarded. The cell pellet dislodged by tapping the tube and 2 ml of 50% PEG 1500 in 75 mM Hepes (pH 8.0, 37° C.) (Boehringer Mannheim) was added over the course of one minute with stirring. An additional 14 ml of serum-free RPMI was subsequently added over the next seven minutes, followed by immediate addition of 16 ml RPMI. The resulting mixture was centrifuged at 200×g for 10 minutes and the supernatant was discarded. The pellet was resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim) and 1.5×10$^6$ thymocytes/ml, and dispensed into ten 96-well flat bottom tissue culture plates (Corning, United Kingdom) at 200 µl/well. Cells were fed on days 2, 4, and 6 days post-fusion by aspirating approximately 100 µl from each well with an 18 G needle (Becton Dickinson), and adding 100 µl/well plating medium described above, except containing 10 units/ml IL-6 and lacking thymocytes.

On day 7–10 post-fusion, supernatant from each well was screened by antibody capture ELISA, testing for the presence of mouse IgG. Immulon® 4 plates (Dynatech, Cambridge, Mass.) were coated with 50 µl/well goat anti-mouse IgA, IgG, or IgM (Organon Teknika) diluted 1:5000 in 50 mM carbonate buffer, pH 9.6, at 4° C. Plates were washed 3× with PBS containing 0.5% Tween® 20 (PBST) and 50 µl culture supernatant from each well was added. After incubation at 37° C. for 30 minutes, wells were washed with PBST as above, and 50 µl of horseradish peroxidase conjugated goat anti-mouse IgG(fc) (Jackson ImmunoResearch, West Grove, Pa.) diluted 1:3500 in PBST was added to each well. Plates were incubated as above, washed 4× with PBST and 100 µl substrate, consisting of 1 mg/ml o-phenylene diamine (Sigma) and 0.1 µl/ml 30% $H_2O_2$ in 100 mM Citrate, pH 4.5, was added. The color reaction was stopped after five minutes with addition of 50 µl 15% $H_2SO_4$. Absorbance at 490 nm was determined for each well using a plate reader (Dynatech).

Hybridomas were further characterized as follows. Supernatants from IgG-producing cultures were analyzed by flow cytometry for reactivity to $\alpha_d$/CD18-transformed CHO cells but not to JY cells (a B-cell line positive for LFA-1, but not other $\beta_2$ integrins as observed in previous in-house staining experiments). Briefly, 5×10$^5$ $\alpha_d$/CD18-transformed CHO or $\alpha_d$/CD18$^-$ JY cells were suspended in 50 µl RPMI containing 2% FBS and 10 mM NaN$_3$ (FACS buffer). Individual cell suspensions were added to 50 µl IgG positive hybridoma culture supernatant in wells of 96-well round bottomed plates (Corning). After a 30 minute incubation on ice, cells were washed twice by pelleting in a clinical centrifuge, supernatant from each well was discarded, and pellets resuspended in 200–300 µl FACS buffer. The last wash was replaced with 50 µl/well of a 1:100 dilution of a F(ab')$_2$ fragment of sheep anti-mouse IgG (H+L)-FITC conjugate (Sigma, St. Louis, Mo.) prepared in FACS Buffer. After incubation as described above, cells were washed twice with Dulbecco's PBS (D-PBS) supplemented with 10 mM NaN$_3$, and finally resuspended in D-PBS containing 1% paraformaldehyde. Samples were then transferred to polystyrene tubes for flow cytometric analysis (FACS) with a Becton Dickinson FACsan analyzer.

The fusion yielded four cultures deemed positive by both criteria. When the secondary screen was repeated on expanded supernatants approximately four days later, three of the four cultures remained positive. The three wells, designated 169A, 169B, 169D were cloned two to three times, successively, by doubling dilution in RPMI, 15% FBS, 100 mM sodium hypoxanthine, 16 mM thymidine, and 10 units/ml IL-6. Wells of clone plates were scored visually after four days and the number of colonies in the least dense wells were recorded. Selected wells of the each cloning were assayed by FACS after 7–10 days. Activity was found in two of the cultures, 169A and 169B. In the final cloning, positive wells containing single colonies were expanded in RPMI with 11% FBS. Antibody from clonal supernatants of 169A and 169B were isotyped using IsoStrip kit (Boehringer Mannheim) according to manufacturer instructions and found to be of the IgG1 isotype.

Immunoprecipitation of $\alpha_d$/CD18 complexes from CHO transfectants and PMA-stimulated HL60 cells was used as a tertiary screen for specificity. Hybridomas 169A and 169B precipitated appropriate bands from CHO lines, and a single a chain species of 150–160 kD from HL60 cells as determined by SDS-PAGE. Hybridomas 169A and 169B were deposited May 31, 1995 with the American Type Culture Collection, 12301 Parklawn Drive, Rockville, Md. 20852 and assigned Accession Numbers HB11907 and HB11906, respectively.

In order to more fully characterize binding properties of 169A and 169B, the ability of each antibody to inhibit binding of the other or the anti-CD18 antibody TS1/18.1 to soluble $\alpha_d$/CD18 was tested. Soluble full length $\alpha_d$/CD18 was immobilized by each unlabeled antibody separately in a 96-well plate format, and biotinylated antibodies were used to detect protein bound by the same or different unlabeled antibodies. Binding was detected using a goat anti-mouse Ig/HRP conjugate followed by addition of OPD substrate. Results indicated that antibody 169A was able to block binding of biotinylated 169A and TS 1/18.1, while the antibody 169B blocked binding only of itself.

4. Another mouse (#2214), immunized by the same protocol as mouse #2212, was selected and further immunized by a pre-fusion boost on day 70 with 30 μg purified $\alpha_d$ from spleen lysates in PBS. The mouse was sacrificed four days later, and the spleen was sterilely removed.

The fusion and cloning of positive cells were carried out as described above. The fusion produced five anti-$\alpha_d$ monoclonal hybridomas designated 170D, 170F, 170E, 170X, and 170H which were isotyped as $IgG_1$ using the IsoStrip kit (Boehringer Mannheim) according to the manufacturer's instructions.

5. Still another mouse, #2211, immunized by the same initial protocol as mouse #2212 and mouse #2214, was selected and further immunized on day 88 with 30 μg immunogen and a pre-fusion boost of 30 μg immunogen on day 203. The mouse was sacrificed four days later, and the spleen was removed and fusion carried out as described above. Hybridoma supernatant was screened by antibody capture ELISA and by flow cytometry as detailed in the above paragraphs.

Fifteen positive hybridomas were identified, designated 188A, 188B, 188C, 188E, 188F, 188G, 188I, 188J, 188K, 188L, 188M, 188N, 188P, 188R and 188T, and isotyped in an ELISA assay. Briefly, Immulon® 4 plates (Dynatech, Cambridge, Mass.) were coated at 4° C. with 50 μl/well goat anti-mouse IgA,G,M (Organon Teknika) diluted 1:5000 in 50 mM carbonate buffer, pH 9.6. Plates were blocked for 30 minutes at 37° C. with 1% BSA in PBS, washed three times with PBS/0.05% Tween® 20 (PBST) and 50 μl culture supernatant (diluted 1:10 in PBST) added. After incubation and washing as above, 50 μl of horseradish peroxidase conjugated rabbit anti-mouse $IgG_1$, $G_{2a}$, or $G_3$ (Zymed, San Francisco, Calif.), diluted 1:1000 in PBST with 1% normal goat serum, was added. Plates were incubated as above, washed four times with PBST, after which 100 μl substrate, consisting of 1 mg/ml o-phenylene diamine (Sigma) and 0.1 μl/ml 30% $H_2O_2$ in 100 mM citrate, pH 4.5, was added. The color reaction was stopped in 5 minutes with the addition of 50 μl of 15% $H_2SO_4$. $A_{490}$ was read on a plate reader (Dynatech) and all fifteen antibodies were determined to be IgG1.

The excess spleen cells from mouse #2211 were frozen in a cryovial and stored in liquid nitrogen. The cryovial was thawed quickly by placing into a 37° C. water bath, and moving it in a circular motion just until contents were melted. Cells were transferred to a 15 ml centrifuge tube where warm RPMI containing 11% FBS was added slowly 1 ml at a time, allowing three to five minutes between additions. Another 5 ml warm RPMI was added and after a five minute wait, the tube was centrifuged at 200×g for five minutes and supernatant aspirated. Cells were resuspended in RPMI and a fusion carried out as described above. Hybridoma supernatant was screened by antibody capture and flow cytometry as described above.

The fusion yielded five clones designated 195A, 195C, 195D, 195E and 195H. The clones were isotyped by the ELISA procedure as described above; monoclonal antibodies 195A, 195C, 195D and 195E were determined to be $IgG_1$ and 195H was determined to be $IgG_{2a}$.

6. In another attempt to generate anti-$\alpha_d$ monoclonal antibodies, mouse #2213 was immunized using the same protocol as mice 2214, 2211, and 2212, but also further immunized on day 414 and 441 with 30 μg of human $\alpha_d$/CD18 leucine zipper (LZ) bound to Sepharose® beads. The immunogen for mouse #2213 was prepared by immunoprecipitating human $\alpha_d$/CD18LZ (Example 14) with an anti-CD18 monoclonal antibody and protein A Sepharose®. The precipitated complex was resuspended as a slurry at a 1:1 ratio with PBS prior to injection. The mouse was sacrificed four days after the booster immunization. The spleen was removed and a fusion carried out as previously described above.

Positive hybridomas were identified by ELISA using human $\alpha_d$/CD18LZ immobilized with the F(ab)'$_2$ fragment of a non-blocking anti-CD18 antibody. Briefly, the F(ab)'$_2$ fragments were coated at 100 ng/well onto Immulon® 4 ELISA plates overnight at 4° C. After the buffer was aspirated, the wells were blocked for 30 minutes at 37° C. with 0.5% fish skin gelatin (Sigma). After washing three times in PBST, 50 μl/well of supernatant from CHO cells, previously transfomed with a plasmid encoding soluble $\alpha_d$/CD18LZ, was added and the plates incubated at 37° C. for 30 minutes. The washing steps were repeated and 50 μl/well hybridoma supernatant was added. Detection of monoclonal antibody was carried out as described above. Positive wells were assayed by flow cytometry using CHO cells transformed with $\alpha_d$/CD18-encoding DNA as described above and two positive hybridomas designated 212A and 212D were identified. Antibodies secreted by the hybridomas were isotyped as IgG1 using the isotype ELISA procedure described above.

7. In yet another method to generate anti-human $\alpha_d$ monoclonal antibodies, mice were immunized with $\alpha_d$/CD18LZ Sepharose® beads, prepared as described above, and each mouse receiving 30 μg immunogen on day 0, day 36, and day 66. Mouse #2477 was selected for fusion after screening the mouse sera by the recombinant protein ELISA format as described above. The fusion, selection, and cloning procedures were carried out using the methods described above for fusion 212. Seven positive hybridomas, 217F, 217G, 217H, 217I, 217K, 217L, and 217M were identified, but hybridoma 217F lost reactivity as determined by flow cytometry during the last round of cloning. Antibodies from the six remaining hybridoma lines were isotyped as previously described and all were found to be IgG1.

8. In another method to generate $\alpha_d$ monoclonal antibodies, mouse #2480 was immunized by the same protocol as mouse #2477 but further immunized by interperitoneal injection on days 217 and 218 with 30 μg $\alpha_d$/CD18LZ. The mouse was sacrificed on day 221, the spleen removed and fusion carried out as described above. Hybridoma supernatant was screened by ELISA as described and flow cytometry to determine reactivity to JY cells previously transfected with DNA encoding $\alpha_d$/CD18. The screening procedures were carried out as described above. The fusion produced three positive hybridomas 240F, 240G, and 240H, which secreted antibodies isotyped by the ELISA method to all be IgG1. A fourth hybridoma, 240I, was later characterized to also be an IgG1 isotype.

9. In order to identify antibodies capable of inhibiting functional $\alpha_d$ binding, soluble $\alpha_d$/CD18LZ (see Example 14) is used for immunization. The protein is isolated on an affinity chromatography resin from supernatant of transiently transfected COS cells and the resin-bound $\alpha_d$ used as an immunogen. A selected mouse is immunized as described above and given a final boost two weeks after the initial immunization. Immunization by this technique prevents possible changes in protein conformation often associated with detergent lysis of cells. Additional mice are immunized with recombinant protein, also resin-bound, but were not initially immunized with protein purified from cell lysate.

Hybridomas, prepared as described above, which result from the immunization are screened by ELISA on the recombinant protein immobilized from a cell supernatant using the Fab fragment of a non-blocking antibody. Alternatively, flow cytomotry is used to assay for reactivity to JY cells previously transfected with $\alpha_d$ cDNA.

10. As another alternative, monoclonal antibodies are generated as follows. Affinity purified $\alpha_d$/CD18 heterodimeric protein from detergent lysates of stably transfected CHO cells is used with 50 µg/ml muramyl dipeptidase to immunize Balb/c mice as described above. Mice receive three immunizations before serum reactivity against $\alpha_d$/CD18 is determined by immunoprecipitation of biotinylated complexes in the CHO transfectants. Hybridomas from positive animals are established according to standard protocols, after which hybridoma cultures are selected by flow cytometry using $\alpha_d$/CD18 transfectants. CD11a/CD18 transfectants are utilized to control for CD18-only reactivity.

11. As another alternative for monoclonal antibody production, Balb/c mice undergo an immunization/immunosuppression protocol designed to reduce reactivity to CHO cell determinants on transfectants used for immunization. This protocol involves immunization with untransfected CHO cells and subsequent killing of CHO-reactive B-cell blasts with cyclophosphamide treatment. After three rounds of immunization and cyclophosphamide treatment are performed, the mice are immunized with $\alpha_d$/CD18 CHO transfected cells as described above.

12. As another alternative, CD18 complexes from detergent lysates of PMA stimulated HL60 cells are enriched by preclearance as described above. Other β2 integrins are cleared on the same columns. Immunization with the resulting complexes, hybridoma production, and screening protocols are performed as described supra.

Production of Polyclonal Sera

Purified $\alpha_d$ I domain/IgG4 chimera (Example 14) was used to generate polyclonal anti-serum in rabbits. The $\alpha_d$ I domain/IgG4 antigen was injected at 100 µg/rabbit initially in complete Freund's adjuvant, followed by three boosts with the same amount of protein in incomplete Freund's adjuvant. Test bleeds were assayed after the third and fourth injections. Rabbit immunoglobulin (Ig) was purified from the serum on a protein A-Sepharose® column and precleared of anti-human IgG reactivity on a human IgG/Affigel® 10 column. Reactivity by ELISA to the I domain chimera, but not to human IgG, was used to confirm complete preclearance.

The precleared polyclonal sera was used to immunoprecipitate protein from detergent lysates of surface-biotinylated CHO cells previously transfected with $\alpha_d$ and CD18 expression vectors. Immunoprecipitation was carried out by the method previously described in Example 10. The precleared sera recognized a protein complex of the same molecular weight as that precipitated by anti-CD18 monoclonal antibody TS 1.18. In addition, the sera recognized a single band of appropriate size in a Western blot of CD18 complexes from $\alpha_d$/CD18 transfected CHO cells. Affinity purified integrins CD11a/CD18, CD11b/CD18, and VLA4 from human spleen were not recognized by the rabbit polyclonal sera. The sera failed to react with $\alpha_d$-transfected CHO cells in solution, as determined by flow cytometry. It was therefore concluded that the polyclonal rabbit sera was only capable of recognizing denatured $\alpha_d$ I domain/IgG4 proteins.

In an attempt to produce polyclonal antisera against $\alpha_d$/CD18, a mouse was immunized 3 times with $\alpha_d$ transfected CHO cells (D6.CHO, $\alpha_d$/CD18) with adjuvant peptide and once with purified $\alpha_d$/CD18 heterodimer. A final boost included only $\alpha_d$/CD18 heterodimer. Approximately 100 µl immunized serum was precleared by addition of approximately $10^8$ LFA-1-transfected CHO cells for 2 hours at 4° C. The resulting serum was assayed for $\alpha_d$ reactivity at dilutions of 115000, 1/10000, 1/20000 and 1/40000 on normal human spleen. The polyclonal antibody was reactive at a dilution of 1/20000, while a 1/40000 dilution stained very weakly.

EXAMPLE 16

Flow Cytometric Analysis Using Anti-$\alpha_d$ Monoclonal Antibodies

Several primary and immortalized cell lines were used in a survey with the anti-$\alpha_d$ monoclonal antibodies 212D, 217K, and 217L. Cell staining was performed and analyzed according to the methods described in Example 17. Primary CD8$^+$/CD56$^-$ and CD4$^-$/CD8$^-$/CD56$^+$ cell lines specific for MAGE-3 (melanoma associated proteins) peptides were strongly positive for CD11b and CD11c, but were not stained by any of the $\alpha_d$ antibodies. MAGE-3 peptide-specific cells are expanded from peripheral blood mononuclear cell populations using peptide-loaded antigen presenting cells (APCs, either dendritic cells or monocytes). Repeated stimulations under limiting dilution conditions, combined with phenotypic selection, result in clonal cytolytic lines which will specifically kill target cells bearing the native protein from which the peptides were derived.

Dendritic cells from peripheral blood, cultured for seven days in the presence of cytokines IL-4 and GM-CSF, were stained strongly by antibodies to CD11a, CD11b, and CD11c, as well as the 217L anti-$\alpha_d$ antibody. The antibodies 212D, 217K, 217I, 217H, and 217M did not react with these cells nor with dendritic cells, obtained from a variety of donors, in repeated experiments. By day 14 of culture, the surface expression of the 217L antigen had waned and the staining disappeared completely by day 21. During the culture period, CD11b and CD11c expression remained at a high level (2 to 3 logs over background staining).

EXAMPLE 17

Human Monocyte Expression of $\alpha_d$ Purification of Human Monocytes from Peripheral Blood Approximately 300 ml of blood was drawn from a volunteer donor into 3.8% sodium citrate buffer (Sigma). The blood was diluted to 480 ml with endotoxin-free PBS (Sigma), and 30 ml of diluted blood was carefully layered onto 17 ml of Histopaque in a 50 ml centrifuge tube. The gradients were spun for 30 minutes at 1500 rpm in a Beckman Tabletop Centrifuge. The cellular layer, representing mononuclear cells, was collected from each gradient and transferred to a new 50 ml tube. The volume was increased to 50 ml with endotoxin-free PBS, 0.1% BSA (endotoxin free), and the tubes centrifuged for 15 minutes at 1500 rpm in a Beckman Tabletop Centrifuge. The supernatant was discarded and the cells resuspended in a small volume of PBS/BSA and subsequently pooled.

A second gradient (which uses Percoll [Denholm and Wolber, *J. Immunol. Meth.* 144:247–251 (1991)]) was required to purify monocytes from the mixed population of cells obtained as described above. Briefly, 10 ml of 10× Hanks buffer (Gibco) was mixed with 600 μl of 1.0 N HCL. To this mixture, 60 ml of Percoll (Pharmacia, Piscataway N.J.) was added and the mixture stirred slowly until all Percoll was in solution. The pH of the Percoll solution was adjusted to 7.0, after which 8.0 ml of gradient mixture was added to six 15 ml round-bottomed polystyrene tubes. Exactly 4.0 ml of cell suspension was added to each gradient and the tubes inverted several times to mix thoroughly. The gradients were centrifuged for 25 minutes in a fixed-angle rotor at 1690 rpm at room temperature. The monocyte fraction, which appeared as a thin white band in the gradients, was collected and transferred to new 50 ml centrifuge tubes. The volume was adjusted to 50 ml with PBS/0.1% BSA and the cells pelleted by centrifugation. The cell pellets were resuspended in a small volume and pooled and cell number determined using a hemacytometer. Cells were resuspended in FACS buffer (RPI 1640, 2.0% FBS, 0.2% sodium azide) and adjusted to one million cells/condition, i.e., one million cells were used for each FACS staining condition to assay for various cellular markers.

FACS Staining and Analysis

Single antibody cell staining was carried out using antibodies immunospecific for $\alpha_d$ or cell markers directly conjugated with a fluorescent tag detectable marker. The mouse anti-human $\alpha_d$ antibodies 212D or 217L were added to cells at 10 μg/ml after which the mixture was incubated on ice for 30 minutes and washed three times. Ten microliters of directly conjugated cell markers, CD3-FITC (Becton-Dickinson) (specific for T cells) or CD33-FITC (Becton-Dickinson) (specific for monocytes) were added to additional cell samples, while 10 μl of a secondary antibody, anti-mouse FITC (Sigma), was added to the 212D and 217L stained cells. All samples were incubated on ice for 30 minutes in the dark, washed three times, and resuspended in 300 μl of 2.0% paraformaldehyde. Samples were processed on a Becton Dickinson FACScan and the data analyzed using Lysys II software (Becton Dickinson).

In the first experiment, monocytes represented 68% and T-cells 18% of the total cells purified using the double-gradient method. There was a significant amount of staining of both cell types cells for $\alpha_d$ by both 212D and 217L, 55% and 65% of the cells respectively. Based on later experiments, there appeared to be some donor-to-donor variation in the relative amount of $\alpha_d$ staining on freshly isolated human monocytes, although the isolated monocytes always stained positive. When human IgG (used at 1 mg/ml for 10 minutes on ice prior to addition of primary antibody) was added to the cells to block any potential Fc receptor binding problems, there was no change in the $\alpha_d$ staining. When these cells were cultured in suspension using Hydron coated dishes (Interferon Sciences) in 10% FBS/RPM-1640 and analyzed for $\alpha_d$ expression, there was loss of surface expression within 24 hours which continued to diminish over a seven day time course. Relative to expression of other integrins on freshly isolated human monocytes, including CD11a, CD11b, and CD11c, the $\alpha_d$ staining was lower.

2-color FACS Staining of Human Monocytes for $\alpha_d$

For 2-color FACS staining, both 212D and 217L antibodies were biotinylated using NHS-LC-biotin (Pierce) according to manufacturer's instruction. In a separate experiment, cells were isolated as described above and stained using biotinylated 212D and 217L antibodies and a biotinylated control IgG1 antibody at 10 μg/ml on ice for 30 minutes. The cells were washed three times in FACS buffer (modified to include D-PBS, 2% FBS, and 0.2% sodium azide), and resuspended in 1.0 ml FACS buffer. Both 10 μl FITC-conjugated CD33 (specific for monocytes) and 5 μl streptavidin PE (PharMingen) were added to cell suspensions. Samples were incubated on ice for 30 minutes in the dark, washed 3 times in FACS buffer, and resuspended in 300 μl 1% paraformaldehyde. Samples were processed by FACS as described above.

Of the two antibodies, 217L showed significant staining on CD33$^+$ cells compared to the control. Antibody 212D also stained this cell type, but the number of CD33$^+$ cells staining was significantly less than observed with antibody 217L. This result was consistent in two separate experiments. In related experiments using biotinylated antibodies 212D and 217L, 217L-biotin consistently stained more cells than 212D-biotin.

Mononuclear cells representing a mixture of lymphocytes and monocytes obtained before Percoll gradient separation were also examined by 2-color analysis as above, and double-stained for 212D and 217L-biotin in combination with FITC-conjugated antibodies immunospecific for CD3 (T cells), CD4 (helper T cells), CD5 (thymocytes, mature T cells, sub-populations of B cells), CD8 (cytotoxic/suppressor T cells), CD14 (monocytes, neutrophils, follicular dendritic reticulum cells), CD20 (B cells), and CD56 (NK cells, subsets of T cells) (Becton Dickinson). No discernible $\alpha_d$ positive populations of cells co-expressed with these cellular markers.

EXAMPLE 18

Analysis of $\alpha_d$ Distribution

Tissue distribution of $\alpha_d$/CD18 was determined using polyclonal anti-serum generated as described in Example 15.

Purified rabbit polyclonal antibody was used at concentrations ranging between 120 ng/ml and 60 μg/ml for immunocytochemical analysis of frozen human spleen sections. Sections of 6 micron thickness were layered onto Superfrost Plus Slides (VWR) and stored at −70° C. Prior to use, slides were removed from −70° C. and placed at 55° C. for 5 minutes. Sections were then fixed in cold acetone for 2 minutes and air dried. Sections were blocked in a solution containing 1% BSA, 30% normal human sera and 5% normal rabbit sera for 30 minutes at room temperature. Primary antibody was applied to each section for 1 hour at room temperature. Unbound antibody was removed by washing the slides 3 times in TBS buffer for 5 minutes per wash. Next, a rabbit anti-mouse IgG link antibody was applied to each section in the same TBS buffer. A mouse alkaline phosphatase anti-alkaline phosphatase (APAAP) antibody, incubated for 30 minutes at room temperature, was used to detect the second antibody. Slides were then washed 3 times in TBS buffer. Fast Blue substrate (Vector Labs) was applied and color development stopped by immersion in water. Slides were counterstained in Nuclear Fast Red (Sigma) and rinsed in water before mounting with Aqua Mount (Baxter). Staining was detected in the splenic red pulp with this reagent, but not with an irrelevant rabbit polyclonal Ig preparation or the unpurified preimmune serum from the same animal.

Once mouse serum was determined to have specific $\alpha_d$ reactivity, it was used to stain various lymphoid and non-lymphoid tissues. Monoclonal antibodies recognizing CD18, CD11a, CD11b, and CD11c were used in the same experiment as controls. Staining of normal spleen sections with $\alpha_d$ polyclonal sera, and monoclonal antibodies to CD11a, CD11b, CD11c, and CD18 revealed the following results. The pattern observed with $\alpha_d$ polyclonal sera did not display the same pattern of labeling as CD11a, CD11b, CD11c, or CD18. There is a distinct pattern of labeling with some cells located in the marginal zone of the white pulp and a distinct labeling of cells peripheral to the marginal zone. This pattern was not observed with the other antibodies. Individual cells scattered throughout the red pulp were also labeled which may or may not be the same population or subset seen with CD11a and CD18.

Labeling with CD11c did display some cells staining in the marginal zone, but the antibody did not show the distinct ring pattern around the white pulp when compared to $\alpha_d$ polyclonal sera, nor did labeling in the red pulp give the same pattern of staining as $\alpha_d$ polyclonal sera.

Therefore, the labeling pattern seen with $\alpha_d$ polyclonal serum was unique compared to that seen using antibodies to the other $\beta_2$ integrins (CD11a, CD11b, CD11c, and CD18), and suggests that the in vivo distribution of $\alpha_d$ in man is distinct from that of other $\beta_2$ integrins.

Characterization of Human $\alpha_d$ Expression With Monoclonal Antibodies

Antibodies secreted by hybridomas 169A and 169B were used to analyze human $\alpha_d$ expression in frozen tissue sections by immunocytochemistry and on cell lines and peripheral blood leukocytes by flow cytometry. Hybridoma supernatants used in both sets of experiments were undiluted.

Tissue Staining

All stains were carried out as described above, except for liver sections which were stained in the following manner. After acetone fixation, sections were quenched in 1% $H_2O_2$ and 1% sodium azide in TBS for 15 minutes at room temperature. After primary antibody staining, a rabbit anti-mouse antibody directly conjugated to peroxidase was applied for 30 minutes at room temperature. Slides were washed 3 times in TBS buffer. A swine anti-rabbit antibody, directly conjugated to peroxidase, was incubated for 30 minutes at room temperature to detect the second antibody. Slides were then washed 3 times in TBS buffer and AEC substrate (Vector Labs) was applied and to allow color development. Slides were counterstained with Hematoxylin Gill's No. 2 (Sigma), and subsequently rinsed in water before dehydration and mounting.

In spleen sections, the majority of expression was localized to the splenic red pulp on cells identified by morphology as granulocytes and macrophages. A large number of granulocytes were stained, while only a subset of macrophages gave signal. A small number of follicular dendritic cells in the white pulp also were weakly stained by the $\alpha_d$ antibodies. CD11a and CD18 staining was detected throughout the red and white pulp. CD11c staining was more pronounced in large cells presumed to be macrophages in the splenic white pulp and in the marginal zone surrounding the white pulp; diffuse staining in the red pulp was also noted. CD11b appeared to have distribution overlapping with but not identical to $\alpha_d$ in the red pulp, with no white pulp involvement.

Integrin expression in normal and (rheumatoid) arthritic synovial tissue was compared. Minimal staining with all anti-integrin antibodies (including antibodies specifically immunoreactive with CD11a, CD11b, CD11c, CD18, as well as $\alpha_d$) was noted in normal tissue, with a widespread distribution on resident cells, presumably macrophages. In the inflamed synovium, expression of all integrins was more localized to cells clustered around lymphatic vessels. While $\alpha_d$ and CD11b expression patterns were similar, CD11c did not appear to be as strongly expressed and was restricted to a subset of leukocytes.

In the dog, CD11b, but not $\alpha_d$, expression was observed on liver macrophages, or Kuppfer cells. Staining of normal human liver sections (as previously described for staining of dog liver section, supra) confirmed the conservation of this staining pattern in humans. In addition, CD11c was detected at low levels. In sections from a hepatitis patient, all leukointegrin staining was higher than observed on normal liver, while $\alpha_d$ expression was detected on macrophages and granulocytes in these samples.

Minimal staining of normal human colon sections was observed with anti-$\alpha_d$ antibodies; faint smooth muscle staining and leukocyte staining was observed. All leukointegrins were detected at higher levels in sections from patients with Crohn's disease.

Normal lung showed a limited number of weakly $\alpha_d$-positive cells; these were determined by morphology to be macrophages and neutrophils. In lung tissue from a patent with emphysema, $\alpha_d$ staining was observed on neutrophils and on macrophages containing hemosiderin, an iron-containing pigment, indicating red cell engulfment by these cells.

Sections of normal brain and plaque lesions from patients with multiple sclerosis (MS) were examined for integrin expression. In normal brain, $\alpha_d$ staining was less intense than that of CD11a, CD11b, and CD11c, and restricted to cells typed as microglial cells by morphology and CD68 staining. CD11b positive cells were located surrounding vessels and throughout the tissue. CD11c$^+$ cells appeared to be located within vessels, whereas $\alpha_d^+$ cells surrounded the vessels. In MS tissue sections, $\alpha_d$ expression was found on both microglial cells and on a non-macrophage leukocyte subset; $\alpha_d^+$ cells were located within plaque lesions, as well as throughout the cortex. The $\alpha_d$ signal was equivalent in intensity to CD11c, but lower than that of CD11b.

Both thoracic aorta and abdominal aorta sections from PDAY (Pathobiological Determinants of Atherosclerosis in Youth, LSU Medical Center) tissue samples were analyzed with anti-leukointegrin and anti-CAM antibodies. The lesions examined were consistent with aortic fatty streaks which consisted of subintimal aggregates of large foam cells (mostly macrophages with ingested lipid) and infiltrates of smaller leukocytes. Single label studies with monoclonal antibodies specific for $\alpha_d$ and the other $\beta_2$ integrin $\alpha$ chains (CD11a, CD11b, and CD11c), plus a macrophage marker (CD68) revealed that the majority of lipid-laden macrophages expressed a moderate level of $\alpha_d$ and CD18, while expressing CD11a and CD11c at weak or weak to moderate levels, respectively. CD11b was faintly expressed, and then by only a subset of macrophages.

Double label studies were conducted to determine the relative localization of $\alpha_d$ and ICAM-R antigens in the aortic sections. Since foam cells in these sections stained with the antibody Ham 56, specific for a macrophage marker, but not with antibodies to smooth muscle actin, it was determined that the foam cells were not derived from subintimal smooth muscle cells. CD68 positive macrophages expressing $\alpha_d$ were surrounded by and interspersed with small ICAM-R positive leukocytes. There appeared to be a limited number of small leukocytes which were CD68 negative but stained with both $\alpha_d$ and ICAM-R antibodies.

Distribution of $\alpha_d$ in normal tissues appeared to be on resident leukocytes in a pattern overlapping with but not identical to that of CD11b and CD11c, two other leukointegrin a chains which have previously been characterized as having restricted leukocyte distribution. Cellular morphology indicated that $\alpha_d$ staining is largely confined to macrophages and granulocytes, with limited lymphocyte staining. Generally, tissue inflammation appeared to increase the number and types of leukocytes observed in a particular tissue, along with increased staining of leukointegrins, including $\alpha_d$. Since the cellular and spatial distribution of the leukointegrins was not identical in pathologic tissues, it was inferred that distinct functions and ligands exist for each family member, including $\alpha_d$, in specific contexts.

Interestingly, $\alpha_d$ expression in early atherosclerotic lesions appeared to be more pronounced than that of CD11a, CD11b, and CD11c, suggesting that $\alpha_d$ may play a central role in the establishment of these lesions. The apposed distribution of $\alpha_d$ and ICAM-R positive cells, supported by evidence suggesting an interaction between $\alpha_d$ and ICAM-R, suggests that $\alpha_d$ may be involved in leukocyte recruitment or activation at early stages in these lesions.

Cell Line and Peripheral Blood Leukocyte Staining

The antibodies 169A and 169B stained a promyeolmonocytic cell line, HL60, by FACS. Surface expression of $\alpha_d$ in these cells is negatively affected by PMA stimulation, which is reported to induce differentiation along a macrophage pathway, but is unaffected by DMSO, which induces granulocyte differentiation [Collins, et al., Blood 70:1233–1244 (1987)]. The FACS profiles of 169A and 169B were antithetical with PMA stimulation to those observed with anti-CD11b and anti-CD11c monoclonal antibodies. A monocyte cell line, THP-1, also exhibited weak staining with 169A and 169B. In addition, a subset of cells in the lymphocyte and monocyte gates of peripheral blood leukocytes appeared to be weakly positive by FACS. A subset of peripheral blood monocytes stained weakly with 169A and 169B, while B lymphocytes were found to have no surface expression of $\alpha_d$. The CD8+ subset of T lymphocytes was $\alpha_d^+$. In addition, antibodies 169A and 169B failed to detect antigen on the B cell lines, JY, Ramos, a basophilic line, KU812, and T cell lines, Jurkat, SKW, and Molt 16.

In light of the results with HL60 cells, granulocytes were isolated from peripheral blood by ficoll/hypaque gradient centrifugation and subsequent red blood cells lysis. All preparations were found to be >90% PMNs by visualization of nuclear morphology in acetic acid. Separate populations were stimulated for 30 minutes with 50 ng/ml PMA or $10^{-8}$ M formyl peptide (fMLP) to release potential intracellular integrin stores. Unstimulated populations exhibited low, but significant expression of 169A and 169B antigens over an IgG1 control, with a detectable increase observed upon stimulation. On PMNs, levels of $\alpha_d$ and CD11c surface expression were more similar than that observed on HL60 cells. The antibody 169B was used subsequently to precipitate a heterodimeric molecule from a detergent lysate of biotinylated PMNs with subunit sizes of approximately 150 and 95 kD appropriate to $\alpha_d$ and CD18, respectively.

The presence of $\alpha_d$ on PMNs could not be anticipated from the information known about canine $\alpha_d$ expression. Canine neutrophils, unlike their human counterparts, express the T helper cell marker CD4, and also integrin VLA-4, and therefore may have different ligands and functions in the dog than in the human.

Staining of PBL Subgroups

The present study was undertaken to determine the distribution of this $\beta_2$ integrin in human peripheral blood leukocytes. In addition, the cell surface density of $\alpha_d$ relative to other $\beta_2$ integrins was compared. Finally, the acute regulation of $\alpha_d$ expression in purified human eosinophils was also evaluated.

Human peripheral blood leukocytes were separated by density gradient centrifugation into a mononuclear cell fraction (containing monocytes, lymphocytes, and basophils) and granulocytes (neutrophils and eosinophils) [Warner, et al., J. Immunol.Meth. 105:107–110 (1987)]. For some experiments, eosinophils were purified using CD16 immunomagnetic selection to purities greater than 95% [Hansel, et al., J.Immunol.Meth. 122:97–103 (1989)]. Skin mast cells were enzymatically dispersed from human skin and enriched as previously described [Lawrence, et al., J.Immunol. 139:3062–3069 (1987)].

Cells were labelled with appropriate dilutions of monoclonal antibody specific for either CD11a (MHM24), CD11b (H5A4), CD11c (BU-15), or $\alpha_d$ (169A). A murine control IgG$_1$ was also employed. Cells were washed and then incubated with phycoerythrin-conjugated goat-anti-mouse IgG. In some experiments, cells were incubated with excess murine IgG and FITC-labelled murine monoclonal antibody or goat polyclonal antibody specific for a particular cell (e.g., CD3, CD4, or CD8 for T-cells; CD16+ lymphocytes for NK cells; anti-IgE for basophils [Bochner, et al., J.Immunol.Meth. 125:265–271 (1989)]. The samples were then examined by flow cytometry (Coulter EPICS Profile) using appropriate gating to identify cell subsets.

For studies with human eosinophils in which acute upregulation of $\alpha_d$ expression was examined, cells were stimulated for 15 minutes at 37° C. with phorbol ester (10 ng/ml), RANTES (100 ng/ml) [Schall, Cytokine 3:165–183 (1991)], or IL-5 (10 ng/ml) prior to labeling with the various monoclonal antibodies as described above.

Results showed that $\alpha_d$ was present on all peripheral blood eosinophils, basophils, neutrophils, monocytes, and NK cells. A small subset (approximately 30%) of CD8+ lymphocytes was also found to express $\alpha_d$. Skin mast cells and CD4+ lymphocytes did not express $\alpha_d$. In general, CD11a and CD11b are present at a higher density on leukocytes then $\alpha_d$, the latter being expressed at relatively low levels similar to CD11c. Among leukocytes, monocytes and CD8+ cells have the highest density of $\alpha_d$, while eosinophils have the lowest level of $\alpha_d$ expression. Expression on neutrophils, basophils, and NK cells was intermediate.

Stimulation of peripheral eosinophils with the CC chemokine RANTES caused no change in the expression of any of the $\beta_2$ integrins. Treatment with phorbol ester, however, produced a two to three fold increase in expression of both CD11b and $\alpha_d$, but did not effect expression of CD11a or CD11c. IL-5 treatment resulted in the selective upregulation of CD11b expression without affecting levels of the other integrin subunits.

Combined, these results indicate that in peripheral blood leukocytes, $\alpha_d$ is generally expressed at a level comparable to CD11c. Highest levels are found on monocytes and a subset of CD8+ lymphocytes. Human skin mast cells do not express $\alpha_d$. Purified eosinophils appear to have pre-formed intracytoplasmic storage pools of CD11b and $\alpha_d$. However, the differential upregulation shown by IL-5 versus PMA suggests that these storage pools are separate from each other.

Staining patterns for peripheral blood leukocyte (PBL) subgroups were also determined by flow cytometry using a combination of gating and surface markers, as described above, in an attempt to more precisely define the 169 A/B negative lymphocyte group. PBL were isolated on Ficoll as previously described and stained separately with 169A, 169B and monoclonal antibodies to CD14 (monocyte/macrophage marker), CD20 (B cell), CD56 (NK cell), T cell receptor α/β (T cell), CD16 (neutrophils, NKs), and α4 (a negative marker for neutrophils). Gates were defined by size and marker distribution. Results indicated that cells in the CD14+ monocyte gate exhibited low levels of 169A and 169B staining. A bimodal expression pattern observed in earlier experiments in the lymphocyte gate was resolved by increasing forward scatter. The mixed TCR⁺/CD20⁺ population appeared to have low, but homogenous levels of 169A/B expression, whereas a population mapped at slightly higher side scatter (cellular complexity), which stained 50% positive for CD56, appeared to have a distinctly 169A/B negative population. The negative population was also not recognized by TCR, CD20, CD14, or CD16 antibodies.

Synovial Distribution of $\alpha_d$

In order to determine cellular distribution of $\alpha_d$, other $\beta_2$ integrins and their counterreceptors in inflammatory and non-inflammatory synovium, monoclonal antibodies to the various $\beta_2$ integrin and immunoglobulin supergene families were used in immunohistological studies. Protein expression was determined in normal, osteoarthritic and rheumatoid synovial tissue samples.

Results indicated that the synovial lining cell layer expressed high levels of VCAM-1, CD11b/CD18 and $\alpha_d$/CD18. In these cells, CD11c/CD18 expression is restricted and CD11a/CD18 is generally not detected. In rheumatoid arthritis synovitis, expression of $\beta_2$ integrins in the synovial cell layer increases in proportion to the degree of hyperplasia. The ratio of cells which express CD11c increases significantly, approaching that of CD11b and $\alpha_d$, but there is no increase in CD11a expression.

In the sublining areas of the tissue, aggregates and diffuse infiltrates of CD3/CD11a/ICAM-R⁺ lymphocytes are interspersed among CD68/CD11b/$\alpha_d^+$ macrophages. A significant number of aggregates demonstrate intense $\alpha_d$ staining, particularly in T cell rich areas.

The synovial endothelium variably expressed ICAM-1 and ICAM-2 with minimal evidence of ICAM-R expression.

Combined, these results indicate that synovial macrophages and macrophage-like synovial cells constitutively express high levels of the $\beta_2$ integrins CD11b and $\alpha_d$. In synovitis, there is an expansion of this subset of cells in both the lining and sublining areas, along with an apparent increase in expression of CD11c. Specific populations of rheumatoid synovial T lymphocytes, in addition to expressing CD11a and ICAM-R, also express high levels of $\alpha_d$, the latter molecule having been shown above to be expressed at low levels by peripheral blood lymphocytes.

$\alpha_d$ Expression in Disease Lung and Liver Tissue

Lung tissue from an individual with sarcoidosis and liver tissue from two individuals with cirrhosis were sectioned at 6 μm thickness and air dried on Superfrost Plus (VWR Scientific) slides for 15 minutes at room temperature. Prior to use, slides were incubated at 50° C. for approximately 5 minutes. Sections were fixed in cold (4° C.) acetone (EM Science) for 2 minutes at room temperature and allowed to air dry at room temperature. Sections were placed in a solution of 100 ml 1×TBS, 1.1 ml 30% H₂O₂ (Sigma), 1.0 ml 10% NaN₃ (Sigma), for 15 minutes at room temperature to remove endogenous peroxidase activity. Each section was blocked with 150 μl of a solution containing 20% normal human serum (Boston Biomedica), 5% normal rat serum (Harlan), and 2% BSA (Sigma) in 1×TBS for 30 minutes at room temperature. After incubation, the solution was gently blotted from the sections. Primary monoclonal antibody was prepared at a protein concentration of 10 μg/ml in blocking solution and 75 μl applied to each tissue section for 1 hour at room temperature. After incubation, sections were washed three times in 1×TBS for 5 minutes each wash to remove unbound antibody. Excess TBS was removed by aspirating around the tissue following the final wash. Biotinylated rat anti-mouse antibody (Jackson Laboratories) was diluted 1:400 in blocking solution and 75 μl was applied to each section for 30 minutes at room temperature. Slides were washed two times with 1×TBS for 5 minutes each wash. Peroxidase conjugated goat anti-biotin antibody (Vector Laboratories) was diluted 1:200 in blocking solution and 75 μl was applied to each section for 30 minutes at room temperature. Slides were washed two times in 1×TBS for 5 minutes each wash. Substrate 3-amino-9-ethylcarbazole (AEC) (Vector Laboratories) or 3,3'-diaminobenzidine (DAB) substrate (Vector Laboratories) was applied and color development stopped by immersion in water. Slides were counterstained in Gill's hematoxylin #2 (Sigma) and rinsed in water before mounting with either Aquamount (Baxter) or Cytoseal (VWR).

In the sarcoidosis lung, only the 217L monoclonal antibody stained cells and the majority of 217L epitope expression was localized to granulomas. Giant cells within the granulomas appeared to be negative for the 217L antigen. Expression of the 217L epitope was localized to cells that morphologically appeared to be epithelioid histiocytes, highly differentiated phagocytic cells of macrophage lineage. Distribution of other integrins was observed to overlap with that of the 217L epitope in the sarcoidosis lung, but the expression patterns were not identical. For example, antibodies immunospecific for all other integrins labeled cells in the granulomas as well as the giant cells which were negative for 217L staining.

Sections from a second patient diagnosed with sarcoidosis were negative for expression of the 217L epitope, however it is unclear from pathology reports whether this patient had received steroidal immunosuppressants, the most common form of treatment.

In sections from the cirrhotic liver tissue, anti-$\alpha_d$ antibodies labeled foam cells in the connective tissue between hepatic nodules as well as a subset of lymphocytes. Distribution of CD11c overlapped with $\alpha_d$ expression but was not identical; anti-CD11c antibody also labeled a subset of foam cells but labeled more macrophages and lymphocytes than anti-$\alpha_d$ antibody. There was no apparent overlap in the distribution of CD11a and CD11b expression with $\alpha_d$ expression.

Antibody 217L also stained phagocytic-type cells which were clustered and isolated from the populations identified by both 212D and 217L. Antibodies to CD11b and CD11c stained the 217L⁺ clusters in a dissimilar fashion.

In related experiments, antibodies 212D and 217L were used to stain human splenic tissue sections as well as serial sections from spleens of the non-human primate *M. nemestrina*. Splenocytes isolated from fresh human and monkey splenic tissue were also evaluated by flow cytometry for $\alpha_d$ expression. Both antibodies 212D and 217L recognized human and monkey splenocytes. By both ICC and FACS, the $\alpha_d^+$ population represented about 20% of total cells, unlike in rodents which exhibit a greater percentage of $\alpha_d^+$ cells. The positive population appeared to be morphologically identical to macrophages.

Human Bone Marrow Staining

Human bone marrow samples were obtained from the iliac bone of healthy bone marrow donors according to standard techniques. The original sample was diluted 1:3 in Iscove's medium and centrifuged for 20 minutes at 2000

RPM. The buffy coat layer was carefully collected, washed once, and hemolyzed using hemolytic buffer (0.83% ammonium chloride, 0.1% sodium bicarbonate, EDTA free). Cells were resuspended in PBS with 15% FBS, aliquoted at 100,000 cells/tube in 100 μl, and put on ice. Immunostaining was performed as previously described. Briefly, monoclonal mouse anti-human $\alpha_d$ antibody 212D or 217L or mouse anti-human CD18 or mouse anti-human CD50 (ICAM-R specific) antibody was individually added to each cell sample at a final concentration of 10 μg/ml and the mixture incubated on ice for 20 minutes. The cells were washed twice and incubated for an additional 20 minutes with goat anti-mouse FITC. Cells were washed twice and resuspended in 1% paraformaldehyde. Fluorescence was measured using a Fluorescence Activated Cell Sorter FACSCAN (Becton Dickinson).

Results from four experiments indicated that $\alpha_d$ expression as determined using antibody 212D was found on 13 to 43% of the cells (median 27%) and on 6 to 55% of cells (median 21%) using antibody 217L. CD18 expression was observed on 60–96% of cells (median 71%) and CD50 on 86–99% of cells (median 94%).

Expression of $\alpha_d$ on Peripheral Blood Mononuclear Cells From Patients with Breast Cancer Peripheral blood mononuclear cells were isolated using Ficoll separation of blood samples from patients with high risk breast cancer, i.e., those patients having breast cancer with poor prognosis features, who had undergone bone marrow transplantation. Cells were screened by immunostaining for the expression of $\alpha_d$ as described above.

Results indicated that $\alpha_d$ expression as determined using antibody 212D was found on 20% of cells and on 13% of the cells using antibody 217L. Antibody 212D also stained a subpopulation of small cells which appeared most likely to be lymphocytes. The percentage of cells expressing $\alpha_d$ were comparable to that generally observed in a normal blood donor.

In addition, antibody 212D appeared to stain not only large cells that were CD14+, but also much smaller cells which were tentatively identified as CD3+. This result was observed both in blood and in bone marrow.

The variation of the number of cells expressing $\alpha_d$ might be explained by a variation in the cell composition of the bone marrow aspirate from donor to donor (e.g., the amount of bone marrow in comparison to the amount of circulating blood).

EXAMPLE 19

Upregulation of $\alpha_d$ Expression

Because leukocyte integrins are generally upregulated during hemodialysis and contribute to the immune alterations observed in chronic renal failure [Rabb, et al., *J. Am. Soc. Nephrol.* 6:1445–1450 (1995) and Rabb, et al., *Am. J. Kidnet Dis.* 23:155–166 (1994)], $\alpha_d$/CD18 surface expression was examined during hemodialysis and chronic renal failure. In addition, expression of $\alpha_d$/CD18 in vitro following PKC stimulation was also investigated.

Whole blood samples were obtained from five randomly chosen hospital patients with non-renal conditions. Blood samples were incubated with PMA at 50 ng/ml for 30 minutes at 37° C. prior to surface staining and flow cytometry. Blood samples were also collected from patients with chronic renal failure. Patients were stable, non-diabetics who were undergoing dialysis three times a week. Baseline samples were obtained prior to beginning dialysis, and subsequent samples were drawn at 15 minutes and 180 minutes during dialysis with a cuprophane membrane. Blood samples from normal subjects having no known diseases were used as negative controls.

For cell staining, 5 μg of antibodies 169A and 169B (and a negative control 1B7) were incubated with 100 μl whole blood in the dark for 15 minutes. Becton Dickinson lysing reagent (2 ml) was added to each mixture and incubation continued for 10 minutes in the dark. Cells were then pelleted and suspended in PBS. The cells were again pelleted by centrifugation and mixed with a secondary FITC-conjugated antibody and incubated for 30 minutes in the dark. Cells were then washed with PBS, centrifuged, aspirated, and resuspended in 1.0% formalin.

Flow cytometry was carried out using the procedure of Rabb, et al. [*J. Am. Soc. Nephrol.* 6:1445–450 (1995)]. Samples were analyzed using Simulset Software (Becton Dickinson) on a FACScan flow cytometer (Becton Dickinson). A minimum of 22,000 cells was analyzed for each sample. Granulocyte, monocyte, and lymphocyte subsets were gated by forward light scatter and side light scatter. Cell subset purity was assessed by CD45 staining and CD14 staining.

Results indicated that $\alpha_d$/CD18 expression can be detected in samples drawn from normal human subjects; expression was greatest on monocytes and lowest on lymphocytes. Expression on neutrophils was intermediate between monocytes and lymphocytes. Staining with antibody 169B was weaker than with antibody 169A. PMA treatment upregulated $\alpha_d$/CD18 expression, particularly on neutrophils and monocytes.

In samples from the renal failure patients, $\alpha_d$/CD18 expression was detectable on neutrophils, monocytes, and lymphocytes prior to the onset of dialysis. After 15 minutes of dialysis using the leukocyte activating membrane, a minor increase in $\alpha_d$/CD18 expression was detected. Expression on monocytes and lymphocytes actually decreased by the end of treatment. This result indicates that $\alpha_d$/CD18 expression is distinct from that observed for CD11a/CD18, CD11b/CD18, and L-selection expression following dialysis.

EXAMPLE 20

Isolation of Rat cDNA Clones

In view of the existence of both canine and human $\alpha_d$ subunits, attempts were made to isolate homologous genes in other species, including rat (this example) and mouse (Example 20, infra).

A partial sequence of a rat cDNA showing homology to the human ad gene was obtained from a rat splenic λgt10 library (Clontech). The library was plated at $2\times10^4$ pfu/plate onto 150 mm LBM/agar plates. The library was lifted onto Hybond® membranes (Amersham), denatured 3 minutes, neutralized 3 minutes and washed 5 minutes with buffers as described in standard protocols [Sambrook, et al., *Molecular Cloning: a laboratory manual*, p.2.110]. The membranes were placed immediately into a Stratalinker (Stratagene) and the DNA crosslinked using the autocrosslinking setting. The membranes were prehybridized and hybridized in 30% or 50% formamide, for low and high stringency conditions, respectively. Membranes were initially screened with a $^{32}$P-labeled probe generated from the human $\alpha_d$ cDNA, corresponding to bases 500 to 2100 in clone 19A2 (SEQ ID NO: 1). The probe was labeled using Boehringer Mannheim's Random Prime Kit according to manufacturer's suggested protocol. Filters were washed with 2×SSC at 55° C.

Two clones, designated 684.3 and 705.1, were identified which showed sequence homology to human $\alpha_d$, human CD11b, and human CD11c. Both clones aligned to the human $\alpha_d$ gene in the 3' region of the gene, starting at base 1871 and extending to base 3012 for clone 684.3, and bases 1551 to 3367 for clone 705.1.

In order to isolate a more complete rat sequence which included the 5' region, the same library was rescreened using the same protocol as employed for the initial screening, but using a mouse probe generated from clone A1160 (See Example 20, infra). Single, isolated plaques were selected from the second screening and maintained as single clones on LBM/agar plates. Sequencing primers 434FL and 434FR (SEQ ID NOS: 34 and 35, respectively) were used in a standard PCR protocol to generate DNA for sequencing.

```
5'-TATAGACTGCTGGGTAGTCCCCAC-3'   (SEQ ID NO: 34)

5'-TGAAGATTGGGGGTAAATAACAGA-3'   (SEQ ID NO: 35)
```

DNA from the PCR was purified using a Quick Spin Column (Qiagen) according to manufacturer's suggested protocol.

Two clones, designated 741.4 and 741.11, were identified which overlapped clones 684.3 and 705.1; in the overlapping regions, clones 741.1 and 741.11 were 100% homologous to clones 684.3 and 705.1. A composite rat cDNA having homology to the human $\alpha_d$ gene is set out in SEQ ID NO: 36; the predicted amino acid sequence is set forth in SEQ ID NO: 37.

Cloning of the 5' end of Rat $\alpha_d$

A 5' cDNA fragment for the rat $\alpha_d$ gene was obtained using a Clonetech rat spleen RACE cloning kit according to manufacturer's suggested protocol. The gene specific oligonucleotides used were designated 741.11#2R and 741.2#1R (SEQ ID NOS: 59 and 58, respectively).

```
5'-CCAAAGCTGGCTGCATCCTCTC-3'   (SEQ ID NO: 59)

5'-GGCCTTGCAGCTGGACAATG-3'     (SEQ ID NO: 58)
```

Oligo 741.11#2R encompasses base pairs 131–152 in SEQ ID NO: 36, in the reverse orientation and 741.2#1R encompasses bases pairs 696–715 in SEQ ID NO: 36, also in the reverse orientation. A primary PCR was carried out using the 3'-most oligo, 741.2#1R. A second PCR followed using oligo 741.11#2R and DNA generated from the primary reaction. A band of approximately 300 base pairs was detected on a 1% agarose gel.

The secondary PCR product was ligated into plasmid pCRTAII (Invitrogen) according to manufacturer's suggested protocol. White (positive) colonies were picked and added to 100 µl LBM containing 1 µl of a 50 mg/ml carbenicillin stock solution and 1 µl M13 K07 phage culture in individual wells in a round bottom 96 well tissue culture plate. The mixture was incubated at 37° C. for 30 minutes to one hour. Following the initial incubation period, 100 µl of LBM (containing 1 µl of 50 mg/ml carbenicillin and a 1:250 dilution of a 10 mg/ml kanamycin stock solution) were added and the incubation was continued overnight at 37° C.

Using a sterile 96 well metal transfer prong, supernatant from the 96 well plate was transferred to four Amersham Hybond® nylon filters. The filters were denatured, neutralized and cross linked by standard protocols. The filters were prehybridized in 20 mls of prehybridization buffer (5×SSPE; 5×Denhardts; 1% SDS; 50 ugs/ml denatured salmon sperm DNA) at 50° C. for several hours while shaking.

Oligo probes 741.11#1 and 741.11#1R (SEQ ID NOS: 56 and 57, respectively), encompassing base pairs 86–105 (SEQ ID NO: 36) in the forward and reverse orientation respectively, were labeled as follows.

```
5'-CCTGTCATGGGTCTAACCTG-3'   (SEQ ID NO: 56)

5'-AGGTTAGACCCATGACAGG-3'    (SEQ ID NO: 57)
```

Approximately 65 WP oligo DNA in 12 µl dH$_2$O was heated to 65° C. for two minutes. Three µl of 10 mCi/ml γ-$^{32}$P-ATP were added to the tube along with 4 µl 5× Kinase Buffer (Gibco) and 1 µl T4 DNA Kinase (Gibco). The mixture was incubated at 37° C. for 30 minutes. Following incubation, 16 µl of each labeled oligo probe were added to the prehybridization buffer and filters and hybridization was continued overnight at 42° C. The filters were washed three times in 5×SSPE; 0.1% SDS for 5 minutes per wash at room temperature, and autoradiographed for 6 hours. Positive clones were expanded and DNA purified using the Magic Mini Prep Kit (Promega) according to manufacturer's suggested protocol. Clone 2F7 was selected for sequencing and showed 100% homology to clone 741.11 in the overlapping region. The complete rat $\alpha_d$ nucleic acid sequence is set out in SEQ ID NO: 54; the amino acid sequence is set out in SEQ ID NO: 55.

Characteristics of the Rat cDNA and Amino Acid Sequences

Neither nucleic acid nor amino acid sequences have previously been reported for rat α subunits in β$_2$ integrins. However sequence comparisons to reported human β$_2$ integrin α subunits suggests that the isolated rat clone and its predicted amino acid sequence are most closely related to $\alpha_d$ nucleotide and amino acid sequences.

At the nucleic acid level, the isolated rat cDNA clone shows 80% identity in comparison to the human $\alpha_d$ cDNA; 68% identity in comparison to human CD11b; 70% identity in comparison to human CD11c; and 65% identity in comparison to mouse CD11b. No significant identity is found in comparison to human CD11a and to mouse CD11a.

At the amino acid level, the predicted rat polypeptide encoded by the isolated cDNA shows 70% identity in comparison to human $\alpha_d$ polypeptide; 28% identity in comparison to human CD11a; 58% identity in comparison to human CD11b; 61% identity in comparison to human CD11c; 28% identity in comparison to mouse CD11a; and 55% identity in comparison to mouse CD11b.

EXAMPLE 21

Northern Analysis of Rat Tissue For $\alpha_d$ Expression

RNA was obtained from a panel of Lewis rat tissues in order to perform Northern analysis using a rat $\alpha_d$ probe. Samples included total RNA from normal spleen, kidney, liver, lung, and bone marrow, in addition to poly(A$^+$) RNA from normal spleen, brain, spinal cord, thymus, skin, small intestine, and rat antigen activated T cells and diseased EAE (experimental allergic encephalomyelitis) spleen and lymph node. The experiments were carried out using the techniques described in Example 6.

The $\alpha_d$ probe was selected from a region of the rat cDNA encompassing nucleotides 1184 to 3008 in SEQ ID NO: 54 which represents the area having the lowest degree of homology with rat CD11c and rat CD11b. The 1124 bp probe was generated by a restriction enzyme digestion with EcoR1 of 10 µg rat $\alpha_d$ cDNA clone 684.3. The fragment was gel purified and used in a random primed labelling reaction as described in Example 6. The Northern blot was prehybridized, hybridized and washed as described in Example 6 except the probe was added to the hybridization buffer at 5.5×10$^5$ cpm/ml.

After autoradiography for five days, bands were detected in lanes containing total spleen RNA as well as poly(A⁺) RNA from a normal rat as well as a spleen from a rat with active EAE, where the amount of RNA was significantly greater than that from normal spleen. The transcript size detected was consistent with the size of the full length rat cDNA clone.

EXAMPLE 22

Production and Characterization of Rodent $\alpha_d$- Specific Antibodies—Antibodies Against Rat $\alpha_d$ I Domain/Hu IgG4 Fusion Proteins In view of the fact that the I domain of human $\beta_2$ integrins has been demonstrated to participate in ligand binding, it was assumed that the same would be true for rat $\alpha_d$ protein. Monoclonal antibodies immunospecific for the rat $\alpha_d$ I domain may therefore be useful in rat models of human disease states wherein $\alpha_d$ binding is implicated.

Oligos "rat alpha-DI5" (SEQ ID NO: 87) and "rat alpha-DI3" (SEQ ID NO: 88) were generated from the rat $\alpha_d$ sequence corresponding to base pairs 469–493 and base pairs 1101–1125 (in the reverse orientation), respectively, in SEQ ID NO: 54. The oligos were used in a standard PCR reaction to generate a rat $\alpha_d$ DNA fragment containing the I domain spanning base pairs 459–1125 in SEQ ID NO: 54. The PCR product was ligated into vector pCRTAII (Invitrogen) according to manufacturer's suggested protocol. A positive colony was selected and expanded for DNA purification using a Qiagen (Chatsworth, Ga.) Midi Prep kit according to manufacturer's protocol. The DNA was digested with XhoI and BglII in a standard restriction enzyme digest and a 600 base pair band was gel purified which was subsequently ligated into pDCS1/HuIgG4 expression vector. A positive colony was selected, expanded and DNA purified with a Quiagen Maxi Prep Kit.

COS cells were plated at half confluence on 100 mm culture dishes and grown overnight at 37° C. in 7% $CO_2$. Cells were rinsed once with 5 ml DMEM. To 5 ml DMEM, 50 µl DEAE-Dextran, 2 µl chloroquine and 15 µg rat $\alpha_d$ I domain/HuIgG4 DNA described above was added. The mixture was added to the COS cells and incubated at 37° C. for 3 hours. Media was then removed and 5 ml 10% DMSO in CMF-PBS was added for exactly one minute. The cells were gently rinsed once with DMEM. Ten ml DMEM containing 10% FBS was added to the cells and incubation continued overnight at 37° C. in 7% $CO_2$. The next day, media was replaced with fresh media and incubation continued for three additional days. The media was harvested and fresh media was added to the plate. After three days, the media was collected again and the plates discarded. The procedure was repeated until 2 liters of culture supernatant were collected.

Supernatant collected as described above was loaded onto a ProsepA® column (Bioprocessing Limited) and protein purified as described below.

The column was initially washed with 15 column volumes of Wash Buffer containing 35 mM Tris and 150 mM NaCl, pH 7.5. Supernatant was loaded at a slow rate of less than approximately 60 column volumes per hour. After loading, the column was washed with 15 column volumes of Wash Buffer, 15 column volumes of 0.55 M diethanolamine, pH 8.5, and 15 column volumes 50 mM citric acid, pH 5.0. Protein was eluted with 50 mM citric acid, pH 3.0. Protein was neutralized with 1.0 M Tris, pH 8.0, and dialyzed in sterile PBS.

The rat $\alpha_d$ I domain protein was analyzed as described in Example 14. The detected protein migrated in the same manner as observed with human I domain protein.

Production of Monoclonal Antibodies to Rat $\alpha_d$ I Domain/ HuIgG4 Fusion Proteins Mice were individually immunized with 50 µg purified rat $\alpha_d$ I domain/HuIgG4 fusion protein previously emulsified in an equal volume of Freunds Complete Adjuvant (FCA) (Sigma). Approximately 200 µl of the antigen/adjuvant preparation was injected at 4 sites in the back and flanks of each of the mice. Two weeks later the mice were boosted with an injection of 100 µl rat $\alpha_d$ I domain/HuIgG4 antigen (50 µg/mouse) previously emulsified in an equal volume of Freunds Incomplete Adjuvant (FIA). After two additional weeks, the mice were boosted with 50 µg antigen in 200 µl PBS injected intravenously.

To evaluate serum titers in the immunized mice, retro-orbital bleeds were performed on the animals ten days following the third immunization. The blood was allowed to clot and serum isolated by centrifugation. The serum was used in an immunoprecipitation on biotinylated (BIP) rat splenocytes. Serum from each mouse immunoprecipitated protein bands of expected molecular weight for rat $\alpha_d$ and rat CD18. One mouse was selected for the fusion and was boosted a fourth time as described above for the third boost.

The hybridoma supernatants were screened by antibody capture, described as follows. Immulon® 4 plates (Dynatech, Cambridge, Mass.) were coated at 4° C. with 50 µl/well goat anti-mouse IgA, IgG or IgM (Organon Teknika) diluted 1:5000 in 50 mM carbonate buffer, pH 9.6. Plates were washed 3× with PBS containing 0.05% Tween® 20 (PBST) and 50 µl culture supernatant was added. After incubation at 37° C. for 30 minutes, and washing as described above, 50 µl horseradish peroxidase-conjugated goat anti-mouse IgG9(Fc) (Jackson ImmunoResearch, West Grove, Pa.) diluted 1:3500 in PBST was added. Plates were incubated as described above and washed 4× with PBST. Immediately thereafter, 100 µl substrate, containing 1 mg/ml o-phenylene diamine (Sigma) and 0.1 µl/ml 30% $H_2O_2$ in 100 mM citrate, pH4.5, was added. The color reaction was stopped after 5 minutes with the addition of 50 µl 15% $H_2SO_4$. Absorbance at 490 nm was read on a Dynatech plate reader.

Supernatant from antibody-containing wells was also analyzed by ELISA with immobilized rat $\alpha_d$ I domain/ HuIgG4 fusion protein. An ELISA with HuIgG4 antibody coated plates served as a control for reactivity against the IgG fusion partner. Positive wells were selected for further screening by BIP on rat splenocyte lysates using techniques described below.

Production of Polyclonal Sera To Rat $\alpha_d$ I Domain/HuIgG4 Fusion Protein

Two rabbits were prebled prior to immunization with 100 µg purified rat $\alpha_d$ I domain/HuIgG4 fusion protein in complete Freund's adjuvant. Injections were repeated at the same dose every three weeks in incomplete Freunds adjuvant (IFA). After three injections the rabbits were test bled and the collected sera used in a standard immunoprecipitation on rat splenocyte lysates. It was determined that sera from both rabbits were immunoreactive with rat $\alpha_d$. The rabbits were boosted again with 100 ug antigen in IFA, and the collected sera assayed for increased immunoreactivity with rat $\alpha_d$ by immunoprecipitation. The animals were given a final boost and 10 days later, bled out and sera collected.

Rat $\alpha_d$ Histology

Rabbit polyclonal sera generated against rat $\alpha_d$ "I" domain was used in immunohistochemical staining of rat tissue sections by the technique described in Example 18. The staining pattern detected on frozen and on paraffin embedded rat spleen sections was essentially identical to that observed with the antibodies against human $\alpha_d$, with staining individual cells throughout the red pulp. The staining pattern differed from that observed with monoclonal antibodies against rat CD11a, CD11b and CD18. In addition, a positive staining pattern was seen in the thymus on individual cells throughout the cortex. Neither of these tissue gave any signal when stained with the rabbit preimmune sera.

Analysis of Antibody Specificity

Rats were sacrificed by asphyxiation with $CO_2$ and spleens were removed using standard surgical techniques. Splenocytes were harvested by gently pushing the spleen through a wire mesh with a 3 cc syringe plunger in 20 mls RPMI. Cells were collected into a 50 ml conical tube and washed in the appropriate buffer.

Cells were washed three times in cold D-PBS and resuspended at a density of $10^8$ to $10^9$ cells in 40 ml PBS. Four mg of NHS-Biotin (Pierce) was added to the cell suspension and the reaction was allowed to continue for exactly 15 minutes at room temperature. The cells were pelleted and washed three times in cold D-PBS.

Cells were resuspended at a density of $10^8$ cells/ml in cold lysis Buffer (1% NP40; 50 mM Tris-HCl, pH 8.0; 150 mM NaCl; 2 mM CaCl; 2 mM MgCl; 1:100 solution of pepstain, leupeptine, and aprotinin, added just before adding to cells; and 0.0001 g PMSF crystals, added just before adding to cells). Lysates were vortexed for approximately 30 seconds, incubated for 5 minute at room temperature, and further incubated for 15 minutes on ice. Lysates were centrifuged for 10 minutes at 10,000×g to pellet the insoluble material. Supernatant was collected into a new tube and stored at between 4° C. and −20° C.

One ml cell lysate was precleared by incubation with 200 µl of a protein A Sepharose® slurry (Zymed) overnight at 4° C. Precleared lysate was aliquoted into Eppendorf tubes at 50 µl/tube for each antibody to be tested. Twenty-five µl of polyclonal serum or 100 to 500 µl of monoclonal antibody supernatant were added to the precleared lysates and the resulting mixture incubated for 2 hours at 4° C. with rotation. One hundred µl rabbit anti-mouse IgG (Jackson) bound to protein A Sepharose® beads in a PBS slurry was then added and incubation continued for 30 minutes at room temperature with rotation. Beads were pelleted with gentle centrifugation, and washed three times with cold Wash Buffer (10 mM HEPES; 0.2 M NaCl; 1% Trition X-100). Supernatant was removed by aspiration, and 20 µl 2×SDS sample buffer containing 10% β-mercaptoethanol was added. The sample was boiled for 2 minutes in a water bath, and the sample loaded onto a 5% SDS PAGE gel. Following separation, the proteins were transferred to nitrocellulose at constant current overnight. The nitrocellulose filters were blocked with 3% BSA in TBS-T for 1 hour at room temperature and the blocking buffer was removed. A 1:6000 dilution of Strepavidin-HRP conjugate (Jackson) in 0.1% BSA TBS-T was added and incubation continued for 30 minutes at room temperature. Filters were washed three times for 15 minutes each with TBS-T and autoradiographed using Amersham's ECL kit according to manufacturer's suggested protocol.

Production of Monoclonal Antibodies To Full Length Rat $\alpha_d$ Protein

Rat $\alpha_d$ was purified from rat splenocytes to prepare an immunogen for generating anti-rat $\alpha_d$ monoclonal antibodies. Spleens from approximately 50 normal female Lewis rats, 12–20 weeks of age, were collected and a single cell suspension was made from the tissue by forcing it through a fine wire screen. Red blood cells were removed by lysis in buffer containing 150 mM $NH_4Cl$, 10 mM $KHCO_3$, 0.1 mM EDTA, pH 7.4, and remaining leukocytes were washed two times with phosphate buffered saline (PBS). The splenocytes were pelleted by centrifugation and lysed in buffer containing 50 mM Tris, 150 mM NaCl, 2 mM CaCl2, 2mM MgCl2, 10 mM PMSF, leupeptin, pepstatin and 1% Triton X-100®. Splenocyte lysis was carried out on ice for 30 minutes with one ml of lysis buffer per $5 \times 10^8$ splenocytes. Insoluble material was removed by centrifugation.

CD11a, CD11b and CD11c were removed from the spleen lysate by immunoprecipitation as follows. A 750 µl volume of a Protein A-Sepharose® slurry was incubated with 2 mg rabbit anti-mouse immunoglobulin at 4° C. for 30 minutes. The rabbit anti-mouse-Protein A-Sepharose® was washed three times with lysis buffer and suspended in a final volume of 1.5 ml of lysis buffer. Approximately 200 µg each of rat $\beta_2$ integrin specific monoclonal antibodies, 515F (specific for rat CD11a), OX-42 (specific for rat CD11b) and 100 g (specific for rat CD11c) were each added to 50 ml of the rat spleen lysate. Following a 30 minute incubation at 4° C., 500 µl of the rabbit anti-mouse-Protein A-Sepharose® was added to the spleen lysates and mixed with end-over-end rotation for 30 minutes at 4° C. The lysate was centrifuged at 2500×g for 10 minutes to pellet the CD11a, CD11b, and CD11c bound to the rabbit anti-mouse-Protein A-Sepharose®, and the supernatant transferred to a clean 50 ml centrifuge tube. Immunoprecipitation with the antibodies 515F, OX-42, and 100 g was repeated two additional times to insure complete removal of CD11a, CD11b, and CD11c.

$\beta_2$ integrins remaining in the lysate were isolated using affinity purification. Approximately 250 µl of a slurry of anti-rat CD18 monoclonal antibody 20C5B conjugated to CNBr-Sepharose® was added to the lysates and mixed with end-over-end rotation for 30 minutes at 4° C. Antibody/antigen complexes were pelleted by centrifugation at 2500×g for ten minutes and the pellet washed three times with lysis buffer before being stored at 4° C.

Immunization of Armenian Hamsters

1. Armenian hamsters, six to eight weeks old, were initially immunized with approximately 50 µg of a recombinant protein consisting of the I domain of rat $\alpha_d$ fused to the human $IgG_4$ heavy chain emulsified in complete Freund's adjuvant. Primary immunization was followed by subsequent immunizations with rat $\alpha_d$ I domain/$HuIgG_4$ emulsified in incomplete Freund's adjuvant on Days 14, 33, and 95. Two separate fusions, designated 197 and 199, were subsequently performed.

Four days prior to fusion 197 (day 306), one hamster was administered a combination of rat $\alpha_d$ protein purified from splenocytes and CHO cells transfected with rat $\alpha_d$. The fusion boost was given three days prior to the fusion (day 307) with purified rat $\alpha_d$ protein and $\alpha_d$ transfected CHO cells. Rat $\alpha_d$ transfected CHO cells were prepared as described below.

A gene segment encoding full length rat $\alpha_d$ protein was inserted into the pDC1 vector and transfected by electroporation into CHO cells together with a human CD18-pRC construct. Transfected cells were grown in the presence of hypoxanthine to select for cells successfully transfected with the pRC construct and in the presence of g418 to select for cells transfected with the pDC1 construct. After 3 weeks, the cells were stained with the rat $\alpha_d$ specific rabbit polyclonal sera and sorted by FACS. A small percentage of the cells which expressed the highest levels of surface $\alpha_d$ (approximately 3% of the total population) were collected and further expanded. FACS selection was repeated several times to provide a population cells with high levels of $\alpha_d$ surface expression.

The $\alpha_d$ transfected cells were also characterized by flow cytometry using a rat $\alpha_d$ specific polyclonal sera and a human CD18 specific monoclonal antibody, TS1.18.1. Results confirmed that the transfected CHO cells expressed high levels of both rat $\alpha_d$ and human CD18.

Finally, $\alpha_d$ and CD18 expression in the cells was evaluated by immunoprecipitation. A rat $\alpha_d$ specific rabbit polyclonal sera was found to immunoprecipitate proteins with two distinct molecular weights: the higher molecular weight protein(s) being approximately 170 kD, and the lower molecular weight protein(s) 95 kD. These findings were consistent with expression of a rat $\alpha_d$/human CD18 heterodimeric complex on the surface of the transfected CHO cells.

On the day of the fusion, the spleen was removed and a single-cell suspension was formed by grinding the tissue between frosted ends of two glass microscope slides submerged in serum free RPMI 1640 supplemented with 2 mM L-glutamine, 1 mM sodium pyruvate, 100 units/ml penicillin, and 100 µg/ml streptomycin (RPM1) (Gibco, Canada). The cell suspension was filtered through sterile 70-mesh Nitex cell strainer (Becton Dickinson, Parsippany, N.J.), and washed twice by centrifuging at 200×g for five minutes and resuspending the pellet in 20 ml serum free RPMI. Thymocytes taken from three naive Balb/c mice were prepared in a similar manner. NS-1 myeloma cells, kept in log phase in RPM1 with 10% Fetaclone serum (FBS) (Hyclone Laboratories, Inc. Logan, Utah) for three days prior to fusion, were centrifuged at 200×g for five minutes, and the pellet was washed twice as previously described.

Approximately $1.15 \times 10^8$ spleen cells were combined with $5.8 \times 10^7$ NS-1 cells, centrifuged and the supernatant removed by aspiration. The cell pellet was dislodged by tapping the tube and seven ml of 37° C. PEG 1500 (50% in 75 mM Hepes, pH 8.0) (Boehringer Mannheim) was added with stirring over the course of one minute, followed by adding 14 ml of serum free RPM1 over seven minutes. An additional eight ml RPMI was added and the cells were centrifuged at 200×g for 10 minutes. The supernatant was removed and the pellet resuspended in 200 ml RPMI containing 15% FBS, 100 mM sodium hypoxanthine, 0.4 mM aminopterin, 16 mM thymidine (HAT) (Gibco), 25 units/ml IL-6 (Boehringer Mannheim) and $1.5 \times 10^6$ thymocytes/ml. The suspension was dispensed into ten 96-well flat bottom tissue culture plates (Corning, United Kingdom) at 200 µl/well and the cells were fed on days 4, 5, 6, and 7 days post fusion by aspirating approximately 100 µl from each well with an 18 G needle (Becton Dickinson) and adding 100 µl plating medium described above except lacking thymocytes.

On day 10, supernatants from the fusion wells were screened by flow cytometry for reactivity to rat $\alpha_d$/human CD18 transfected CHO cells. Approximately $5 \times 10^5$ rat $\alpha_d$ transfected CHO cells were suspended in 50 µl RPMI containing 2.0% FBS and 0.05% sodium azide and added to approximately 100 µl of hybridoma culture supernatant in 96-well, round-bottomed plates. Positive controls for staining included rabbit anti-$\alpha_d$ polyclonal sera and TS1/18 (anti-human CD18). Cells were incubated for 30 minutes on ice, washed three times in FACS buffer (RPM1, 2.0% FBS, 0.05% NaAzide), and incubated for 30 minutes on ice with a FITC-conjugated goat anti-hamster antibody (Jackson ImmunolResearch Labs) at a final dilution of 1:200 in FACS buffer. Cells were washed three times in FACS buffer and resuspended in 200 ml of FACS buffer. Samples were analyzed with a Becton Dickinson FACscan analyzer. To insure that positive clone wells were specific for rat $\alpha_d$, the screen was repeated with non-transfected CHO cells. Wells which met the criteria of reacting with rat $\alpha_d$ CHO transfectants and not the untransfected CHO cells were cloned.

Following primary screening, cells from positive wells were cloned initially by doubling dilution and subsequently by limiting dilution in RPM1, 15% FBS 100 mM sodium hypoxanthine, 16 mM thymidine, and 10 units/ml IL-6. In the limiting dilution step, the percentage of wells showing growth was determined and clonality was predicted using a Poisson distribution analysis. Wells showing growth were analyzed by FACS after 10–12 days. After final cloning, positive wells were expanded in RPMI and 11% FBS. Cloning yielded one culture deemed positive by these criteria, from which four separate subclones designated 197A-1, 197A-2, 197A-3, and 197A-4 were expanded.

Prior to fusion 199, a second hamster was boosted on day 307 with $2.3 \times 10^6$ rat $\alpha_d$ (RAD)-transfected CHO cells. Two final immunizations were administered four days prior to the fusion (day 334) and again three days prior to the fusion (day 335). The boost on day 334 consisted of $2 \times 10^6$ rat $\alpha_d$ transfected CHO cells and 200 µl of purified rat $\alpha_d$ bound to Sepharose® (described previously) administered by intraperitoneal injection. The day 335 boost consisted of $5 \times 10^6$ rat $\alpha_d$ transfected CHO cells, also administered by intraperitoneal injection. The fusion and screening protocols for fusion 199 were identical to fusion 197, and three hybridomas, designated 199A, 199H, and 199M, with supernatant reactive with rat $\alpha_d$ were identified and cloned.

2. A second immunization was carried out using the same protocols which led up to fusions 197 and 199. After the day 334 boost, there were no further immunizations until days 394 and 395. Prior to the fusion, the hamsters were administered $2 \times 10^6$ RAD-transfected CHO cells along with 300 µl of purified rat $\alpha_d$-Sepharose® which was administered interpertoneally. The fusion and screening protocols for the subsequent fusion 205 were identical to those of fusions 199 and 197, except that during cloning, Armenian hamster ELISA reagents, e.g. goat anti-Armenian hamster antibodies (Jackson ImmunolResearch Labs), were used as an initial screen. Positive wells identified by this method were subsequently screened by FACS as described. Fusion 205 yielded three separate positive clones named 205A, 205C, 205E.

3. In another method to generate anti-rat $\alpha_d$ monoclonal antibodies, 6 to 12 week old BALB/c mice were immunized on day I with purified rat $\alpha_d$-Sepharose® administered subcutaneously in complete Fruend's adjuvant. A second boost was administered by the same route on day 25 with the same immunogen in incomplete Freund's adjuvant. A third boost identical to the second was performed on day 42. No further boosts were carried out until the pre-fusion boosts which consisted of 400 µl (for fusion 226) and 250 µl (for fusion 236) purified rat $\alpha_d$-Sepharose® injected intraperitoneally. Each volume contained approximately 10 to 15 µg antigen as determined by Coomassie staining. The prefusion boosts for fusion 226 occurred on days 62 and 63 and the fusion was performed on day 66. For fusion 236, the preflusion boosts were performed on days 132 and 133 and the fusion was performed on day 136. Both fusion protocols differed from that used for the Armenian hamster fusions described above in that a 5:1 ratio of splenocytes to NS-1 cells was used as compared to a ratio of 2:1 in the Armenian hamster fusions. The fusion protocol was otherwise identical to the Armenian hamster protocol.

The screening and cloning protocols for fusions 226 and 236 were identical to those used in fusions 197, 199, and 205, except that an initial screen by ELISA was performed. In the ELISA, a goat anti-mouse whole molecule was employed to capture the mouse antibody from hybridoma supernatant and a goat anti-mouse horse radish peroxidase conjugate was used to detect mouse antibody. Positive supernatants were subsequently screened by FACS as described for fusions 197 through 205.

Fusion 226 yielded nine positive clones designated 226A, 226B, 226C, 226D, 226E, 226F, 226G, 226H, and 226I. Fusion 236 yielded ten positive clones designated 236A, 236B, 236C, 236F, 236G, 236H, 236I, 236K, 236L, and 236M. Monoclonal antibodies generated from these clones were isotyped by ELISA as described in Example 15. All antibodies were found to be of the IgG1 isotype.

Characterization of Monoclonal Antibodies to Rat $\alpha_d$

In order to characterize the anti-rat $\alpha_d$ antibodies, biotin labeled spleens lysates were prepared as described in Example 22, section D, above. Lysates were precleared prior to use in immunoprecipitations. Initially, 50 μg/ml of normal murine immunoglobulin was added to the lysate and the resulting solution mixed with end-over-end rotation for 30 minutes at 4° C. A 75 μl slurry of a protein A-Sepharose® coated with rabbit anti-mouse immunoglobulin was added and mixing was continued with end-over-end rotation for 30 minutes. The rabbit anti-mouse coated protein A beads were pelleted by centrifugation at 15,000 rpm in a table-top microfuge for five minutes at 4° C. and the supernatant collected. The pelleted material was discarded.

For each cloned hybridoma, approximately 300 μl of supernatant was placed into a Eppendorf microfuge tube, to which was added 30 μl 10% Triton X-100®, 30 μl of a 100× stock solution of pepstatin, leupeptin and aprotinin, 100 μg PMSF crystals, and 50 μl of precleared biotinylated rat spleen lysate. Samples were vortexed gently and placed onto an end-over-end rotator at 4° C. for 30 minutes. A control sample was prepared by adding 10 mg/ml of a rabbit anti-rat $\alpha_d$ specific polyclonal antibody to 50 μl of rat spleen lysate.

Following a 30 minute incubation, 75 μl of protein A-Sepharose® beads in a PBS slurry was added to each sample and incubated with end-over-end rotation at 4° C. for 30 minutes. The protein A-coupled beads were pelleted by centrifugation at 15,000 rpm in a table-top microfuge for 5 minutes at 4° C. and the supernatant was collected. The pelleted beads were washed sequentially with a series of 1 ml detergent washes as follows: buffer #1 containing 10 mM Tris, 400 mM NaCl, 1.0% Triton X-100®, pH 8.0; buffer #2 containing 10 mM Tris, 400 mM NaCl, 0.5% Triton X-100®, pH 8.0; buffer #3 containing 10 mM Tris, 400 mM NaCl, 1.0% Triton X-100®, 0.1% deoxycholate, pH 8.0; and buffer #4 containing 10 mM Tris, 400 mM NaCl, 0.5 M LiCl$_2$, pH 8.0. A final washed was carried out with wash buffer #1. Beads were vortexed gently between each wash and pelleted using a tabletop microfuge. Supernatants were removed by transfer pipette, and after the final wash, all remaining buffer was removed from the beads by Hamilton syringe. A 50 μl aliquot of SDS sample buffer containing Bromphenol Blue and Pyronine Y dyes and β-mercaptoethanol at a final concentration of 10% was added to each pellet. The mixture was vortexed vigorously for 1–2 minutes and incubated at room temperature for 5–10 minutes. Samples were centrifuged for 5 minutes at 15,000 rpm in a table-top microftige at 4° C. and released protein was collected and transferred to a new microfuge tube. Aliquots from each sample were boiled for four minutes in a water bath before loading onto 7.5% SDS-PAGE gels.

Following separation by PAGE, proteins were transferred to nitrocellulose filters for one hour at 200 mAmps, and the filters were blocked in a solution of 3.0% BSA/TBS-T overnight at 4° C. A solution of 0.1% BSA-TBS-T containing a 1:6000 dilution of streptavidin-OPD was added to each filter and incubation allowed to continue for one hour at room temperature. The filters were washed five times for ten minutes each in TBS-T, and developed using Amersham's ECL kit according to the manufacturer's suggested protocol.

Clone 199M was found to immunoprecipitate a heterodimeric protein. The larger protein subunit had an approximate molecular weight of 170–175 kD which was consistent with the size of the protein immunoprecipitated by the rabbit anti-rat $\alpha_d$ polyclonal control. A second protein was also precipitated with an approximate molecular weight of 95 kD, consistent with the weight of CD18.

EXAMPLE 23

Specificity of Monoclonal Antibody 199M

A CNBr-Sepharose® affinity column with conjugated 199M monoclonal antibody was used to affinity purify rat $\alpha_d$ from spleen cell lysates. Briefly, approximately $1.3 \times 10^{10}$ rat spleen cells were lysed in buffer consisting of 150 mM NaCl, 10 mM PMSF, 10 mM Tris, 1% Triton X-100®, pH 8.0. Cells in the buffer were incubated for 30 minutes on ice and centrifuged at approximately 10,000×g for 30 minutes at 4° C.

Antibody 199M was conjugated to CNBr-activated Sepharose® 4B (Pharmacia) by the following method. One gram of the activated resin was suspended in 1 mM HCl for 15 minutes and washed three times with 15 ml of 1 mM HCl and once with 15 ml coupling buffer containing 0.1 mM HCO$_3$, 0.5 M NaCl, pH 8.0. Antibody 199M in coupling buffer was added to resin suspension at a final concentration of approximately 10–20 mg/ml and the mixture incubated overnight at 4° C. The following day the conjugated resin was pelleted by centrifugation and the supernatant removed. Unreacted groups on the resin were blocked by incubation in 0.1 M Tris, pH 8.0 for one hour at room temperature. The conjugated resin was washed with 0.1 M citric acid, pH 3, and stored in lysis buffer as a 1:2 slurry containing 0.1% sodium azide.

For affinity purification, spleen cells were incubated with end-over-end mixing overnight with 0.4 ml of the 199M-conjugated Sepharose® resin. The resin was then pelleted by centrifugation and washed four times with 15 ml lysis buffer. Aliquots of approximately 100 μl of each gel were boiled briefly in reducing sample buffer containing 0.1 M Tris-HCl, pH 6.8, 2.0% SDS, 20% glycerol, 0.0002% bromophenol blue, 10% β-mercaptoethanol (final concentration 5%) and loaded onto and proteins resolved using a 6.0% polyacrylamide SDS gel (SDS-PAGE).

The affinity purified material was found to contain two major and one minor protein species when separated on SDS-PAGE. A prominent protein band with a molecular weight of 90 kD was consistent with the known size of CD18 and this band was not sequenced. A second prominent band of 160 kD was detected which was consistent with the predicted molecular weight for $\alpha_d$. In addition, a minor band with an apparent molecular weight of 200 kD was also detected. Both the 160 kD and 200 kD species were further analyzed by amino terminal protein sequencing with the results compared to the amino acid sequence predicted by the rat $\alpha_d$ cDNA, as well as to the known amino acid sequences for CD11c and CD11b. The sequence of both the 160 and 200 kD bands were found to be consistent with the amino acid sequence predicted by cloned rat $\alpha_d$, suggesting that there may be two forms of $\alpha_d$, perhaps resulting from splice variants or glycosylation differences.

EXAMPLE 24

T Cell Proliferation Assay Using Rat $\alpha_d$-Expressing Macrophages

Macrophages expressing $\alpha_d$ isolated from rat spleens were used as antigen presenting cells (APC) to stimulate a myelin basic protein specific T cell line designated LR-21. Briefly, rats were injected intravenously with a 100 µl volume of iron particles (BioMag, Cambridge, Mass.). The following day a single cell suspension was prepared from the spleens and $\alpha_d^+$ macrophages which had phagocytosed iron particles were collected using a magnet. Flow cytomotery and immunoprecipitation indicated that 50 to 80% of the cells which phagocytose iron are $\alpha_d^+$.

The results indicated that spleen macrophages expressing $\alpha_d$ were very poor APC's compared to other APC such as thymic macrophages. The monoclonal antibody designated 205C was also tested in the proliferation assay with the $\alpha_d$ positive macrophages and the LR-21 cell line. Proliferation assays were then carried out as follows.

Spleen macrophages positive for $\alpha_d$ expression were suspended at a density of $6 \times 10^6$ cells/ml in RPMI containing 5% normal rat serum and 100 µl of the macrophage suspension was added to each well. Cells from the LR-21 line were suspended at $1 \times 10^6$ cell/ml in RPMI with 5% normal rat serum and 50 µl of the suspension was added to each well. Monoclonal antibody 205C was added to each well in a volume of 50 µl to a final concentration of 50, 10 and 2 µg/ml. Plates were incubated at 37° C. for 72 hours and 1 µCi $^3$H-thymidine was added for the final 24 hours of incubation. Cells were harvested onto glass fiber mats and $^3$H incorporation determined using a Direct Beta Counter (Packard Matrix 96).

Results from the experiments indicate that high concentrations of antibody 205C (10 and 50 µg/ml) are able to reduce T cell proliferation in a dose dependent manner.

EXAMPLE 25

Immunoprecipitation of $\alpha_d$ from Rat Bone Marrow

Bone marrow cells were harvested from a Lewis rat by flushing the femur bone with PBS. The cells were washed, biotinylated, and immunoprecipitated, essentially as described in Example 18, using 20 µg purified monoclonal antibodies to immunoprecipitate protein from 100 µl of precleared cell lysates. Detection of immunoprecipitated protein was carried out in the manner as previously described.

The rat $\alpha_d$ monoclonal antibody 205C immunoprecipitated two bands which migrated at 160 kD and 95 kD. Bands of this size were consistent with the size for the $\alpha$ and $\beta$ chains in $\alpha_d$/CD18 as observed in immunoprecipitation of proteins from spleen cell lysates using the same antibody. Antibodies against rat CD11a, CD11b, or CD11c immunoprecipitated alpha chains distinct from $\alpha_d$ and all antibodies co-immunoprecipitated a protein having a molecular weight consistent with that known for CD18.

EXAMPLE 26

Expression of $\alpha_d$ in Animal Models

Preliminary results indicated that rat $\alpha_d$ is selectively expressed by subpopulations of macrophages, including cortical macrophages in the thymus, Kupffer cells in the liver, perivascular cells in the central nervous system, a subset of peritoneal macrophages, and resident bone marrow macrophages. In addition, a subset of thioglycolate macrophages showed upregulation of $\alpha_d$ expression following stimulation with dexamethasone. The observed macrophage-restricted expression of rat $\alpha_d$ suggested further analysis of expression in various animal models.

Expression of Rat $\alpha_d$ in Phenylhydrazine Model

The administration of phenylhydrazine to animals results in massive red blood cell (rbc) damage which leads to a transient anemia. Damaged rbcs are cleared from circulation by red pulp macrophages, resulting in significant splenomegaly. It is proposed that macrophages which express $\alpha_d$ may be involved in the clearance of damaged rbcs and other foreign material from circulation.

To test this hypothesis, groups of rats were treated with saline alone or phenylhydrazine dissolved in saline and administrated by intraperitoneal injection at a dosage of 100 mg/kg body weight. In some experiments rats were treated with a polyclonal antiserum generated to the "I domain" of rat $\alpha_d$.

At various time points following phenylhydrazine administration, animals were sacrificed. Spleen weight and hematocrit were used as parameters of rbcs clearance. In addition, kidney, spleen and liver were collected for histopathologic evaluation, which included immunostaining for CD11a, CD11b, CD11c and $\alpha_d$.

Gross findings indicated that four days following treatment with phenylhydrazine (saline controls and $\alpha_d$ treatment) rats developed a dramatic splenomegaly, while hematocrit levels dropped. Treatment with the $\alpha_d$ polyclonal serum had no effect on spleen weight or the drop in hematocrit induced with phenylhydrazine.

Tissue from saline and day 4 phenylhydrazine treated rats were sectioned at 4 µm thickness and air dried on Superfrost Plus (VWR Scientific) slides at room temperature for 15 minutes. Prior to use, slides were incubated at 50° C. for approximately 5 minutes. Sections were fixed in cold (4° C.) acetone (EM Science) for 2 minutes at room temperature and allowed to dry at room temperature. Sections were placed in 100 ml 1×TBS, 1.1 ml 30% $H_2O_2$ (Sigma), 1 ml 10% $NaN_3$ (Sigma) for 15 minutes at room temperature to remove endogenous peroxidase activity. Each section was blocked using 150 µl of a solution containing 30% normal rat serum (Harlan Bioproducts), 2% BSA (Sigma) in 1×TBS for 30 minutes at room temperature, after which the solution was gently blotted from the sections. Each section received 75 µl of biotinylated hamster anti-rat $\alpha_d$ antibody 205C at a protein concentration of 13.3 µg/ml diluted in blocking solution, for 1 hour at room temperature. After incubation, the sections were washed three times in 1×TBS for 5 minutes each to remove any unbound antibody. Excess TBS was removed by aspirating around the tissue following the final wash. Peroxidase-conjugated goat anti-biotin antibody (Vector Laboratories) was diluted 1:200 in blocking solution and 75 µl was applied to each section for 30 minutes at room temperature. After incubation, slides were washed two times in 1×TBS for 5 minutes each wash. AEC substrate (Vector Laboratories) was applied and color development stopped by immersion in water. Slides were counterstained in Gill's hematoxylin #2 (Sigma) and rinsed in water, after which they were successively dehydrated in 70%, 95%, 100% EtOH, and Xylene. Sections were then mounted with cytoseal (VWR).

In the saline-treated rat spleen sections, the majority of $\alpha_d$ expression was localized in the splenic red pulp on cells identified morphologically as macrophages, granulocytes, and a subpopulation of lymphocytes. In the phenylhydrazine-treated rat spleens, however, the splenic red pulp had undergone morphological changes such that the only cell type identified was a population of large macrophages which had engulfed damaged red blood cells. The majority of these large macrophages were observed to expressed $\alpha_d$. Also in the phenylhydrazine-treated rat, there appeared to be an increase in the number of macrophages in the splenic white pulp that expressed $\alpha_d$.

A double label experiment to determine expression of $\alpha_d$ and CD11c was also performed on a phenylhydrazine-treated rat spleen. As previously described, $\alpha_d$ expression was detected on large macrophages in the splenic red pulp that appeared to have engulfed damaged red blood cells. CD11c expression was also detected on large macrophages in the splenic red pulp and there appeared to be more CD11c positive cells in the red pulp than $\alpha_d$ Positive cells. The majority of macrophages expressing $\alpha_d$ also expressed CD11c even though a small subset of $\alpha_d$ positive macrophages were observed that did not express CD11c. There was also a population of CD11c positive macrophages that did not express $\alpha_d$.

Immunohistology analysis therefore indicates that there appears to be an upregulation of CD11c expression in the spleen of phenylhydrazine treated animals compared to the saline controls on day 4. Expression of the other integrins, CD11a, CD11b and $\alpha_d$, however, appears to be unaffected by the phenylhydrazine treatment. Treatment with polyclonal "I" domain $\alpha_d$ antibody also showed no effect on the uptake of rbcs by the red pulp macrophages, but the majority of macrophages that are engulfing rbcs are $\alpha_d$ positive. The $\alpha_d$ positive macrophages which had engulfed damaged rbcs were not present in spleens collected 7 days after phenylhydrazine administration.

A double label experiment was then performed on the day 4 phenylhydrazine-treated rat spleens using an apoptosis assay and ICC with biotin-conjugated antibody 205C. Tissue from normal rat and day four phenylhydrazine-treated rats were sectioned at 4 microns thickness and air dried on Superfrost Plus slides (VWR Scientific) at room temperature for 15 minutes and stored at −20° C. Prior to use, slides were warmed to 50° C. Warmed slides were placed in buffer containing 100 ml 1×TBS, 1.1 ml 30% $H_2O_2$ (Sigma), 1 ml 10% $NaN_3$ (Sigma) for 15 minutes at room temperature to remove endogenous peroxidase activity. Each section was blocked using 150 μl of a solution containing 20% normal rat serum (Harlan Bioproducts), 2% BSA (Sigma) in 1×TBS for 10 minutes at 37° C., after which the Solution was gently blotted from the sections. Each section was incubated for 30 minutes at 37° C. with 75 μl biotinylated hamster anti-rat $\alpha_d$ antibody 205C at a protein concentration of 26.6 μg/ml diluted in blocking solution. Sections were then washed three times for five minutes each in 1×TBS to remove unbound antibody. Excess TBS was removed by aspirating around the tissue following the final wash. Alkaline phosphatase-conjugated avidin/biotin complex (Vector Laboratories) prepared according to the manufacturer's instructions was applied to each section for 20 minutes at 37° C. After incubation, slides were washed two times for five minutes each in 1×TBS. Sections were fixed for five minutes with 4% paraformaldehyde (Sigma) at 4° C. Sections were then rinsed in 1×PBS and placed in CSK buffer (100 mM NaCl, 300 mM sucrose, 10 mM pipes pH 6.8, 3 mM $MgCl_2$, 0.5% Triton-X-100®) for two minutes at 4° C. Sections were rinsed in 1×PBS for two minutes at room temperature after which the sections were washed three times for five minutes each with 1×PBS. TUNEL reaction mixture (Boehringer Mannheim) was applied to each section for 60 minutes at 37° C. After incubation, the sections were washed three times in 1×PBS for 5 minutes each wash. The apoptosis kit methodology is similar to in situ hybridization; the TUNEL reagent (which is FITC conjugated) hybridizes to "nicked" DNA. Converter-POD (a peroxidase conjugated antibody which recognizes the FITC tag on the TUNEL reagent) was applied to each section for 30 minutes at 37° C. and the sections were washed three times for five minutes each with 1×PBS. AEC (Vector Laboratories) was applied and color development stopped by immersion in water. Sections were mounted with Aquamount (VWR).

In the model, numerous cells in both the red and white pulp regions of the spleen were undergoing apoptosis, but large macrophages in the red pulp (which expressed $\alpha_d$ and disappeared on day 7 of the model) that had engulfed RBCs were not found to be undergoing apoptosis.

Cell Type Analysis of Rat $\alpha_d$ Expression on Normal Rat Spleen

In order to determine which rat cell types express $\alpha_d$, a double label staining was performed on normal rat spleen. Sections of normal rat spleen were prepared as described above through the rat serum blocking step. After the addition of primary cell marker antibodies, alkaline phosphatase-conjugated goat anti-mouse antibody (Jackson Laboratories) was diluted 1:500, in the same diluent used for the primary antibodies, and 75 μl was applied to each section for 30 minutes at room temperature. Slides were washed two times in 1×TBS for five minutes each wash. Alkaline phosphatase conjugated donkey anti-goat antibody (Jackson Laboratories) was diluted 1:300, in antibody diluent, and 75 μl was applied to each section for 30 minutes at room temperature. After washing and blocking as above, each section received 75 μl of biotinylated hamster anti-rat $\alpha_d$ antibody (205C), at a protein concentration of 20 μg/ml, for 1 hour 45 minutes each and then washed to remove unbound antibody. Excess TBS was removed by aspirating around the tissue following the final wash. Peroxidase conjugated goat anti-biotin (Vector Laboratories) was diluted 1:200, in antibody diluent, and 75 μl was applied to each section for 45 minutes at room temperature. Slides were washed two times 1×TBS for five minutes each wash. AEC substrate (Vector Laboratories) was applied and color development was stopped by immersion in water. Fast Blue substrate (Vector Laboratories) was then applied and color development was stopped by immersion in water. Slides were then mounted with Aquamount (Baxter).

Dual antibody immunocytochemistry was performed using antibodies to CD5, CD2, CD4, CD8, NK marker, or HIS 45 (a T cell marker) in conjunction with anti-$\alpha_d$ antibody in an attempt to determine the phenotype of cells expressing $\alpha_d$. No double labeled cells were detected with CD2/$\alpha_d$ or HIS 45/$\alpha_d$. In the splenic red pulp of a normal rat $\alpha_d$ labeled clusters of small cells which were found to also express CD5. It was not determined if the CD5 positive cells were T cells or B cells. A small population of $\alpha_d$ expressing cells in the red pulp were also determined to express CD4. In addition, a subset of NK cells and CD8 positive cells were also identified that expressed $\alpha_d$. Therefore, $\alpha_d$ expression in the spleen was found on a subset of T cells, possibly a subset of B cells, a subset of NK cells, and subset of macrophages.

Expression of $\alpha_d$ on Large Granulocytic Leukocytes (LGL) Tumor Cells from the F344 Rat Model A rat model for LGL-leukemia was designed in the F344 rat using tumor cells received from the National Cancer Institute which were injected intravenously into 3 male F344 rats (1 million cells each). The disease took three months to manifest, at which time several of the animals were sacrificed and tissues examined by FACS and histochemical analysis.

For FACS analysis, a portion of the spleen was removed and a single-cell suspension prepared as described in example below. Briefly, the splenic tissue was minced into smaller pieces with scissors and passed through a wire mesh screen in the presence of D-PBS. The cells were pelleted by centrifugation and resuspended in 30 ml D-PBS. Histopaque gradients (Sigma) were prepared by layering 5.0 ml of the cell suspension over 5.0 ml of Histopaque within a 15 ml centrifuge tube. The gradients were centrifuged for 30 minutes at 1500 rpm using a Beckman Tabletop Centrifuge and the cellular layer collected, washed once in D-PBS, and counted by hemacytometer. The cells were resuspended in FACS buffer (RPMI-1640/2% FBS, 0.2% sodium azide) to a density of $1 \times 10^6$ cells/sample.

The cells were two-color stained by incubation with the hamster anti-rat $\alpha_d$ antibody 205C conjugated to biotin (10 $\mu$g/ml) and one of a series of antibodies against rat cellular markers that were FITC conjugated. These second antibodies included anti-macrophage-FITC, anti-CD3-FITC, and anti-IgM (B-cell)-FITC antibodies (all from PharMingen), in addition to a FITC-conjugated antibody with NK cell specificity (Harlan). The FITC conjugated antibodies were each used at 10 $\mu$l/sample.

The samples were first incubated on ice for 30 minutes with 205C-biotin antibody, washed three times in FACS buffer, and resuspended in 1.0 ml FACS buffer. The FITC conjugates were added along with 5 $\mu$l streptavidin-PE (Pharmigen) and the samples placed on ice for 30 minutes. After incubation, the samples were washed three times in FACS buffer and resuspended in 200 $\mu$l FACS buffer. Samples were examined using a Becton Dickinson FACscan and the data analyzed using Lysis II software (Becton Dickinson).

The results overwhelmingly demonstrated expression of $\alpha_d$ on the surface of NK, or LGL, cells. Cells which stained positive for B-cell and T-cell markers did not reveal $\alpha_d$ expression and cells which stained using the macrophage marker showed only a slight degree of $\alpha_d$ expression. It is believed that, at this point in the disease, the spleen is composed predominantly of NK tumor cells, consistent with the observation that a large population of spleen cells stained for expression of both the NK marker and $\alpha_d$.

These observations were also consistent with results from a parallel experiment using peripheral blood cells also collected from the same animals and processed as above for FACS. Results using peripheral blood cells indicated that circulating NK cells also express $\alpha_d$, while cells expressing other cellular markers in the blood did not show $\alpha_d$ expression. Results using peripheral blood cells, however, were not as dramatic as the splenic cell results presumably due to a difference in the percentage of different cell types present in the spleen and peripheral blood.

In subsequent FACS analysis of rat spleen cells from these model animals, identical results were obtained. Upon further analysis using the above method of cell preparation, the LGL tumor cells have also shown staining for expression of CD18 as well as CD11a, CD11b, and CD11c.

Histochemical analysis was carried out on both normal and NK F344 diseased tissue using the ICC procedure described above. Preliminary data indicated that $\alpha_d$ was expressed in NK F344 tumor lung and liver tissue, but was either not detected or was expressed in very low levels in normal respective tissue. Diseased lung tissue showed expression of $\alpha_d$ on small and large clusters of cells, as well as individual cells throughout the lung. The NK F344 liver showed weak labeling around vessels and other cells throughout the tissue. Antibodies to the other $\beta_2$ integrins indicated these molecules are expressed at similar levels in both normal and diseased tissue although labeling patterns did vary.

In parallel analyses, the normal rat thymus showed slight $\alpha_d$ expression in scattered cells in the cortex, while the F344 NK thymus showed an increased level of $\alpha_d$ expression. While the normal spleen showed expression in the red pulp, the NK spleen had cluster labeling throughout the tissue.

The NK spleen was then tested at weekly intervals from onset of the disease which indicated that the level of expression of $\alpha_d$ increased up until the third week and then dropped off at the fourth week.

EXAMPLE 27

Assay for Inhibition of NK-Tumor Cell-Induced Target Cell Lysis Using Anti-$\alpha_d$ Monoclonal Antibodies A specific function of NK cells is to target and kill virally-infected and foreign cells. To assay the ability of NK cells to lyse a specific target cell, target cells are labeled with $^{51}$chromium and as lysis occurs, increasing radioactivity is detected in the medium. It was postulated that $\alpha_d$, previously shown to be expressed on NK cells, might participate in NK targeted cell killing. To test this hypothesis, tumor cells were pre-incubated with $\alpha_d$ antibodies in order to assess the role of $\alpha_d$ in a functional assay.

Preparation of $\alpha_d$ Positive NK-tumor Effector Cells

F344 rats were injected with NK tumor cells, originally obtained from the National Cancer Institute and passaged through animals three to four weeks prior to removal of the spleen. The spleen was removed and was minced into small pieces which were passed through a wire-mesh screen in the presence of D-PBS. The resultant cell suspension was centrifuged at 1500 rpm in a Beckman tabletop centrifuge for 10 minutes at room temperature. The supernatant was aspirated and the cell pellet resuspended in 30 ml D-PBS.

Histopaque separation of mononuclear cells from blood was then carried out as follows. Five ml Histopaque (Sigma) was added to six 15 ml centrifuge tubes on top of which was layered 5.0 ml of the cell suspension described above. The cells were centrifuged at 1500 rpm for 30 minutes in a Beckman Tabletop centrifuge at room temperature. The cellular layer was collected, pooled and counted by hemacytometer. Several dilutions of the isolated tumor cells were prepared in D-PBS buffer and subsequently incubated in the presence or absence of anti-rat $\alpha_d$ antibodies at a concentration of 50 $\mu$g/ml Control antibodies included an anti-rat CD18 antibody and an anti-rat ICAM-I antibody which were also incubated with the cells at 50 $\mu$g/ml concentration. Tumor cells were pre-incubated with antibodies at 37° C. for approximately 30 minutes prior to the assay.

Chromium Labeling of Yak-1 Target Cells

Yak-1 cells (ATCC), a mouse lynphoma cell line, were cultured in 10% FBS/RPMI 1640. Cells were harvested by centrifugation and resuspended at a density of approximately $1 \times 10^7$ cells in 1.5 to 4.0 ml of RPMI "test media" made from 500 ml RPMI 1640, 5 ml Pen-Strep antibiotic solution, and 10 ml FBS. Approximately 200 to 300 $\mu$Ci of $^{51}$chromium was added to the Yak-1 cell suspension which were then incubated at 37° C. for 45 to 60 minutes with gentle mixing. Following incubation, the volume was increased to 50 ml with test media and the cells pelleted by centrifugation. The supernatant was discarded and cells were suspended in 1 to 3 ml test media and adjusted to a density of $5\times10^4$ cells/ml. Non-labeled Yak-1 cells were also prepared at a concentration of $1\times10^7$ cell/ml to use as autologous controls.

The activity of labeled cells was determined by assaying 100 µl of the labeled cell suspension in triplicate using a gamma counter.

Short-Term Chromium Release Assay

NK effector cells of each dilution were plated in triplicate in a volume of 100 µl test media in a 96-well microtiter plate and 100 µl labeled Yak-1 cells were added to each well. Autologous, i.e., spontaneous or background, release was obtained by incubating 100 µl of labeled cells with non-labeled Yak cells at each of the effector dilutions. Total $^{51}$chromium release was obtained by adding 1.0% Triton® to target cells in one set of wells. Spontaneous release was measured by the amount of $^{51}$chromium found in wells with only target cells. Incubation of effector/target cells was carried out for four hours at 37° C. after which the plates were centrifuged and 100 µl supernatant collected from each well and radioactivity measured.

Cytolytic activity was calculated by using the following formula:

$$\frac{\% \text{ cytolytic}}{\text{activity}} = \frac{\text{cmp of sample} - \text{spontaneous release cpm}}{100\% \text{ release cmp} - \text{spontaneous release cmp}} \times 100$$

Results indicated that neither hamster anti-rat $\alpha_d$ antibodies (including 199M and 205C) nor mouse anti-rat $\alpha_d$ antibodies (226A, 226B, 226C, 226D, 226F, 226G, 226H, and 226I) effected the ability of NK tumor cells to kill or lyse the labeled target cells.

EXAMPLE 28

Isolation of Mouse cDNA Clones

Isolation of a mouse $\alpha_d$ homolog was attempted.

Cross-species hybridization was performed using two PCR-generated probes: a 1.5 kb fragment corresponding to bases 522 to 2047 from human clone 19A2 (SEQ ID NO: 1), and a 1.0 kb rat fragment which corresponds to bases 1900 to 2900 in human clone 19A2 (SEQ ID NO: 1). The human probe was generated by PCR using primer pairs designated ATM-2 and 9-10.1 set out in SEQ ID NOS: 38 and 39, respectively; the rat probe was generated using primer pairs 434L and 434R, set out in SEQ ID NOS: 34 and 35, respectively. Samples were incubated at 94° C. for 4 minutes and subjected to 30 cycles of the temperature step sequence: 94° C.; 50° C. 2 minutes; 72° C., 4 minutes.

```
5'-GTCCAAGCTGTCATGGGCCAG-3'     (SEQ ID NO: 38)

5'-GTCCAGCAGACTGAAGAGCACGG-3'   (SEQ ID NO: 39)
```

The PCR products were purified using the Qiagen Quick Spin kit according to manufacturer's suggested protocol, and approximately 180 ng DNA was labeled with 200 µCi [$^{32}$P]-dCTP using a Boehringer Mannheim Random Primer Labeling kit according to manufacturer's suggested protocol. Unincorporated isotope was removed using a Centri-sep Spin Column (Princeton Separations, Adelphia, N.J.) according to manufacturer's suggested protocol. The probes were denatured with 0.2 N NaOH and neutralized with 0.4 M Tris-HCl, pH 8.0, before use.

A mouse thymic oligo dT-primed cDNA library in lambda ZAP® II (Stratagene) was plated at approximately 30,000 plaques per 15 cm plate. Plaque lifts on nitrocellulose filters (Schleicher & Schuell, Keene, N.H.) were incubated at 50° C. with agitation for 1 hour in a prehybridization solution (8 ml/lift) containing 30% formamide. Labeled human and rat probes were added to the prehybridization solution and incubation continued overnight at 50° C. Filters were washed twice in 2×SSC/0.1% at room temperature, once in 2×SSC/0.1% SDS at 37° C., and once in 2×SSC/0.1% SDS at 42° C. Filters were exposed on Kodak X-Omat AR film at –80° C. for 27 hours with an intensifying screen.

Four plaques giving positive signals on duplicate lifts were restreaked on LB medium with magnesium (LBM)/carbenicillin (100 mg/ml) plates and incubated overnight at 37° C. The phage plaques were lifted with Hybond® filters (Amersham), probed as in the initial screen, and exposed on Kodak X-Omat AR film for 24 hours at –80° C. with an intensifying screen.

Twelve plaques giving positive signals were transferred into low Mg$^{++}$ phage diluent containing 10 mM Tris-HCl and 1 mM MgCl$_2$. Insert size was determined by PCR amplification using T3 and T7 primers (SEQ ID NOS: 13 and 14, respectively) and the following reaction conditions. Samples were incubated at 94° C. for 4 minutes and subjected to 30 cycles of the temperature step sequence: 94° C., for 15 seconds; 50° C., for 30 seconds; and 72° C. for 1 minute.

Six samples produced distinct bands that ranged in size from 300 bases to 1 kb. Phagemids were released via co-infection with helper phage and recircularized to generate Bluescript® SK$^-$ (Stratagene). The resulting colonies were cultured in LBM/carbenicillin (100 mg/ml) overnight. DNA was isolated with a Promega Wizard miniprep kit (Madison, Wis.) according to manufacturer's suggested protocol. EcoRI restriction analysis of purified DNA confirmed the molecular weights which were detected using PCR. Insert DNA was sequenced with M13 and M13 reverse. I primers set out in SEQ ID NOS: 40 and 41, respectively.

```
5'-TGTAAAACGACGGCCAGT-3'    (SEQ ID NO: 40)

5'-GGAAACAGCTATGACCATG-3'   (SEQ ID NO: 41)
```

Sequencing was performed as described in Example 4.

Of the six clones, only two, designated 10.3-1 and 10.5-2, provided sequence information and were identical 600 bp fragments. The 600 bp sequence was 68% identical to a corresponding region of human $\alpha_d$, 40% identical to human CD11a, 58% identical to human CD11c, and 54% identical to mouse CD11b. This 600 bp fragment was then utilized to isolate a more complete cDNA encoding a putative mouse $\alpha_d$ homolog.

A mouse splenic cDNA library (oligo dT$^-$ and random-primed) in lambda Zap® II (Stratagene) was plated at $2.5\times10^4$ phage/15 cm LBM plate. Plaques were lifted on Hybond® nylon transfer membranes (Amersham), denatured with 0.5 M NaOH/1.5 M NaCl, neutralized with 0.5 M Tris Base/1.5 M NaCl/11.6 HCl, and washed in 2×SSC. The DNA was cross-linked to filters by ultraviolet irradiation.

Approximately 500,000 plaques were screened using probes 10.3-1 and 10.5-2 previously labeled as described supra. Probes were added to a prehybridization solution and incubated overnight at 50° C. The filters were washed twice in 2×SSC/0.1% SDS at room temperature, once in 2×SSC/0.1% SDS at 37° C., and once in 2×SSC/0.1% SDS at 42° C. Filters were exposed on Kodak X-Omat AR film for 24 hours at –80° C. with an intensifying screen. Fourteen plaques giving positive signals on duplicate lifts were subjected to a secondary screen identical to that for the initial screen except for additional final high stringency washes in 2×SSC/0.1% SDS at 50° C., in 0.5×SSC/0.1% SDS at 50° C., and at 55° C. in 0.2×SSC/0.1% SDS. The filters were exposed on Kodak X-Omat AR film at −80° C. for 13 hours with an intensifying screen.

Eighteen positive plaques were transferred into low Mg$^{++}$ phage diluent and insert size determined by PCR amplification as described above. Seven of the samples gave single bands that ranged in size from 600 bp to 4 kb. EcoRI restriction analysis of purified DNA confirmed the sizes observed from PCR and the DNA was sequenced with primers M13 and M13 reverse.1 (SEQ ID NOS: 40 and 41, respectively).

One clone designated B3800 contained a 4 kb insert which corresponded to a region 200 bases downstream of the 5' end of the human $\alpha_d$ 19A2 clone and includes 553 bases of a 3' untranslated region. Clone B3800 showed 77% identity to a corresponding region of human $\alpha_d$, 44% identity to a corresponding region of human CD11a, 59% identity to a corresponding region of human CD11c, and 51% identity to a corresponding region of mouse CD11b. The second clone A1160 was a 1.2 kb insert which aligned to the 5' end of the coding region of human $\alpha_d$ approximately 12 nucleic acids downstream of the initiating methionine. Clone A1160 showed 75% identity to a corresponding region of human $\alpha_d$, 46% identity to a corresponding region of human CD11a, 62% identity to a corresponding region of human CD11c, and 66% identity to a corresponding region of mouse CD11b.

Clone A1160, the fragment closer to the 5' end of human clone 19A2, is 1160 bases in length, and shares a region of overlap with clone B3800 starting at base 205 and continuing to base 1134. Clone A1160 has a 110-base insertion (bases 704–814 of clone A1160) not present in the overlapping region of clone B3800. This insertion occurs at a probable exon-intron boundary [Fleming, et al., *J.Immunol.* 150:480–490 (1993)] and was removed before subsequent ligation of clones A1160 and B3800.

Rapid Amnplification of 5' cDNA End of the Putative Mouse $\alpha_d$ Clone

RACE PCR [Frohman, "RACE: Rapid Amplification of cDNA Ends," in PCR Protocols: A Guide to Methods and Applications, Innis, et al. (eds.) pp. 28–38, Academic Press-:New York (1990)] was used to obtain missing 5' sequences of the putative mouse $\alpha_d$ clone, including 5' untranslated sequence and initiating methionine. A mouse splenic RACE-Ready kit (Clontech, Palo Alto, Calif.) was used according to the manufacturer's suggested protocol. Two antisense, gene-specific primers, A1160 RACE1-primary and A1160 RACE2-nested (SEQ ID NOS: 42 and 43), were designed to perform primary and nested PCR.

```
5'-CGACATCTTCACTGCCTCTAGG-3'      (SEQ ID NO: 42)

5'-GGCGGACAGTCAGACGACTGTCCTG-3'   (SEQ ID NO: 43)
```

The primers, SEQ ID NOS: 42 and 43, correspond to regions starting 302 and 247 bases from the 5' end, respectively. PCR was performed as described, supra, using the 5' anchor primer (SEQ ID NO: 44) and mouse spleen cDNA supplied with the kit.

CTGGTTCGGCCCACCTCTGAAGGTTCCA-GAATCGATAG (SEQ ID NO: 44)

Electrophoresis of the PCR product revealed a band approximately 280 bases in size, which was subcloned using a TA cloning kit (Invitrogen) according to manufacturer's suggested protocol. Ten resulting colonies were cultured, and the DNA isolated and sequenced. An additional 60 bases of 5' sequence were identified by this method, which correspond to bases 1 to 60 in SEQ ID NO: 45.

Characteristics of the Mouse cDNA and Predicted Amino Acid Sequence

A composite sequence of the mouse cDNA encoding a putative homolog of human $\alpha_d$ is set out in SEQ ID NO: 45. Although homology between the external domains of the human and mouse clones is high, homology between the cytoplasmic domains is only 30%. The observed variation may indicate C-terminal functional differences between the human and mouse proteins. Alternatively, the variation in the cytoplasmic domains may result from splice variation, or may indicate the existence of an additional $\beta_2$ integrin gene(s).

At the amino acid level, the mouse cDNA predicts a protein (SEQ ID NO: 46) with 28% identity to mouse CD11a, 53% identity to mouse CD11b, 28% identity to human CD11a, 55% identity to human CD11b, 59% identity to human CD11c, and 70% identity to human $\alpha_d$. Comparison of the amino acid sequences of the cytoplasmic domains of human $\alpha_d$ and the putative mouse homolog indicates regions of the same length, but having divergent primary structure. Similar sequence length in these regions suggests species variation rather than splice variant forms. When compared to the predicted rat polypeptide, Example 20, supra, mouse and rat cytoplasmic domains show greater than 60% identity.

EXAMPLE 29

Isolation of Additional Mouse $\alpha_d$ cDNA Clones for Sequence Verification

In order to verify the nucleic and amino acids sequences describe in Example 28 for mouse $\alpha_d$, additional mouse sequences were isolated for the purposes of confirmation.

Isolation of mouse cDNA by hybridization with two homologous $\alpha_d$ probes (3' and 5') was performed using both a mouse splenic random primed library and an oligo dT-primed cDNA library in lambda ZAP® II (Strategene). The library was plated at 5×10⁵ phage per 15 cm LBM plate. Plaques were lifted on Hybond® nylon membranes (Amersham), and the membranes were denatured (0.5 M NaOH/1.5 M NaCl), neutralized (0.5 M Tris Base/1.5 M NaCl/11.6 M HCl) and washed (2×SSC salt solution). DNA was cross-lined to filters by ultraviolet irradiation.

Probes were generated using primers described below in a PCR reaction under the following conditions. Samples were held at 94° C. for 4 minutes and then run through 30 cycles of the temperature step sequence (94° C. for 15 seconds; 50° C. for 30 seconds; 72° C. for 1 minute in a Perkin-Elmer 9600 thennocycler).

The 3' probe was approximately 900 bases long and spanned a region from nucleotides 2752 to 3651 (in SEQ ID NO: 1) (5'3') and was produced with primers 11.b-1/2FOR11 and 11.b-1/2REV2 as shown in SEQ ID NOS: 69 and 74, respectively. This probe was used in a first set of lifts.

The 5' probe was approximately 800 bases long and spanned a region from nucleotides 149 to 946 (in SEQ ID NO: 1) (5'→3') arid was produced with primers 11.b-1/2FOR1 and 11.a-1/1REV1 as shown in SEQ ID NOS: 50 and 85, respectively). This probe was used in a second set of lifts.

In a third set of lifts, both probes described above were used together on the same plates.

Approximately 500,000 plaques were screened using the two probes from above which were labeled in the same way as described in Example 20. Labeled probes were added to a prehybridization solution, containing 45% formamide, and incubated overnight at 50° C. Filters were washed twice in 2×SSC/0.1% SDS at room temperature (22° C.). A final wash was carried out in 2×SSC/0.1% SDS at 50° C. Autoradiography was for 19 hours at −80° C. on Kodak X-Omat AR film with an intensifying screen.

Thirteen plaques giving positive signals on at least duplicate lifts were subjected to a secondary screen performed as described for the initial screen except that both the 3' and 5' labeled probes were used for hybridization and an additional final wash was incorporated using 2×SSC/0.1% SDS at 65° C. Autoradiography was performed as described above for 2.5 hours.

Thirteen plaques (designated MS2P1 through MS2P13) giving positive signals were transferred into low Mg$^{-+}$ phage diluent. Insert size was detennined by PCR amplification (Perkin-Elmer 9600 thermocycler) using T3 and T7 primers which anneal to Bluescript phagemid in ZAP® II (sequence previously described) under the same conditions shown above. Band sizes ranged from 500 bases to 4 Kb.

Phagemids were isolated, prepared, and sequenced with M13 and M13 reverse.1 primers (SEQ ID NOS: 40 and 41, respectively). Five of the thirteen clones; MS2P-3, MS2P-6, MS2P-9, MS2P-12, and MS2P-13, were sequenced, and together, represented a region from approximately base 200 at the 5' end to about 300 bases past a first stop codon at the 3' end.

Automated sequencing was performed as described in Example 4 by first using M13 and M13 reverse.1 primers (SEQ ID NOS: 40 and 41, respectively) to sequence the ends of each clone and to determine its position relative to construct #17 (SEQ ID NO: 45). Each clone was then completely sequenced using the appropriate primers (listed below) for that particular region.

```
                                         (SEQ ID NO: 50)
11.b-1/2FOR1      5'-GCAGCCAGCTTCGGACAGAC-3'

(SEQ ID NO: 60)
11.a-1/1FOR2      5'-CCGCCTGCCACTGGCGTGTGC-3'

(SEQ ID NO: 61)
11.a-1/1FOR3      5'-CCCAGATGAAGGACTTCGTCAA-3'

(SEQ ID NO: 62)
11.b-1/2FOR4      5'-GCTGGGATCATTCGCTATGC-3'

(SEQ ID NO: 63)
11.b-1/2FOR5      5'-CAATGGATGGACCAGTTCTGG-3'

(SEQ ID NO: 64)
11.b-1/2FOR6      5'-CAGATCGGCTCCTACTTTGG-3'

(SEQ ID NO: 65)
11.b-1/2FOR7      5'-CATGGAGCCTCGAGACAGG-3'

(SEQ ID NO: 66)
11.b-1/2FOR8      5'-CCACTGTCCTCGAAGCTGGAG-3'

(SEQ ID NO: 67)
11.b-1/2FOR9      5'-CTTCGTCCTGTGCTGGCTGTGGGCTC-3

(SEQ ID NO: 68)
11.b-1/2FOR10     5'-CGCCCTGGCATGTGAGGCTGAG-3'

(SEQ ID NO: 69)
11.b-1/2FOR11     5'-CCGTGATCAGTAGGCAGGAAG-3'

(SEQ ID NO: 70)
11.b-1/2FOR12     5'-GTCACAGAGGGAACCTCC-3'

(SEQ ID NO: 71)
11.b-1/2FOR13     5'-GCTCCTGAGTGAGGCTGAAATCA-3'

(SEQ ID NO: 72)
11.b-1/2FOR14     5'-GAGATGCTGGATCTACCATCTGC-3'

(SEQ ID NO: 73)
11.b-1/2FOR15     5'-CTGAGCTGGGAGATTTTTATGG-3'

(SEQ ID NO: 74)
11.b-1/2REV2      5'-GTGGATCAGCACTGAAATCTG-3'

(SEQ ID NO: 75)
11.b-1/2REV3      5'-CGTTTGAAGAAGCCAAGCTTG-3'

(SEQ ID NO: 76)
11.b-1/2REV4      5'-CACAGCGGAGGTGCAGGCAG-3'

(SEQ ID NO: 77)
11.b-1/2REV5      5'-CTCACTGCTTGCGCTGGC-3'

(SEQ ID NO: 78)
11.b-1/2REV6      5'-CGGTAAGATAGCTCTGCTGG-3'

(SEQ ID NO: 79)
11.b-1/2REV7      5'-GAGCCCACAGCCAGCACAGG-3'

(SEQ ID NO: 80)
11.b-1/2REV8      5'-GATCCAACGCCAGATCATACC-3'

(SEQ ID NO: 81)
11.b-1/2REV9      5'-CACGGCCAGGTCCACCAGGC-3'

(SEQ ID NO: 82)
11.b-1/2REV10     5'-CACGTCCCCTAGCACTGTCAG-3'

(SEQ ID NO: 83)
11.b-1/2REV11     5'-CCATGTCCACAGAACAGAGAG-3'

(SEQ ID NO: 83)
11.b-1/2REV12     5'-TTGACGAAGTCCTTCATCTGGG-3'

(SEQ ID NO: 84)
11.b-1/2REV13     5'-GAACTGCAAGCTGGAGCCCAG-3'

(SEQ ID NO: 85)
11.a-1/1REV1      5'-CTGGATGCTGCGAAGTGCTAC-3'

(SEQ ID NO: 86)
11.a-1/1REV2      5'-GCCTTGGAGCTGGACGATGGC-3'
```

Sequences were edited, aligned, and compared to a previously isolated mouse $\alpha_d$ sequence (construct #17, SEQ ID NO: 45).

Alignment of the new sequences revealed an 18 base deletion in construct #17 beginning at nucleotide 2308; the deletion did not cause a shift in the reading frame. Clone MS2P-9, sequenced as described above, also revealed the same 18 base deletion. The deletion has been observed to occur in 50% of mouse clones that include the region but has not been detected in rat or human $\alpha_d$ clones. The eighteen base deletion is characterized by a 12 base palindromic sequence AAGCAGGAGCTCCTGTGT (SEQ ID NO: 91). This inverted repeat in the nucleic acid sequence is self-complementary and may form a loop out, causing cleavage during reverse transcription. The mouse $\alpha_d$ sequence which includes the additional 18 bases is set forth in SEQ ID NO: 52; the deduced amino acid sequence is set forth in SEQ ID NO: 53.

EXAMPLE 30
In situ Hybridizations in Mouse

Tissue distribution was then determined for mouse $\alpha_d$ in order to provide a comparison to that in humans, described in Example 6.

A single stranded 200 bp mRNA probe was generated from a DNA template, corresponding to nucleotides 3460 to 3707 in the cytoplasmic tail region of the murine cDNA, by in vitro RNA transcription incorporating $^{35}$S-UTP (Amersham).

Whole mouse embryos (harvested at days 11–18 after fertilization) and various mouse tissues, including spleen, kidney, liver, intestine, and thymus, were hybridized in situ with the radiolabeled single-stranded mRNA probe.

Tissues were sectioned at 6 µm thickness, adhered to Vectabond (Vector Laboratories, Inc., Burlingame, Calif.) coated slides, and stored at −70° C. Prior to use, slides were removed from −70° C. and placed at 50° C. for approximately 5 minutes. Sections were fixed in 4% parafornaldehyde for 20 minutes at 4° C., dehydrated with an increasing ethanol gradient (70–95–100%) for 1 minute at 4° C. at each concentration, and air dried for 30 minutes at room temperature. Sections were denatured for 2 minutes at 70° C. in 70% formamide/2xSSC, rinsed twice in 2xSSC, dehydrated with the ethanol gradient described supra and air dried for 30 minutes. Hybridization was carried out overnight (12–16 hours) at 55° C. in a solution containing $^{35}$S-labeled riboprobes at 6x10$^5$ cpm/section and diethylpyrocarbonate (DEPC)-treated water to give a final concentration of 50% formamide, 0.3 M NaCl, 20 mM Tris-HCl, pH 7.5, 10% dextran sulfate, 1xDenhardt's solution, 100 mM dithiothreitol (DTT) and 5 mM EDTA. After hybridization, sections were washed for 1 hour at room temperature in 4xSSC/10 mM DTT, 40 minutes at 60° C. in 50% formamide/2xSSC/10 mM DTT, 30 minutes at room temperature in 2xSSC, and 30 minutes at room temperature in 0.1xSSC. The sections were dehydrated, air dried for 2 hours, coated with Kodak NTB2 photographic emulsion, air dried for 2 hours, developed (after storage at 4° C. in complete darkness) and counterstained with hematoxylin/eosin.

Spleen tissue showed a strong signal primarily in the red pulp. This pattern is consistent with that of tissue macrophage distribution in the spleen, but does not exclude other cell types.

EXAMPLE 31

Generation of Mouse Expression Constructs

In order to construct an expression plasmid including mouse cDNA sequences exhibiting homology to human $\alpha_d$, inserts from clones A1160 and B3800 were ligated. Prior to this ligation, however, a 5' leader sequence, including an initiating methionine, was added to clone A1160. A primer designated "5' PCR leader" (SEQ ID NO: 47) was designed to contain: (1) identical nonspecific bases at positions 1–6 allowing for digestion; (2) a BamHI site (underlined in SEQ ID NO: 47) from positions 7–12 to facilitate subcloning into an expression vector; (3) a consensus Kozak sequence from positions 13–18, (4) a signal sequence including a codon for an initiating methionine (bold in SEQ ID NO: 47), and (5) an additional 31 bases of specifically overlapping 5' sequence from clone A1160 to allow primer annealing. A second primer designated "3' end frag" (SEQ ID NO: 48) was used with primer "5' PCR leader" to amplify the insert from clone A1160.

```
5'-AGTTACGGATCCGGCACCATGAC-         (SEQ ID NO:47)
   -CTTCGGCACTGTGATCCTCCTGTGTG-3'

5'-GCTGGACGATGGCATCCAC-3'            (SEQ ID NO:48)
```

The resulting PCR product did not digest with BamHI, suggesting that an insufficient number of bases preceded the restriction site, prohibiting recognition by the enzyme. The length of the "tail" sequence preceding the BamHI site in the 5' primer (SEQ ID NO: 47) was increased and PCR was repeated on the amplification product from the first PCR. A 5' primer, designated mAD.5'.2 (SEQ ID NO: 49), was designed with additional nonspecific bases at positions 1–4 and an additional 20 bases specifically overlapping the previously employed "5' PCR leader" primer sequences.

5'-GTAGAGTTACGGATCCGGCACCAT-3' (SEQ ID NO: 49).

Primers "mAD.5'.2" and "3' end frag" were used together in PCR with the product from the first amplification as template. A resulting secondary PCR product was subcloned into plasmid pCRtmII (Invitrogen) according to manufacturer's suggested protocol and transfomed into competent One shot cells (Invitrogen). One clone containing the PCR product was identified by restriction enzyme analysis using BamHI and EcoRI and sequenced. After the sequence was verified, the insert was isolated by digestion with BamHI and EcoRI and gel purified.

The insert from clone B3800 was isolated by digestion with EcoRI and NotI, gel purified, and added to a ligation reaction which included the augmented A1160 BamHI/EcoRI fragment. Ligation was allowed to proceed for 14 hours at 14° C. Vector pcDNA.3 (Invitrogen), digested with BamHI and NotI, was added to the ligation reaction with additional ligase and the reaction was continued for another 12 hours. An aliquot of the reaction mixture was transformed into competent E. coli cells, the resulting colonies cultured, and one positive clone identified by PCR analysis with the primers 11.b-1/2FOR1 and 11.b-1/2REV11 (SEQ ID NOS: 50 and 51, respectively). These primers bridge the A1160 and B3800 fragments, therefore detection of an amplification product indicates the two fragments were ligated. The sequence of the positive clone was verified with the primers set out in SEQ ID NOS: 50 and 51, which amplify from base 100 to 1405 after the initiating methionine.

EXAMPLE 32

Construction of a Knock-out Mouse

In order to more accurately assess the immunological role of the protein encoded by the putative mouse $\alpha_d$ cDNA, a "knock-out" mouse is designed wherein the genomic DNA sequence encoding the putative $\alpha_d$ homolog is disrupted by homologous recombination. The significance of the protein encoded by the disrupted gene is thereby assessed by the absence of the encoded protein. Generation of "knock-out" mice is described in Deng, et al., *Mol.Cell.Biol.* 13:2134–2140 (1993).

Design of such a mouse begins with construction of a plasmid containing sequences to be "knocked out" by homologous recombination events. A 750 base pair fragment of the mouse cDNA (corresponding to nucleotides 1985 to 2733 in SEQ ID NO: 45) was used to identify a mouse genomic sequence encoding the putative mouse $\alpha_d$ homolog from a λFIXII genomic library. Primary screening resulted in 14 positive plaques, seven of which were confirmed by secondary screening. Liquid lysates were obtained from two of the plaques giving the strongest signal and the λ DNA was isolated by conventional methods. Restriction mapping and Southern analysis confirmed the authenticity of one clone, designated 14-1, and the insert DNA was isolated by digestion with NotI. This fragment was cloned into Bluescript® SKII+.

In order to identify a restriction fragment of approximately 9 to 14 kb, a length reported to optimize the probability of homologous recombination events, Southern hybridization was performed with the 750 bp cDNA probe. Prior to hybridization, a restriction map was constructed for clone 14-1. A 12 kb fragment was identified as a possible candidate and this fragment was subcloned into pBluescript® SKII⁺ in a position wherein the mouse DNA is flanked by thymidine kinase encoding cassettes. Further analysis of this clone with an I domain probe (corresponding to nucleotides 454–1064 in SEQ ID NO: 45) indicated that the clone did not contain I domain encoding sequences.

Using the same I domain probe, the λFIXII genomic library was rescreened. Initially, six positive clones were detected, one of which remained positive upon secondary screening. DNA isolated from this clone reacted strongly in Southern analysis with an I domain probe. No reactivity was detected using the original 750 bp probe, however, indicating that this clone included regions 5' to nucleotides 1985–2773 of SEQ ID NO: 45.

Alternatively, the lack of hybridization to the 750 bp probe may have suggested that the clone was another member of the integrin family of proteins. To determine if this explanation was plausible, the 13 kb insert was subcloned into pBluescript® SKII⁺. Purified DNA was sequenced using primers corresponding to $\alpha_d$ I domain nucleic acid sequences 441–461, 591–612, 717–739, and reverse 898–918 in SEQ ID NO: 52. Sequence information was obtained using only the first 4441–4461 primer, and only the 5'-most exon of the I domain was efficiently amplified. The remainder of the I domain was not amplified. The resulting clone therefore comprised exon 6 of the mouse $\alpha_d$ gene, and intronic sequences to the 3' and 5' end of the exon. Exon 7 was not represented in the clone. After sequencing, a construct is generated containing neomycin resistance and thymidine kinase genes.

The neomycin resistance (neo$^r$) gene is inserted into the resulting plasmid in a manner that interrupts the protein coding sequence of the genomic mouse DNA. The resulting plasmid therefore contains a neo$^r$ gene within the mouse genomic DNA sequences, all of which are positioned within a thymidine kinase encoding region. Plasmid construction in this manner is required to favor homologous recombination over random recombination [Chisaka, et al., *Nature* 355:516–520 (1992)].

An alternative strategy was used to generate constructs useful for production of $\alpha_d$ knock out mice. Two sets of oligonucleotide primers were submitted to Genome Systems, Inc. (St. Louis, Mo.) for high stringency PCR analysis of a large-insert library made from genomic DNA of embryonic stem cells. The primers corresponded to the first and last exons of the I domain in $\alpha_d$. Three clones were identified, two of which, designated 1117 and 1118, were reactive with both primers and one, designated 1119, which only the primers from the last exon could amplify.

Identification of a Mouse Genomic $\alpha_d$ DNA

Plasmid DNA was prepared from bacterial lysates of clones 1117 and 1118 according to manufacturer's instructions (Genome Systems, Inc.) The $\alpha_d$ inserts were verified by PCR using the oligonucleotides madk.f1 (SEQ ID NO: 104) and madk.r1 (SEQ ID NO: 105) and madk.r2 (SEQ ID NO: 106).

```
madk.f1   TGTCCAGGACAAGAGATGGACATTGC   SEQ ID NO: 104
madk.r1   GAGCTATTTCATAGCAAGAATGGG     SEQ ID NO: 105
madk.r2   TATAGCATAGCGAATGATCC         SEQ ID NO: 106
```

Aliquots of both plasmids were digested with restriction enzymes BamHI, PstI, SacI, SalI, SmaI, XbaI, and XhoI (Boehringer Mannheim). Each digest sample was resolved on 0.8% agarose gel and the polynucleotides transferred onto Hybond®-N⁺ nucleic acid transfer membrane (Amersham) for analysis. The blot was probed with ³²P-random primed DNA generated using a 1.6 kb template obtained by PCR using oligos madfor 1 (SEQ ID NO: 107) and madrev 1 (SEQ ID NO: 108).

```
madfor 1   ATGGTCCGTGGAGTTGTGATC   SEQ ID NO: 107
madrev 1   TCGAGATCCACCAAACTGCAC   SEQ ID NO: 108
```

Hybridization was carried out at 42° C. overnight in SSPE buffer with 50% formamide. The labeled blot was washed five times in 2×SSPE at room temperature. Radiolabeled bands were visualized by exposure of the blot to Kodak X-Omat autoradiography film at −70° C. for two hours.

Two fragments of interest were identified from clone 1118: a SacI fragment of 4.1 kb and an XbaI fragment of 8.3 kb. The entire sample contents from the SacI and XbaI digests of clone 1118 were ligated into the vector pBluescriptR KS⁺ without further purification, and following ligation, the entire reaction contents were transformed into calcium-competent preparations of the *E. coli* strain TG1/lambda SmR. Resulting colonies were isolated and cultured overnight in 200 μl selective medium containing M13KO7 helper virus to replicate single stranded DNA. A 10 μl aliquot of supernatant from each well was then blotted onto Hybond®-N⁺ transfer membrane and hybridized with the same probe and protocol as described above. Cultures were expanded from nine positive clones and plasmid DNA was isolated from each culture using a Wizard® Plus Miniprep DNA Purification System (Promega). Restriction digests and PCR were used to confirm presence and size of inserts in the isolated plasmids.

Three clones were subjected to sequence analysis using the vector primers T3 and T7 and oligonucleotide primers corresponding to murine $\alpha_d$ sequences. Sequence comparison of these three clones with the murine cDNA using Geneworks software indicated that all three contained both exons 1 and 2 of murine $\alpha_d$. The longest clone, referred to as A, was an XbaI clone of 8280 kb length, and the two shorter clones, referred to as E and H, were identical SacI clones of 4112 kb length. The 8280 kb XbaI clone was selected for further development.

EXAMPLE 33

Cloning of Rabbit $\alpha_d$

Construction and Screening of the Rabbit cDNA Library

Identification of human $\alpha_d$ homologs in rats and mice led to the investigation of the existence of a rabbit homolog which would be useful in rabbit models of human disease states described infra.

Poly A⁺ RNA was prepared from a whole rabbit spleen using an Invitrogen FastTrack kit (San Diego, Calif.) according to manufacturer's suggested protocol and reagents supplied with the kit. From 1.65 g tissue, 73 μg poly A⁺ RNA were isolated. The rabbit spleen RNA was used to construct a ZAP® Express cDNA library using a kit from Stratagene (La Jolla, Calif.). Resulting cDNA was directionally cloned into EcoRI and XhoI sites in the lambda arms of a pBK-CMV phagemid vector. Gigapack® II Gold (Stratagene) was used to package the lambda arms into phage particles. The resulting library titer was estimated to be approximately 8×10⁵ particles, with an average insert size of 1.2 kb.

The library was amplified once by plating for confluent plaque growth and cell lysate was collected. The amplified library was plated at approximately 30,000 plaque forming units (pfu) per 150 mm plate with *E. coli* and the resulting mixture incubated for 12–16 hrs at 37° C. to allow plaque formation. Phage DNA was transferred onto Hybond® N+ nylon membranes (Amersham, Arlington Heights, Ill.). The membranes were hybridized with a mixture of two random primed radiolabeled mouse $\alpha_d$ PCR DNA probes. The first probe was generated from a PCR product spanning nucleotides 149–946 in SEQ ID NO: 52. The second probe was from a PCR product spanning nucleotides 2752–3651 in SEQ ID NO: 52. Probes were labeled by random priming (Boehringer Mannheim Random Primed DNA Labeling Kit) and the reaction mixture was passed over a Sephadex® G-50 column to remove unincorporated nucleotides. The hybridization solution was composed of 5×SSPE, 5×Denhardts, 1% SDS, 40% Formamide and the labeled probes at $1 \times 10^6$ dpm/ml. Hybridization was carried out at 42° C. for 16–18 hours. Filters were washed extensively in 2×SSPE/0.1% SDS at room temperature and exposed to X-ray film to visualize any hybridizing plaques.

Two clones with significant sequence homology to human $\alpha_d$ were identified. Clone #2 was approximately 800 bp in length and mapped to the 5' end of human $\alpha_d$. Clone #2 includes an initiating methionine and complete leader sequence. Clone #7 was approximately 1.5 kb and includes an initiating methionine. The 5' end of clone #7 overlapped that of clone #2, while the 3' sequences terminated at a point beyond the I domain sequences. Clone #7 was completely sequenced by the primer walking method. The nucleotide and deduced amino acid sequences for clone #7 are set out in SEQ ID NOs: 100 and 101, respectively.

The predicted N terminal amino acid sequence for rabbit $\alpha_d$ as determined from clones #2 and #7 indicated a protein with 73% identity with human $\alpha_d$, 65% identity with mouse $\alpha_d$, and 58% identity with mouse CD11b, human CD11b, and human CD11c. The nucleic acid sequence for clone #2 is set out in SEQ ID NO: 92; the predicted amino acid sequence is set out in SEQ ID NO: 93.

Isolation of a full length rabbit $\alpha_d$ cDNA was attempted using labeled rabbit clone # 7 and rescreening the cDNA library from which the fragment was derived. Twenty-five additional clones were identified with one, designated clone 49, determined to be the largest. Clone 49 was completely sequenced using the nested deletions technique. The nucleotide and amino acid sequences for clone 49 are set out in SEQ ID NOs: 102 and 103, respectively. Since clones #7 and #49 did not overlap, oligonucleotides were designed to be used as primers in a PCR with first strand rabbit spleen cDNA to isolate the missing sequence.

The relationship of the putative amino acid sequence of these two partial clones with that of other leukointegrins is described in Table 1.

TABLE 1

Percent identity of $\beta_2$ integrin family members on the amino acid level.

| | Human $\alpha_d$ | Rabbit #7 | Rabbit #49 |
|---|---|---|---|
| Human $\alpha_d$ | 100 | 74 | 80 |
| Mouse $\alpha_d$ | 70 | 67 | 74 |
| Rat $\alpha_d$ | 70 | 66 | 73 |
| Mouse CD11a | random* | 28 | 28 |
| Mouse CD11b | 55 | 59 | 53 |
| Human CD11a | 36 | 28 | 28 |
| Human CD11b | 60 | 58 | 55 |
| Human CD11c | 66 | 59 | 62 |

*If < 25% identity, it is just random alignment and not significant.

Isolation of a rabbit $\alpha_d$ clone allows expression of the protein, either on the surface of transfectants or as a soluble full length or truncated form. This protein is then used as an immunogen for the production of monoclonal antibodies for use in rabbit models of human disease states.

EXAMPLE 34

Isolation of Monkey $\alpha_d$

Preparation of Affinity Columns

In order to prepare an affinity column resin to isolate $\alpha_d$ from monkey spleen, 10 mg each of the anti-human $\alpha_d$ antibodies 212D and 217L were dialyzed overnight against coupling buffer containing 0.1 M $NaHCO_3$, 0.5 M NaCl, pH 8.3. Approximately 1.0 g of CNBr Sepharose® 4B (Pharmacia, Piscataway N.J.) was prepared according to the manufacturer's recommended protocol and 1.0 ml of the resin combined with each of the dialyzed antibodies. The resulting slurry was mixed by rotation overnight at 4° C. and coupled resin obtained by centrifugation for 5 minutes at 1000 rpm in a Beckman tabletop centrifuge. The nonabsorbed supernatant fraction was collected and assayed for the presence of uncoupled protein by spectrophotometer. Results indicated that all available antibody had bound to the gel matrix. Uncoupled active groups on the resins were blocked with 1 M ethanolamine for 2 hours at room temperature and the resins washed in a series of alternating high and low pH changes in Coupling buffer followed by a final wash using acetate buffer containing 0.1 M $NaC_2H_3O_2.3H_2O$ and 0.5 M NaCl, pH 4.0. Both resins were stored at 4° C. in Coupling buffer.

Preparation of Monkey Spleen

Female macaque spleens were obtained from the University of Washington's Regional Primate Center. Spleen tissue was injected with 100 U/ml collagenase D (Sigma) and minced into small pieces. Tissue pieces were then suspended in a small volume of Lysis Buffer containing 50 mM Tris, 150 mM NaCl, 2 mM $CaCl_2$, 2 mM $MgCl_2$, pH 8.0, with 1.0% Triton-X100 detergent and stored at −70° C. Protease inhibitors PLA (a mixture of Pepstatin A, leupeptin, and aprotinin, each from Sigma) and 4-(2-aminoethyl) benzene sulfonyl fluoride-HCl (AEBSF) (Nova Biochem, La Jolla, Calif.) were added to prevent proteolysis of protein during storage. Tissue was stored until a total of six macaque spleens was obtained.

Spleen tissue from the six monkeys was pooled and homogenized in a Waring blender, three cycles of ten seconds each, in TSA Lysis Buffer containing 25 mM Tris, 0.15 M NaCl, 0.02% $NaN_3$, 1.0% Triton®, 1×PLA and 0.1 mM AEBSF. Lysate was collected and placed on a rocking platform for one hour at 4° C., and then centrifuged for 15 minutes at 3000 rpm in a Beckman tabletop centrifuge. Supernatant was collected and the pelleted cellular debris discarded. A total volume of 550 ml of lysate was collected and precleared by incubating the lysate for 2 hours at 4° C. with CNBr Sepharose® previously treated in 1 M ethanolamine in order to block reactive sites. Following incubation, the resin was removed by centrifugation and the supernatant collected.

Affinity Purification and Sequencing

The spleen lysate prepared as described above was divided in half and combined individually with the 212D- and 217L-prepared CNBr Sepharose® gels. The resulting slurries were mixed with rotation for three days at 4° C., after which the nonabsorbed fraction was collected by centrifugation at 10 minutes 1500 rpm in a Beckman tabletop centrifuge and saved. The gels were transferred to 15 ml centrifuge tubes and washed sequentially in several volumes of D-PBS. Aliquots of approximately 100 μl of each gel were boiled briefly in reducing sample buffer containing 0.1 M Tris-HCl, pH 6.8, 2.0% SDS, 20% glycerol, 0.0002% bromophenol blue, 10% β-mercaptoethanol (final concentration 5%) and loaded onto and proteins resolved using a 6.0% polyacrylamide SDS gel (SDS-PAGE). The gel was Coomasie stained and proteins having molecular weights consistent with $\alpha_d$ and CD18 were detected along with a number of background proteins.

In an attempt to improve purification of the protein having the molecular weight similar to $\alpha_d$, two 100 μl aliquots of each gel with bound protein were washed by different means. In one method, gels were washed several times in buffer containing 150 mM NaCl, 10 mM Tris, 1.0% Triton-X100®, pH 8.0, and in a second method, gels were washed identically, but bound protein was eluted in a final wash with 0.05 M glycine, pH 2.4. As before, the eluted protein was boiled briefly in reducing sample buffer and resolved on a 6.0% SDS-PAGE gel. Coomasie staining detected only proteins consistent with $\alpha_d$ and CD18 from the resin washed in low pH glycine buffer, thus this isolation method was chosen. In order to isolate protein for sequencing, the remaining CNBr Sepharose® resin was washed four times as described above and approximately three quarters of the resin suspended in 2.0 ml 0.05 M glycine, pH 2.4, and vortexed vigorously. The resin was pelleted by centrifugation for 3 minutes and the nonabsorbed fraction collected. The gel was then washed once more in glycine buffer and this wash pooled with the previous nonabsorbed fraction. The pooled fractions were dialyzed against D-PBS overnight at 4° C. with two changes. After dialysis, the samples were dried down to reduce volumes to 1.0 ml.

For sequencing, the eluates were separated on 7.0% resolving gels and proteins transferred to Immobilon (PVDF) membranes (Millipore, Bedford Mass.) as described in Example 2. Briefly, the gels were washed once in deionized water and equilibrated for 15 to 45 minutes in 10 mM cyclohexylamino-propanesulfoic acid buffer (CAPS), pH 10.5, with 10% methanol. PVDF membranes were rinsed in both methanol and distilled water, then equilibrated in CAPS transfer buffer for 15 to 30 minutes. Proteins were transferred to PVDF membranes for 3 hours at 70 volts after which they were stained in filtered 0. 1% R250 Coomasie stain for 10 minutes. Membranes were washed to destained in 50% methanol/10% acetic acid three times, 10 minutes each wash, washed once more in filtered water, and dried.

Two predominant protein bands of approximately 150 kD and 95 kD were detected from both the 212D- and 217L-coupled resins which were consistent with proteins detected on the previously run analytical scale gels. A less distinct band was observed on the membrane derived from 217L-coupled resin located directly beneath the protein at 150 kD, but the band was not detected after the membrane was dried. The 150 kD band from each membrane was excised from the membrane and directly sequenced with an Applied Biosystems (Foster City, Calif.) Model 473A protein sequencer according to the manufacturer's suggested method.

Results indicated that the amino tenninal sequence of the monkey protein isolated using 212D-coupled resin had the amino acid sequence as set out in SEQ ID NO: 109, and the amino terminus of the protein isolated using 217L-coupled resin had the sequence shown in SEQ ID NO: 110. The "X" in SEQ ID NO: 110 indicates an indeterminable residue.

| 212D-Couple Protein | NLDVEEPTIFQEDA | SEQ ID NO: 109 |
|---|---|---|
| 217L-Coupled Protein | NLDVEEPTIFXEDA | SEQ ID NO: 110 |

A comparison of the monkey sequences with the amino terminal sequences of human $\alpha_d$ and other a chains in the $\beta_2$ integrin family is shown in Table 2.

TABLE 2

Comparison of Monkey $\alpha_d$ Amino Terminal Sequence With Human $\beta_2$ Subunits

| PROTEIN | SEQ ID NO: | AMINO TERMINAL SEQUENCE |
|---|---|---|
| Monkey $\alpha_d$ | 111 | F N L D V E E P T I F Q E D A |
| Human $\alpha_d$ | 112 | F N L D V E E P T I F Q E D A G G |
| Human CD11c | 113 | F N L D T E E L T A F V D S A G |
| Human CD11b | 114 | F N L D T E N A M T F Q E N A R G |

Based on the sequence identify, it can be concluded that both 212D and 217L recognize $\alpha_d$ in both macaque and human.

EXAMPLE 35

Characterization of 217L Antigen

Based on the N-terminal sequence of protein precipitated from monkey spleen in the previous example, it can be concluded that antibodies 217L and 212D recognize $\alpha_d$ protein in both monkey and human. Immunocytochemical (ICC) analysis and immunoprecipitation experiments, however, indicate that 217L has additional reactivity unshared by 212D. FACS and ICC experiments using antibodies to all a chains ruled out cross-reactivity of 217L with CD11c, the most closely related leukointegrin α chain, and CD11b. Therefore, it may be that the 217L antibody also recognizes either a conformational, glycosylation, or splice variant of $\alpha_d$ or a novel α chain which shares sequence homology with $\alpha_d$.

The unique distribution of the antigen recognized by antibody 217L in sarcoid lung tissue (see Example 18), with a non-overlapping staining pattern in relationship to CD11c, suggests that the antigen may have biological significance. Therefore, in order to more fully understand the significance of the 217L antigen, analysis of the protein and underlying DNA encoding the protein are required and various approaches are contemplated.

Immunoprecipitation of a protein complex from human dendritic cells or peripheral blood is carried out using the antibody 217L, followed by N-terminal sequence of the precipitated proteins. Sequence analysis will reveal whether the protein recognized on peripheral blood cells shares amino terminal identity with $\alpha_d$. The protein precipitated from dendritic cells or peripheral blood cells is then treated with deglycosylating enzymes and compared to CD11c and $\alpha_d$ precipitated from other sources to provide a comparison of molecular weight of the primary amino acid sequence.

Additionally, a cDNA library generated from dendritic cell RNA is probed with the entire $\alpha_d$ cDNA under low stringency. Reactive clones are analyzed by nucleic acid sequencing over the entire length of the clone in order to determine if non-$\alpha_d$ sequences exist in the clones.

EXAMPLE 36

Animal Models For Determining $\alpha_d$ Therapeutic Utility

Immunohistologic data in dog and in situ hybridization in rats and mice has determined that in spleen $\alpha_d$ is expressed primarily by macrophages present in red pulp and in lymph nodes, $\alpha_d$ is found in medullary cords and sinuses. The expression pattern is remarkably similar to what has been reported for two murine antigens defined by the monoclonal antibodies F4/80 and SK39. While biochemical characterization of these murine antigens has demonstrated that they are distinct from $\alpha_d$, it is highly probably that $\alpha_d$ defines the same macrophage subset as the murine F4/80 and SK39 antigens.

In mouse, SK39-positive macrophages have been identified in splenic red pulp where they may participate in the clearance of foreign materials from circulation, and in medulla of lymph nodes [Jutila, et al., *J.Leukocyte Biol.* 54:30–39 (1993)]. SK39-positive macrophages have also been reported at sites of both acute and chronic inflammation. Furthermore, monocytes recruited to thioglycolate-inflamed peritoneal cavities also express the SK39 antigen. Collectively, these findings suggest that, if SK39$^+$ cells are also $\alpha_d^+$, then these cells are responsible for the clearance of foreign materials in the spleen and participate in inflammation where macrophages play a significant role.

While the function of $\alpha_d$ remains unclear, other more well characterized $\beta_2$ integrins have been shown to participate in a wide variety of adhesion events that facilitate cell migration, enhance phagocytosis, and promote cell—cell interactions, events which all lead to upregulation of inflammatory processes. Therefore, it is highly plausible that interfering with the normal $\alpha_d$ function may also interfere with inflammation where macrophages play a significant role. Such an anti-inflammatory effect could result from: i) blocking macrophage recruitment to sites of inflammation, ii) preventing macrophage activation at the site of inflammation or iii) interfering with macrophage effector functions which damage normal host tissue through either specific autoimmune responses or as a result of bystander cell damage.

Disease states in which there is evidence of macrophages playing a significant role in the disease process include multiple sclerosis, arthritis, graft atherosclerosis, some forms of diabetes and inflammatory bowel disease. Animal models, discussed below, have been shown to reproduce many of the aspects of these human disorders. Inhibitors of $\alpha_d$ function are tested in these model systems to determine if the potential exists for treating the corresponding human diseases.

Graft Arteriosclerosis

Cardiac transplantation is now the accepted form of therapeutic intervention for some types of end-state heart disease. As the use of cyclosporin A has increased one year survival rates to 80%, the development of progressive graft arteriosclerosis has emerged as the leading cause of death in cardiac transplants surviving beyond the first year. Recent studies have found that the incidence of significant graft arteriosclerosis 3 years following a cardiac transplant is in the range of 36–44% [Adams, et al., *Transplantation* 53:1115–1119 (1992); Adams, et al., *Transplantation* 56:794–799 (1993)].

Graft arteriosclerosis typically consists of diffuse, occlusive, intimal lesions which affect the entire coronary vessel wall, and are often accompanied by lipid deposition. While the pathogenesis of graft arteriosclerosis remains unknown, it is presumably linked to histocompatibility differences between donor and recipient, and is immunologic in nature. Histologically, the areas of intimal thickening are composed primarily of macrophages, although T cells are occasionally seen. It is therefore possible that macrophages expressing $\alpha_d$ may play a significant role in the induction and/or development of graft arteriosclerosis. In such a case, monoclonal antibodies or small molecule inhibitors (for example, soluble ICAM-R) of $\alpha_d$ function could be given prophylactically to individuals who received heart transplants and are at risk of developing graft arteriosclerosis.

Although atherosclerosis in heart transplants presents the greatest threat to life, graft arteriosclerosis is also seen in other solid organ transplants, including kidneys and livers. Therapeutic use of $\alpha_d$ blocking agents could prevent graft arteriosclerosis in other organ transplants and reduce complications resulting from graft failure.

One model for graft arteriosclerosis in the rat involves heterotopic cardiac allografts transplanted across minor histocompatibility barriers. When Lewis cardiac allografts are transplanted into MHC class I and II compatible F-344 recipients, 80% of the allografts survive at least 3 weeks, while 25% of the grafts survive indefinitely. During this low-grade graft rejection, arteriosclerosis lesions form in the donor heart. Arterial lesions in 120 day old allografts typically have diffuse fibrotic intimal thickening indistinguishable in appearance from graft arteriosclerosis lesions found in rejecting human cardiac allografts.

Rats are transplanted with hearts mismatched at minor histocompatibility antigens, for example Lewis into F-344. Monoclonal antibodies specific for rat $\alpha_d$ or small molecule inhibitors of $\alpha_d$ are given periodically to transplant recipients. Treatment is expected to reduce the incidence of graft arteriosclerosis in non-rejecting donor hearts. Treatment of rats with $\alpha_d$ monoclonal antibodies or small molecule inhibitors may not be limited to prophylactic treatments. Blocking $\alpha_d$ function is also be expected to reduce macrophage mediated inflammation and allow reversal of arterial damage in the graft.

Atherosclerosis in Rabbits Fed Cholesterol

Rabbits fed an atherogenic diet containing a cholesterol supplement for approximately 12–16 weeks develop intimal lesions that cover most of the lumenal surface of the ascending aorta [Rosenfeld, et al., *Arteriosclerosis* 7:9–23 (1987); Rosenfeld, et al., *Arteriosclerosis* 7:24–34 (1987)]. The atherosclerotic lesions seen in these rabbits are simmer to those in humans. Lesions contain large numbers of T cells, most of which express CD45RO, a marker associated with memory T cells. Approximately half of the infiltrating T cells also express MHC class II antigen and some express the IL-2 receptor suggesting that many of the cells are in an activated state.

One feature of the atherosclerotic lesions found in cholesterol fed rabbits, but apparently absent in rodent models, is the accumulation of foam cell-rich lesions. Foam cell macrophages are believed to result from the uptake of oxidized low-density lipoprotein (LDL) by specific receptors. Oxidized LDL particles have been found to be toxic for some cell types including endothelial cells and smooth muscle cells. The uptake of potentially toxic, oxidized LDL particles by macrophages serves as an irritant and drives macrophage activation, contributing to the inflammation associated with atherosclerotic lesions.

Once monoclonal antibodies have been generated to rabbit $\alpha_d$, cholesterol fed rabbits are treated. Treatments include prophylactic administration of ad monoclonal antibodies or small molecule inhibitors, to demonstrate that $\alpha_d^+$ macrophages are involved in the disease process. Additional studies would demonstrate that monoclonal antibodies to $\alpha_d$ or small molecule inhibitors are capable of reversing vessel damage detected in rabbits fed an atherogenic diet.

Insulin-dependent Diabetes

BB rats spontaneously develop insulin-dependent diabetes at 70–150 days of age. Using immunohistochemistry, MHC class II$^+$, ED1$^+$ macrophages can be detected infiltrating the islets early in the disease. Many of the macrophages appear to be engaged in phagocytosis of cell debris or normal cells. As the disease progresses, larger numbers of macrophages are found infiltrating the islets, although significant numbers of T cells, and later B cells, also appear to be recruited to the site [Hanenberg, et al., *Diabetologia* 32:126–134 (1989)].

Development of diabetes in BB rats appears to depend on both early macrophage infiltration and subsequent T cells recruitment. Treatment of BB rats with silica particles, which are toxic to macrophages, has been effective in blocking the early macrophage infiltration of the islets. In the absence of early macrophage infiltration, subsequent tissue damage by an autoaggressive lymphocyte population fails to occur. Administration of monoclonal antibody OX-19 (specific for rat CD5) or monoclonal antibody OX-8 (specific for rat CD8), which block the T cell-associated phase of the disease, is also effective in suppressing the development of diabetes.

The central role of macrophages in the pathology of this model makes it attractive for testing inhibitors of $\alpha_d$ function. Rats genetically predisposed to the development of insulin-dependent diabetes are treated with monoclonal antibodies to $\alpha_d$ or small molecule inhibitors and evaluated for the development of the disease. Preventing or delaying clinical onset is evidence that $\alpha_d$ plays a pivotal role in macrophage damage to the islet cells.

Inflammatory Bowel Disease (Crohn's Disease, Ulcerative Colitis)

Animal models used in the study of inflammatory bowel disease (IBD) are generally elicited by intrarectal administration of noxious irritants (e.g. acetic acid or trinitrobenzene sulfonic acid/ethanol). Colonic inflammation induced by these agents is the result of chemical or metabolic injury and lacks the chronic and spontaneously relapsing inflammation associated with human IBD. However, a recently described model using subserosal injections of purified peptidoglycan-polysaccharide (PG-PS) polymers from either group A or group D streptococci appears to be a more physiologically relevant model for human IBD [Yamada, et al., *Gastroenterology* 104:759–771 (1993)].

In this model PG-PS is injected into the subserosal layer of the distal colon. The resulting inflammatory response is biphasic with an initial acute episode three days after injection, which is followed by a spontaneous chronic phase three to four weeks later. The late phase response is granulomatous in nature, and results in colonic thickening, adhesions, colonic nodules and mucosal lesions. In addition to mucosal injury, PG-PS colitis frequently leads to arthritis anemia and granulomatous hepatitis. The extraintestinal manifestations of the disease make the model attractive for studying Crohn's colitis in that a significant number of patients with active Crohn's disease suffer from arthritic joint disease and hepatobillary inflammation.

Granulomatous lesions are the result of chronic inflammation which leads to the recruitment and subsequent activation of cells of the monocyte/macrophage lineage. Presence of granulomatous lesions in Crohn's disease and the above animal model make this an attractive clinical target for $\alpha_d$ monoclonal antibodies or other inhibitors of $\alpha_d$ function. Inhibitors of $\alpha_d$ function are expected to block the formation of lesions associated with IBD or even reverse tissue damage seen in the disease.

Arthritis

Arthritis appears to be a multi-factorial disease process involving a variety of inflammatory cell types including neutrophils, T lymphocytes and phagocytic macrophages. Although a variety of arthritis models exist, preparations of streptococcal cell wall proteoglycan produce a disorder most similar to the human disease.

In rats, streptococcal cell wall induces inflammation of peripheral joints characterized by repeated episodes of disease progression followed by remission and eventually resulting in joint destruction over a period of several months [Cromartie, et al., *J.Exp.Med.* 146:1585–1602 (1977); Schwab et al., *Infection and Immunity* 59:4436–4442 (1991)]. During the chronic phase of the disease, mononuclear phagocytes or macrophages are believed to play a major role in destruction of the synovium. Furthermore, agents which suppress the recruitment of macrophages into the synovium effectively reduce the inflammation and pathology characteristic of arthritis.

A central role for the macrophage in synovium destruction that leads to arthritis predicts that monoclonal antibodies to $\alpha_d$ or inhibitors of $\alpha_d$ function may have therapeutic potential in the treatment of this disease. As in other models previously described, $\alpha_d$ monoclonal antibodies or small molecule inhibitors administered prophylactically are expected to block or moderate joint inflammation and prevent destruction of the synovium. Agents that interfere with $\alpha_d$ function may also moderate ongoing inflammation by preventing the recruitment of additional macrophages to the joint or blocking macrophage activation. The net result would be to reverse ongoing destruction of the joint and facilitate tissue repair.

Multiple Sclerosis

Although pathogenesis of multiple sclerosis (MS) remains unclear, it is generally accepted that the disease is mediated by CD4$^+$ T cells which recognize autoantigens in the central nervous system and initiate an inflammatory cascade. The resulting immune response results in the recruitment of additional inflammatory cells, including activated macrophages which contribute to the disease. Experimental autoimmune encephalomyelitis (EAE) is an animal model which reproduces some aspects of MS. Recently, monoclonal antibodies reactive with CD11b/CD18 [Huitinga, et al., *Eur.J.Immunol.* 23:709–715 (1993)] present on inflammatory macrophages have been shown to block both clinical and histologic disease. The results suggest that monoclonal antibodies or small molecule inhibitors to $\alpha_d$ are likely to be effective in blocking the inflammatory response in EAE. Such agents also have important therapeutic applications in the treatment of MS.

Immune Complex Alveolitis

Alveolar macrophages located in the alveolar ducts, airways, connective tissue, and pleural spaces of the lung represent the lung's first line of defense against inhaled environmental agents. In response to stimulation by agents, including bacterial-derived LPS, IFN-γ and immune complexes, alveolar macrophages release a variety of potent inflammatory mediators, including highly reactive oxygen radicals and nitrogen intermediates. While superoxide anions, hydrogen peroxide and nitric oxide (NO$^+$) have important functions in eradicating pathogens and lysing tumor targets, these agents can have injurious effects on normal tissues.

In a rat model of immune complex alveolitis, NO$^+$ release from alveolar macrophages has been shown to mediate much of the lung damage [Mulligan, et al., *Proc.Natl.Acad.Sci.(USA)* 88:638–6342 (1991)]. NO$^+$ has also been implicated as a mediator in other immune complex mediated injuries including dermal vasculitis [Mulligan, et al., supra] and could potentially play a role in diseases such as glomerulonephritis.

$NO^+$ mediated tissue damage is not limited to inflammation involving immune complexes. For example, microglial cell stimulated, by agents such as PMA, LPS or IFN-γ, produce $NO^+$ at levels capable of killing oligodendrocytes [Merrill, et al., *Immunol*. 151:2132 (1993)]. Pancreatic islet cells have also been found to be sensitive to $NO^+$, and macrophage release of this mediator has been implicated in the tissue damage which leads to diabetes [Kroncke, et al., *BBRC* 175:752–758 (1991)]. More recently, it was conclusively demonstrated that $NO^+$ release plays a role in endotoxic shock [MacMicking, et al., *Cell* 81:641–650 (1995)]. When administered lipopolysaccharide (LPS), normal wild-type mice experience a severe, progressive decline in arterial pressure resulting in death. Mice deficient in inducible nitric oxide, however, experience a much less severe decline in arterial pressure in response to LPS, and all survive the treatment.

In vitro assays indicate that blockage of $\alpha_d$ is effective at blocking some aspects of macrophage (or leukocyte which express $\alpha_d$, in general) activation, including $NO^+$ release. Alveolar macrophages stimulated with IFN-γ in the presence of anti-$\alpha_d$ polyclonal anti-serum (generated in rabbits against a rat $\alpha_d$ I domain polypeptide) were found to produce significantly less nitrite/nitrate—breakdown products of $NO^+$ than macrophages treated with control anti-serum. This finding indicates that monoclonal antibodies to $\alpha_d$, particularly to the I-domain, may be potent anti-inflammatory agents with potential uses in MS, diabetes, lung inflammation and endotoxic shock. Furthermore, in contrast to CD18, which effects the function of a wide variety of leukocyte types, the limited distribution of $\alpha_d$ may make this a more attractive target than CD18 for preventing macrophage (or leukocyte which express $\alpha_d$, in general) activation.

Rat IgG immune complex-induced alveolitis is a widely used experimental model important in understanding acute lung injury. The injury is elicited by instilling anti-bovine serum albumin (BSA) antibodies into lungs via tracheal cannulation, followed by an intravenous injection of BSA. The formation of immune complexes in the microvasculature of the lung leads to complement activation and the recruitment of neutrophils into the lung. Presumably, formation of immune complexes in the lung following extravasation of leukocytes from the blood and subsequent leukocyte movement across lung epithelium. The subsequent release of mediators, including radicals, TNF-α and nitric oxide ($NO^+$), from activated endothelial cells, neutrophils and macrophages which participate in progression of the disease. Pathologic features of the disease include increased vascular permeability leading to edema and the presence of large numbers of erythrocytes and PMNs present in the alveolar spaces.

Polyclonal anti-serum specific for the I domain of $\alpha_d$ was tested in a rat model of immune complex-induced alveolitis. The anti-$\alpha_d$ polyclonal serum was administered via tracheal cannulation at the same time anti-BSA was introduced into the lungs. Lung injury was subsequently elicited by intravenous administration of BSA along with a trace amount of $^{125}$I-labeled BSA (approximately 800,000 cpm) to quantitate edema resulting from lung injury. Lung injury was allowed to proceed for four hours and damage was assessed using a lung permeability value, is defined as the ratio of $^{125}$I-labeled BSA in the lung compared to the amount of label present in the 1.0 ml of blood. Typically lung permeability values for positive control rates range between 0.6 and 0.8, while negative controls (rats not receiving BSA) have permeability index values in the range of 0.1–0.2.

Initial studies indicated that treatment with anti-$\alpha_d$ polyclonal anti-serum reduced lung permeability values by greater that 50%, representing a dramatic moderation of lung injury. Historically, treatments with anti-CD18 have reduced permeability values by 60%. These findings indicate that $\alpha_d$ may be the most important $\beta_2$ integrin during acute lung injury, however it cannot be precisely determined if the effect of the anti-sera prohibits leukocyte extravasation from the blood, or movement across lung epithelia.

As additional proof that $\alpha_d$ moderates lung injury, TNF-alpha levels in the bronchoalveolar lavage fluid were evaluated. Treatment with the anti-$\alpha_d$ anti-serum was found to reduce TNF-alpha levels approximately four-fold. TNF-alpha has long been viewed as an important mediator in acute lung inflammation, and responsible for the recruitment of inflammatory cells into sites of inflammation, cell activation and tissue damage. Presumably, anti-$\alpha_d$ anti-serum blocks activation of resident alveolar macrophages during the formation of immune complex alveolitis, and thereby moderates the release of TNF-α and $NO^+$, and reduces subsequent tissue damage caused by these agents and the recruitment of neutrophils.

F344 Rat Model of LGL leukemia

LGL leukemia in the F344 rat was first described in the early to mid 1980's as a transplantable leukemia with stable NK cell activity. This leukemia has been suggested as a possible model for human T gamma lymphoma and T-cell Chronic Lymphocytic Leukemia [Ward and Reynolds, *Am. J. Pathol*. 111:1–10 (1982); Stromberg, *Am. J. Pathol*. 119:517–519 (1985); Reynolds, et al. *J.Immunol*. 132:534–540 (1984)]. This model provides abundant cells for studies of LGL and NK cell function. Of particular interest is the presence of $\alpha_d$ on the surface of these cells as detected using hamster anti-rat antibody 205C through FACS analysis described in Example 26. In view of this observation, the roles of $\alpha_d$ in vitro (for example, using the cytolytic assays previously described) and in vivo were examined.

The pathologic features of LGL leukemia include severe splenomegaly, a pale mottled liver, enlargement of peripheral lymph nodes and petechial hemorrhages in lung, brain, and lymph node. Because $\alpha_d$ is present in the red pulp of normal rat spleen (on splenic macrophages), and the hallmark of LGL leukemia is severe splenomegaly, it was hypothesized that the $\alpha_d$ positive NK tumor cells may also "home" or tether to a yet defined ligand and proliferate here. To test this hypothesis, tumor cells were radiolabeled and injected with and without $\alpha_d$ antibody treatment into recipient rats. Spleens from these animals were removed after three hours and the presence of NK tumor cells determined. A more complete description of the methods used and experimental results are as follows.

Tumor cells, obtained from the spleens of rats with LGL leukemia and prepared as described below, were adoptively transferred to recipient rats 2 to 4 weeks prior to each experiment. From previous studies by histology and FACS analysis, it was known that a rapid proliferation of the tumor and resulting splenomegaly occurs about three to four weeks after adoptive transfer. In the first experiment, a spleen was removed from an animal that had been exposed to tumor cells for four weeks. A single-cell suspension was made by mincing up the spleen into smaller pieces with scissors and passing these pieces through a mesh screen in the presence of D-PBS. The cell suspension was collected in a 50 ml tube and centrifuged for 10 minutes at 1500 rpm in a Beckman tabletop centrifuge at room temperature. The supernatant was discarded, and the cells resuspended in 30 ml of D-PBS. Approximately 5.0 ml of this cell suspension was layered onto 5.0 ml of Histopaque, and the gradients centrifuged for 30 minutes at 1500 rpm. The cellular layer from these gradients was collected, pooled, and counted by hemacytometer. The cell number was adjusted so that each recipient rat received $1.0 \times 10^7$ cells, with a slight overestimation to account for cell loss during washes and preparing syringes. The cells were suspended in NK "test media" (RPMI-1640 plus antibiotics, plus 2% FBS) and labeled with 10 mCi of $^{51}$chromium for one hour at 37° C. After incubation, the volume of the cell suspension was increased to 50 ml with test media and the cells pelleted by centrifugation for 10 minutes, 1200 rpm. The supernatant was discarded and the cells washed two more times as described. The labeled cells were suspended at a final concentration of $1 \times 10^7$ cells/ml and preincubated in the presence or absence of anti-rat $\alpha_d$ antibodies as well as a control IgG1 antibody prior to injection into recipient rats. The final concentration of antibody used per animal was adjusted to 5.5 mg/kg, or approximately 1 mg/animal. A minimum of four animals was used for each condition.

Recipient rats were weighed and injected subcutaneously with 150 to 200 µl ACE solution (containing 0.25 ml Ketamine, 0.2 ml Ace and 0.8 ml Rompin) to anesthetize. From each antibody treatment, $1.0 \times 10^7$ cells were injected intravenously into animals. Approximately 300 µl of each cell suspension was examined using a gamma counter to determine the total cpm injected/rat. The labeled NK cells were allowed to circulate in the rats for three hours after which the animals were sacrificed and 1.0 ml of peripheral blood drawn by aortic puncture. Spleens were removed from each animal, weighed, and counted using a gamma counter. To determine the percentage of cells returning to the spleen, the counts per minute (cpm)/spleen were divided by the total known cpm injected into the rat. To determine the cpm in peripheral blood, an assumption was made that blood represents about 6.0% of the total rat's weight. The cpm in 1.0 ml blood was multiplied by 6.0% of the animal's total weight to determine total cpm in blood. This number was then divided by the total number of cpm's injected into each animal to obtain the percentage of cpm remaining in blood.

In the first experiment, antibodies 226B, 226G, 226H, 226I, 20C5B (a non-blocking CD18 antibody) and a control antibody were used. Antibodies 226B and 226G appeared to significantly reduce the number of cells returning to the spleen as compared to the control antibody and the other two 226 antibodies; approximately 7 to 8% of the labeled cells returned to the spleen after incubation with the control antibodies, while approximately 6% of the cells returned to the spleen after incubation with 226B and 226G antibodies. The percentage of total cpm in blood, between 0.9 and 1.4%, did not show a marked difference between treatment groups with the exception of 226B, which had lower values than all other groups.

In a second experiment, several adjustments were made to the protocol defined above. First, an increase to four animals per condition was made, and second, the spleen from a tumor-bearing rat was removed at 2.5 weeks post-$\alpha_d$ optive transfer rather than four weeks as above. The NK cells were prepared in exactly the same manner and injected into recipient animals following incubation with either antibody 226B or 226G or a control antibody at the doses defined above. Again, the labeled cells were allowed to circulate for three hours after which the animals were sacrificed and blood and spleens collected as above. In addition, the tissues from two of the animals/condition were removed to determine other locations of the tumor cells. These tissues included liver, brain, thymus, lung, long bone (for bone marrow) and kidney.

The results indicated that, in the control IgG1, approximately 32% of tumor cells were in the spleen, whereas both 226B and 226G showed reduced numbers, 28% and 29%, respectively, of labeled cells in the spleen. The percentage of cells in the blood were similar for each antibody, approximately 3 to 4% of the total cpm's were found in blood, with 226G antibody treatment slightly less than the other two groups.

The tissue distribution was similar between treatment groups with liver showing 27% of total cpm, brain 0.05%, thymus 0.10%, lung 15%, kidney 0.80%, and long bone 1.3%.

In a third experiment, an increase in the number of animal per condition (n=6 or 7) was made in an attempt to detect statistical differences between the three treatment groups above. Again, the spleen from an animal injected with tumor cells two weeks prior to the experiment was used and prepared by the same method described above. The cells were labeled in the same manner and injected into the animals and allowed to circulate for three hours. In this experiment, only blood samples and spleens were collected from animals due to the large number of animals used.

The results were consistent with the second experiment in that approximately 30% of labeled cells were observed to have returned to the spleen in the control group, while only 25% in 226B antibody-treated cells and 27% in 226G antibody-treated cells were found in the spleen. The blood values again did not show major differences between groups, with approximately 17% of the total cpm's found in blood in the control group and 15.8% and 14.75%, respectively. were found for 226B and 226G treated groups.

To determine if three hours was an optimum time point to examine differences between treatment groups, a small adjustment was made in a fourth experiment. Again, cells were isolated and prepared in the same way for injection into recipient animals, except that an additional anti-CD18 antibody 20C5B was added to the panel of test antibodies. In addition, only four animal were used for each condition. In this experiment, the cells were allowed to circulate for only 30 minutes after injection, at which point blood samples were drawn and spleen removed from the animals.

At the 30 minute time point, the total cpm in the spleen was reduced from values observed in the second and third experiments to 12 to 13%. There were no apparent differences between all treatment groups in the spleen samples, although two of the four animal in the group treated with antibody 226B did have slightly lower values. The blood values were again similar between all groups, with approximately 6 to 7% of the total cpm found in blood. The only marked difference between blood groups was a larger spread in data points from 226B and 226G antibody-treated animals. These findings suggest that $\alpha_d$ plays a role in the homing of leukemia cells to the spleen. Experiments indicate that homing requires several hours and maximum inhibition with the $\alpha_d$ specific monoclonal antibodies occurs at 3 hours.

Macaque Models for Multiple Sclerosis and Atherosclerosis

Monoclonal antibodies 212D and 217L were shown by immunocytochemical staining and immunoprecipitation to cross-react with macaque splenocytes. The specificity of recognition was confirmed by immunoprecipitation and amino terminal sequencing of an $\alpha_d$ species homolog from macaque spleen (Example 34). In view of these previous observations, the two antibodies were used to stain tissues obtained from macaques in either experimental autoimmune encephalitis (EAE) or atherosclerosis studies. Both of these diseases are marked by infiltration into lesions of phagocytotic macrophages which take up myelin basic protein (MBP) in the EAE or low density lipoprotein in atherosclerosis. MBP or lipid-laden macrophages can be identified morphorologically or by staining with Oil Red O (ORO) or antibody Ham 56 (Dako, Carpinteria, Calif.). The protocol employed in these studies is as described in Example 18 to characterize $\alpha_d$ expression in human tissues.

Sections from macaque brains with EAE were marked by infiltration of lymphocytes and macrophages. Expression of $\alpha_d$ was localized to a subset of macrophages in lesions which stained with ORO indicating previous uptake of MBP. Lesions which were negative for ORO staining were also negative for $\alpha_d$ expression. This result suggested a direct correlation between ORO staining and $\alpha_d$. Similar results were observed using antibodies 217K, 217I, and 217H.

Atherosclerosis lesions were obtained from either thoracic or abdominal arteries of macaques on high fat diets. Lesions occur in both locations in humans, but those which progress pathologically are more often located in the abdominal aorta. The lesions tested in this study were separated into five different stages (I through V) and normal. Stage (IV/V) lesions were derived from the abdominal aorta and the remainder were derived from the thoracic aorta.

Early stage lesions (I/II) showed little macrophage infiltration and low or even absent levels of $\alpha_d$ expression. In later stage lesions, foam cell infiltration was greater and $\alpha_d$ expression was detectable.

Staining patterns for other leukointegrin a chain subunits were overlapping with, but not identical to, $\alpha_d$ expression in both tissues. Most notably, expression of $\alpha$ subunits of non-$\alpha_d$ leukointegrins was detected on lymphocytes that did not stain with anti-$\alpha_d$ antibodies.

These results suggest that $\alpha_d$ expression may be characteristic of phagocytotic macrophages in both animal models. It is unclear, however, whether $\alpha_d$ is directly involved in phagocytosis or some downstream process such as antigen presentation.

EXAMPLE 37

Expression of $\alpha_d$ in Preclinical Models

In order to assess differential expression of $\alpha_d$ in various disease states, tissue sections from animal disease models were stained with anti-$\alpha_d$ polyclonal serum produced as described above (see Example 22). Tissue from normal and diseased rats was sectioned at 6 $\mu$m thickness and air dried on Superfrost Plus (VWR Scientific) slides at room temperature overnight. After drying, sections were stored at −70° C. until use. Prior to use, slides were removed from −70° C. and placed at 50° C. for approximately 5 minutes. Sections were fixed in cold (4° C.) acetone (Stephens Scientific) for 10 minutes at room temperature and allowed to dry at room temperature. Each section was blocked with 150 $\mu$l of a solution containing 30% normal rat serum (Harlan Bioproducts), 5% normal goat serum (Vector Laboratories) and 1% bovine serum (BSA) (Sigma Chemical Company) in 1×TBS for 30 minutes at room temperature, after which the solution was gently blotted from the sections. Rabbit polyclonal serum, at a protein concentration of 34 $\mu$g/ml, and preimmune serum from the same rabbit, at a protein concentration of 38.5 $\mu$g/ml, were diluted in the blocking solution and 100 $\mu$l separately applied to each tissue section for 30 minutes 37° C. The serum solution was blotted from the sections and unbound antibody removed by washing three times in 1×TBS for 5 minutes. Excess TBS was removed by blotting following the final wash. Biotinylated goat anti-rabbit antibody from a Elite Rabbit IgG Vectastain® ABC kit (Vector) was prepared according to manufacturer's suggested protocol and 100 $\mu$l of the resulting solution was applied to each section for 15 minutes at 37° C. Slides were washed two times in 1×TBS for five minutes in each wash, after which 100 $\mu$l of streptavidin-gold conjugate (Goldmark Biologicals), diluted 1:100 in 5% normal rat serum and 1% BSA, was applied to each section for one hour at room temperature. Slides were washed three times with TBS for five minutes each wash, and 100 $\mu$l of 1% glutaraldehyde (Sigma) in TBS buffer was applied for five minutes at room temperature. Slides were again washed three times in TBS for five minutes each wash, and five times in sterile deionized water for three minutes each wash. Excess liquid was blotted from each slide and two drops each of silver enhancing and initiating solution (Goldmark Biologicals) were applied to each section. The reaction was allowed to proceed for 20–30 minutes at room temperature, after which the sections were rinsed thoroughly in sterile deionized water, air dried overnight at room temperature and mounted with Cytoseal 60 (VWR). As controls, tissue sections were labeled with monoclonal antibodies recognizing CD11a, CD11b, CD11c and CD18 in the same experiments by identical protocols.

Labeling with $\alpha_d$ polyclonal sera and monoclonal antibodies to CD11a, CD11b, CD11c, and CD18 revealed a staining pattern for $\alpha_d$ different from than observed for the other $\alpha$ subunits.

In normal lung tissue, $\alpha_d$ expression was detected on respiratory epithelium of the bronchi (but not the epithelium in the alveolar spaces) and on individual cells which appear to be alveolar macrophages within the airspaces. The signal observed with the polyclonal serum was significantly higher than the background signal level with the pre-immune serum control. In pulmonary granuloma tissue, 24 and 96 hours after administration of glycan, a different signal was detected with the $\alpha_d$ staining respiratory epithelium throughout the alveolar area and a stronger signal detected on what appear to be alveolar macrophages throughout the airways. In the lung tissue from animals which had presumably recovered from the disease (sacrificed 16 days after administration of glycan), no signal was observed with the $\alpha_d$ antibody. Very little background was observed with the pre-immunization serum in each of these tissues.

Using rat lung tissue from an antigen-induced asthma model, a very strong signal was detected with $\alpha_d$ antibody in the respiratory epithelium of both the bronchi and the alveolar spaces. The signal was significantly higher than the background signal level in the pre-immunization serum control.

Preclinical Model—*L. monocytogenes*

Evidence suggests that $\alpha_d$ positive macrophages in the spleen red pulp are involved in the clearance of damaged rbcs and other particles from circulation. It is hypothesized that bacterial agents are also cleared from circulation by the $\alpha_d$ positive macrophages in the spleen red pulp. Non-infectious agents which would not require the induction of an antigen-specific T cell response would be eliminated directly by the red pulp macrophages. In contrast, opportunistic infectious agents cleared by the red pulp macrophage do require a product T cell immune response for the eradication of the bacteria. It was therefore proposed that $\alpha_d$ expression on red pulp macrophages may serve to regulate macrophage/T cell interactions either by regulating the movement of macrophages from the red pulp into the marginal zones or by acting as an accessory molecule involved in macrophage/T cell interactions leading T cell activation.

To investigate the role of $\alpha_d$ during immune responses to infectious agents, $\alpha_d$ expression is evaluated in the spleen using a murine model of *Listeria monocytogens*. Expression of $\alpha_d$ is examined on red pulp macrophages which have phagocytosed bacteria. Antibodies to $\alpha_d$ are also tested in the model to determine the role played by $\alpha_d$ in the induction of a protective T cell response to *L. monocytogenes*.

EXAMPLE 38

The Role of $\alpha_d$ in Spinal Cord Injury

After central nervous system (CNS) trauma, the immune response involves a mixture of invading neutrophils, natural killer cells and phagocytic monocytes/macrophages [Means, et al., *J. Neurophathol. & Exp. Neurol.*, 42:707–719 (1983)]. This response includes the release of inflammatory mediators, induction of reactive microglia, infiltration of platelets, endothelial damage with enhanced vascular permeability and development of edema. Recent observations suggest that post-traumatic inflammation in the spinal cord contributes to chronic deficits, partly through demyelination or through more direct damage to neurons and axons [Blight, A. R., *Central Nervous System Trauma*, 2:299–315 (1985)]. In addition, a recent study reported that the number of macrophages/microglia was significantly correlated with the amount of tissue damage at each level of the spinal cord following impact injury [Carlson, et al., *Exp. Neurol.*, 151:71–81 (1998)]. Both neutrophils and macrophages phagocytose debris which in turn induces an oxidative burst resulting in the production of reactive oxygen species. These antibacterial agents, although efficacious, can lead to damage in surrounding healthy tissue. Thus, it is possible that the infiltration of leukocytes and concomitant production of reactive oxygen species is involved with the spread of secondary injury beyond the initial impact site. This hypothesis is supported by studies in which blocking of neutrophil or macrophage infiltration led to decreases in the extent of injury following stroke or spinal cord injury [Blight, *Neurosci*, 60:263–273 (1994)].

Complete Transection Model

In order to assess the role of $\alpha_d$ in spinal cord injury, a rat transection model was utilized in combination with monoclonal antibodies to $\alpha_d$, some of which block binding to its ligand VCAM-1. In this model, complete transection at the fourth thoracic (T) spinal cord segment is introduced, which consistently produces autonomic dysreflexia [Krassioukov, et al., *Am. J. Physiol.* 268:H2077–H2083 (1995)]. This model is advantageous because the small surgical lesion produces a well-defined, narrow zone of primary tissue destruction that facilitates analysis of the effects of cord injury on the area.

All experiments were carried out in accordance with policies established in the "Guide to Care and Use of Experimental Animals" as prepared by the Canadian Counsel on Animal Care. Forty-two male Wistar rats (Charles River) weighing 270–320 grams were initially administered atropine (0.5 mg/kg) and diazepam (2.5 mg/kg) by intraperitoneal injection. After ten minutes, the rats were anaesthetized by intraperitoneal injection with sodium phenobarbital (35 mg/kg). Supplemental injections of anaesthetic (2 mg/kg) were administered during surgery as necessary. The rats were placed on a heating pad during surgery and the body temperature was kept close to 37° C. The dorsal process of the third thoracic (T3) vertebra was removed and a laminectomy was performed to expose the spinal cord under microscopic guidance. The cord was completely transected at the T4 spinal segment with a scalpel blade. The muscles and skin above the laminectomy were closed and the animals recovered tinder a heat lamp. Postoperative care of the paraplegic rats was conducted as previously described [Krassioukov et al., *Neurosci.* 70:211–226 (1996)]. After recovery from surgery, food and water were provided ad libitum. Animals survived for two days following surgery.

The rats (four to five per group) were divided into the following treatment groups: (1) 1 mg/kg of either $\alpha_d$ monoclonal antibodies 226H, 236L, 226B, or an irrelevant isotype-matched IgG1 kappa antibody 1B7 and (2) 5 mg/kg of either $\alpha_d$ monoclonal antibodies 226H, 236L, or the control 1B7. Each mouse received only one antibody in the treatment regimen.

Antibodies were selected following in vitro binding assays using recombinant human VCAM-1 fused to an immunoglobulin region and a CHO cell line expressing rat $\alpha_d$ and human CD18. A panel of antibodies was examined for the ability of individual antibodies to block $\alpha_d$ binding to VCAM-1. Results from the binding assays indicated that some antibodies did not block binding ("non-blockers"), some block binding in the range of 50% ("medium blockers"), while others block binding in the range of 75% to 85% ("strong blockers"). Representative antibodies from the non-blocking, medium blocking and strong blocking groups were chosen for use as described below.

All monoclonal antibodies were administered via tail vein injection 24 hours before surgery, 2 hours and 24 hours after surgery. Antibodies were diluted in phosphate buffered saline, pH 7.2, without calcium chloride or magnesium chloride to ensure an adequate volume for ease of injection. In another control group, methylprednisolone (MP) was injected via the tail vein at a concentration of 30 mg/kg at 30 minutes, and at a concentration of 15 mg/kg at 2 hours, and 24 hours following a complete transection of the spinal cord. An additional control group of rats had transected spinal cords as described above, but received no accompanying treatment.

Two days after surgery, the animals were deeply anaesthetized with an intraperitoneal injection of 3 g/kg urethane (Aldrich Chemical Company, Inc., Milwaukee, Wis., USA) prior to transcardial perfusion. After opening of the thoracic cavity, heparin was injected into the left ventricle. The rats were perfused with 250 ml of oxygenated tissue culture medium, pH 7.4, (Dulbecco's modified Eagle medium; Gibco BRL) followed by 500 ml of 4% formaldehyde fixative in 0.1 M phosphate buffer (pH 7.4). The thoracic spinal cord caudal to the transection (T4-8) was removed for examination as described previously [Krenz and Weaver, *Neurosci* 85:443–458 (1998)]. Following overnight postfixation in the same fixative, the spinal cord portions were cryoprotected with 10%, 20%, and 30% sucrose solutions in PBS at 4° C. The spinal cord portions were then cut into horizontal sections (50 μm) on a cryostat. Sections were stained with 1% cresyl violet, pH 4, using standard procedures to visualize the polymorphonuclear leukocytes, cleared in xylene, and coverslipped with DPX mountant (BDH Laboratory Supplies, Poole, U.K.). The number of macrophages/microglia exhibiting a rounded, phagocytic morphology and neutrophils exhibiting the characteristic multilobed nuclei following cresyl violet staining were counted in the area of the cord at the lesion site. Quantitation of immune cells was performed using bright field microscopy and a 40× objective lens fitted with a grid (total area of 0.08 mm$^2$). Three sample areas, starting at the edge of the transected cord and moving caudally and from one lateral edge to the other were examined for immune cells. The procedure resulted in an average total quantified area of spinal cord of 2.72 mm$^2$. The process was then repeated in another spinal cord section. The sample areas were selected from horizontal sections of the cord with the largest grey matter (border between lamina V and VII) because the inflammatory response was most prominent in the grey matter. The total number of macrophages and neutrophils counted in each sample area was divided by the total sample area (mm$^2$) to acquire the mean number of macrophages and neutrophils per mm$^2$ in each treatment group. The antibody-treated groups (1 mg/kg and 5 mg/kg) were compared to the respective irrelevant IgG-matched control at the same dose and to a non-drug treated transection control. In a further comparison, the groups most significantly lowering the mean number of immune cells were compared to MP treated animals and to surgery control animals. All cell counting was carried out blind with respect to the identification of the treatment group.

Results indicated that activated microglia and/or blood macrophages identified as mononuclear, round cells with large translucent cytoplasm were evident in the lesion site two days after transection. Control animals that received no accompanying $\alpha_d$ antibody or corticosteroid treatment were found to have an average of 396±26 macrophage/microglia per mm$^2$ at the site of the cord injury. Treatment with the irrelevant IgG1 antibody 1B7 at the lower dose (1 mg/kg) increased the number of macrophage/microglia to 362±43 per mm$^2$, but this value was not significantly different than control animals which received no antibody treatment. Of the $\alpha_d$ antibodies tested, 226H and 236L at 1 mg/kg each led to significant reductions in the average number of macrophages per mm$^2$ compared to the 1B7 antibody and to the transection control. Specifically, 226H administration reduced macrophage/microglia per mm$^2$ to 147±17 and 236L administration reduced macrophage/microglia per mm$^2$ to 131±4 compared to both 1B7 and animals receiving no treatment. In contrast, injection of $\alpha_d$ antibody 226B at 1 mg/kg reduced the number of macrophages/microglia per mm$^2$ to 327±65, which was not significantly different from the control values. MP treatment led to an observation of 250±24 macrophage/microglia per mm$^2$, which was significantly less than control animals but greater than that detected in animals treated with 226H and 236L $\alpha_d$ antibodies. This result was unexpected since methylprednisolone is the most widely used drug for clinical treatment of acute spinal cord injury.

When the dose of $\alpha_d$ antibodies was increased to 5 mg/kg, the average number of macrophage/microglia per mm$^2$ with 226H and 236L treatment was significantly lower than the control, but the number was not significantly different from the number in animals treated with the irrelevant IgG1 isotype matched control antibody.

The results with respect to neutrophilic leukocytes (NLs) indicated that the majority was detected either singly or in aggregates throughout the gray matter. Only a small portion of the visible NLs were detected in the white matter on each side of the grey matter. Moreover, some neutrophils were found adhering to the lumenal surface of venules and arterioles in the spinal tissue sections. In animals that received no treatment, the average number of NLs per mm$^2$ was 295±56 and in those treated with 1 mg/kg 1B7, the number of NLs increased significantly to 416±63. No $\alpha_d$ antibody treatment significantly reduced the number of NLs when compared to the control animals that received no treatment. Specifically, 226H and 226B at 1 mg/kg provided an increased number of NLs per mm$^2$ to 361±80 and 332±43, respectively. Compared to 1B7 treated animals, treatment with 236L at 1 mg/kg and MP both significantly decreased the number of NLs per mm$^2$ to 270±39 and 193±39, respectively. These observations, however, were not significantly different from the control group which received no treatment.

At 5 mg/kg, 1B7 treatment increased the average number of NLs to 343±37, but the observed increase was not significant compared to the non-treated animal group. Compared to 1B7 treatment, antibody 226H decreased the average number of NL present to 236±38, but the reduction was not significant compared to animals that received no treatment. In contrast, 236L reduced the number of NL to 190±17 per mm$^2$ which was significant compared to animals receiving 1B7 treatment.

These results indicate that $\alpha_d$ monoclonal antibodies at low doses reduce the number of leukocytes in injured spinal cord, possibly through the disruption of an interaction with VCAM-1 which would be consistent with previously reported observations. Other reports using antibodies against the best known counterreceptor for VCAM-1, VLA-4, showed decreased infiltration of VLA-4 positive cells into the brain and prevention of clinical and pathological signs of experimental allergic encephalomyelitis (EAE). Similarly anti-TNFα treatment was shown to inhibit the incidence and severity of EAE and one mechanism of action was by inhibiting VCAM-1 expression on spinal cord vessels leading to significant reduction in leukocyte entry into the CNS. These previous observations suggest that blocking the interaction of $\alpha_d$ on the surface of leukocytes with VCAM-1 on the surface of endothelial cells or glial cells may be responsible for the observed attenuated inflammatory response.

Because one of the antibodies, 226H, that blocked macrophage infiltration did not block binding between $\alpha_d$ and VCAM-1, these results suggest that the mode of inhibition by the antibody can include blocking between $\alpha_d$ binding partners other than VCAM-1. One possibility is the existence of a rat counterpart to ICAM-R. Previous observations have indicated that, in addition to VCAM-1, $\alpha_d$ also binds to TCAM-R, although with much less affinity that to VCAM-. Interestingly, ICAM-R appears to be absent on endothelial cells and is expressed primarily on resting monocytes, lymphocytes and neutrophils precluding its involvement in leukocyte-endothelial adhesion under normal circumstances. It has been suggested that ICAM-R has a role in the initial phases of leukocyte cell—cell contact and that ICAM-R is involved in the regulation of the LFA-1/ICAM-1 leukocyte intercellular interaction. The role of ICAM-R in the early leukocyte interaction has been shown to be induction of cell aggregation. Disruption of the initial contacts which give rise to aggregation reduces the effectiveness of the immune response. It has also been shown that the interaction of another ligand for ICAM-R, LFA-1 induces a switch of LFA-1 to its activated state at the intercellular contact site. It is possible that co-expression of $\alpha_d$ and ICAM-R on resting leukocytes could work in much the same way and that interaction between the two proteins may promote contact-dependent leukocyte activation events. Conversely, disruption of the interactions, for example, through use of an $\alpha_d$ antibody, could account for the reduced entry of leukocytes into the spinal cord.

Several explanations could account for the increase in macrophage infiltration. Most simply, the result may be a phenomenon of the system. Alternatively, the higher dose of antibody may have resulted in cross-linking of FcγR on the mature macrophages, resulting in an initial burst of chemokine production that attracted additional leukocytes to the injury site. In the same way, chemokine production could explain the greater numbers of both neutrophils and macrophages at the injury site after treatment with 1B7 that occurred in the majority of cases. Another possible explanation for the observed results is inter-animal variability since the ad antibodies were tested in outbred strains of Wistar rats. For example, different groups of rats could have slightly different states of immunocompetence. In order to test this possibility, the experiments are replicated using both a low and high dose of the monoclonal antibodies at the same time in animals from the same or related litters.

Clip Compression Injury (CCI) Model

An alternative animal model for spinal cord injury that is clinically more relevant is the clip compression injury (CCI) model [Rivlin, et al., *Surg. Neurol.* 10:38–43 (1978); Maiorov, et al., J Neurotrauma 15:365–74 (1998)]. Briefly, rats are prepared as described above for the complete cord transection by exposing the spinal cord by a dorsal laminectomy at thoracic segments T3 and T4. A modified aneurysm clip is used to compress the spinal cord by slipping the bottom part of the clip under the spinal cord between the dorsal roots of T3 and T4. The clip is then snapped shut for a period of one minute after which the clip is opened and removed. The rat is then closed with sutures. These aneurysm slips have been specifically modified so that they close with a calibrated force. In this way, a clip can be calibrated to induce a severe, moderate, or mild spinal cord injury. The severe, moderate and mild clip compression models of spinal cord injury accurately and consistently reproduce all of the pathophysiological aspects of human spinal cord injury including ischemia.

All experiments were carried out using the procedures described above with respect to animal care and administration of treatments. Rats subjected to severe CCI (50 g) were treated at 2, 24, and 48 hr post injury with one of the following (i) anti-$\alpha_d$ monoclonal antibody 217L (at 1 mg/ml), (ii) anti-$\alpha_d$ monoclonal antibody 226H (at 1 mg/ml), (iii) anti-$\alpha_d$ monoclonal antibody 236L (at 1 mg/ml), (iv) isotype control antibody 1B7, or (v) PBS (no treatment control). A sixth group of rats were given methylprednisolone (MP) at 30 mg/ml at 24 hr and 15 mg/ml at 24 and 48 hr post CCI. Four or five rats were examined for each of the treatment groups. At 72 hr, the animals were sacrificed and perfused with a fixative, after which spinal cords were removed for further processing. The effectiveness of anti-$\alpha_d$ monoclonal antibodies (217L, 226H, and 236L) to reduce the infiltration of ED1$^+$ (i.e., monocytes/macrophages) and MPO$^+$ (i.e., phagocytes) cells to the site of injury was analyzed. ED1$^+$ and MPO$^+$ cells were identified by immunocytochemistry double staining methods using two different fluorochromes. Since it was sometimes difficult to distinguish between cells with a neutrophilic-like morphology and cells with a macrophage-like morphology, both were counted as MPO$^+$ cells. In general, most MPO$^+$ cells appeared to be neutrophils. Cells were counted on the one side (usually on the caudal side) of the injury. For each animal, one 16 μm section out of every 10 serial, horizontal sections cut through the entire spinal cord segment spanning the injury was counted. This procedure resulted in a total of 6 to 10 sections per animal being counted.

Results of this analysis showed a 40–55% reduction of infiltrating ED1$^+$ cells at the site of injury following treatment with antibodies 217L and 226H compared to animals that were treated with PBS or the control 1B7 antibody or 236L antibody. Control animals that received either PBS or 1B7 antibody were found to have 681.3±47.4 and 641.8±77.8 ED1$^+$ cells, respectively, that infiltrated the site of the severe CCI. Rats treated with 217L, 226H or 236L antibody showed 388.6±52.8, 291.9±67.7, and 692.7±98.4 infiltrating ED1$^+$ cells, respectively, at the site of injury. Rats treated with methylprednisolone showed 409.0±42.6 infiltrating ED1$^+$ cells at the site of injury. Statistical analysis of these results using two-way Anova indicated that animals treated with either 217L or 226H antibody showed significant improvements different from control groups (p<0.05). Similar analysis of infiltrating MPO$^+$ cells indicate that 217L most consistently reduces migration of these cells to the site of injury when compared to untreated animals or to animals treated with the control antibody 1B7. Rats treated with 217L, 226H or 236L antibody were found to have 156.5±163.3, 191.3±39.0, and 299.1±44.0 infiltrating MPO$^+$ cells, respectively, at the site of injury. Control animals treated with either PBS or 1B7 antibody showed 615.3±45.7 and 260.9±48.92 infiltrating MPO$^+$ cells, respectively at the injury site. However, since the peak time of neutrophil infiltration is normally around 18 hours after CCI, the data taken at 72 hours post-injury may not reflect the effectiveness of anti-$\alpha_d$ monoclonal antibodies in reducing neutrophil infiltration.

Similar experiments using rats subjected to moderate CCI (35 g) were also performed. Results from this experiment show that animals that were administered 217L antibody showed significantly reduced numbers of infiltrating ED1$^+$ cells as well as MPO$^+$ cells at the site of injury. Control animals that were administered either PBS or 1B7 antibody showed 832.3±69 and 1075±87.94 infiltrating ED1$^+$ cells. Rats treated with 217L, 226H, or 236L antibody showed 507.0±51.4, 797.4±65.1, and 761.2±88.2 ED1$^+$ cells respectively at the site of injury. Examination of infiltrating MPO$^+$ cells at the site of injury in these animals showed that rats treated with 217L, 226H or 236L antibody had 190.5±28.4, 253.7±45.2, and 301.4±36.6 MPO$^+$ cells, respectively, at the injury site. Control animals treated with PBS or 1B7 antibody showed 611.7±140.5 and 247.6±18.1 MPO$^+$ cells, respectively, at the site of injury.

Locomotor Scores for anti-$\alpha_d$ mAb Treated Rats

Four rats were subjected to severe CCI and treated with antibodies as described above. At days 1, 7, 10, 14, 17, and 19 post injury, the rats were assessed for restored locomotor ability as assessed by the Basso, Beattie, Bresnahan (BBB) 21 point scoring system [Basso, et al., *J. Neurotrauma* 12:1–21 (1995)]. Briefly, the BBB scoring system is based on the three general phases of recovery following spinal cord injury. The early phase where little or no hindlimb movement is observed, the intermediate phase characterized by uncoordinated stepping, and the late phase in which animals show dragging of toes and tails, trunk instability and rotation of paws. Each of the three phases are further divided into categories characterized by specific behavior. Rats 41C450 and 42C50 were assessed over a 19 day period and rats 44C50 and 45C50 were assessed over a 17 day period. The horizontal bar on the 14 day assessment indicated the average BBB score achieved by untreated rats with the same severe injury. Scores for both sides of each rat indicated that the compression injury was evenly applied over the spinal cord.

Three of the four rats tested exhibited clear increases in locomotor recovery were observed compared to non-treated rats. It should be noted that by day 17, all four rats had also recovered a certain degree of bladder control.

Assessment of Autonomic Dysreflexia in Rats with CCI

The same four rats described above were assessed for autonomic dysreflexia by distending the colon [Maiorov, D. N. et al., *J. Neurotrauma* 15:365–374 (1998)]. This assessment was carried out starting on day 17 for rats 44C50 and 45C50 and on day 19 for rats 41C50 and 45C50. Simultaneous recording of heart rate (HR), arterial pressure (AR), and mean arterial pressure (MAP) were obtained twice on two consecutive days beginning with the day of arterial cannulation. Administration of 217L antibody to severely injured rats showed approximately 50% decrease in the effect of colon distension on arterial pressure. Untreated injured rats showed an average increase in MAP of 42±3 mmHg from a basal pressure of approximately 100 mm Hg. In contrast, similarly injured animals treated with 217L antibody showed an average increase in MAP of 22±3 mmHg. The average heart rate (HR) of an untreated resting rat with CCI was 515±16 beats/min. This HR value dropped by 124±13 beats/min following induction of autonomic dysreflexia upon colon distension. The average heart rate of the four resting rats treated with 217L antibody was 544±9 beats/min. This dropped by 117.7±18 after induction of autonomic dysreflexia resulting from colon distension. Thus, there was no statistically significant differences between the HR of treated versus untreated rats before or after induction of autonomic dysreflexia, which may be due to the fact that heart rate changes in response to colon distension occur via the parasympathetic vagus nerve which functions independently of the spinal cord injury.

Examination of Rats Treated with Anti-$\alpha_d$ Monoclonal Antibody at 12, 24 or 48 Hours After Injury If initial administration of anti-$\alpha_d$ antibody can be delayed to 12, 24 or 48 hours after spinal cord injury and still be effective, this would be useful because the time frame for delivery of effective treatment will be widened. To investigate this possibility, rats subjected to severe or moderate CC1 are treated with (i) PBS, (ii) 1B7 antibody or (iii) anti-$\alpha_d$ monoclonal antibody as described above, except that antibodies are administered 12 hours post CCI (followed by injections of the antibodies at 24 hours and 48 hours post CCI) or 24 hours post CCI (followed by another injection of antibodies at 48 hours post CCI). Similar experiments are also carried out in which antibodies are only administered once at 48 hours after CCI. The number of ED1$^+$ and MPO$^+$ cells is assessed using the methods described above. If administration of anti-$\alpha_d$ antibody is delayed to 12, 24, or 48 hours after CCI and the animals display a significant reduction in the number of infiltrating ED1+ and MPO+ cells, then treatment using this antibody can be initiated at a later time point after injury.

Comparison of the Effectiveness of a Single Injection of Anti-$\alpha_d$ Monoclonal Antibody with a Three-Injection Regimen to Reduce the Infiltration of ED1$^+$ and MPO$^+$ Cells to the Site of Injury Treatments using a single dose of antibody would be advantageous over those using a three-dose regimen. A single dose treatment would reduce costs, simplify the treatment procedure and may also reduce the occurrence of possible side effects. Based on results from experiments carried out above, the optimal time for antibody administration is determined. Rats subjected to severe or moderate CCI are given a single injection of anti-$\alpha_d$ monoclonal antibody, control 1B7 antibody or PBS at 2 hours post-CCI or at the optimal time as determined by analysis of results from above. Rats are sacrificed at 72 hours post injury and the number of ED1$^+$ and MPO$^+$ cells at the site of injury will be assayed. Results of animals given a single dose are compared to that from animals treated with a three-dose regimen to determine the effectiveness of the single dose treatment.

Examination of Effectiveness of Anti-$\alpha_d$ Monoclonal Antibody Treatment in Reducing Peak Neutrophil Infiltration to the Site of Injury.

The normal peak of neutophil infiltration occurs at 18 hours post injury and then declines rapidly to much lower sustained levels. To determine if treatment with anti-$\alpha_d$ antibody can reduce neutrophil infiltration to the site of injury, rats are treated with anti-$\alpha_d$ antibody, control 1B7 antibody or PBS at 2 or 12 hours post CCI (severe or moderate) and then sacrificed at 18–20 hours post CCI. The number of neutrophils infiltrating the site of injury is then assayed to analyze the effect of anti-$\alpha_d$ antibody administration during peak neutrophil infiltration.

Examination of Locomoter Ability and Autonomic Dysreflexia in Rats Subjected to CCI and Treated with Anti-$\alpha_d$ Antibody Based on results of experiments outlined above, the optimal treatment regimen is determined. Rats are subjected to severe or moderate CCI treated with PBS, control 1B7 antibody or anti-$\alpha_d$ antibody using the optimal treatment regimen. Every three days post-injury, rats are assessed for locomoter ability using the standard BBB scoring system as described above. Three weeks after CCI, a subset of the animals is tested for autonomic dysreflexia while the remaining rats are assessed for locomoter ability for another three weeks. Autonomic dysreflexia is assayed as described above.

EXAMPLE 39

Expression of $\alpha_d$ in Crohn's Disease

Previous work (Example 18) indicated that leukointegrins are detected at higher levels in tissue sections from patients with Crohn's disease. In order to assess the degree to which $\alpha_d$ expression is modulated in Crohn's disease, expression was examined in tissue sections from diseased and normal colon as follows.

Colon tissue from five individuals with Crohn's disease and a normal colon were sectioned at 6 μm thickness and air dried on Superfrost Plus (VWR Scientific) slides for five minutes at room temperature. Slides were stored at −20° C. until the assay was performed. Prior to use, slides were incubated at 50° C. for approximately two minutes. Sections were fixed in cold (4° C.) acetone (EM Science) for two minutes and allowed to air dry at room temperature. Sections were placed in buffer containing 100 ml 1×TBS, 1.1 ml 30% $H_2O_2$ (Sigma), and 1.0 ml 10% $NaN_3$ (Sigma) for 15 minutes at room temperature to remove endogenous peroxidase activity. Each section was incubated in 150 μl of a blocking solution containing 20% normal human serum (Boston Biomedica), 5% normal rat serum (Harlan), and 2% BSA (Sigma) in 1×TBS for 30 minutes at room temperature. After incubation, the solution was gently blotted from the sections. Primary monoclonal antibody was prepared at a protein concentration of 10 μg/ml in blocking solution and 75 μl was applied to each tissue section for one hour at room temperature. After incubation, sections were washed three times for five minutes each in 1×TBS to remove unbound antibody. Excess TBS was removed by aspirating around the tissue following the final wash. Biotinylated rat anti-mouse antibody (Jackson Laboratories) was diluted 1:400 in blocking solution and 75 μl was applied to each section for 30 minutes at room temperature. Slides were washed two times with 1×TBS for five minutes each wash. Peroxidase-conjugated avidin/biotin complex (Vector Laboratories) was prepared by adding 9 μl reagent A and 9 μl reagent B, both reagents supplied by the manufacturer, to 782 μl 1×TBS, and 75 μl of the resulting mixture was applied to each section for 30 minutes at room temperature. Slides were washed two times in 1×TBS for five minutes each wash. Substrate 3,3'-diaminobenzidine (DAB) (Vector Laboratories) was applied and color development was stopped by immersion in water. One drop of 1% osmic acid (VWR) was applied to each section for approximately 15 seconds to enhance the signal intensity and the reaction was stopped by immersion in water. Sections were counterstained in Gill's hematoxylin #2 (Sigma) and rinsed in water before dehydrating and mounting with Cytoseal (VWR).

In the normal colon, no labeling was detected with antibodies 217L, 217K, or 212D. Antibody 240I labeled numerous cells in lymphoid aggregates as well as lymphocytes and eosinophils scattered in the lamina propria. Antibody 240I also labeled cell types that appeared to be either macrophages or activated lymphocytes. Staining with antibody 169A was similar to that of antibody 240I. Antibody 169B labeled lymphocytes and macrophages scattered in the lamina propria and submucosa, in addition to a subset of smooth muscle cells around arteries and in the muscularis externa.

With the Crohn's colon samples, the labeling patterns observed with the individual antibodies overlapped but the expression patterns were not identical. No labeling was detected with antibodies 212D or 217K. Antibody 240I labeled granulomas with differential expression on the multinucleated giant cells in the lyrnphoid aggregates and labeled lymphocytes in the lymphoid aggregates. Antibody 240I labeled eosinophils and lymphocytes scattered in the lamina propria. Antibody 217L also labeled granulomas with different expression on the multinucleated giant cells in the lymphoid aggregates. Antibody 217L labeled a small subset of lymphomas in the lamina propia and submucosa which were also labeled with 240I. The staining pattern of antibody 169A was very similar to that found for 240I except that 169A labeled fewer lymphocytes. Antibody 169B staining was similar to the 169A pattern except that 169B also labeled a subset of smooth muscle cells around the vessels and in the muscularis externa.

EXAMPLE 40

TNFα Release from Rat Spleen $\alpha_d^+$ Cells

In order to characterize a unique splenic subpopulation of $\alpha_d^+$ cells with respect to the ability to produce cytokine upon stimulation, the following experiments were conducted.

Lewis rats were injected subcutaneously in the rear flank with 100 μl of a 1:1 emulsion of Complete Freund's Adjuvant (CFA) in PBS and the animals were sacrificed seven days later. The spleens were harvested and a single cell suspension was prepared by standard procedures. B cells, CD4$^+$ T helper cells, and macrophages were selectively removed using monoclonal antibodies against CD4 (antibody W3/25, E.A.A.C.C. No: 84112002), CD11b (antibody OX42, E.A.A.C.C. No: 87081803) and CD45Ra/b (antibody OX33, Pharmingen) pre-armed onto an anti-mouse IgG magnetic bead conjugate. The CD4 antibody identifies T cells, the CD11b antibody identifies macrophage, monocytes, granulocytes, and natural killer cells, and the CD45Ra/b antibody recognizes B cells, T cell subsets, monocytes, granulocytes, and macrophage. A magnet was then used to remove the antibody-coated cells. The non-$\alpha_d$ herent cells were collected and a positive selection was carried out using biotinylated rat anti-$\alpha_d$ monoclonal antibodies 205C and 226G, followed by incubation with Streptavidin magnetic beads. The antibody-coated cells were collected using a magnet and suspended at 5×10$^5$ cells/ml in growth media (RPMI 1640 including 2% normal Lewis rat serum, penicillin/streptomycin sodium pyruvate; L-glutamine).

Two ml of cell suspension was added to individual wells on a 24 well plate coated with 3 μg/ml anti-rat CD3 monoclonal antibody (G418, Pharmingen), irrelevant control antibody, or no antibody. The plate was incubated at 37° C. in 7% $CO_2$ and supernatants from each well were collected after 20 hours, 48 hours, and 72 hours. Supernatants were aliquoted and stored at −70° C. immediately upon collection. Prior to the assay, supernatants were diluted 1:2 and placed into an anti-rat TNFα detection assay (Biosource).

Results indicated that after stimulation with the anti-CD3 monoclonal antibody, the $\alpha_d^+$ cells released approximately 280 pg/ml TNFα after 20 hours compared to approximately 40 pg/ml with the antibody control and media only treatment groups.

EXAMPLE 41

Modulation of TNFα Release from Activated Splenocytes With $\alpha_d$ Antibodies In order to assess the role of $\alpha_d^+$ phagocytic splenocytes in an inflammatory response, the following experiments were performed.

Because it has previously been shown that $\alpha_d^+$ splenic macrophages phagocytose magnetic particles injected into rats, cells of this type were collected in the following manner. Four mice were injected intravenously with 200 μl of a magnetic bead suspension (amine-conjugated, Perspective Biosystems). After 24 hours, spleens were removed and a single-cell suspension was prepared by passing the tissue through a wire-mesh screen. The cells were isolated using a magnet and washed one time in PBS containing magnesium and calcium, placed into culture in RPMI/10% FBS medium, and grown under the following six conditions: (i) no treatment; (ii) with hamster anti-rat $\alpha_d$ monoclonal antibody 205C (10 μg/ml) that crossreacts with mouse $\alpha_d$; (iii) with hamster anti-rat $\alpha_d$ monoclonal antibody 205E (10 μg/ml) which also crossreacts with mouse $\alpha_d$; (iv) with lipopolysaccharide (LPS); (v) with LPS and monoclonal antibody 205C (10 μg/ml); and (vi) with LPS and monoclonal antibody 205E (10 μg/ml) that also crossreacts with mouse $\alpha_d$.

Where indicated, the cells were first treated with the antibody for 30 minutes after which a 200 μl sample of conditioned medium was collected to represent the initial time point (t=0). LPS (10 ng/ml) was then added to wells as indicated above and aliquots of media were collected at 0.5 hour, 1 hour, 2 hours, and 4 hours and assayed for released TNFα by ELISA using a murine TNFα kit (ENDOGEN, #005452). Upon collection, samples were immediately frozen until assay. Just prior to assay, the conditioned media was diluted 1:1 and assayed according to the manufacturer's suggested protocol.

Results indicated that splenocytes which had not been activated with LPS showed no significant release of TNFα into the media regardless of prior antibody treatment. Splenocytes which had been treated with LPS released TNFα into the media at a detectable level, while the LPS-activated cells treated with either 205C or 205E antibody showed significantly lower levels of TNFα release. These results were consistent over all time points tested and confirmed in subsequently repeated assays. In addition, the same results were observed in later experiments with splenocytes that were not isolated using magnetic beads. Finally, preliminary results indicated that IL-1β release from splenocytes was similarly inhibited by the anti-$\alpha_d$ monoclonal antibodies.

EXAMPLE 42

Characterization of $\alpha_d$ Expression on Eosinophils

Previous observations indicated that $\alpha_d$ is expressed on all peripheral blood eosinophils (Example 18). In order to further examine the expression and function of $\alpha_d$ on human eosinophils, the following analyses were carried out.
Expression of $\alpha_d$ Integrin on Human Granulocytes Expression of $\alpha_d$ on human granulocytes was examined on cells prepared as follows. Normodense eosinophils (i.e., those with a normal specific gravity of greater than 1.09) were isolated from peripheral blood of allergic volunteers by density gradient centrifugation, hypotonic erythrocyte lysis, and immunomagnetic negative selection as previously described [Hansel, et al., *J. Immunol. Meth.* 145:105 (1991)]. Neutrophils were purified from peripheral blood of normal volunteers by density gradient centrifugation and hypotonic erythrocyte lysis alone [Bochner, et al., *J. Immunol;.* 145:1832 (1990)]. Respective purities of the cell types always exceeded 95%. Enrichment of peripheral blood for basophils was performed using a double-percoll density gradient separation which increased the number of basophils to 3–10% of the total leukocyte count [Bochner, et al, *J. Immunol. Meth.* 125:265 (1989)]. Expression of integrins on the freshly isolated cells from blood following stimulation in culture was evaluated using single color indirect immunofluorescence and flow cytometry as previously described [Bochner, et al., *J. Immunol. Meth.* 125:265 (1989); Matsumoto, et al., *Blood* 86:1437 (1995)]. Dual color detection of basophils (using anti-IgE) was also performed. All samples were fixed in 0.1% paraformaldehyde (Sigma) and analyzed using an EPICS Profile II flow cytometer (Coulter). Approximately 10,000 events were collected and displayed on a four-log scale yielding values for means fluorescence intensity (MFI).

Results indicated that eosinophils express all four of the $\beta_2$ integrins.

The level of surface expression of $\alpha_d$ integrin was greater than that of CD11c, but less than expression of $\alpha_4$ integrin (CD49d), CD11a, or CD11b. Results also indicated that basophils have slightly higher levels of $\alpha_d$ integrin expression as compared to neutrophils.
Regulation of $\alpha_d$ Integrin Surface Expression on Human Eosinophils Initial studies were performed to determine whether eosinophils could rapidly mobilize intracellular stores of $\alpha_d\beta_2$ as has been reported for neutrophils [Van der Vieren, et al., *Immunity* 3:683 (1995)]. Purified peripheral blood eosinophils (prepared as described above) were incubated for 15 minutes with either PMA or the calcium ionophore A23187 and the surface expression of several a chains of the $\beta_2$ integrin family was measured by indirect immunofluorescence (described above).

Results indicated that both PMA at 50 ng/ml and calcium ionophore at 1 μM significantly increased expression of $\alpha_d$ and CD11b. Within minutes of adding PMA, expression increased and reached significantly increased levels by ten minutes.

This observation suggested that eosinophils have cytoplasmic stores of $\alpha_d\beta_2$ which, similar to CD11b stores, can be rapidly mobilized to the cell surface.

In view of these results, other eosinophil-active stimuli were tested for acute effects on $\alpha_d\beta_2$ expression. Incubation of eosinophils for fifteen minutes with MDC (100 nM), IL-5 (10 ng/ml), RANTES (100 ng/ml), and eotaxin (100 μM) failed to alter $\alpha_d$ integrin expression.

Previous observations have indicated that many eosinophil responses can be enhanced by prolonged exposure to certain cytokines, such as IL-5, in a phenomenon referred to as "priming" [Walsh, et al., *Immunol.* 71:258 (1990)]. Experiments were therefore designed to examine if priming eosinophil cultures with IL-5 would lead to changes in surface expression of $\alpha_d$ integrin. Purified eosinophils, prepared as described above, were incubated for four days with 10 ng/ml IL-5 and expression of various integrins assayed as described above.

Results indicated that while expression of $\alpha_d$ integrin on the cell surface increased four to five fold, the level of $\alpha 4$ integrin expression remained unchanged. The kinetics of the increase in $\alpha_d$ integrin expression indicated a statistically significant increase in expression after four to seven days of culture. In contrast, levels of $\alpha_4$ integrin did not change significantly. The kinetics of enhanced $\alpha_d$ expression with PMA exposure was similar to that of CD11b, suggesting that these two leukointegrins might exist in similar or identical intracellular compartments. The location of this compartment for either integrin in eosinophils is not known; however, in neutrophils, preformed stores of CD11b have been localized to specific granules [Todd, et al., *J. Clin. Invest.* 74:1280 (1984); Bainton, et al., *J. Exp. Med.* 166:1641 (1641)].

Because late phase bronchoalveolar lavage (BAL) eosinophils express many characteristics of cytokine-primed eosinophils [Kroegel, et al., *Ann. Rev. Respir. Dis.* 143:A45 (1991); Sedgewick, et al., *J. Immunol.* 149:3710 (1992)], expression of $\alpha_d$ on this cell type was also examined. BAL cells were obtained from allergic patients who had undergone an endobronchial segmental allergen challenge with either ragweed or *D. petrynissinus* extract 18 hours previously as described [Kroegel, et al., *J. Clin. Allergy Immunol.* 93725 (1994)]. Eosinophil purity in the late phase BAL fluid was 19±4%.

Results indicated that late phase BAL eosinophils also showed a statistically significant increase in $\alpha_d$ integrin expression, with levels similar to those seen after three days of culture stimulated with IL-5. In examining levels of $\alpha_d$ integrin on late phase BAL eosinophils, i.e., cells which have already undergone cell adhesion and migration to get to the airway lumen, levels of expression intermediate to those seen on freshly isolated and IL-5 cultured eosinophils were observed. These data suggest that at least a portion of the elevated levels of $\alpha_d$ found after IL-5 culture is likely due to increased transcription and translation of $\alpha_d$ integrin.
Eosinophils Expressing $\alpha_d$ Bind to VCAM-1

Although $\alpha_d$ integrin has been shown to bind ICAM-R and possibly mediate leukocyte-leukocyte adhesion [Van der Vieren, et al., *Immunity* 3:683 (1995)], experiments were designed to examine other possible ligands for $\alpha_d$ expressed on eosinophils. In part because of previous studies suggesting $\beta_2$ integrin-dependent, CD11b-independent eosinophil adhesion to VCAM-1 [Matsumoto, et al., *Blood* 86:1437 (1995)], initial studies were performed using immobilized recombinant VCAM-1.

For both freshly purified and cultured eosinophils, $^{51}Cr$-labeled cell adhesion to VCAM-1 (250 ng/ml) or BSA (1%)

coated wells was performed for 30 minutes at 37° C. as previously described [Matsumoto, et al., *Blood* 86:1437 (1995)]. In some experiments, cells were preincubated for 30 minutes at 4° C. with saturating concentrations of one or more of the following blocking monoclonal antibodies prior to examining adhesion: anti-CD18 (7E4), anti-CD11a (MHM24), anti-CD11b (clone 44), anti-CD11c (BU-15), anti-$\alpha_d$ (240I), and anti-$\alpha_4$ (HP2/1).

For transfected and parental CHO cells, adhesion was performed using coated plates identical to those employed for eosinophil adhesion. Examination of the transformed CHO cells indicated that $\alpha_d$ expression was relatively low, and as a result, the interaction between CHO transfectants and VCAM-1 was not as strongly detected as that between eosinophils and VCAM-1. A modification of a previously described gentle washing technique [Shanley, et al., *J. Immunol.* 160:1014 (1998)] was therefore employed. This technique allowed non-$\alpha_d$ herent cells to be dislodged from the inverted plate with centrifugation at 1×g for 30 minutes at 20° C. Remaining adherent cells were then removed using 0.1 M EDTA (Sigma) and counted by flow cytometry. In addition to VCAM-1, E-selection (100 ng/ml) was also used to coat wells in some adhesion experiments. In addition to the blocking monoclonal antibodies used in the eosinophil studies, immobilized VCAM-1 was pretreated with an appropriate dilution of F(ab')$_2$ anti-VCAM-1 monoclonal antibody prior to the addition of CHO cells.

Results indicated that freshly isolated eosinophils adhered to VCAM-1 and monoclonal antibody blocking of $\alpha_4$ integrin effectively inhibited adhesion. Blocking with the anti-CD11b antibody had no effect. Adhesion could also be significantly and consistently inhibited by anti-$\alpha_d$ monoclonal antibody 240I, albeit to a lesser degree (approximately 30% inhibition) than that observed using the anti-$\alpha_4$ antibody.

Even more striking were results of VCAM-1 adhesion experiments in which IL-5 cultured eosinophils, expressing enhanced levels of $\alpha_d$ integrin, were employed. Under these conditions, monoclonal antibodies to CD18, $\alpha_d$, or $\alpha_4$ integrins were equally effective in reducing adhesion to background levels, while a combination of blocking antibodies to CD11a, CD11b, and CD11c had no effect. It was also observed that IL-5 cultured eosinophils displayed enhanced background adhesion and reduced VCAM-1 adhesion compared to that seen with freshly isolated eosinophils. Based on monoclonal antibody blocking studies with freshly isolated eosinophils, adhesion to VCAM-1 was mainly mediated through $\alpha_4$ integrins. However, in IL-5-cultured eosinophils, adhesion to VCAM-1 was equally mediated by $\alpha_4$ and $\alpha_d$ integrins. Together, these data are the first to demonstrate activation-dependent regulation of $\alpha_d\beta_2$ integrin expression and function on human eosinophils and document a novel function for $\alpha_d\beta_2$ as an alternative ligand for VCAM-1.

Based on the result that $\alpha_d$ integrins on eosinophils bind to VCAM-1 and can be upregulated with IL-5, this leuko-integrin may play a role in cytokine-primed eosinophil recruitment to inflammatory sites.

EXAMPLE 43

CHO Cells Expressing $\alpha_d$ Bind VCAM-1

To further verify that $\alpha_d\beta_2$ functions as a ligand VCAM-1, CHO transfectants were generated expressing human $\alpha_d$ and $\beta_2$ integrin chains as follows.

Chinese hamster ovary cells were transfected as described in Example 11. The $\alpha_d\beta_2$-transfected CHO cells were cultured in DMEM/F12 media with 1 mM pyruvate and 2 mM L-glutamine (Biofluids) supplemented with 10% dialyzed FBS, 100 U/ml penicillin, 100 µg/ml streptomycin, and 600 µg/ml G418 (all from Life Technologies). Media for culture of the parental CHO cell line was similar except that non-dialyzed FBS (Life Technologies) was used and 0.1 mM hypoxanthine and 16 nM thymidine (Sigma) were used in place of the G418. The transfected cells expressed $\alpha_d$ and $\beta_2$ integrin chains at:modest levels and did not express CD11a, CD11b, CD11c, or $\alpha_4$ integrins. The parental CHO cell line failed to express any of these integrins. Adhesion assays were performed as described above in Example 42.

Results indicated that the $\alpha_d\beta_2$-transfected CHO cells adhered to VCAM-1-coated wells. Adhesion was effectively blocked by an F(ab')$_2$ monoclonal antibody against the first domain of VCAM-1 as well as by monoclonal antibodies against either CD18 or $\alpha_d$. In contrast, parental non-transfected CHO cells failed to adhere to VCAM-1 and neither cell type displayed significant adherence to wells coated with E-selectin.

The finding that the monoclonal antibody to the $\alpha_4$ integrin binding site in the first domain of VCAM-1 completely blocked $\alpha_d\beta_2$ integrin dependent VCAM-1 adhesion strongly suggested that the $\alpha_d\beta_2$ binding site is near or identical to that for $\alpha_4$ integrins. Since there is little amino acid homology between $\alpha_d$ and $\alpha_4$ integrins, this result was unexpected. Whether $\alpha_d\beta_2$ integrins can bind to other $\alpha_4$ integrin ligands, such as fibronectin or mucosal addressin cell adhesion molecule-1, is unknown.

VCAM-1 Regions Required for $\alpha_d$ Binding

The first two domains of VCAM-1 have been shown to support binding of $\alpha_4$ integrins and relevant amino acids in those domains have been identified. In order to determine whether $\alpha_d$ shares similar sites of recognition in the VCAM-1 molecules, a plasmid was constructed containing sequences for domains I and 2 of VCAM-1 fused to human immunoglobulin Fc. In addition, a modified version of the two domain VCAM-1 expression construct was generated by PCR to include a substitution mutation wherein alanine at residue 40 was replaced with an aspartate residue. The two expression constructs were transiently transfected into COS cells using the DEAE-Dextran protocol previously described. Protein was purified from the culture supernatant using Protein A Sepharose® as previously described.

The ability of CHO cells expressing either $\alpha_4\beta_1$ or $\alpha_d\beta_2$ to bind a five domain VCAM-1/Ig fusion protein or ICAM-1/Ig fusion protein was tested as follows. CAMs were immobilized on 96 well microtiter plates at 0.5 µg/well in bicarbonate buffer (pH 9.5). Plates were blocked with 1% fish gelatin and treated with either buffer, irrelevant antibody or a blocking VCAM-1 antibody. The $\alpha_d$ or $\alpha_4$ transformed CHO cells were treated with either buffer only, irrelevant antibody of a monoclonal antibody specific for the alpha chain (130K or 217I for $\alpha_d$ or $\alpha_{4.1}$ for $\alpha_4$) or a blocking alpha chain antibody. Cells were washed before addition to the CAM-coated wells at a density of 100,000 cells per well. Cells were incubated in the presence of the immobilized antibody for twenty minutes before addition of 5% glutaraldehyde. Following fixation, plates were washed with distilled water and cells were stained with 1% crystal violet, After destaining with 66% ethanol for several hours, absorbance at 570 nm was measured on a Dynatech plate reader.

Results indicated that both $\alpha_d\beta_2$ and $\alpha_4\beta_1$ recognized the five domain and two domain forms of VCAM-1 to equivalent degrees indicating that additional domains might not be required for binding. While differences were detected between the $\alpha_d$/VCAM-1 binding and $\alpha_4$/VCAM-12 binding, it is likely that the differences resulted from differential expression in the transformed CHO cells. Binding of both cell lines was blocked by the VCAM-1 antibody (50 to 100%), $\alpha_4$ antibody (100%) and $\alpha_d$ antibody (50%). The $\alpha_4$ transfected line did not recognize the mutant VCAM-1 and binding of the $\alpha_d$ cell line to the mutant was 50% of that detected with wild-type VCAM-1. Neither CHO cell line exhibited binding of ICAM-1/Ig. Combined, these results suggest that both $\alpha_d$ and $\alpha_4$ recognize domains 1 and 2 of VCAM-1 and recognize overlapping, but not identical, epitopes.

EXAMPLE 44

Targeting $\alpha_d$ as a Tumor Antigen

Spatially and temporally restricted expression of $\alpha_d$ suggests that the molecule may serve as a target for removal of pathogenic cell populations that express $\alpha_d$ on the surface. Several previous observations lead to this possibility.

For example, compared to other leukointegrins, $\alpha_d$ expression is less widespread. Expression of ad appears to be limited to a specialized and/or highly differentiated subset of leukocytes. Unlike other leukointegrins, $\alpha_d$ expression appears to be subject to regulation as evidenced by rapid down regulation on primary or transformed cells in culture. Monoclonal antibodies to $\alpha_d$ show variable reactivity even though the antibodies are specific for $\alpha_d$. For example, the anti $\alpha_d$ antibody 212D shows limited reactivity with normal tissue and highly differentiated myeloid cells as compared to reactivity observed with another anti-$\alpha_d$ monoclonal antibody 217L. Interestingly, knockout $\alpha_d$ mice survive until birth and beyond, but this observation provides little information relating to the biological function of $\alpha_d$. Finally, $\alpha_d$ expression has been detected on an estimated 70% of canine leukemias, and high levels of $\alpha_d$ expression have been detected on freshly isolated NK leukemia cells from F344 rats (Example 26). While tumor cells would be a preferred population for clearance using $\alpha_d$ as the target, any undesirable cell type that expresses $\alpha_d$ might also be cleared in the manner described below.

One or more antibodies are selected with preference for those exhibiting low level reactivity with normal tissue. One possibility would be antibody 212D for reasons discussed above. Appropriate control antibodies are also selected, including an irrelevant antibody as negative control. Blood and tumor samples are obtained from leukemia and lymphoma patients and screened by immunocytochemistry and for cell surface expression with analysis by FAScan, immunoprecipitation and Western blot analysis using the selected antibodies. Detection of positive staining would then lead to alternative procedures in developing the clearance method.

In one approach, the hypervariable region of the positive staining antibody selected above is cloned and expressed in the context of a complement-fixing human isotype. After subcloning and isotype switching, specification and reactivity is again assessed as described above including, for example, FACS analysis, histology on normal tissue, and immunoprecipitation. A cassette vector was developed for the purpose of expressing a chosen hypervariable region in a human IgG1 context. In addition, a series of primers were designed and synthesized to facilitate amplification of a hypervariable region of an antibody of interest from a hybridoma cell line [Gavilondo-Cowley, et al., in HYBRIDOMA, Vol 9 No; 5, 1990, Mary Anne Leibert Inc., Publishers, Media, Philadelphia, pp.407–417]. The resulting antibody is then tested in vitro to determine if its binding in the presence of complement results in cell death. Preferably, the in vitro assay is carried out using tumor cells. Control assays will determine if the monoclonal antibody exhibits the same activity in cell cultures that do not express $\alpha_d$.

The monoclonal antibody is also tested to determine if binding results in internalization which indicates that the antibody can be conjugated with a cytotoxic drug.

A preclinical model is developed wherein in vivo cytolytic activity is examined. In one example, equivalency is examined in the F344 rat model (Example 26). Another model is the SCID/Hu system wherein human cells have been transplanted. For example, myeloid U937 cells, Jurkat T cells, or human colon carcinoma HTC166 cells are transplanted into mice, tumors are harvested, and the tumors are stained for surface antigens using anti-$\alpha_d$ antibodies (e.g., 212D and 217L). Detection of $\alpha_d$ expression leads to use of the antibodies in vivo to remove tumors.

EXAMPLE 44

Human Anti-$\alpha_d$ Monoclonal Antibodies

Human monoclonal antibodies are identified by screening antibody repertoires displayed on filamentous phage as previously described [Waterhouse, et al., Nucl. Acids Res. 21:2265–2266 (1993); Parsons, et al., Protein Engineering 9:1043–1049 (1996)]. Briefly, functional V-gene segments from non-immunized human donors are used to construct a repertoire of single-chain Fv (scFv) fragments displayed on the surface of phage. Fragments are cloned in a phagemid vector which permits both phage displayed and soluble scFv to be produced without subcloning. A histidine tag has been incorporated to allow rapid purification of scFv by nickel chelate chromatography. Use of this library format generally permits isolation of human monoclonal antibody fragments in less than two weeks. Isolation is carried out as previously described [Marks, et al., J. Mol. Biol. 222:581–597 (1991), Vaughan, et al., Nature Biotechnol. 14:309–314 (1996)]. Preferably antibodies are identified that specifically recognize the I domain

EXAMPLE 45

Anti-$\alpha_d$ Antibody Treatment in Motheaten Mice

In motheaten mutant mice [Koo, et al., J. Immunol. 147:1194–1200 (1992); Koo. et al., J. Immunol. 151.6733–6741 (1993)], the autosomal recessive me$^v$ gene occurs spontaneously as a point mutation of the hematopoietic cell protein tyrosine phosphatase in C57BL/6 mice. Homozygotes develop a chronic myelomonocytic inflammation involving accumulation of myelomonocytic cells in the lung and skin which results in interstitial pneumonitis, thymic atrophy, and T cell and NK cell dysfunction. The inflammatory condition is transferable by bone marrow cell of these mice indicating that the me$^v$ mutation is due to a stem cell defect in the myelomonocytic pathway. Since $\alpha_d$ is present in mycloid cells, a procedure was undertaken to assess any inhibitory effects on the immunopathologic changes with anti-$\alpha_d$ monoclonal antibody treatment in normal mice following bone marrow transplant from motheaten mutant mice.

C57BL/6J (B6)-me$^v$/me$^v$ and their normal +/−siblings (B6)-+/− mice were obtained from the Jackson Laboratory, Bar Harbor, Me. Mice were maintained in a pathogen free environment with food and water provided ad libitum. All mice were six to ten weeks old.

At Day-1, all mice received 2 µg/ml α-NK1.1 antibody, PK136, Pharmingen) in 0.5 ml PBS via intraperitoneal injection. At Day 0, all B6+/− mice were irradiated with 750 Rad. Bone marrow was harvested from (B6) me$^v$/me$^v$ as previously described. Cells removed from tibia and femur were transferred to supplemented RPMI culture media and incubated for two hours prior to intravenous injection into the irradiated mice. Mice were immediately treated with either anti-$\alpha_d$ antibody 205C or irrelevant antibody at 5 mg/kg in 200 µl PBS via intraperitoneal injection. Purified 205C hamster anti-rat cross-reactive to mouse $\alpha_d$ monoclonal antibody has been described above. As a negative control, one group of mice received an equal volume saline injection. On Days 4 through 25, mice were treated with either antibody or saline injection every other day for a total of ten treatments and animals were monitored for changes in weight and signs of disease. In general, observations for each group were continued for a total of two months.

A moribund state is the endpoint in the assay. Animals that become very sick, however, are sacrificed. Survival rate among the groups are assessed and histological analyses of tissue are used as additional indicators of the efficacy of $\alpha_d$ antibody treatment. A similar study looking at the therapeutic properties of $\alpha_d$ antibodies is conducted to complement the prophylactic study described above.

As of day 35, none of the mice treated with the $\alpha_d$ antibody had dies, while two of the nine mice in the saline treated group had died and three of the remaining seven were developing conditions typical of the syndrome. In the group treated with irrelevant antibody, three of the eight had died.

EXAMPLE 46

Expression of $\alpha_d$ on Human Leukemias

Leukemias can be divided into two classes, myeloid and lymphoid, according to cell lineage and both of these classes can be further distinguished as acute or chronic. Because of the apparent restriction of $\alpha_d$ expression to myeloid lineage cells, it was hypothesized that myeloid, but not lymphocytic, leukemias express $\alpha_d$. A second line of inquiry, if the first hypothesis was correct, was to determine if $\alpha_d$ expression varied according to pathogenicity, thereby implying a disease-related function for $\alpha_d$ on these cells.

Expression of $\alpha_d$ on peripheral blood cells has been detected using antibodies 212D and 217L as described in Example 18. In the examination of leukemia cells, normal bone marrow cells were first analyzed by flow cytometric methods for $\alpha_d$ expression to establish a baseline for this cell type. Antibodies 212D and 217L were used to stain patient samples according to standard protocols and both antibodies exhibited weak reactivity with monocytes in the marrow. Antibody 212D was only marginally positive.

Flow cytometric analysis of leukemic cells from either peripheral blood or bone marrow of patients indicated the presence of 212D and 217L epitopes on myeloid blasts and monoblasts in three actue myelogenous leukemia (AML) patients. Expression was also observed on cells from a patient with chronic lymphocytic leukemia (CLL). Cells from another AML patient were evaluated at a later date and found to be $\alpha_d$ positive. Expression of $\alpha_d$ on the cells was 50 to 100% higher than control monoclonal antibodies, but significantly lower than CD11a, CD11b, and CD11c expression levels.

In light of these results, the U937 cell line, a myeloid lineage leukemia equivalent to stage M-4 (on a differentiation scale of M1–M5) AML cells, was also evaluated. The expression patterns of CD11a, CD11b, CD11c, and $\alpha_d$ were similar to those of AML patient cells. Interestingly, the presence of cell-surface $\alpha_d$ protein was dependent on culture conditions. Rich medium with high serum levels (Iscove's Modified Dulbecco's Medium, 20% FBS) supported $\alpha_d$ expression, while basic culture medium (RPMI, 10% FBS) did not.

The finding that $\alpha_d$ expression was detected on lymphoblasts from a CLL patient indicates that $\alpha_d$ can be expressed in lymphocyte-lineage cells and is consistent with other data (i.e., $\alpha_d$ expression on rat CD5$^+$ cells and canine CD8$^+$ cells). The relatively high level expression of other leukointegrins on these cells would preclude use of these cells to examine $\alpha_d$ function in a reproducible fashion, and suggests that the functional redundancy of this family would compensate for inhibition of one member in these cell types. In fact, $\alpha_d$ expression by these cells may be coincidental to aberrant transcription.

While these experiments did not fully support the initial hypotheses, the presence of $\alpha_d$ protein on both myeloid and lymphoid lineage leukemias suggests that a broad patient population may benefit from use of anti-$\alpha_d$ therapies aimed at tumor removal rather than functional inhibition.

Numerous modifications and variations in the invention as set forth in the above illustrative examples are expected to occur to those skilled in the art. Consequently only such limitations as appear in the appended claims should be placed on the invention.

What is claimed is:

1. A method for promoting locomotor recovery following spinal cord injury comprising the step of administering to a spinal cord injury victim an effective amount of an anti-$\alpha_d$ monoclonal antibody.

2. A method for inhibiting locomotor damage following spinal cord injury comprising the step of administering to a spinal cord injury victim an effective amount of an anti-$\alpha_d$ monoclonal antibody.

3. A method of limiting locomotor impairment following spinal cord injury comprising the step of administering to a spinal cord injury victim an effective amount of an anti-$\alpha_d$ monoclonal antibody.

4. A method of limiting autonomic and sensory dysfunction following spinal cord injury comprising the step of administering to a spinal cord injury victim an effective amount of an anti-$\alpha_d$ monoclonal antibody.

5. The method of any one of claims 1, 2, 3, or 4 wherein the anti-$\alpha_d$ monoclonal antibody is secreted by a hybridoma selected from the group consisting of 217L (ATCC Accession No: HB12701) and 226H (ATCC Accession No: 12502).

6. The method of any one of claims 1, 2, 3, or 4 wherein the anti-$\alpha_d$ monoclonal antibody competes with 217L (ATCC Accession No: HB 12701) or 226H (ATCC Accession No: 12502) for binding to $\alpha_d$.

7. The method of any one of claims 1, 2, 3, or 4 wherein the anti-$\alpha_d$ monoclonal antibody inhibits $\alpha_d$ binding to an $\alpha_d$ ligand.

8. The method according to any one of claims 1, 2, 3, or 4 wherein the spinal cord injury comprises compression to the spinal cord.

9. The method of claim 7 wherein the $\alpha_d$ ligand is selected from the group consisting of ICAM-R and VCAM-1.

* * * * *

UNITED STATES PATENT AND TRADEMARK OFFICE
CERTIFICATE OF CORRECTION

PATENT NO. : 6,432,404 B1
DATED : August 13, 2002
INVENTOR(S) : Michael W. Gallatin et al.

It is certified that error appears in the above-identified patent and that said Letters Patent is hereby corrected as shown below:

Column 2,
Line 67, replace "of the a chains" with -- of the α chains --.

Column 3,
Line 52, replace "integrin a subunit," with -- integrin α subunit, --.

Column 7,
Line 32, replace "transfonnants described" with -- transformants described --.

Column 9,
Line 38, replace "226H, 2261, 236A" with -- 226H, 226I, 236A --.

Column 14,
Line 44, replace "parafornaldehyde" with -- paraformaldehyde --.
Line 64, replace "for N-Terminal" with -- For N-Terminal --.

Column 19,
Line 60, replace "conserved a subunit" with -- conserved α subunit --.

Column 21,
Line 1, replace "[Larson and Springer, supra], [Shaw, et al." with -- Larson and Springer, supra], $\alpha_E$ [Shaw, et al." --.
Line 23, replace "all a integrins" with -- all α integrins --

Column 22,
Line 28, replace "2'SSC/0.1% SDS" with -- 2X SSC/0.1% SDS --.
Line 46, replace "A.7Q AND A.8Q" with -- A.7Q and A.8Q --.

Column 26,
Line 56, replace "100 μl sample" with -- 100μl/sample --.

Column 27,
Line 11, replace "and an a chain" with -- and an α chain --.

Column 28,
Line 17, replace "ofanti-CD18" with -- of anti-CD18 --.

Column 30,
Line 16, replace "$\alpha_d/iC^3b$" with -- $\alpha_d$/iC3b --.

UNITED STATES PATENT AND TRADEMARK OFFICE
CERTIFICATE OF CORRECTION

PATENT NO. : 6,432,404 B1
DATED : August 13, 2002
INVENTOR(S) : Michael W. Gallatin et al.

It is certified that error appears in the above-identified patent and that said Letters Patent is hereby corrected as shown below:

Column 33,
Line 20, replace "on the a chain" with -- on the α chain --.

Column 34,
Line 5, replace "ICAM-R/g" with -- ICAM-R/Ig --.

Column 35,
Line 54, replace "pDCS 1" with -- pDCS1 --.

Column 38,
Line 60, replace "a chain species" with -- α chain species --.

Column 39,
Line 9, replace "TS 1/18.1" with -- TS1/18.1 --.
Line 41, replace "supematant" with -- supernatant --.

Column 42,
Line 15, replace "dilutions of 115000" with -- dilutions of 1/5000 --.

Column 47,
Line 2, replace "a chains" with -- α chains --.

Column 52,
Line 50, replace "human ad gene" with -- human $α_d$ gene --.

Column 60,
Line 61, replace "perflusion boosts" with -- perfusion boosts --.

Column 61,
Line 64, replace "table-top microftige" with -- table-top microfuge --.

Column 65,
Line 18, replace "Positive cells" with -- positive cells. --.
Line 49, replace "the Solution" with -- the solution --.

Column 71,
Line 56, replace "5'-CGACATGTTCACTGCCTCTAGG-3'" with
-- 5'-GGACATCTTCACTGCCTCTAGG-3' --.

UNITED STATES PATENT AND TRADEMARK OFFICE
CERTIFICATE OF CORRECTION

PATENT NO.    : 6,432,404 B1
DATED         : August 13, 2002
INVENTOR(S)   : Michael W. Gallatin et al.

It is certified that error appears in the above-identified patent and that said Letters Patent is hereby corrected as shown below:

Column 72,
Line 54, replace "9600 thennocycler" with -- 9600 thermocycler --.
Line 57, replace "(5'3')" with -- (5'-3') --.

Column 73,
Line 19, replace "$Mg^{-+}$" with -- $Mg^{++}$ --.
Line 63, replace "11.b-1/2FOR10 5'-CGCCCT… (SEQ ID NO 68)" with
-- 11.b-1/2FOR10 5'-CGCCT… (SEQ ID NO 68) --.

Column 74,
Line 35, replace "(SEQ ID NO 83)" with -- (SEQ ID NO 51) --.

Column 75,
Line 34, replace "hematoxylin/cosin" with -- hematoxylin/eosin --.

Column 80,
Line 29, replace "$NaC_2H_3O_2.3H_2O$" with -- $NaC_2H_3O_23H_2O$ --.

Column 81,
Line 62, replace "tenninal" with -- terminal --.

Column 82,
Line 8, replace "other a chains" with -- other α chains --.
Line 13, replace "Human $β_2$ Subunits" with -- Human $β_2$ α Subunits --.
Line 33, replace "to all a chains" with -- to all α chains --.

Column 84,
Line 62, replace "ad monoclonal" with -- $α_d$ monoclonal --.

Column 86,
Lines 60, 64 and 67, replace "(NO+)" with -- (NO·) --.

Column 87,
Lines 5, 8, 10, 14, 24 and 51, replace "(NO+)" with -- (NO·) --.

Column 88,
Line 24, replace "(NO+)" with -- (NO·) --.

UNITED STATES PATENT AND TRADEMARK OFFICE
CERTIFICATE OF CORRECTION

PATENT NO. : 6,432,404 B1
DATED : August 13, 2002
INVENTOR(S) : Michael W. Gallatin et al.

It is certified that error appears in the above-identified patent and that said Letters Patent is hereby corrected as shown below:

Column 89,
Line 62, replace "post-αd optive" with -- post-adoptive --.

Column 91,
Line 34, replace "a chains" with -- α chains --.

Column 94,
Line 8, replace "tinder a heat lamp" with -- under a heat lamp --.

Column 96,
Line 44, replace "TCAM-R" with -- ICAM-R --.

Column 97,
Line 10, replace "the ad antibodies" with -- the $\alpha_d$ antibodies --.

Column 98,
Line 18, replace "156.5±163.3," with -- 156.5±63.3, --.

Column 102
Line 1, replace "non-αd herent" with -- non-adherent --.

Column 103,
Line 60, replace "a chains" with -- α chains --.

Column 104,
Line 20, replace "α4 integrin" with -- $\alpha_4$ integrin --.

Column 105,
Line 18, replace "non-αd herent" with -- non-adherent --.
Line 34, replace "cbserved" with -- observed --.

Column 106,
Line 8, replace "at:modest" with -- at modest --.
Line 35, replace "domains I and 2" with -- domains 1 and 2 --.
Line 53, replace "$\alpha_{4.1}$" with -- α4.1 --.

UNITED STATES PATENT AND TRADEMARK OFFICE
CERTIFICATE OF CORRECTION

PATENT NO.     : 6,432,404 B1
DATED          : August 13, 2002
INVENTOR(S)    : Michael W. Gallatin et al.

It is certified that error appears in the above-identified patent and that said Letters Patent is hereby corrected as shown below:

<u>Column 107,</u>
Line 20, replace "widesprea$\alpha_d$" with -- widespread --.
Line 20, replace "ofad" with -- of $\alpha_d$ --.

Signed and Sealed this

Twenty-fourth Day of February, 2004

JON W. DUDAS
*Acting Director of the United States Patent and Trademark Office*

SEQUENCE LISTING

<160> NUMBER OF SEQ ID NOS: 114

<210> SEQ ID NO 1
<211> LENGTH: 3726
<212> TYPE: DNA
<213> ORGANISM: Homo sapiens
<220> FEATURE:
<221> NAME/KEY: CDS
<222> LOCATION: (3)..(3485)

<400> SEQUENCE: 1

```
tg acc ttc ggc act gtg ctt ctt ctg agt gtc ctg gct tct tat cat        47
   Thr Phe Gly Thr Val Leu Leu Leu Ser Val Leu Ala Ser Tyr His
   1               5                   10                  15
```

| | |
|---|---|
| gga ttc aac ctg gat gtg gag gag cct acg atc ttc cag gag gat gca<br>Gly Phe Asn Leu Asp Val Glu Glu Pro Thr Ile Phe Gln Glu Asp Ala<br>20                          25                     30 | 95 |
| ggc ggc ttt ggg cag agc gtg gtg cag ttc ggt gga tct cga ctc gtg<br>Gly Gly Phe Gly Gln Ser Val Val Gln Phe Gly Gly Ser Arg Leu Val<br>35                       40                     45 | 143 |
| gtg gga gca ccc ctg gag gtg gtg gcg gcc aac cag acg gga cgg ctg<br>Val Gly Ala Pro Leu Glu Val Val Ala Ala Asn Gln Thr Gly Arg Leu<br>50                       55                     60 | 191 |
| tat gac tgc gca gct gcc acc ggc atg tgc cag ccc atc ccg ctg cac<br>Tyr Asp Cys Ala Ala Ala Thr Gly Met Cys Gln Pro Ile Pro Leu His<br>65                       70                     75 | 239 |
| atc cgc cct gag gcc gtg aac atg tcc ttg ggc ctg acc ctg gca gcc<br>Ile Arg Pro Glu Ala Val Asn Met Ser Leu Gly Leu Thr Leu Ala Ala<br>80                       85                     90                     95 | 287 |
| tcc acc aac ggc tcc cgg ctc ctg gcc tgt ggc ccg acc ctg cac aga<br>Ser Thr Asn Gly Ser Arg Leu Leu Ala Cys Gly Pro Thr Leu His Arg<br>100                     105                    110 | 335 |
| gtc tgt ggg gag aac tca tac tca aag ggt tcc tgc ctc ctg ctg ggc<br>Val Cys Gly Glu Asn Ser Tyr Ser Lys Gly Ser Cys Leu Leu Leu Gly<br>115                     120                    125 | 383 |
| tcg cgc tgg gag atc atc cag aca gtc ccc gac gcc acg cca gag tgt<br>Ser Arg Trp Glu Ile Ile Gln Thr Val Pro Asp Ala Thr Pro Glu Cys<br>130                     135                    140 | 431 |
| cca cat caa gag atg gac atc gtc ttc ctg att gac ggc tct gga agc<br>Pro His Gln Glu Met Asp Ile Val Phe Leu Ile Asp Gly Ser Gly Ser<br>145                     150                    155 | 479 |
| att gac caa aat gac ttt aac cag atg aag ggc ttt gtc caa gct gtc<br>Ile Asp Gln Asn Asp Phe Asn Gln Met Lys Gly Phe Val Gln Ala Val<br>160                     165                    170                    175 | 527 |
| atg ggc cag ttt gag ggc act gac acc ctg ttt gca ctg atg cag tac<br>Met Gly Gln Phe Glu Gly Thr Asp Thr Leu Phe Ala Leu Met Gln Tyr<br>180                     185                    190 | 575 |
| tca aac ctc ctg aag atc cac ttc acc ttc acc caa ttc cgg acc agc<br>Ser Asn Leu Leu Lys Ile His Phe Thr Phe Thr Gln Phe Arg Thr Ser<br>195                     200                    205 | 623 |
| ccg agc cag cag agc ctg gtg gat ccc atc gtc caa ctg aaa ggc ctg<br>Pro Ser Gln Gln Ser Leu Val Asp Pro Ile Val Gln Leu Lys Gly Leu<br>210                     215                    220 | 671 |
| acg ttc acg gcc acg ggc atc ctg aca gtg gtg aca cag cta ttt cat<br>Thr Phe Thr Ala Thr Gly Ile Leu Thr Val Val Thr Gln Leu Phe His<br>225                     230                    235 | 719 |
| cat aag aat ggg gcc cga aaa agt gcc aag aag atc ctc att gtc atc<br>His Lys Asn Gly Ala Arg Lys Ser Ala Lys Lys Ile Leu Ile Val Ile<br>240                     245                    250                    255 | 767 |
| aca gat ggg cag aag tac aaa gac ccc ctg gaa tac agt gat gtc atc<br>Thr Asp Gly Gln Lys Tyr Lys Asp Pro Leu Glu Tyr Ser Asp Val Ile<br>260                     265                    270 | 815 |
| ccc cag gca gag aag gct ggc atc atc cgc tac gct atc ggg gtg gga<br>Pro Gln Ala Glu Lys Ala Gly Ile Ile Arg Tyr Ala Ile Gly Val Gly<br>275                     280                    285 | 863 |
| cac gct ttc cag gga ccc act gcc agg cag gag ctg aat acc atc agc<br>His Ala Phe Gln Gly Pro Thr Ala Arg Gln Glu Leu Asn Thr Ile Ser<br>290                     295                    300 | 911 |
| tca gcg cct ccg cag gac cac gtg ttc aag gtg gac aac ttt gca gcc<br>Ser Ala Pro Pro Gln Asp His Val Phe Lys Val Asp Asn Phe Ala Ala<br>305                     310                    315 | 959 |
| ctt ggc agc atc cag aag cag ctg cag gag aag atc tat gca gtt gag<br>Leu Gly Ser Ile Gln Lys Gln Leu Gln Glu Lys Ile Tyr Ala Val Glu<br>320                     325                    330                    335 | 1007 |

```
gga acc cag tcc agg gca agc agc tcc ttc cag cac gag atg tcc caa    1055
Gly Thr Gln Ser Arg Ala Ser Ser Ser Phe Gln His Glu Met Ser Gln
            340                 345                 350 gaa ggc ttc agc aca gcc ctc aca atg gat ggc ctc ttc ctg ggg gct    1103
Glu Gly Phe Ser Thr Ala Leu Thr Met Asp Gly Leu Phe Leu Gly Ala
            355                 360                 365 gtg ggg agc ttt agc tgg tct gga ggt gcc ttc ctg tat ccc cca aat    1151
Val Gly Ser Phe Ser Trp Ser Gly Gly Ala Phe Leu Tyr Pro Pro Asn
        370                 375                 380 atg agc ccc acc ttc atc aac atg tct cag gag aat gtg gac atg agg    1199
Met Ser Pro Thr Phe Ile Asn Met Ser Gln Glu Asn Val Asp Met Arg
    385                 390                 395 gac tct tac ctg ggt tac tcc acc gag cta gcc ctg tgg aag ggg gta    1247
Asp Ser Tyr Leu Gly Tyr Ser Thr Glu Leu Ala Leu Trp Lys Gly Val
400                 405                 410                 415 cag aac ctg gtc ctg ggg gcc ccc cgc tac cag cat acc ggg aag gct    1295
Gln Asn Leu Val Leu Gly Ala Pro Arg Tyr Gln His Thr Gly Lys Ala
                420                 425                 430 gtc atc ttc acc cag gtg tcc agg caa tgg agg aag aag gcc gaa gtc    1343
Val Ile Phe Thr Gln Val Ser Arg Gln Trp Arg Lys Lys Ala Glu Val
            435                 440                 445 aca ggg acg cag atc ggc tcc tac ttc ggg gcc tcc ctc tgc tcc gtg    1391
Thr Gly Thr Gln Ile Gly Ser Tyr Phe Gly Ala Ser Leu Cys Ser Val
            450                 455                 460 gat gtg gac agc gat ggc agc acc gac ctg atc ctc att ggg gcc ccc    1439
Asp Val Asp Ser Asp Gly Ser Thr Asp Leu Ile Leu Ile Gly Ala Pro
        465                 470                 475 cat tac tat gag cag acc cga ggg ggc cag gtg tcc gtg tgt ccc ttg    1487
His Tyr Tyr Glu Gln Thr Arg Gly Gly Gln Val Ser Val Cys Pro Leu
480                 485                 490                 495 cct agg ggg cag agg gtg cag tgg cag tgt gac gct gtt ctc cgt ggt    1535
Pro Arg Gly Gln Arg Val Gln Trp Gln Cys Asp Ala Val Leu Arg Gly
                500                 505                 510 gag cag ggc cac ccc tgg ggc cgc ttt ggg gca gcc ctg aca gtg ttg    1583
Glu Gln Gly His Pro Trp Gly Arg Phe Gly Ala Ala Leu Thr Val Leu
            515                 520                 525 ggg gat gtg aat gag gac aag ctg ata gac gtg gcc att ggg gcc ccg    1631
Gly Asp Val Asn Glu Asp Lys Leu Ile Asp Val Ala Ile Gly Ala Pro
            530                 535                 540 gga gag cag gag aac cgg ggt gct gtc tac ctg ttt cac gga gcc tca    1679
Gly Glu Gln Glu Asn Arg Gly Ala Val Tyr Leu Phe His Gly Ala Ser
545                 550                 555 gaa tcc ggc atc agc ccc tcc cac agc cag cgg att gcc agc tcc cag    1727
Glu Ser Gly Ile Ser Pro Ser His Ser Gln Arg Ile Ala Ser Ser Gln
560                 565                 570                 575 ctc tcc ccc agg ctg cag tat ttt ggg cag gcg ctg agt ggg ggt cag    1775
Leu Ser Pro Arg Leu Gln Tyr Phe Gly Gln Ala Leu Ser Gly Gly Gln
                580                 585                 590 gac ctc acc cag gat gga ctg atg gac ctg gcc gtg ggg gcc cgg ggc    1823
Asp Leu Thr Gln Asp Gly Leu Met Asp Leu Ala Val Gly Ala Arg Gly
            595                 600                 605 cag gtg ctc ctg ctc agg agt ctg ccg gtg ctg aaa gtg ggg gtg gcc    1871
Gln Val Leu Leu Leu Arg Ser Leu Pro Val Leu Lys Val Gly Val Ala
            610                 615                 620 atg aga ttc agc cct gtg gag gtg gcc aag gct gtg tac cgg tgc tgg    1919
Met Arg Phe Ser Pro Val Glu Val Ala Lys Ala Val Tyr Arg Cys Trp
            625                 630                 635 gaa gag aag ccc agt gcc ctg gaa gct ggg gac gcc acc gtc tgt ctc    1967
Glu Glu Lys Pro Ser Ala Leu Glu Ala Gly Asp Ala Thr Val Cys Leu
```

-continued

```
640                645                650                655
acc atc cag aaa agc tca ctg gac cag cta ggt gac atc caa agc tct    2015
Thr Ile Gln Lys Ser Ser Leu Asp Gln Leu Gly Asp Ile Gln Ser Ser
                660                665                670 gtc agg ttt gat ctg gca ctg gac cca ggt cgt ctg act tct cgt gcc    2063
Val Arg Phe Asp Leu Ala Leu Asp Pro Gly Arg Leu Thr Ser Arg Ala
            675                680                685 att ttc aat gaa acc aag aac ccc act ttg act cga aga aaa acc ctg    2111
Ile Phe Asn Glu Thr Lys Asn Pro Thr Leu Thr Arg Arg Lys Thr Leu
        690                695                700 gga ctg ggg att cac tgt gaa acc ctg aag ctg ctt ttg cca gat tgt    2159
Gly Leu Gly Ile His Cys Glu Thr Leu Lys Leu Leu Leu Pro Asp Cys
    705                710                715 gtg gag gat gtg gtg agc ccc atc att ctg cac ctc aac ttc tca ctg    2207
Val Glu Asp Val Val Ser Pro Ile Ile Leu His Leu Asn Phe Ser Leu
720                725                730                735 gtg aga gag ccc atc ccc tcc ccc cag aac ctg cgt cct gtg ctg gcc    2255
Val Arg Glu Pro Ile Pro Ser Pro Gln Asn Leu Arg Pro Val Leu Ala
            740                745                750 gtg ggc tca caa gac ctc ttc act gct tct ctc ccc ttc gag aag aac    2303
Val Gly Ser Gln Asp Leu Phe Thr Ala Ser Leu Pro Phe Glu Lys Asn
        755                760                765 tgt ggg caa gat ggc ctc tgt gaa ggg gac ctg ggt gtc acc ctc agc    2351
Cys Gly Gln Asp Gly Leu Cys Glu Gly Asp Leu Gly Val Thr Leu Ser
    770                775                780 ttc tca ggc ctg cag acc ctg acc gtg ggg agc tcc ctg gag ctc aac    2399
Phe Ser Gly Leu Gln Thr Leu Thr Val Gly Ser Ser Leu Glu Leu Asn
785                790                795 gtg att gtg act gtg tgg aac gca ggt gag gat tcc tac gga acc gtg    2447
Val Ile Val Thr Val Trp Asn Ala Gly Glu Asp Ser Tyr Gly Thr Val
800                805                810                815 gtc agc ctc tac tat cca gca ggg ctg tcg cac cga cgg gtg tca gga    2495
Val Ser Leu Tyr Tyr Pro Ala Gly Leu Ser His Arg Arg Val Ser Gly
            820                825                830 gcc cag aag cag ccc cat cag agt gcc ctg cgc ctg gca tgt gag aca    2543
Ala Gln Lys Gln Pro His Gln Ser Ala Leu Arg Leu Ala Cys Glu Thr
        835                840                845 gtg ccc act gag gat gag ggc cta aga agc agc cgc tgc agt gtc aac    2591
Val Pro Thr Glu Asp Glu Gly Leu Arg Ser Ser Arg Cys Ser Val Asn
    850                855                860 cac ccc atc ttc cat gag ggc tct aac ggc acc ttc ata gtc aca ttc    2639
His Pro Ile Phe His Glu Gly Ser Asn Gly Thr Phe Ile Val Thr Phe
    865                870                875 gat gtc tcc tac aag gcc acc ctg gga gac agg atg ctt atg agg gcc    2687
Asp Val Ser Tyr Lys Ala Thr Leu Gly Asp Arg Met Leu Met Arg Ala
880                885                890                895 agt gca agc agt gag aac aat aag gct tca agc agc aag gcc acc ttc    2735
Ser Ala Ser Ser Glu Asn Asn Lys Ala Ser Ser Ser Lys Ala Thr Phe
            900                905                910 cag ctg gag ctc ccg gtg aag tat gca gtc tac acc atg atc agc agg    2783
Gln Leu Glu Leu Pro Val Lys Tyr Ala Val Tyr Thr Met Ile Ser Arg
        915                920                925 cag gaa gaa tcc acc aag tac ttc aac ttt gca acc tcc gat gag aag    2831
Gln Glu Glu Ser Thr Lys Tyr Phe Asn Phe Ala Thr Ser Asp Glu Lys
    930                935                940 aaa atg aaa gag gct gag cat cga tac cgt gtg aat aac ctc agc cag    2879
Lys Met Lys Glu Ala Glu His Arg Tyr Arg Val Asn Asn Leu Ser Gln
945                950                955 cga gat ctg gcc atc agc att aac ttc tgg gtt cct gtc ctg ctg aac    2927
```

-continued

```
Arg Asp Leu Ala Ile Ser Ile Asn Phe Trp Val Pro Val Leu Leu Asn
960                 965                 970                 975 ggg gtg gct gtg tgg gat gtg gtc atg gag gcc cca tct cag agt ctc     2975
Gly Val Ala Val Trp Asp Val Val Met Glu Ala Pro Ser Gln Ser Leu
                980                 985                 990 ccc tgt gtt tca gag aga aaa cct ccc cag cat tct gac ttc ctg acc     3023
Pro Cys Val Ser Glu Arg Lys Pro Pro Gln His Ser Asp Phe Leu Thr
            995                 1000                1005 cag att tca aga agt ccc atg ctg gac tgc tcc att gct gac tgc ctg     3071
Gln Ile Ser Arg Ser Pro Met Leu Asp Cys Ser Ile Ala Asp Cys Leu
        1010                1015                1020 cag ttc cgc tgt gac gtc ccc tcc ttc agc gtc cag gag gag ctg gat     3119
Gln Phe Arg Cys Asp Val Pro Ser Phe Ser Val Gln Glu Glu Leu Asp
    1025                1030                1035 ttc acc ctg aag ggc aat ctc agt ttc ggc tgg gtc cgc gag aca ttg     3167
Phe Thr Leu Lys Gly Asn Leu Ser Phe Gly Trp Val Arg Glu Thr Leu
1040                1045                1050                1055 cag aag aag gtg ttg gtc gtg agt gtg gct gaa att acg ttc gac aca     3215
Gln Lys Lys Val Leu Val Val Ser Val Ala Glu Ile Thr Phe Asp Thr
                1060                1065                1070 tcc gtg tac tcc cag ctt cca gga cag gag gca ttt atg aga gct cag     3263
Ser Val Tyr Ser Gln Leu Pro Gly Gln Glu Ala Phe Met Arg Ala Gln
            1075                1080                1085 atg gag atg gtg cta gaa gaa gac gag gtc tac aat gcc att ccc atc     3311
Met Glu Met Val Leu Glu Glu Asp Glu Val Tyr Asn Ala Ile Pro Ile
        1090                1095                1100 atc atg ggc agc tct gtg ggg gct ctg cta ctg ctg gcg ctc atc aca     3359
Ile Met Gly Ser Ser Val Gly Ala Leu Leu Leu Leu Ala Leu Ile Thr
    1105                1110                1115 gcc aca ctg tac aag ctt ggc ttc ttc aaa cgc cac tac aag gaa atg     3407
Ala Thr Leu Tyr Lys Leu Gly Phe Phe Lys Arg His Tyr Lys Glu Met
1120                1125                1130                1135 ctg gag gac aag cct gaa gac act gcc aca ttc agt ggg gac gat ttc     3455
Leu Glu Asp Lys Pro Glu Asp Thr Ala Thr Phe Ser Gly Asp Asp Phe
                1140                1145                1150 agc tgt gtg gcc cca aat gtg cct ttg tcc taataatcca ctttcctgtt       3505
Ser Cys Val Ala Pro Asn Val Pro Leu Ser
            1155                1160 tatctctacc actgtgggct ggacttgctt gcaaccataa atcaacttac atggaaacaa   3565
cttctgcata gatctgcact ggcctaagca acctaccagg tgctaagcac cttctcggag   3625
agatagagat tgtaatgttt ttacatatct gtccatcttt ttcagcaatg acccactttt   3685
tacagaagca ggcatggtgc cagcataaat tttcatatgc t                      3726
```

<210> SEQ ID NO 2
<211> LENGTH: 1161
<212> TYPE: PRT
<213> ORGANISM: Homo sapiens

<400> SEQUENCE: 2

```
Thr Phe Gly Thr Val Leu Leu Leu Ser Val Leu Ala Ser Tyr His Gly
 1               5                   10                  15

Phe Asn Leu Asp Val Glu Glu Pro Thr Ile Phe Gln Glu Asp Ala Gly
            20                  25                  30

Gly Phe Gly Gln Ser Val Val Gln Phe Gly Gly Ser Arg Leu Val Val
        35                  40                  45

Gly Ala Pro Leu Glu Val Val Ala Ala Asn Gln Thr Gly Arg Leu Tyr
    50                  55                  60
```

-continued

```
Asp Cys Ala Ala Ala Thr Gly Met Cys Gln Pro Ile Pro Leu His Ile
 65                  70                  75                  80

Arg Pro Glu Ala Val Asn Met Ser Leu Gly Leu Thr Leu Ala Ala Ser
                 85                  90                  95

Thr Asn Gly Ser Arg Leu Leu Ala Cys Gly Pro Thr Leu His Arg Val
            100                 105                 110

Cys Gly Glu Asn Ser Tyr Ser Lys Gly Ser Cys Leu Leu Leu Gly Ser
        115                 120                 125

Arg Trp Glu Ile Ile Gln Thr Val Pro Asp Ala Thr Pro Glu Cys Pro
    130                 135                 140

His Gln Glu Met Asp Ile Val Phe Leu Ile Asp Gly Ser Gly Ser Ile
145                 150                 155                 160

Asp Gln Asn Asp Phe Asn Gln Met Lys Gly Phe Val Gln Ala Val Met
                165                 170                 175

Gly Gln Phe Glu Gly Thr Asp Thr Leu Phe Ala Leu Met Gln Tyr Ser
            180                 185                 190

Asn Leu Leu Lys Ile His Phe Thr Phe Thr Gln Phe Arg Thr Ser Pro
        195                 200                 205

Ser Gln Gln Ser Leu Val Asp Pro Ile Val Gln Leu Lys Gly Leu Thr
    210                 215                 220

Phe Thr Ala Thr Gly Ile Leu Thr Val Val Thr Gln Leu Phe His His
225                 230                 235                 240

Lys Asn Gly Ala Arg Lys Ser Ala Lys Lys Ile Leu Ile Val Ile Thr
                245                 250                 255

Asp Gly Gln Lys Tyr Lys Asp Pro Leu Glu Tyr Ser Asp Val Ile Pro
            260                 265                 270

Gln Ala Glu Lys Ala Gly Ile Ile Arg Tyr Ala Ile Gly Val Gly His
        275                 280                 285

Ala Phe Gln Gly Pro Thr Ala Arg Gln Glu Leu Asn Thr Ile Ser Ser
    290                 295                 300

Ala Pro Pro Gln Asp His Val Phe Lys Val Asp Asn Phe Ala Ala Leu
305                 310                 315                 320

Gly Ser Ile Gln Lys Gln Leu Gln Glu Lys Ile Tyr Ala Val Glu Gly
                325                 330                 335

Thr Gln Ser Arg Ala Ser Ser Phe Gln His Glu Met Ser Gln Glu
            340                 345                 350

Gly Phe Ser Thr Ala Leu Thr Met Asp Gly Leu Phe Leu Gly Ala Val
        355                 360                 365

Gly Ser Phe Ser Trp Ser Gly Gly Ala Phe Leu Tyr Pro Pro Asn Met
    370                 375                 380

Ser Pro Thr Phe Ile Asn Met Ser Gln Glu Asn Val Asp Met Arg Asp
385                 390                 395                 400

Ser Tyr Leu Gly Tyr Ser Thr Glu Leu Ala Leu Trp Lys Gly Val Gln
                405                 410                 415

Asn Leu Val Leu Gly Ala Pro Arg Tyr Gln His Thr Gly Lys Ala Val
            420                 425                 430

Ile Phe Thr Gln Val Ser Arg Gln Trp Arg Lys Lys Ala Glu Val Thr
        435                 440                 445

Gly Thr Gln Ile Gly Ser Tyr Phe Gly Ala Ser Leu Cys Ser Val Asp
    450                 455                 460

Val Asp Ser Asp Gly Ser Thr Asp Leu Ile Leu Ile Gly Ala Pro His
465                 470                 475                 480

Tyr Tyr Glu Gln Thr Arg Gly Gly Gln Val Ser Val Cys Pro Leu Pro
```

-continued

```
                485                 490                 495
Arg Gly Gln Arg Val Gln Trp Gln Cys Asp Ala Val Leu Arg Gly Glu
                500                 505                 510

Gln Gly His Pro Trp Gly Arg Phe Gly Ala Ala Leu Thr Val Leu Gly
                515                 520                 525

Asp Val Asn Glu Asp Lys Leu Ile Asp Val Ala Ile Gly Ala Pro Gly
                530                 535                 540

Glu Gln Glu Asn Arg Gly Ala Val Tyr Leu Phe His Gly Ala Ser Glu
545                 550                 555                 560

Ser Gly Ile Ser Pro Ser His Ser Gln Arg Ile Ala Ser Ser Gln Leu
                565                 570                 575

Ser Pro Arg Leu Gln Tyr Phe Gly Gln Ala Leu Ser Gly Gly Gln Asp
                580                 585                 590

Leu Thr Gln Asp Gly Leu Met Asp Leu Ala Val Gly Ala Arg Gly Gln
                595                 600                 605

Val Leu Leu Leu Arg Ser Leu Pro Val Leu Lys Val Gly Val Ala Met
        610                 615                 620

Arg Phe Ser Pro Val Glu Val Ala Lys Ala Val Tyr Arg Cys Trp Glu
625                 630                 635                 640

Glu Lys Pro Ser Ala Leu Glu Ala Gly Asp Ala Thr Val Cys Leu Thr
                645                 650                 655

Ile Gln Lys Ser Ser Leu Asp Gln Leu Gly Asp Ile Gln Ser Ser Val
                660                 665                 670

Arg Phe Asp Leu Ala Leu Asp Pro Gly Arg Leu Thr Ser Arg Ala Ile
                675                 680                 685

Phe Asn Glu Thr Lys Asn Pro Thr Leu Thr Arg Arg Lys Thr Leu Gly
                690                 695                 700

Leu Gly Ile His Cys Glu Thr Leu Lys Leu Leu Leu Pro Asp Cys Val
705                 710                 715                 720

Glu Asp Val Val Ser Pro Ile Ile Leu His Leu Asn Phe Ser Leu Val
                        725                 730                 735

Arg Glu Pro Ile Pro Ser Pro Gln Asn Leu Arg Pro Val Leu Ala Val
                740                 745                 750

Gly Ser Gln Asp Leu Phe Thr Ala Ser Leu Pro Phe Glu Lys Asn Cys
                755                 760                 765

Gly Gln Asp Gly Leu Cys Glu Gly Asp Leu Gly Val Thr Leu Ser Phe
                770                 775                 780

Ser Gly Leu Gln Thr Leu Thr Val Gly Ser Ser Leu Glu Leu Asn Val
785                 790                 795                 800

Ile Val Thr Val Trp Asn Ala Gly Glu Asp Ser Tyr Gly Thr Val Val
                        805                 810                 815

Ser Leu Tyr Tyr Pro Ala Gly Leu Ser His Arg Arg Val Ser Gly Ala
                820                 825                 830

Gln Lys Gln Pro His Gln Ser Ala Leu Arg Leu Ala Cys Glu Thr Val
                835                 840                 845

Pro Thr Glu Asp Glu Gly Leu Arg Ser Ser Arg Cys Ser Val Asn His
            850                 855                 860

Pro Ile Phe His Glu Gly Ser Asn Gly Thr Phe Ile Val Thr Phe Asp
865                 870                 875                 880

Val Ser Tyr Lys Ala Thr Leu Gly Asp Arg Met Leu Met Arg Ala Ser
                    885                 890                 895

Ala Ser Ser Glu Asn Asn Lys Ala Ser Ser Lys Ala Thr Phe Gln
                900                 905                 910
```

-continued

```
Leu Glu Leu Pro Val Lys Tyr Ala Val Tyr Thr Met Ile Ser Arg Gln
        915                 920                 925

Glu Glu Ser Thr Lys Tyr Phe Asn Phe Ala Thr Ser Asp Glu Lys Lys
        930                 935                 940

Met Lys Glu Ala Glu His Arg Tyr Arg Val Asn Asn Leu Ser Gln Arg
945                 950                 955                 960

Asp Leu Ala Ile Ser Ile Asn Phe Trp Val Pro Val Leu Leu Asn Gly
                965                 970                 975

Val Ala Val Trp Asp Val Val Met Glu Ala Pro Ser Gln Ser Leu Pro
            980                 985                 990

Cys Val Ser Glu Arg Lys Pro Pro Gln His Ser Asp Phe Leu Thr Gln
        995                 1000                1005

Ile Ser Arg Ser Pro Met Leu Asp Cys Ser Ile Ala Asp Cys Leu Gln
        1010                1015                1020

Phe Arg Cys Asp Val Pro Ser Phe Ser Val Gln Glu Glu Leu Asp Phe
1025                1030                1035                1040

Thr Leu Lys Gly Asn Leu Ser Phe Gly Trp Val Arg Glu Thr Leu Gln
                1045                1050                1055

Lys Lys Val Leu Val Val Ser Val Ala Glu Ile Thr Phe Asp Thr Ser
                1060                1065                1070

Val Tyr Ser Gln Leu Pro Gly Gln Glu Ala Phe Met Arg Ala Gln Met
        1075                1080                1085

Glu Met Val Leu Glu Glu Asp Val Tyr Asn Ala Ile Pro Ile Ile
        1090                1095                1100

Met Gly Ser Ser Val Gly Ala Leu Leu Leu Ala Leu Ile Thr Ala
1105                1110                1115                1120

Thr Leu Tyr Lys Leu Gly Phe Phe Lys Arg His Tyr Lys Glu Met Leu
                1125                1130                1135

Glu Asp Lys Pro Glu Asp Thr Ala Thr Phe Ser Gly Asp Asp Phe Ser
                1140                1145                1150

Cys Val Ala Pro Asn Val Pro Leu Ser
        1155                1160

<210> SEQ ID NO 3
<211> LENGTH: 1153
<212> TYPE: PRT
<213> ORGANISM: Homo sapiens

<400> SEQUENCE: 3

Met Ala Leu Arg Val Leu Leu Thr Ala Leu Thr Leu Cys His Gly
  1             5                  10                  15

Phe Asn Leu Asp Thr Glu Asn Ala Met Thr Phe Gln Glu Asn Ala Arg
                 20                  25                  30

Gly Phe Gly Gln Ser Val Gln Leu Gln Gly Ser Arg Val Val Val
            35                  40                  45

Gly Ala Pro Gln Glu Ile Val Ala Ala Asn Gln Arg Gly Ser Leu Tyr
        50                  55                  60

Gln Cys Asp Tyr Ser Thr Gly Ser Cys Glu Pro Ile Arg Leu Gln Val
65                  70                  75                  80

Pro Val Glu Ala Val Asn Met Ser Leu Gly Leu Ser Leu Ala Ala Thr
                85                  90                  95

Thr Ser Pro Pro Gln Leu Leu Ala Cys Gly Pro Thr Val His Gln Thr
                100                 105                 110

Cys Ser Glu Asn Thr Tyr Val Lys Gly Leu Cys Phe Leu Phe Gly Ser
```

-continued

```
                115                 120                 125
Asn Leu Arg Gln Gln Pro Gln Lys Phe Pro Glu Ala Leu Arg Gly Cys
    130                 135                 140
Pro Gln Glu Asp Ser Asp Ile Ala Phe Leu Ile Asp Gly Ser Gly Ser
145                 150                 155                 160
Ile Ile Pro His Asp Phe Arg Arg Met Lys Glu Phe Val Ser Thr Val
                165                 170                 175
Met Glu Gln Leu Lys Lys Ser Lys Thr Leu Phe Ser Leu Met Gln Tyr
            180                 185                 190
Ser Glu Glu Phe Arg Ile His Phe Thr Phe Lys Glu Phe Gln Asn Asn
        195                 200                 205
Pro Asn Pro Arg Ser Leu Val Lys Pro Ile Thr Gln Leu Leu Gly Arg
    210                 215                 220
Thr His Thr Ala Thr Gly Ile Arg Lys Val Val Arg Glu Leu Phe Asn
225                 230                 235                 240
Ile Thr Asn Gly Ala Arg Lys Asn Ala Phe Lys Ile Leu Val Val Ile
                245                 250                 255
Thr Asp Gly Glu Lys Phe Gly Asp Pro Leu Gly Tyr Glu Asp Val Ile
            260                 265                 270
Pro Glu Ala Asp Arg Glu Gly Val Ile Arg Tyr Val Ile Gly Val Gly
        275                 280                 285
Asp Ala Phe Arg Ser Glu Lys Ser Arg Gln Glu Leu Asn Thr Ile Ala
    290                 295                 300
Ser Lys Pro Pro Arg Asp His Val Phe Gln Val Asn Asn Phe Glu Ala
305                 310                 315                 320
Leu Lys Thr Ile Gln Asn Gln Leu Arg Glu Lys Ile Phe Ala Ile Glu
                325                 330                 335
Gly Thr Gln Thr Gly Ser Ser Ser Phe Glu His Glu Met Ser Gln
            340                 345                 350
Glu Gly Phe Ser Ala Ala Ile Thr Ser Asn Gly Pro Leu Leu Ser Thr
        355                 360                 365
Val Gly Ser Tyr Asp Trp Ala Gly Gly Val Phe Leu Tyr Thr Ser Lys
    370                 375                 380
Glu Lys Ser Thr Phe Ile Asn Met Thr Arg Val Asp Ser Asp Met Asn
385                 390                 395                 400
Asp Ala Tyr Leu Gly Tyr Ala Ala Ala Ile Ile Leu Arg Asn Arg Val
                405                 410                 415
Gln Ser Leu Val Leu Gly Ala Pro Arg Tyr Gln His Ile Gly Leu Val
            420                 425                 430
Ala Met Phe Arg Gln Asn Thr Gly Met Trp Glu Ser Asn Ala Asn Val
        435                 440                 445
Lys Gly Thr Gln Ile Gly Ala Tyr Phe Gly Ala Ser Leu Cys Ser Val
    450                 455                 460
Asp Val Asp Ser Asn Gly Ser Thr Asp Leu Val Leu Ile Gly Ala Pro
465                 470                 475                 480
His Tyr Tyr Glu Gln Thr Arg Gly Gly Gln Val Ser Val Cys Pro Leu
                485                 490                 495
Pro Arg Gly Gln Arg Ala Arg Trp Gln Cys Asp Ala Val Leu Tyr Gly
            500                 505                 510
Glu Gln Gly Gln Pro Trp Gly Arg Phe Gly Ala Ala Leu Thr Val Leu
        515                 520                 525
Gly Asp Val Asn Gly Asp Lys Leu Thr Asp Val Ala Ile Gly Ala Pro
    530                 535                 540
```

-continued

Gly Glu Glu Asp Asn Arg Gly Ala Val Tyr Leu Phe His Gly Thr Ser
545                 550                 555                 560

Gly Ser Gly Ile Ser Pro Ser His Ser Gln Arg Ile Ala Gly Ser Lys
            565                 570                 575

Leu Ser Pro Arg Leu Gln Tyr Phe Gly Gln Ser Leu Ser Gly Gly Gln
            580                 585                 590

Asp Leu Thr Met Asp Gly Leu Val Asp Leu Thr Val Gly Ala Gln Gly
            595                 600                 605

His Val Leu Leu Leu Arg Ser Gln Pro Val Leu Arg Val Lys Ala Ile
            610                 615                 620

Met Glu Phe Asn Pro Arg Glu Val Ala Arg Asn Val Phe Glu Cys Asn
625                 630                 635                 640

Asp Gln Val Val Lys Gly Lys Glu Ala Gly Glu Val Arg Val Cys Leu
                645                 650                 655

His Val Gln Lys Ser Thr Arg Asp Arg Leu Arg Glu Gly Gln Ile Gln
                660                 665                 670

Ser Val Val Thr Tyr Asp Leu Ala Leu Asp Ser Gly Arg Pro His Ser
            675                 680                 685

Arg Ala Val Phe Asn Glu Thr Lys Asn Ser Thr Arg Arg Gln Thr Gln
690                 695                 700

Val Leu Gly Leu Thr Gln Thr Cys Glu Thr Leu Lys Leu Gln Leu Pro
705                 710                 715                 720

Asn Cys Ile Glu Asp Pro Val Ser Pro Ile Val Leu Arg Leu Asn Phe
                725                 730                 735

Ser Leu Val Gly Thr Pro Leu Ser Ala Phe Gly Asn Leu Arg Pro Val
            740                 745                 750

Leu Ala Glu Asp Ala Gln Arg Leu Phe Thr Ala Leu Phe Pro Phe Glu
            755                 760                 765

Lys Asn Cys Gly Asn Asp Asn Ile Cys Gln Asp Asp Leu Ser Ile Thr
770                 775                 780

Phe Ser Phe Met Ser Leu Asp Cys Leu Val Val Gly Gly Pro Arg Glu
785                 790                 795                 800

Phe Asn Val Thr Val Thr Val Arg Asn Asp Gly Glu Asp Ser Tyr Arg
                805                 810                 815

Thr Gln Val Thr Phe Phe Pro Leu Asp Leu Ser Tyr Arg Lys Val
                820                 825                 830

Ser Thr Leu Gln Asn Gln Arg Ser Gln Arg Ser Trp Arg Leu Ala Cys
            835                 840                 845

Glu Ser Ala Ser Ser Thr Glu Val Ser Gly Ala Leu Lys Ser Thr Ser
850                 855                 860

Cys Ser Ile Asn His Pro Ile Phe Pro Glu Asn Ser Glu Val Thr Phe
865                 870                 875                 880

Asn Ile Thr Phe Asp Val Asp Ser Lys Ala Ser Leu Gly Asn Lys Leu
                885                 890                 895

Leu Leu Lys Ala Asn Val Thr Ser Glu Asn Asn Met Pro Arg Thr Asn
            900                 905                 910

Lys Thr Glu Phe Gln Leu Glu Leu Pro Val Lys Tyr Ala Val Tyr Met
            915                 920                 925

Val Val Thr Ser His Gly Val Ser Thr Lys Tyr Leu Asn Phe Thr Ala
            930                 935                 940

Ser Glu Asn Thr Ser Arg Val Met Gln His Gln Tyr Gln Val Ser Asn
945                 950                 955                 960

-continued

```
Leu Gly Gln Arg Ser Leu Pro Ile Ser Leu Val Phe Leu Val Pro Val
                965                 970                 975
Arg Leu Asn Gln Thr Val Ile Trp Asp Arg Pro Gln Val Thr Phe Ser
            980                 985                 990
Glu Asn Leu Ser Ser Thr Cys His Thr Lys Glu Arg Leu Pro Ser His
        995                 1000                1005
Ser Asp Phe Leu Ala Glu Leu Arg Lys Ala Pro Val Val Asn Cys Ser
    1010                1015                1020
Ile Ala Val Cys Gln Arg Ile Gln Cys Asp Ile Pro Phe Phe Gly Ile
1025                1030                1035                1040
Gln Glu Glu Phe Asn Ala Thr Leu Lys Gly Asn Leu Ser Phe Asp Trp
                1045                1050                1055
Tyr Ile Lys Thr Ser His Asn His Leu Leu Ile Val Ser Thr Ala Glu
            1060                1065                1070
Ile Leu Phe Asn Asp Ser Val Phe Thr Leu Leu Pro Gly Gln Gly Ala
        1075                1080                1085
Phe Val Arg Ser Gln Thr Glu Thr Lys Val Glu Pro Phe Glu Val Pro
    1090                1095                1100
Asn Pro Leu Pro Leu Ile Val Gly Ser Ser Val Gly Gly Leu Leu Leu
1105                1110                1115                1120
Leu Ala Leu Ile Thr Ala Ala Leu Tyr Lys Leu Gly Phe Phe Lys Arg
                1125                1130                1135
Gln Tyr Lys Asp Met Met Ser Glu Gly Gly Pro Pro Gly Ala Glu Pro
            1140                1145                1150
Gln
```

```
<210> SEQ ID NO 4
<211> LENGTH: 1163
<212> TYPE: PRT
<213> ORGANISM: Homo sapiens

<400> SEQUENCE: 4
```

```
Met Thr Arg Thr Arg Ala Ala Leu Leu Leu Phe Thr Ala Leu Ala Thr
 1               5                  10                  15
Ser Leu Gly Phe Asn Leu Asp Thr Glu Glu Leu Thr Ala Phe Arg Val
            20                  25                  30
Asp Ser Ala Gly Phe Gly Asp Ser Val Val Gln Tyr Ala Asn Ser Trp
        35                  40                  45
Val Val Val Gly Ala Pro Gln Lys Ile Ile Ala Ala Asn Gln Ile Gly
    50                  55                  60
Gly Leu Tyr Gln Cys Gly Tyr Ser Thr Gly Ala Cys Glu Pro Ile Gly
65                  70                  75                  80
Leu Gln Val Pro Pro Glu Ala Val Asn Met Ser Leu Gly Leu Ser Leu
                85                  90                  95
Ala Ser Thr Thr Ser Pro Ser Gln Leu Leu Ala Cys Gly Pro Thr Val
            100                 105                 110
His His Glu Cys Gly Arg Asn Met Tyr Leu Thr Gly Leu Cys Phe Leu
        115                 120                 125
Leu Gly Pro Thr Gln Leu Thr Gln Arg Leu Pro Val Ser Arg Gln Glu
    130                 135                 140
Cys Pro Arg Gln Glu Gln Asp Ile Val Phe Leu Ile Asp Gly Ser Gly
145                 150                 155                 160
Ser Ile Ser Ser Arg Asn Phe Ala Thr Met Met Asn Phe Val Arg Ala
                165                 170                 175
```

-continued

```
Val Ile Ser Gln Phe Gln Arg Pro Ser Thr Gln Phe Ser Leu Met Gln
            180                 185                 190

Phe Ser Asn Lys Phe Gln Thr His Phe Thr Phe Glu Glu Phe Arg Arg
            195                 200                 205

Thr Ser Asn Pro Leu Ser Leu Leu Ala Ser Val His Gln Leu Gln Gly
            210                 215                 220

Phe Thr Tyr Thr Ala Thr Ala Ile Gln Asn Val Val His Arg Leu Phe
225                 230                 235                 240

His Ala Ser Tyr Gly Ala Arg Arg Asp Ala Ile Lys Ile Leu Ile Val
                245                 250                 255

Ile Thr Asp Gly Lys Lys Glu Gly Asp Ser Leu Asp Tyr Lys Asp Val
                260                 265                 270

Ile Pro Met Ala Asp Ala Ala Gly Ile Ile Arg Tyr Ala Ile Gly Val
            275                 280                 285

Gly Leu Ala Phe Gln Asn Arg Asn Ser Trp Lys Glu Leu Asn Asp Ile
            290                 295                 300

Ala Ser Lys Pro Ser Gln Glu His Ile Phe Lys Val Glu Asp Phe Asp
305                 310                 315                 320

Ala Leu Lys Asp Ile Gln Asn Gln Leu Lys Glu Lys Ile Phe Ala Ile
                325                 330                 335

Glu Gly Thr Glu Thr Ile Ser Ser Ser Phe Glu Leu Glu Met Ala
                340                 345                 350

Gln Glu Gly Phe Ser Ala Val Phe Thr Pro Asp Gly Pro Val Leu Gly
            355                 360                 365

Ala Val Gly Ser Phe Thr Trp Ser Gly Gly Ala Phe Leu Tyr Pro Pro
            370                 375                 380

Asn Met Ser Pro Thr Phe Ile Asn Met Ser Gln Glu Asn Val Asp Met
385                 390                 395                 400

Arg Asp Ser Tyr Leu Gly Tyr Ser Thr Glu Leu Ala Leu Trp Lys Gly
                405                 410                 415

Val Gln Ser Leu Val Leu Gly Ala Pro Arg Tyr Gln His Ile Gly Lys
            420                 425                 430

Ala Val Ile Phe Ile Gln Val Ser Arg Gln Trp Arg Met Lys Ala Glu
            435                 440                 445

Val Ile Gly Thr Gln Ile Gly Ser Tyr Phe Gly Ala Ser Leu Cys Ser
            450                 455                 460

Val Asp Val Asp Thr Asp Gly Ser Thr Asp Leu Val Leu Ile Gly Ala
465                 470                 475                 480

Pro His Tyr Tyr Glu Gln Thr Arg Gly Gly Gln Val Ser Val Cys Pro
                485                 490                 495

Leu Pro Arg Gly Trp Arg Arg Trp Trp Cys Asp Ala Val Leu Tyr Gly
                500                 505                 510

Glu Gln Gly His Pro Trp Gly Arg Phe Gly Ala Ala Leu Thr Val Leu
            515                 520                 525

Gly Asp Val Asn Gly Asp Lys Leu Thr Asp Val Val Ile Gly Ala Pro
530                 535                 540

Gly Glu Glu Glu Asn Arg Gly Ala Val Tyr Leu Phe His Gly Val Leu
545                 550                 555                 560

Gly Pro Ser Ile Ser Pro Ser His Ser Gln Arg Ile Ala Gly Ser Gln
                565                 570                 575

Leu Ser Ser Arg Leu Gln Tyr Phe Gly Gln Ala Leu Ser Gly Gly Gln
                580                 585                 590

Asp Leu Thr Gln Asp Gly Leu Val Asp Leu Ala Val Gly Ala Arg Gly
```

```
                  595                 600                 605
Gln Val Leu Leu Arg Thr Arg Pro Val Leu Trp Val Gly Val Ser
            610                 615                 620
Met Gln Phe Ile Pro Ala Glu Ile Pro Arg Ser Ala Phe Glu Cys Arg
625                 630                 635                 640
Glu Gln Val Val Ser Glu Gln Thr Leu Val Gln Ser Asn Ile Cys Leu
                645                 650                 655
Tyr Ile Asp Lys Arg Ser Lys Asn Leu Leu Gly Ser Arg Asp Leu Gln
            660                 665                 670
Ser Ser Val Thr Leu Asp Leu Ala Leu Ala Pro Gly Arg Leu Ser Pro
                675                 680                 685
Arg Ala Ile Phe Gln Glu Thr Lys Asn Arg Ser Leu Ser Arg Val Arg
            690                 695                 700
Val Leu Gly Leu Lys Ala His Cys Glu Asn Phe Asn Leu Leu Leu Pro
705                 710                 715                 720
Ser Cys Val Glu Asp Ser Val Ile Pro Ile Ile Leu Arg Leu Asn Phe
                725                 730                 735
Thr Leu Val Gly Lys Pro Leu Leu Ala Phe Arg Asn Leu Arg Pro Met
            740                 745                 750
Leu Ala Ala Leu Ala Gln Arg Tyr Phe Thr Ala Ser Leu Pro Phe Glu
            755                 760                 765
Lys Asn Cys Gly Ala Asp His Ile Cys Gln Asp Asn Leu Gly Ile Ser
770                 775                 780
Phe Ser Phe Pro Gly Leu Lys Ser Leu Leu Val Gly Ser Asn Leu Glu
785                 790                 795                 800
Leu Asn Ala Glu Val Met Val Trp Asn Asp Gly Glu Asp Ser Tyr Gly
                805                 810                 815
Thr Thr Ile Thr Phe Ser His Pro Ala Gly Leu Ser Tyr Arg Tyr Val
                820                 825                 830
Ala Glu Gly Gln Lys Gln Gly Gln Leu Arg Ser Leu His Leu Thr Cys
            835                 840                 845
Cys Ser Ala Pro Val Gly Ser Gln Gly Thr Trp Ser Thr Ser Cys Arg
            850                 855                 860
Ile Asn His Leu Ile Phe Arg Gly Gly Ala Gln Ile Thr Phe Leu Ala
865                 870                 875                 880
Thr Phe Asp Val Ser Pro Lys Ala Val Gly Leu Asp Arg Leu Leu Leu
                885                 890                 895
Ile Ala Asn Val Ser Ser Glu Asn Asn Ile Pro Arg Thr Ser Lys Thr
                900                 905                 910
Ile Phe Gln Leu Glu Leu Pro Val Lys Tyr Ala Val Tyr Ile Val Val
            915                 920                 925
Ser Ser His Glu Gln Phe Thr Lys Tyr Leu Asn Phe Ser Glu Ser Glu
            930                 935                 940
Glu Lys Glu Ser His Val Ala Met His Arg Tyr Gln Val Asn Asn Leu
945                 950                 955                 960
Gly Gln Arg Asp Leu Pro Val Ser Ile Asn Phe Trp Val Pro Val Glu
                965                 970                 975
Leu Asn Gln Glu Ala Val Trp Met Asp Val Glu Val Ser His Pro Gln
            980                 985                 990
Asn Pro Ser Leu Arg Cys Ser Ser Glu Lys Ile Ala Pro Pro Ala Ser
            995                 1000                1005
Asp Phe Leu Ala His Ile Gln Lys Asn Pro Val Leu Asp Cys Ser Ile
1010                1015                1020
```

Ala Gly Cys Leu Arg Phe Arg Cys Asp Val Pro Ser Phe Ser Val Gln
1025                1030                1035                1040

Glu Glu Leu Asp Phe Thr Leu Lys Gly Asn Leu Ser Phe Gly Trp Val
            1045                1050                1055

Arg Gln Ile Leu Gln Lys Lys Val Ser Val Ser Val Ala Glu Ile
        1060                1065                1070

Ile Phe Asp Thr Ser Val Tyr Ser Gln Leu Pro Gly Gln Glu Ala Phe
        1075                1080                1085

Met Arg Ala Gln Thr Ile Thr Val Leu Glu Lys Tyr Lys Val His Asn
    1090                1095                1100

Pro Ile Pro Leu Ile Val Gly Ser Ser Ile Gly Leu Leu Leu Leu
1105                1110                1115                1120

Ala Leu Ile Thr Ala Val Leu Tyr Lys Val Gly Phe Phe Lys Arg Gln
            1125                1130                1135

Tyr Lys Glu Met Met Glu Glu Ala Asn Gly Gln Ile Ala Pro Glu Asn
            1140                1145                1150

Gly Thr Gln Thr Pro Ser Pro Pro Ser Glu Lys
        1155                1160

<210> SEQ ID NO 5
<211> LENGTH: 12
<212> TYPE: PRT
<213> ORGANISM: dog

<400> SEQUENCE: 5

Phe Asn Leu Asp Val Glu Glu Pro Met Val Phe Gln
 1               5                  10

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: primer
<221> NAME/KEY: misc_feature
<222> LOCATION: 15
<223> OTHER INFORMATION: n = A or T or G or C
<221> NAME/KEY: misc_feature
<222> LOCATION: 24
<223> OTHER INFORMATION: n = A or T or G or C
<221> NAME/KEY: misc_feature
<222> LOCATION: 30
<223> OTHER INFORMATION: n = A or T or G or C

<400> SEQUENCE: 6
ttyaayytgg aygtngarga rccnatggtn ttyca                35

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 7
ttcaacctgg acgtggagga gcccatggtg ttccaa               36

<210> SEQ ID NO 8
<211> LENGTH: 36
<212> TYPE: DNA
<213> ORGANISM: Artificial Sequence
<220> FEATURE:
<223> OTHER INFORMATION: Description of Artificial Sequence: primer

```
<221> NAME/KEY: misc_feature
<222> LOCATION: 15
<223> OTHER INFORMATION: n = A or T or G or C
<221> NAME/KEY: misc_feature
<222> LOCATION: 21
<223> OTHER INFORMATION: n = A or T or G or C

<400> SEQUENCE: 8
ttcaacctgg acgtngaasa ncccatggtc ttccaa                                36

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: primer
<221> NAME/KEY: misc_feature
<222> LOCATION: 9
<223> OTHER INFORMATION: n = A or T or G or C
<221> NAME/KEY: misc_feature
<222> LOCATION: 15
<223> OTHER INFORMATION: n = A or T or G or C

<400> SEQUENCE: 9
ttyaayytng aygtngarga rcc                                              23

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: primer
<221> NAME/KEY: misc_feature
<222> LOCATION: 15
<223> OTHER INFORMATION: n = A or T or G or C

<400> SEQUENCE: 10
ttyaayytgg acgtngaaga                                                  20

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: primer
<221> NAME/KEY: misc_feature
<222> LOCATION: 6
<223> OTHER INFORMATION: n = A or T or G or C
<221> NAME/KEY: misc_feature
<222> LOCATION: 12
<223> OTHER INFORMATION: n = A or T or G or C

<400> SEQUENCE: 11
tgraanacca tnggytc                                                     17

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: primer
<221> NAME/KEY: misc_feature
<222> LOCATION: 13
<223> OTHER INFORMATION: n = A or T or G or C

<400> SEQUENCE: 12
ttggaagacc atnggytc                                                    18

<210> SEQ ID NO 13
```

```
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 13
attaaccctc actaaag                                                    17

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 14
aatacgactc actatag                                                    17

<210> SEQ ID NO 15
<211> LENGTH: 11
<212> TYPE: PRT
<213> ORGANISM: dog
<220> FEATURE:
<221> NAME/KEY: misc_feature
<222> LOCATION: 5
<223> OTHER INFORMATION: Xaa = any or unknown amino acid

<400> SEQUENCE: 15

Val Phe Gln Glu Xaa Gly Ala Gly Phe Gly Gln
  1               5                  10

<210> SEQ ID NO 16
<211> LENGTH: 14
<212> TYPE: PRT
<213> ORGANISM: dog
<220> FEATURE:
<221> NAME/KEY: misc_feature
<222> LOCATION: 4
<223> OTHER INFORMATION: Xaa = any or unknown amino acid
<221> NAME/KEY: misc_feature
<222> LOCATION: 11
<223> OTHER INFORMATION: Xaa = any or unknown amino acid

<400> SEQUENCE: 16

Leu Tyr Asp Xaa Val Ala Ala Thr Gly Leu Xaa Gln Pro Ile
  1               5                  10

<210> SEQ ID NO 17
<211> LENGTH: 12
<212> TYPE: PRT
<213> ORGANISM: dog
<220> FEATURE:
<221> NAME/KEY: misc_feature
<222> LOCATION: 5
<223> OTHER INFORMATION: Xaa = any or unknown amino acid

<400> SEQUENCE: 17

Pro Leu Glu Tyr Xaa Asp Val Ile Pro Gln Ala Glu
  1               5                  10

<210> SEQ ID NO 18
<211> LENGTH: 10
<212> TYPE: PRT
<213> ORGANISM: dog
<220> FEATURE:
<221> NAME/KEY: misc_feature
<222> LOCATION: 7
<223> OTHER INFORMATION: Xaa = any or unknown amino acid
```

```
<221> NAME/KEY: misc_feature
<222> LOCATION: 10
<223> OTHER INFORMATION: Xaa = any or unknown amino acid

<400> SEQUENCE: 18

Phe Gln Glu Gly Phe Ser Xaa Val Leu Xaa
 1               5                  10

<210> SEQ ID NO 19
<211> LENGTH: 14
<212> TYPE: PRT
<213> ORGANISM: dog
<220> FEATURE:
<221> NAME/KEY: misc_feature
<222> LOCATION: 7
<223> OTHER INFORMATION: Xaa = any or unknown amino acid

<400> SEQUENCE: 19

Thr Ser Pro Thr Phe Ile Xaa Met Ser Gln Glu Asn Val Asp
 1               5                  10

<210> SEQ ID NO 20
<211> LENGTH: 17
<212> TYPE: PRT
<213> ORGANISM: dog
<220> FEATURE:
<221> NAME/KEY: misc_feature
<222> LOCATION: 13
<223> OTHER INFORMATION: Xaa = any or unknown amino acid

<400> SEQUENCE: 20

Leu Val Val Gly Ala Pro Leu Glu Val Val Ala Val Xaa Gln Thr Gly
 1               5                  10                  15

Arg

<210> SEQ ID NO 21
<211> LENGTH: 9
<212> TYPE: PRT
<213> ORGANISM: dog
<220> FEATURE:
<221> NAME/KEY: misc_feature
<222> LOCATION: 3
<223> OTHER INFORMATION: Xaa = any or unknown amino acid
<221> NAME/KEY: misc_feature
<222> LOCATION: 6
<223> OTHER INFORMATION: Xaa = any or unknown amino acid

<400> SEQUENCE: 21

Leu Asp Xaa Lys Pro Xaa Asp Thr Ala
 1               5

<210> SEQ ID NO 22
<211> LENGTH: 7
<212> TYPE: PRT
<213> ORGANISM: dog

<400> SEQUENCE: 22

Phe Gly Glu Gln Phe Ser Glu
 1               5

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: primer
<221> NAME/KEY: misc_feature
<222> LOCATION: 4
```

-continued

<223> OTHER INFORMATION: n = A or T or G or C

<400> SEQUENCE: 23
raanccytcy tgraaactyt c                                              21

<210> SEQ ID NO 24
<211> LENGTH: 1006
<212> TYPE: DNA
<213> ORGANISM: dog

<400> SEQUENCE: 24
ttcaacctgg acgtggagga gcccatggtg ttcaagagga tggagctggc tttggacaga      60
gcgtggccca gcttggcgga tctagactcg tggtgggagc cccctggag gtggtggcgg     120
tcaaccaaac aggaaggttg tatgactgtg tggctgccac tggccttgtc aacccatacc    180
cctgcacaca cccccagatg ctgtgaacat gtccctgggt ctgtccctgt cagccgccgc    240
cagtcgcccc tggctgctgg cctgtggccc aaccatgcac agagcctgtg gggagaatat    300
gtatgcagaa ggcttttgcc tcctgttgga ctcccatctg cagaccattt ggacagtacc    360
tgctgcccta ccagagtgtc caagtcaaga gatggacatt gtcttcctga ttgatggttc    420
tggcagtatg agcaaagtga ctttaaacaa atgaaggatt tgtgagagct gtgatgggac    480
agtttgaggg cacccaaacc ctgttctcac tgatacagta tcccacctcc ctgaagatcc    540
acttcacctt cacgcaattc cagagcagct ggaaccctct gagcctggtg gatcccattg    600
tccaactgga cggcctgaca tatacagcca cgggcatccg gaaagtggtg gaggaactgt    660
ttcatagtaa gaatggggcc cgtaaaagtg ccaagaagat cctcattgtc atcacagatg    720
gcaaaaatac aaagaccccc tggagtacga ggacgtatcc ccaggcagag agagcggatc    780
atccgctatg ccattggggt gggagatgct ttctggaaac ccagtgccaa gcaggagctg    840
gacaacattg gctcagagcc ggctcaggac catgtgttca gggtggacaa ctttgcagca    900
ctcagcagca tccaggagca gctgcaggag aagatctttg cactcgaagg aacccagtcg    960
acgacaagta gctctttcca acatgagatg ttccaagaag ggttca                 1006

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: primer
<221> NAME/KEY: misc_feature
<222> LOCATION: 3
<223> OTHER INFORMATION: n = A or T or G or C

<400> SEQUENCE: 25
gtnttycarg argaygg                                                   17

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 26
ccactgtcag gatgcccgtg                                                20

<210> SEQ ID NO 27
<211> LENGTH: 42
<212> TYPE: DNA

<213> ORGANISM: Artificial Sequence
<220> FEATURE:
<223> OTHER INFORMATION: Description of Artificial Sequence: primer

<400> SEQUENCE: 27
agttacgaat tcgccaccat ggctctacgg gtgcttcttc tg          42

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: primer

<400> SEQUENCE: 28
agttacgaat tcgccaccat gactcggact gtgcttcttc tg          42

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 29
agttacgaat tcgccaccat gaccttcggc actgtg                 36

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 30
ttgctgactg cctgcagttc                                   20

<210> SEQ ID NO 31
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 31
gttctgacgc gtaatggcat tgtagacctc gtcttc                 36

<210> SEQ ID NO 32
<211> LENGTH: 36
<212> TYPE: DNA
<213> ORGANISM: Artificial Sequence
<220> FEATURE:
<223> OTHER INFORMATION: Description of Artificial Sequence: primer

<400> SEQUENCE: 32
acgtatgcag gatcccatca agagatggac atcgct                 36

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 33
actgcatgtc tcgaggctga agccttcttg ggacatc                37

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 34
tatagactgc tgggtagtcc ccac                                         24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 35
tgaagattgg gggtaaataa caga                                         24

<210> SEQ ID NO 36
<211> LENGTH: 3528
<212> TYPE: DNA
<213> ORGANISM: Rattus rattus
<220> FEATURE:
<221> NAME/KEY: CDS
<222> LOCATION: (1)..(3453)
<223> OTHER INFORMATION: Description of Artificial Sequence: primer
<221> NAME/KEY: misc_feature
<222> LOCATION: 361
<223> OTHER INFORMATION: Xaa = any or unknown amino acid
<221> NAME/KEY: misc_feature
<222> LOCATION: 464
<223> OTHER INFORMATION: Xaa = any or unknown amino acid
<221> NAME/KEY: misc_feature
<222> LOCATION: 486
<223> OTHER INFORMATION: Xaa = any or unknown amino acid
<221> NAME/KEY: misc_feature
<222> LOCATION: 506
<223> OTHER INFORMATION: Xaa = any or unknown amino acid
<221> NAME/KEY: misc_feature
<222> LOCATION: 1117
<223> OTHER INFORMATION: Xaa = any or unknown amino acid
<221> NAME/KEY: misc_feature
<222> LOCATION: 1118
<223> OTHER INFORMATION: Xaa = any or unknown amino acid

<400> SEQUENCE: 36

| ggc | tgg | gcc | ctg | gct | tcc | tgt | cat | ggg | tct | aac | ctg | gat | gtg | gag | gaa | 48 |
| Gly | Trp | Ala | Leu | Ala | Ser | Cys | His | Gly | Ser | Asn | Leu | Asp | Val | Glu | Glu | |
| 1 | | | | 5 | | | | | 10 | | | | | 15 | | |

| ccc | atc | gtg | ttc | aga | gag | gat | gca | gcc | agc | ttt | gga | cag | act | gtg | gtg | 96 |
| Pro | Ile | Val | Phe | Arg | Glu | Asp | Ala | Ala | Ser | Phe | Gly | Gln | Thr | Val | Val | |
| | | | 20 | | | | | 25 | | | | | 30 | | | |

| cag | ttt | ggt | gga | tct | cga | ctc | gtg | gtg | gga | gcc | cct | ctg | gag | gcg | gtg | 144 |
| Gln | Phe | Gly | Gly | Ser | Arg | Leu | Val | Val | Gly | Ala | Pro | Leu | Glu | Ala | Val | |
| | | 35 | | | | | 40 | | | | | 45 | | | | |

| gca | gtc | aac | caa | aca | gga | cgg | ttg | tat | gac | tgt | gca | cct | gcc | act | ggc | 192 |
| Ala | Val | Asn | Gln | Thr | Gly | Arg | Leu | Tyr | Asp | Cys | Ala | Pro | Ala | Thr | Gly | |
| | 50 | | | | | 55 | | | | | 60 | | | | | |

| atg | tgc | cag | ccc | atc | gta | ctg | cgc | agt | ccc | cta | gag | gca | gtg | aac | atg | 240 |
| Met | Cys | Gln | Pro | Ile | Val | Leu | Arg | Ser | Pro | Leu | Glu | Ala | Val | Asn | Met | |
| 65 | | | | 70 | | | | | 75 | | | | | 80 | | |

| tcc | ctg | ggc | ctg | tct | ctg | gtg | act | gcc | acc | aat | aac | gcc | cag | ttg | ctg | 288 |
| Ser | Leu | Gly | Leu | Ser | Leu | Val | Thr | Ala | Thr | Asn | Asn | Ala | Gln | Leu | Leu | |
| | | | 85 | | | | | 90 | | | | | 95 | | | |

```
gct tgt ggt cca act gca cag aga gct tgt gtg aag aac atg tat gcg      336
Ala Cys Gly Pro Thr Ala Gln Arg Ala Cys Val Lys Asn Met Tyr Ala
            100                 105                 110 aaa ggt tcc tgc ctc ctt ctc ggc tcc agc ttg cag ttc atc cag gca      384
Lys Gly Ser Cys Leu Leu Leu Gly Ser Ser Leu Gln Phe Ile Gln Ala
        115                 120                 125 gtc cct gcc tcc atg cca gag tgt cca aga caa gag atg gac att gct      432
Val Pro Ala Ser Met Pro Glu Cys Pro Arg Gln Glu Met Asp Ile Ala
130                 135                 140 ttc ctg att gat ggt tct ggc agc att aac caa agg gac ttt gcc cag      480
Phe Leu Ile Asp Gly Ser Gly Ser Ile Asn Gln Arg Asp Phe Ala Gln
145                 150                 155                 160 atg aag gac ttt gtc aaa gct ttg atg gga gag ttt gcg agc acc agc      528
Met Lys Asp Phe Val Lys Ala Leu Met Gly Glu Phe Ala Ser Thr Ser
                165                 170                 175 acc ttg ttc tcc ctg atg caa tac tcg aac atc ctg aag acc cat ttt      576
Thr Leu Phe Ser Leu Met Gln Tyr Ser Asn Ile Leu Lys Thr His Phe
            180                 185                 190 acc ttc act gaa ttc aag aac atc ctg gac cct cag agc ctg gtg gat      624
Thr Phe Thr Glu Phe Lys Asn Ile Leu Asp Pro Gln Ser Leu Val Asp
        195                 200                 205 ccc att gtc cag ctg caa ggc ctg acc tac aca gcc aca ggc atc cgg      672
Pro Ile Val Gln Leu Gln Gly Leu Thr Tyr Thr Ala Thr Gly Ile Arg
210                 215                 220 aca gtg atg gaa gag cta ttt cat agc aag aat ggg tcc cgt aaa agt      720
Thr Val Met Glu Glu Leu Phe His Ser Lys Asn Gly Ser Arg Lys Ser
225                 230                 235                 240 gcc aag aag atc ctc ctt gtc atc aca gat ggg cag aaa tac aga gac      768
Ala Lys Lys Ile Leu Leu Val Ile Thr Asp Gly Gln Lys Tyr Arg Asp
                245                 250                 255 ccc ctg gag tat agt gat gtc att ccc gcc gca gac aaa gct ggc atc      816
Pro Leu Glu Tyr Ser Asp Val Ile Pro Ala Ala Asp Lys Ala Gly Ile
            260                 265                 270 att cgt tat gct att ggg gtg gga gat gcc ttc cag gag ccc act gcc      864
Ile Arg Tyr Ala Ile Gly Val Gly Asp Ala Phe Gln Glu Pro Thr Ala
        275                 280                 285 ctg aag gag ctg aac acc att ggc tca gct ccc cca cag gac cac gtg      912
Leu Lys Glu Leu Asn Thr Ile Gly Ser Ala Pro Pro Gln Asp His Val
290                 295                 300 ttc aag gta ggc aac ttt gca gca ctt cgc agc atc cag agg caa ctt      960
Phe Lys Val Gly Asn Phe Ala Ala Leu Arg Ser Ile Gln Arg Gln Leu
305                 310                 315                 320 cag gag aaa atc ttc gcc att gag gga act caa tca agg tca agt agt     1008
Gln Glu Lys Ile Phe Ala Ile Glu Gly Thr Gln Ser Arg Ser Ser Ser
                325                 330                 335 tcc ttt cag cac gag atg tca caa gaa ggt ttc agt tca gct ctc aca     1056
Ser Phe Gln His Glu Met Ser Gln Glu Gly Phe Ser Ser Ala Leu Thr
            340                 345                 350 tcg gat gga ccc gtt ctg ggg gcc gyg gga agc ttc agc tgg tcc gga     1104
Ser Asp Gly Pro Val Leu Gly Ala Xaa Gly Ser Phe Ser Trp Ser Gly
        355                 360                 365 ggt gcc ttc tta tat ccc cca aat acg aga ccc acc ttt atc aac atg     1152
Gly Ala Phe Leu Tyr Pro Pro Asn Thr Arg Pro Thr Phe Ile Asn Met
370                 375                 380 tct cag gag aat gtg gac atg aga gac tcc tac ctg ggt tac tcc acc     1200
Ser Gln Glu Asn Val Asp Met Arg Asp Ser Tyr Leu Gly Tyr Ser Thr
385                 390                 395                 400 gca gtg gcc ttt tgg aag ggg gtt cac agc ctg atc ctg ggg gcc ccg     1248
Ala Val Ala Phe Trp Lys Gly Val His Ser Leu Ile Leu Gly Ala Pro
                405                 410                 415
```

```
cgt cac cag cac acg ggg aag gtt gtc atc ttt acc cag gaa gcc agg    1296
Arg His Gln His Thr Gly Lys Val Val Ile Phe Thr Gln Glu Ala Arg
            420                 425                 430 cat tgg agg ccc aag tct gaa gtc aga ggg aca cag atc ggc tcc tac    1344
His Trp Arg Pro Lys Ser Glu Val Arg Gly Thr Gln Ile Gly Ser Tyr
            435                 440                 445 ttc ggg gcc tct ctc tgt tct gtg gac gtg gat aga gat ggc agc acy    1392
Phe Gly Ala Ser Leu Cys Ser Val Asp Val Asp Arg Asp Gly Ser Xaa
        450                 455                 460 gac ctg gtc ctg atc gga gcc ccc cat tac tat gag cag acc cga ggg    1440
Asp Leu Val Leu Ile Gly Ala Pro His Tyr Tyr Glu Gln Thr Arg Gly
465                 470                 475                 480 ggg cag gtc tca gtg tkc ccc gtg ccc ggt gtg agg ggc agg tgg cag    1488
Gly Gln Val Ser Val Xaa Pro Val Pro Gly Val Arg Gly Arg Trp Gln
                485                 490                 495 tgt gag gcc acc ctc cac ggg gag cag grc cat cct tgg ggc cgc ttt    1536
Cys Glu Ala Thr Leu His Gly Glu Gln Xaa His Pro Trp Gly Arg Phe
            500                 505                 510 ggg gtg gct ctg aca gtg ctg ggg gac gta aac ggg gac aat ctg gca    1584
Gly Val Ala Leu Thr Val Leu Gly Asp Val Asn Gly Asp Asn Leu Ala
            515                 520                 525 gac gtg gct att ggt gcc cct gga gag gag gag agc aga ggt gct gtc    1632
Asp Val Ala Ile Gly Ala Pro Gly Glu Glu Glu Ser Arg Gly Ala Val
        530                 535                 540 tac ata ttt cat gga gcc tcg aga ctg gag atc atg ccc tca ccc agc    1680
Tyr Ile Phe His Gly Ala Ser Arg Leu Glu Ile Met Pro Ser Pro Ser
545                 550                 555                 560 cag cgg gtc act ggc tcc cag ctc tcc ctg aga ctg cag tat ttt ggg    1728
Gln Arg Val Thr Gly Ser Gln Leu Ser Leu Arg Leu Gln Tyr Phe Gly
                565                 570                 575 cag tca ttg agt ggg ggt cag gac ctt aca cag gat ggc ctg gtg gac    1776
Gln Ser Leu Ser Gly Gly Gln Asp Leu Thr Gln Asp Gly Leu Val Asp
            580                 585                 590 ctg gcc gtg gga gcc cag ggg cac gta ctg ctc agg agt ctg cct        1824
Leu Ala Val Gly Ala Gln Gly His Val Leu Leu Arg Ser Leu Pro
            595                 600                 605 ctg ctg aaa gtg gag ctc tcc ata aga ttc gcc ccc atg gag gtg gca    1872
Leu Leu Lys Val Glu Leu Ser Ile Arg Phe Ala Pro Met Glu Val Ala
610                 615                 620 aag gct gtg tac cag tgc tgg gaa agg act ccc act gtc ctc gaa gct    1920
Lys Ala Val Tyr Gln Cys Trp Glu Arg Thr Pro Thr Val Leu Glu Ala
625                 630                 635                 640 gga gag gcc act gtc tgt ctc act gtc cac aaa ggc tca cct gac ctg    1968
Gly Glu Ala Thr Val Cys Leu Thr Val His Lys Gly Ser Pro Asp Leu
                645                 650                 655 tta ggt aat gtc caa ggc tct gtc agg tat gat ctg gcg tta gat ccg    2016
Leu Gly Asn Val Gln Gly Ser Val Arg Tyr Asp Leu Ala Leu Asp Pro
            660                 665                 670 ggc cgc ctg att tct cgt gcc att ttt gat gag act aag aac tgc act    2064
Gly Arg Leu Ile Ser Arg Ala Ile Phe Asp Glu Thr Lys Asn Cys Thr
            675                 680                 685 ttg acg gga agg aag act ctg ggg ctt ggt gat cac tgc gaa aca gtg    2112
Leu Thr Gly Arg Lys Thr Leu Gly Leu Gly Asp His Cys Glu Thr Val
690                 695                 700 aag ctg ctt ttg ccg gac tgt gtg gaa gat gca gtg agc cct atc atc    2160
Lys Leu Leu Leu Pro Asp Cys Val Glu Asp Ala Val Ser Pro Ile Ile
705                 710                 715                 720 ctg cgc ctc aac ttt tcc ctg gtg aga gac tct gct tca ccc agg aac    2208
Leu Arg Leu Asn Phe Ser Leu Val Arg Asp Ser Ala Ser Pro Arg Asn
```

-continued

```
                725                     730                       735
ctg cat cct gtg ctg gct gtg ggc tca caa gac cac ata act gct tct      2256
Leu His Pro Val Leu Ala Val Gly Ser Gln Asp His Ile Thr Ala Ser
            740                 745                 750 ctg ccg ttt gag aag aac tgt aag caa gaa ctc ctg tgt gag ggg gac      2304
Leu Pro Phe Glu Lys Asn Cys Lys Gln Glu Leu Leu Cys Glu Gly Asp
        755                 760                 765 ctg ggc atc agc ttt aac ttc tca ggc ctg cag gtc ttg gtg gtg gga      2352
Leu Gly Ile Ser Phe Asn Phe Ser Gly Leu Gln Val Leu Val Val Gly
    770                 775                 780 ggc tcc cca gag ctc act gtg aca gtc act gtg tgg aat gag ggt gag      2400
Gly Ser Pro Glu Leu Thr Val Thr Val Thr Val Trp Asn Glu Gly Glu
785                 790                 795                 800 gac agc tat gga act tta gtc aag ttc tac tac cca gca ggg cta tct      2448
Asp Ser Tyr Gly Thr Leu Val Lys Phe Tyr Tyr Pro Ala Gly Leu Ser
                805                 810                 815 tac cga cgg gta aca ggg act cag caa cct cat cag tac cca cta cgc      2496
Tyr Arg Arg Val Thr Gly Thr Gln Gln Pro His Gln Tyr Pro Leu Arg
            820                 825                 830 ttg gcc tgt gag gct gag ccc gct gcc cag gag gac ctg agg agc agc      2544
Leu Ala Cys Glu Ala Glu Pro Ala Ala Gln Glu Asp Leu Arg Ser Ser
        835                 840                 845 agc tgt agc att aat cac ccc atc ttc cga gaa ggt gca aag acc acc      2592
Ser Cys Ser Ile Asn His Pro Ile Phe Arg Glu Gly Ala Lys Thr Thr
    850                 855                 860 ttc atg atc aca ttc gat gtc tcc tac aag gcc ttc cta gga gac agg      2640
Phe Met Ile Thr Phe Asp Val Ser Tyr Lys Ala Phe Leu Gly Asp Arg
865                 870                 875                 880 ttg ctt ctg agg gcc aaa gcc agc agt gag aat aat aag cct gat acc      2688
Leu Leu Leu Arg Ala Lys Ala Ser Ser Glu Asn Asn Lys Pro Asp Thr
                885                 890                 895 aac aag act gcc ttc cag ctg gag ctc cca gtg aag tac acc gtc tat      2736
Asn Lys Thr Ala Phe Gln Leu Glu Leu Pro Val Lys Tyr Thr Val Tyr
            900                 905                 910 acc ctg atc agt agg caa gaa gat tcc acc aac cat gtc aac ttt tca      2784
Thr Leu Ile Ser Arg Gln Glu Asp Ser Thr Asn His Val Asn Phe Ser
        915                 920                 925 tct tcc cac ggg ggg aga agg caa gaa gcc gca cat cgc tat cgt gtg      2832
Ser Ser His Gly Gly Arg Arg Gln Glu Ala Ala His Arg Tyr Arg Val
    930                 935                 940 aat aac ctg agt cca ctg aag ctg gcc gtc aga gtt aac ttc tgg gtc      2880
Asn Asn Leu Ser Pro Leu Lys Leu Ala Val Arg Val Asn Phe Trp Val
945                 950                 955                 960 cct gtc ctt ctg aac ggt gtg gct gtg tgg gac gtg act ctg agc agc      2928
Pro Val Leu Leu Asn Gly Val Ala Val Trp Asp Val Thr Leu Ser Ser
                965                 970                 975 cca gca cag ggt gtc tcc tgc gtg tcc cag atg aaa cct cct cag aat      2976
Pro Ala Gln Gly Val Ser Cys Val Ser Gln Met Lys Pro Pro Gln Asn
            980                 985                 990 ccc gac ttt ctg acc cag att cag aga cgt tct gtg ctg gac tgc tcc      3024
Pro Asp Phe Leu Thr Gln Ile Gln Arg Arg Ser Val Leu Asp Cys Ser
        995                 1000                1005 att gct gac tgc ctg cac tcc cgc tgt gac atc ccc tcc ttg gac atc      3072
Ile Ala Asp Cys Leu His Ser Arg Cys Asp Ile Pro Ser Leu Asp Ile
    1010                1015                1020 cag gat gaa ctt gac ttc att ctg agg ggc aac ctc agc ttc ggc tgg      3120
Gln Asp Glu Leu Asp Phe Ile Leu Arg Gly Asn Leu Ser Phe Gly Trp
1025                1030                1035                1040 gtc agt cag aca ttg cag gaa aag gtg ttg ctt gtg agt gag gct gaa      3168
```

```
Val Ser Gln Thr Leu Gln Glu Lys Val Leu Leu Val Ser Glu Ala Glu
                1045                1050                1055 atc act ttc gac aca tct gtg tac tcc cag ctg cca gga cag gag gca      3216
Ile Thr Phe Asp Thr Ser Val Tyr Ser Gln Leu Pro Gly Gln Glu Ala
            1060                1065                1070 ttt ctg aga gcc cag gtg gag aca acg tta gaa gaa tac gtg gtc tat      3264
Phe Leu Arg Ala Gln Val Glu Thr Thr Leu Glu Glu Tyr Val Val Tyr
        1075                1080                1085 gag ccc atc ttc ctc gtg gcg ggc agc tcg gtg gga ggt ctg ctg tta      3312
Glu Pro Ile Phe Leu Val Ala Gly Ser Ser Val Gly Gly Leu Leu Leu
    1090                1095                1100 ctg gct ctc atc aca gtg gta ctg tac aag ctt ggc tyc tyc aaa cgt      3360
Leu Ala Leu Ile Thr Val Val Leu Tyr Lys Leu Gly Xaa Xaa Lys Arg
1105                1110                1115                1120 cag tac aaa gaa atg ctg gac ggc aag gct gca gat cct gtc aca gcc      3408
Gln Tyr Lys Glu Met Leu Asp Gly Lys Ala Ala Asp Pro Val Thr Ala
            1125                1130                1135 ggc cag gca gat ttc ggc tgt gag act cct cca tat ctc gtg agc          3453
Gly Gln Ala Asp Phe Gly Cys Glu Thr Pro Pro Tyr Leu Val Ser
        1140                1145                1150 taggaatcca ctctcctgcc tatctctgna atgaagattg gtcctgccta tgagtctact    3513
ggcatgggaa cgagt                                                     3528

<210> SEQ ID NO 37
<211> LENGTH: 1151
<212> TYPE: PRT
<213> ORGANISM: Rattus rattus
<220> FEATURE:
<221> NAME/KEY: misc_feature
<222> LOCATION: 361
<223> OTHER INFORMATION: Xaa = any or unknown amino acid
<221> NAME/KEY: misc_feature
<222> LOCATION: 464
<223> OTHER INFORMATION: Xaa = any or unknown amino acid
<221> NAME/KEY: misc_feature
<222> LOCATION: 486
<223> OTHER INFORMATION: Xaa = any or unknown amino acid
<221> NAME/KEY: misc_feature
<222> LOCATION: 506
<223> OTHER INFORMATION: Xaa = any or unknown amino acid
<221> NAME/KEY: misc_feature
<222> LOCATION: 1117
<223> OTHER INFORMATION: Xaa = any or unknown amino acid
<221> NAME/KEY: misc_feature
<222> LOCATION: 1118
<223> OTHER INFORMATION: Xaa = any or unknown amino acid

<400> SEQUENCE: 37

Gly Trp Ala Leu Ala Ser Cys His Gly Ser Asn Leu Asp Val Glu Glu
  1               5                  10                  15

Pro Ile Val Phe Arg Glu Asp Ala Ala Ser Phe Gly Gln Thr Val Val
                20                  25                  30

Gln Phe Gly Gly Ser Arg Leu Val Val Gly Ala Pro Leu Glu Ala Val
            35                  40                  45

Ala Val Asn Gln Thr Gly Arg Leu Tyr Asp Cys Ala Pro Ala Thr Gly
        50                  55                  60

Met Cys Gln Pro Ile Val Leu Arg Ser Pro Leu Glu Ala Val Asn Met
 65                  70                  75                  80

Ser Leu Gly Leu Ser Leu Val Thr Ala Thr Asn Asn Ala Gln Leu Leu
                85                  90                  95

Ala Cys Gly Pro Thr Ala Gln Arg Ala Cys Val Lys Asn Met Tyr Ala
            100                 105                 110
```

-continued

```
Lys Gly Ser Cys Leu Leu Gly Ser Ser Leu Gln Phe Ile Gln Ala
        115                 120                 125

Val Pro Ala Ser Met Pro Glu Cys Pro Arg Gln Glu Met Asp Ile Ala
130                 135                 140

Phe Leu Ile Asp Gly Ser Gly Ser Ile Asn Gln Arg Asp Phe Ala Gln
145                 150                 155                 160

Met Lys Asp Phe Val Lys Ala Leu Met Gly Glu Phe Ala Ser Thr Ser
                165                 170                 175

Thr Leu Phe Ser Leu Met Gln Tyr Ser Asn Ile Leu Lys Thr His Phe
            180                 185                 190

Thr Phe Thr Glu Phe Lys Asn Ile Leu Asp Pro Gln Ser Leu Val Asp
        195                 200                 205

Pro Ile Val Gln Leu Gln Gly Leu Thr Tyr Thr Ala Thr Gly Ile Arg
210                 215                 220

Thr Val Met Glu Glu Leu Phe His Ser Lys Asn Gly Ser Arg Lys Ser
225                 230                 235                 240

Ala Lys Lys Ile Leu Leu Val Ile Thr Asp Gly Gln Lys Tyr Arg Asp
                245                 250                 255

Pro Leu Glu Tyr Ser Asp Val Ile Pro Ala Ala Asp Lys Ala Gly Ile
            260                 265                 270

Ile Arg Tyr Ala Ile Gly Val Gly Asp Ala Phe Gln Glu Pro Thr Ala
        275                 280                 285

Leu Lys Glu Leu Asn Thr Ile Gly Ser Ala Pro Pro Gln Asp His Val
290                 295                 300

Phe Lys Val Gly Asn Phe Ala Ala Leu Arg Ser Ile Gln Arg Gln Leu
305                 310                 315                 320

Gln Glu Lys Ile Phe Ala Ile Glu Gly Thr Gln Ser Arg Ser Ser Ser
                325                 330                 335

Ser Phe Gln His Glu Met Ser Gln Glu Gly Phe Ser Ser Ala Leu Thr
            340                 345                 350

Ser Asp Gly Pro Val Leu Gly Ala Xaa Gly Ser Phe Ser Trp Ser Gly
        355                 360                 365

Gly Ala Phe Leu Tyr Pro Pro Asn Thr Arg Pro Thr Phe Ile Asn Met
370                 375                 380

Ser Gln Glu Asn Val Asp Met Arg Asp Ser Tyr Leu Gly Tyr Ser Thr
385                 390                 395                 400

Ala Val Ala Phe Trp Lys Gly Val His Ser Leu Ile Leu Gly Ala Pro
                405                 410                 415

Arg His Gln His Thr Gly Lys Val Val Ile Phe Thr Gln Glu Ala Arg
            420                 425                 430

His Trp Arg Pro Lys Ser Glu Val Arg Gly Thr Gln Ile Gly Ser Tyr
        435                 440                 445

Phe Gly Ala Ser Leu Cys Ser Val Asp Val Asp Arg Asp Gly Ser Xaa
450                 455                 460

Asp Leu Val Leu Ile Gly Ala Pro His Tyr Tyr Glu Gln Thr Arg Gly
465                 470                 475                 480

Gly Gln Val Ser Val Xaa Pro Val Pro Gly Val Arg Gly Arg Trp Gln
                485                 490                 495

Cys Glu Ala Thr Leu His Gly Glu Gln Xaa His Pro Trp Gly Arg Phe
            500                 505                 510

Gly Val Ala Leu Thr Val Leu Gly Asp Val Asn Gly Asp Asn Leu Ala
        515                 520                 525

Asp Val Ala Ile Gly Ala Pro Gly Glu Glu Glu Ser Arg Gly Ala Val
```

```
              530            535            540
Tyr Ile Phe His Gly Ala Ser Arg Leu Glu Ile Met Pro Ser Pro Ser
545                 550                 555                 560

Gln Arg Val Thr Gly Ser Gln Leu Ser Leu Arg Leu Gln Tyr Phe Gly
                565                 570                 575

Gln Ser Leu Ser Gly Gly Gln Asp Leu Thr Gln Asp Gly Leu Val Asp
            580                 585                 590

Leu Ala Val Gly Ala Gln Gly His Val Leu Leu Arg Ser Leu Pro
            595                 600                 605

Leu Leu Lys Val Glu Leu Ser Ile Arg Phe Ala Pro Met Glu Val Ala
        610                 615                 620

Lys Ala Val Tyr Gln Cys Trp Glu Arg Thr Pro Thr Val Leu Glu Ala
625                 630                 635                 640

Gly Glu Ala Thr Val Cys Leu Thr Val His Lys Gly Ser Pro Asp Leu
                645                 650                 655

Leu Gly Asn Val Gln Gly Ser Val Arg Tyr Asp Leu Ala Leu Asp Pro
                660                 665                 670

Gly Arg Leu Ile Ser Arg Ala Ile Phe Asp Glu Thr Lys Asn Cys Thr
            675                 680                 685

Leu Thr Gly Arg Lys Thr Leu Gly Leu Gly Asp His Cys Glu Thr Val
        690                 695                 700

Lys Leu Leu Leu Pro Asp Cys Val Glu Asp Ala Val Ser Pro Ile Ile
705                 710                 715                 720

Leu Arg Leu Asn Phe Ser Leu Val Arg Asp Ser Ala Ser Pro Arg Asn
                725                 730                 735

Leu His Pro Val Leu Ala Val Gly Ser Gln Asp His Ile Thr Ala Ser
                740                 745                 750

Leu Pro Phe Glu Lys Asn Cys Lys Gln Glu Leu Leu Cys Glu Gly Asp
        755                 760                 765

Leu Gly Ile Ser Phe Asn Phe Ser Gly Leu Gln Val Leu Val Val Gly
        770                 775                 780

Gly Ser Pro Glu Leu Thr Val Thr Val Thr Val Trp Asn Glu Gly Glu
785                 790                 795                 800

Asp Ser Tyr Gly Thr Leu Val Lys Phe Tyr Tyr Pro Ala Gly Leu Ser
                805                 810                 815

Tyr Arg Arg Val Thr Gly Thr Gln Gln Pro His Gln Tyr Pro Leu Arg
                820                 825                 830

Leu Ala Cys Glu Ala Glu Pro Ala Ala Gln Glu Asp Leu Arg Ser Ser
            835                 840                 845

Ser Cys Ser Ile Asn His Pro Ile Phe Arg Glu Gly Ala Lys Thr Thr
850                 855                 860

Phe Met Ile Thr Phe Asp Val Ser Tyr Lys Ala Phe Leu Gly Asp Arg
865                 870                 875                 880

Leu Leu Leu Arg Ala Lys Ala Ser Ser Glu Asn Asn Lys Pro Asp Thr
                885                 890                 895

Asn Lys Thr Ala Phe Gln Leu Glu Leu Pro Val Lys Tyr Thr Val Tyr
                900                 905                 910

Thr Leu Ile Ser Arg Gln Glu Asp Ser Thr Asn His Val Asn Phe Ser
            915                 920                 925

Ser Ser His Gly Gly Arg Arg Gln Glu Ala Ala His Arg Tyr Arg Val
            930                 935                 940

Asn Asn Leu Ser Pro Leu Lys Leu Ala Val Arg Val Asn Phe Trp Val
945                 950                 955                 960
```

```
Pro Val Leu Leu Asn Gly Val Ala Val Trp Asp Val Thr Leu Ser Ser
                965                 970                 975
Pro Ala Gln Gly Val Ser Cys Val Ser Gln Met Lys Pro Pro Gln Asn
            980                 985                 990
Pro Asp Phe Leu Thr Gln Ile Gln Arg Arg Ser Val Leu Asp Cys Ser
        995                1000                1005
Ile Ala Asp Cys Leu His Ser Arg Cys Asp Ile Pro Ser Leu Asp Ile
1010                1015                1020
Gln Asp Glu Leu Asp Phe Ile Leu Arg Gly Asn Leu Ser Phe Gly Trp
1025                1030                1035                1040
Val Ser Gln Thr Leu Gln Glu Lys Val Leu Leu Val Ser Glu Ala Glu
                1045                1050                1055
Ile Thr Phe Asp Thr Ser Val Tyr Ser Gln Leu Pro Gly Gln Glu Ala
            1060                1065                1070
Phe Leu Arg Ala Gln Val Glu Thr Thr Leu Glu Glu Tyr Val Val Tyr
        1075                1080                1085
Glu Pro Ile Phe Leu Val Ala Gly Ser Ser Val Gly Gly Leu Leu Leu
    1090                1095                1100
Leu Ala Leu Ile Thr Val Val Leu Tyr Lys Leu Gly Xaa Xaa Lys Arg
1105                1110                1115                1120
Gln Tyr Lys Glu Met Leu Asp Gly Lys Ala Ala Asp Pro Val Thr Ala
                1125                1130                1135
Gly Gln Ala Asp Phe Gly Cys Glu Thr Pro Pro Tyr Leu Val Ser
            1140                1145                1150

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 38
gtccaagctg tcatgggcca g                                          21

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 39
gtccagcaga ctgaagagca cgg                                        23

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 40
tgtaaaacga cggccagt                                              18

<210> SEQ ID NO 41
<211> LENGTH: 19
<212> TYPE: DNA
<213> ORGANISM: Artificial Sequence
<220> FEATURE:
```

```
<223> OTHER INFORMATION: Description of Artificial Sequence: primer

<400> SEQUENCE: 41
ggaaacagct atgaccatg                                                  19

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 42
ggacatgttc actgcctcta gg                                              22

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: primer

<400> SEQUENCE: 43
ggcggacagt cagacgactg tcctg                                           25

<210> SEQ ID NO 44
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 44
ctggttcggc ccacctctga aggttccaga atcgatag                             38

<210> SEQ ID NO 45
<211> LENGTH: 3519
<212> TYPE: DNA
<213> ORGANISM: Mus musculus
<220> FEATURE:
<221> NAME/KEY: CDS
<222> LOCATION: (52)..(3516)
<223> OTHER INFORMATION: Description of Artificial Sequence: primer

<400> SEQUENCE: 45
gctttctgaa ggttccagaa tcgatagtga attcgtgggc actgctcaga t atg gtc       57
                                                        Met Val
                                                          1 cgt gga gtt gtg atc ctc ctg tgt ggc tgg gcc ctg gct tcc tgt cat       105
Arg Gly Val Val Ile Leu Leu Cys Gly Trp Ala Leu Ala Ser Cys His
          5                  10                  15 ggg tct aac ctg gat gtg gag aag ccc gtc gtg ttc aaa gag gat gca       153
Gly Ser Asn Leu Asp Val Glu Lys Pro Val Val Phe Lys Glu Asp Ala
     20                  25                  30 gcc agc ttc gga cag act gtg gtg cag ttt ggt gga tct cga ctc gtg       201
Ala Ser Phe Gly Gln Thr Val Val Gln Phe Gly Gly Ser Arg Leu Val
 35                  40                  45                  50 gtg gga gcc cct ctg gag gcg gtg gca gtc aac caa aca gga cag tcg       249
Val Gly Ala Pro Leu Glu Ala Val Ala Val Asn Gln Thr Gly Gln Ser
                 55                  60                  65 tct gac tgt ccg cct gcc act ggc gtg tgc cag ccc atc tta ctg cac       297
Ser Asp Cys Pro Pro Ala Thr Gly Val Cys Gln Pro Ile Leu Leu His
             70                  75                  80 att ccc cta gag gca gtg aac atg tcc ctg ggc ctg tct ctg gtg gct       345
```

-continued

```
Ile Pro Leu Glu Ala Val Asn Met Ser Leu Gly Leu Ser Leu Val Ala
        85                  90                  95 gac acc aat aac tcc cag ttg ctg gct tgt ggt cca act gca cag aga         393
Asp Thr Asn Asn Ser Gln Leu Leu Ala Cys Gly Pro Thr Ala Gln Arg
100                 105                 110 gct tgt gca aag aac atg tat gca aaa ggt tcc tgc ctc ctt ctg ggc         441
Ala Cys Ala Lys Asn Met Tyr Ala Lys Gly Ser Cys Leu Leu Leu Gly
115                 120                 125                 130 tcc agc ttg cag ttc atc cag gca atc cct gct acc atg cca gag tgt         489
Ser Ser Leu Gln Phe Ile Gln Ala Ile Pro Ala Thr Met Pro Glu Cys
                135                 140                 145 cca gga caa gag atg gac att gct ttc ctg att gat ggc tcc ggc agc         537
Pro Gly Gln Glu Met Asp Ile Ala Phe Leu Ile Asp Gly Ser Gly Ser
            150                 155                 160 att gat caa agt gac ttt acc cag atg aag gac ttc gtc aaa gct ttg         585
Ile Asp Gln Ser Asp Phe Thr Gln Met Lys Asp Phe Val Lys Ala Leu
        165                 170                 175 atg ggc cag ttg gcg agc acc agc acc tcg ttc tcc ctg atg caa tac         633
Met Gly Gln Leu Ala Ser Thr Ser Thr Ser Phe Ser Leu Met Gln Tyr
    180                 185                 190 tca aac atc ctg aag act cat ttt acc ttc acg gaa ttc aag agc agc         681
Ser Asn Ile Leu Lys Thr His Phe Thr Phe Thr Glu Phe Lys Ser Ser
195                 200                 205                 210 ctg agc cct cag agc ctg gtg gat gcc atc gtc cag ctc caa ggc ctg         729
Leu Ser Pro Gln Ser Leu Val Asp Ala Ile Val Gln Leu Gln Gly Leu
                215                 220                 225 acg tac aca gcc tcg ggc atc cag aaa gtg gtg aaa gag cta ttt cat         777
Thr Tyr Thr Ala Ser Gly Ile Gln Lys Val Val Lys Glu Leu Phe His
            230                 235                 240 agc aag aat ggg gcc cga aaa agt gcc aag aag ata cta att gtc atc         825
Ser Lys Asn Gly Ala Arg Lys Ser Ala Lys Lys Ile Leu Ile Val Ile
        245                 250                 255 aca gat ggg cag aaa ttc aga gac ccc ctg gag tat aga cat gtc atc         873
Thr Asp Gly Gln Lys Phe Arg Asp Pro Leu Glu Tyr Arg His Val Ile
    260                 265                 270 cct gaa gca gag aaa gct ggg atc att cgc tat gct ata ggg gtg gga         921
Pro Glu Ala Glu Lys Ala Gly Ile Ile Arg Tyr Ala Ile Gly Val Gly
275                 280                 285                 290 gat gcc ttc cgg gaa ccc act gcc cta cag gag ctg aac acc att ggc         969
Asp Ala Phe Arg Glu Pro Thr Ala Leu Gln Glu Leu Asn Thr Ile Gly
                295                 300                 305 tca gct ccc tcg cag gac cac gtg ttc aag gtg ggc aat ttt gta gca        1017
Ser Ala Pro Ser Gln Asp His Val Phe Lys Val Gly Asn Phe Val Ala
            310                 315                 320 ctt cgc agc atc cag cgg caa att cag gag aaa atc ttt gcc att gaa        1065
Leu Arg Ser Ile Gln Arg Gln Ile Gln Glu Lys Ile Phe Ala Ile Glu
        325                 330                 335 gga acc gaa tca agg tca agt agt tcc ttt cag cac gag atg tca caa        1113
Gly Thr Glu Ser Arg Ser Ser Ser Phe Gln His Glu Met Ser Gln
    340                 345                 350 gaa ggt ttc agc tca gct ctc tca atg gat gga cca gtt ctg ggg gct        1161
Glu Gly Phe Ser Ser Ala Leu Ser Met Asp Gly Pro Val Leu Gly Ala
355                 360                 365                 370 gtg gga ggc ttc agc tgg tct gga ggt gcc ttc ttg tac ccc tca aat        1209
Val Gly Gly Phe Ser Trp Ser Gly Gly Ala Phe Leu Tyr Pro Ser Asn
                375                 380                 385 atg aga tcc acc ttc atc aac atg tct cag gag aac gag gat atg agg        1257
Met Arg Ser Thr Phe Ile Asn Met Ser Gln Glu Asn Glu Asp Met Arg
            390                 395                 400
```

-continued

```
gac gct tac ctg ggt tac tcc acc gca ctg gcc ttt tgg aag ggg gtc        1305
Asp Ala Tyr Leu Gly Tyr Ser Thr Ala Leu Ala Phe Trp Lys Gly Val
        405                 410                 415 cac agc ctg atc ctg ggg gcc cct cgc cac cag cac acg ggg aag gtt        1353
His Ser Leu Ile Leu Gly Ala Pro Arg His Gln His Thr Gly Lys Val
420                 425                 430 gtc atc ttt acc cag gaa tcc agg cac tgg agg ccc aag tct gaa gtc        1401
Val Ile Phe Thr Gln Glu Ser Arg His Trp Arg Pro Lys Ser Glu Val
435                 440                 445                 450 aga ggg aca cag atc ggc tcc tac ttt ggg gca tct ctc tgt tct gtg        1449
Arg Gly Thr Gln Ile Gly Ser Tyr Phe Gly Ala Ser Leu Cys Ser Val
                455                 460                 465 gac atg gat aga gat ggc agc act gac ctg gtc ctg att gga gtc ccc        1497
Asp Met Asp Arg Asp Gly Ser Thr Asp Leu Val Leu Ile Gly Val Pro
            470                 475                 480 cat tac tat gag cac acc cga ggg ggg cag gtg tcg gtg tgc ccc atg        1545
His Tyr Tyr Glu His Thr Arg Gly Gly Gln Val Ser Val Cys Pro Met
        485                 490                 495 cct ggt gtg agg agc agg tgg cat tgt ggg acc acc ctc cat ggg gag        1593
Pro Gly Val Arg Ser Arg Trp His Cys Gly Thr Thr Leu His Gly Glu
500                 505                 510 cag ggc cat cct tgg ggc cgc ttt ggg gcg gct ctg aca gtg cta ggg        1641
Gln Gly His Pro Trp Gly Arg Phe Gly Ala Ala Leu Thr Val Leu Gly
515                 520                 525                 530 gac gtg aat ggg gac agt ctg gcg gat gtg gct att ggt gca ccc gga        1689
Asp Val Asn Gly Asp Ser Leu Ala Asp Val Ala Ile Gly Ala Pro Gly
                535                 540                 545 gag gag gag aac aga ggt gct gtc tac ata ttt cat gga gcc tcg aga        1737
Glu Glu Glu Asn Arg Gly Ala Val Tyr Ile Phe His Gly Ala Ser Arg
            550                 555                 560 cag gac atc gct ccc tcg cct agc cag cgg gtc act ggc tcc cag ctc        1785
Gln Asp Ile Ala Pro Ser Pro Ser Gln Arg Val Thr Gly Ser Gln Leu
        565                 570                 575 ttc ctg agg ctc caa tat ttt ggg cag tca tta agt ggg ggt cag gac        1833
Phe Leu Arg Leu Gln Tyr Phe Gly Gln Ser Leu Ser Gly Gly Gln Asp
580                 585                 590 ctt aca cag gat ggc ctg gtg gac ctg gcc gtg gga gcc cag ggg cac        1881
Leu Thr Gln Asp Gly Leu Val Asp Leu Ala Val Gly Ala Gln Gly His
595                 600                 605                 610 gtg ctg ctg ctt agg agt ctg cct ttg ctg aaa gtg ggg atc tcc att        1929
Val Leu Leu Leu Arg Ser Leu Pro Leu Leu Lys Val Gly Ile Ser Ile
                615                 620                 625 aga ttt gcc ccc tca gag gtg gca aag act gtg tac cag tgc tgg gga        1977
Arg Phe Ala Pro Ser Glu Val Ala Lys Thr Val Tyr Gln Cys Trp Gly
            630                 635                 640 agg act ccc act gtc ctc gaa gct gga gag gcc acc gtc tgt ctc act        2025
Arg Thr Pro Thr Val Leu Glu Ala Gly Glu Ala Thr Val Cys Leu Thr
        645                 650                 655 gtc cgc aaa ggt tca cct gac ctg tta ggt gat gtc caa agc tct gtc        2073
Val Arg Lys Gly Ser Pro Asp Leu Leu Gly Asp Val Gln Ser Ser Val
660                 665                 670 agg tat gat ctg gcg ttg gat ccg ggc cgt ctg att tct cgt gcc att        2121
Arg Tyr Asp Leu Ala Leu Asp Pro Gly Arg Leu Ile Ser Arg Ala Ile
675                 680                 685                 690 ttt gat gag acg aag aac tgc act ttg acc cga agg aag act ctg ggg        2169
Phe Asp Glu Thr Lys Asn Cys Thr Leu Thr Arg Arg Lys Thr Leu Gly
                695                 700                 705 ctt ggt gat cac tgc gaa aca atg aag ctg ctt ttg cca gac tgt gtg        2217
Leu Gly Asp His Cys Glu Thr Met Lys Leu Leu Leu Pro Asp Cys Val
            710                 715                 720
```

```
gag gat gca gtg acc cct atc atc ctg cgc ctt aac tta tcc ctg gca    2265
Glu Asp Ala Val Thr Pro Ile Ile Leu Arg Leu Asn Leu Ser Leu Ala
        725                 730                 735 ggg gac tct gct cca tcc agg aac ctt cgt cct gtg ctg gct gtg ggc    2313
Gly Asp Ser Ala Pro Ser Arg Asn Leu Arg Pro Val Leu Ala Val Gly
    740                 745                 750 tca caa gac cat gta aca gct tct ttc ccg ttt gag aag aac tgt gag    2361
Ser Gln Asp His Val Thr Ala Ser Phe Pro Phe Glu Lys Asn Cys Glu
755                 760                 765                 770 ggg aac ctg ggc gtc agc ttc aac ttc tca ggc ctg cag gtc ttg gag    2409
Gly Asn Leu Gly Val Ser Phe Asn Phe Ser Gly Leu Gln Val Leu Glu
                775                 780                 785 gta gga agc tcc cca gag ctc act gtg aca gta aca gtt tgg aat gag    2457
Val Gly Ser Ser Pro Glu Leu Thr Val Thr Val Thr Val Trp Asn Glu
        790                 795                 800 ggt gag gac agc tat gga acc tta atc aag ttc tac tac cca gca gag    2505
Gly Glu Asp Ser Tyr Gly Thr Leu Ile Lys Phe Tyr Tyr Pro Ala Glu
    805                 810                 815 cta tct tac cga cgg gtg aca aga gcc cag caa cct cat ccg tac cca    2553
Leu Ser Tyr Arg Arg Val Thr Arg Ala Gln Gln Pro His Pro Tyr Pro
820                 825                 830 cta cgc ctg gca tgt gag gct gag ccc acg ggc cag gag agc ctg agg    2601
Leu Arg Leu Ala Cys Glu Ala Glu Pro Thr Gly Gln Glu Ser Leu Arg
835                 840                 845                 850 agc agc agc tgt agc atc aat cac ccc atc ttc cga gaa ggt gcc aag    2649
Ser Ser Ser Cys Ser Ile Asn His Pro Ile Phe Arg Glu Gly Ala Lys
                855                 860                 865 gcc acc ttc atg atc aca ttt gat gtc tcc tac aag gcc ttc ctg gga    2697
Ala Thr Phe Met Ile Thr Phe Asp Val Ser Tyr Lys Ala Phe Leu Gly
        870                 875                 880 gac agg ttg ctt ctg agg gcc agc gca agc agt gag aat aat aag cct    2745
Asp Arg Leu Leu Leu Arg Ala Ser Ala Ser Ser Glu Asn Asn Lys Pro
    885                 890                 895 gaa acc agc aag act gcc ttc cag ctg gag ctt ccg gtg aag tac acg    2793
Glu Thr Ser Lys Thr Ala Phe Gln Leu Glu Leu Pro Val Lys Tyr Thr
900                 905                 910 gtc tat acc gtg atc agt agg cag gaa gat tct acc aag cat ttc aac    2841
Val Tyr Thr Val Ile Ser Arg Gln Glu Asp Ser Thr Lys His Phe Asn
915                 920                 925                 930 ttc tca tct tcc cac ggg gag aga cag aaa gag gcc gaa cat cga tat    2889
Phe Ser Ser Ser His Gly Glu Arg Gln Lys Glu Ala Glu His Arg Tyr
                935                 940                 945 cgt gtg aat aac ctg agt cca ttg acg ctg gcc atc agc gtt aac ttc    2937
Arg Val Asn Asn Leu Ser Pro Leu Thr Leu Ala Ile Ser Val Asn Phe
        950                 955                 960 tgg gtc ccc atc ctt ctg aat ggt gtg gcc gtg tgg gat gtg act ctg    2985
Trp Val Pro Ile Leu Leu Asn Gly Val Ala Val Trp Asp Val Thr Leu
    965                 970                 975 agg agc cca gca cag ggt gtc tcc tgt gtg tca cag agg gaa cct cct    3033
Arg Ser Pro Ala Gln Gly Val Ser Cys Val Ser Gln Arg Glu Pro Pro
980                 985                 990 caa cat tcc gac ctt ctg acc cag atc caa gga cgc tct gtg ctg gac    3081
Gln His Ser Asp Leu Leu Thr Gln Ile Gln Gly Arg Ser Val Leu Asp
995                 1000                1005                1010 tgc gcc atc gcc gac tgc ctg cac ctc cgc tgt gac atc ccc tcc ttg    3129
Cys Ala Ile Ala Asp Cys Leu His Leu Arg Cys Asp Ile Pro Ser Leu
            1015                1020                1025 ggc acc ctg gat gag ctt gac ttc att ctg aag ggc aac ctc agc ttc    3177
Gly Thr Leu Asp Glu Leu Asp Phe Ile Leu Lys Gly Asn Leu Ser Phe
```

|  |  |
|---|---|
| ggc tgg atc agt cag aca ttg cag aaa aag gtg ttg ctc ctg agt gag<br>Gly Trp Ile Ser Gln Thr Leu Gln Lys Lys Val Leu Leu Leu Ser Glu<br>         1045                       1050                1055 | 3225 |
| gct gaa atc aca ttc aac aca tct gtg tat tcc cag ctg ccg gga cag<br>Ala Glu Ile Thr Phe Asn Thr Ser Val Tyr Ser Gln Leu Pro Gly Gln<br>1060                       1065                     1070 | 3273 |
| gag gca ttt ctg aga gcc cag gtg tca acg atg cta gaa gaa tac gtg<br>Glu Ala Phe Leu Arg Ala Gln Val Ser Thr Met Leu Glu Glu Tyr Val<br>1075                       1080                    1085                1090 | 3321 |
| gtc tat gag ccc gtc ttc ctc atg gtg ttc agc tca gtg gga ggt ctg<br>Val Tyr Glu Pro Val Phe Leu Met Val Phe Ser Ser Val Gly Gly Leu<br>         1095                     1100                    1105 | 3369 |
| ctg tta ctg gct ctc atc act gtg gcg ctg tac aag ctt ggc ttc ttc<br>Leu Leu Leu Ala Leu Ile Thr Val Ala Leu Tyr Lys Leu Gly Phe Phe<br>         1110                     1115                    1120 | 3417 |
| aaa cgt cag tat aaa gag atg ctg gat cta cca tct gca gat cct gac<br>Lys Arg Gln Tyr Lys Glu Met Leu Asp Leu Pro Ser Ala Asp Pro Asp<br>1125                       1130                    1135 | 3465 |
| cca gcc ggc cag gca gat tcc aac cat gag act cct cca cat ctc acg<br>Pro Ala Gly Gln Ala Asp Ser Asn His Glu Thr Pro Pro His Leu Thr<br>    1140                     1145                    1150 | 3513 |
| tcc tag<br>Ser<br>1155 | 3519 |

<210> SEQ ID NO 46
<211> LENGTH: 1155
<212> TYPE: PRT
<213> ORGANISM: Mus musculus

<400> SEQUENCE: 46

Met Val Arg Gly Val Val Ile Leu Leu Cys Gly Trp Ala Leu Ala Ser
1               5                   10                  15

Cys His Gly Ser Asn Leu Asp Val Glu Lys Pro Val Val Phe Lys Glu
            20                  25                  30

Asp Ala Ala Ser Phe Gly Gln Thr Val Val Gln Phe Gly Gly Ser Arg
        35                  40                  45

Leu Val Val Gly Ala Pro Leu Glu Ala Val Ala Val Asn Gln Thr Gly
    50                  55                  60

Gln Ser Ser Asp Cys Pro Pro Ala Thr Gly Val Cys Gln Pro Ile Leu
65                  70                  75                  80

Leu His Ile Pro Leu Glu Ala Val Asn Met Ser Leu Gly Leu Ser Leu
                85                  90                  95

Val Ala Asp Thr Asn Asn Ser Gln Leu Leu Ala Cys Gly Pro Thr Ala
            100                 105                 110

Gln Arg Ala Cys Ala Lys Asn Met Tyr Ala Lys Gly Ser Cys Leu Leu
        115                 120                 125

Leu Gly Ser Ser Leu Gln Phe Ile Gln Ala Ile Pro Ala Thr Met Pro
    130                 135                 140

Glu Cys Pro Gly Gln Glu Met Asp Ile Ala Phe Leu Ile Asp Gly Ser
145                 150                 155                 160

Gly Ser Ile Asp Gln Ser Asp Phe Thr Gln Met Lys Asp Phe Val Lys
                165                 170                 175

Ala Leu Met Gly Gln Leu Ala Ser Thr Ser Thr Ser Phe Ser Leu Met
            180                 185                 190

Gln Tyr Ser Asn Ile Leu Lys Thr His Phe Thr Phe Thr Glu Phe Lys

-continued

```
                195                 200                 205
Ser Ser Leu Ser Pro Gln Ser Leu Val Asp Ala Ile Val Gln Leu Gln
        210                 215                 220
Gly Leu Thr Tyr Thr Ala Ser Gly Ile Gln Lys Val Val Lys Glu Leu
225                 230                 235                 240
Phe His Ser Lys Asn Gly Ala Arg Lys Ser Ala Lys Lys Ile Leu Ile
                245                 250                 255
Val Ile Thr Asp Gly Gln Lys Phe Arg Asp Pro Leu Glu Tyr Arg His
                260                 265                 270
Val Ile Pro Glu Ala Glu Lys Ala Gly Ile Ile Arg Tyr Ala Ile Gly
                275                 280                 285
Val Gly Asp Ala Phe Arg Glu Pro Thr Ala Leu Gln Glu Leu Asn Thr
            290                 295                 300
Ile Gly Ser Ala Pro Ser Gln Asp His Val Phe Lys Val Gly Asn Phe
305                 310                 315                 320
Val Ala Leu Arg Ser Ile Gln Arg Gln Ile Gln Glu Lys Ile Phe Ala
                325                 330                 335
Ile Glu Gly Thr Glu Ser Arg Ser Ser Ser Phe Gln His Glu Met
            340                 345                 350
Ser Gln Glu Gly Phe Ser Ser Ala Leu Ser Met Asp Gly Pro Val Leu
            355                 360                 365
Gly Ala Val Gly Gly Phe Ser Trp Ser Gly Gly Ala Phe Leu Tyr Pro
370                 375                 380
Ser Asn Met Arg Ser Thr Phe Ile Asn Met Ser Gln Glu Asn Glu Asp
385                 390                 395                 400
Met Arg Asp Ala Tyr Leu Gly Tyr Ser Thr Ala Leu Ala Phe Trp Lys
                405                 410                 415
Gly Val His Ser Leu Ile Leu Gly Ala Pro Arg His Gln His Thr Gly
                420                 425                 430
Lys Val Val Ile Phe Thr Gln Glu Ser Arg His Trp Arg Pro Lys Ser
                435                 440                 445
Glu Val Arg Gly Thr Gln Ile Gly Ser Tyr Phe Gly Ala Ser Leu Cys
            450                 455                 460
Ser Val Asp Met Asp Arg Asp Gly Ser Thr Asp Leu Val Leu Ile Gly
465                 470                 475                 480
Val Pro His Tyr Tyr Glu His Thr Arg Gly Gly Gln Val Ser Val Cys
                485                 490                 495
Pro Met Pro Gly Val Arg Ser Arg Trp His Cys Gly Thr Thr Leu His
            500                 505                 510
Gly Glu Gln Gly His Pro Trp Gly Arg Phe Gly Ala Ala Leu Thr Val
            515                 520                 525
Leu Gly Asp Val Asn Gly Asp Ser Leu Ala Asp Val Ala Ile Gly Ala
            530                 535                 540
Pro Gly Glu Glu Glu Asn Arg Gly Ala Val Tyr Ile Phe His Gly Ala
545                 550                 555                 560
Ser Arg Gln Asp Ile Ala Pro Ser Pro Ser Gln Arg Val Thr Gly Ser
                565                 570                 575
Gln Leu Phe Leu Arg Leu Gln Tyr Phe Gly Gln Ser Leu Ser Gly Gly
            580                 585                 590
Gln Asp Leu Thr Gln Asp Gly Leu Val Asp Leu Ala Val Gly Ala Gln
            595                 600                 605
Gly His Val Leu Leu Leu Arg Ser Leu Pro Leu Leu Lys Val Gly Ile
            610                 615                 620
```

-continued

```
Ser Ile Arg Phe Ala Pro Ser Glu Val Ala Lys Thr Val Tyr Gln Cys
625                 630                 635                 640

Trp Gly Arg Thr Pro Thr Val Leu Glu Ala Gly Glu Ala Thr Val Cys
            645                 650                 655

Leu Thr Val Arg Lys Gly Ser Pro Asp Leu Leu Gly Asp Val Gln Ser
        660                 665                 670

Ser Val Arg Tyr Asp Leu Ala Leu Asp Pro Gly Arg Leu Ile Ser Arg
    675                 680                 685

Ala Ile Phe Asp Glu Thr Lys Asn Cys Thr Leu Thr Arg Arg Lys Thr
690                 695                 700

Leu Gly Leu Gly Asp His Cys Glu Thr Met Lys Leu Leu Pro Asp
705                 710                 715                 720

Cys Val Glu Asp Ala Val Thr Pro Ile Ile Leu Arg Leu Asn Leu Ser
                725                 730                 735

Leu Ala Gly Asp Ser Ala Pro Ser Arg Asn Leu Arg Pro Val Leu Ala
            740                 745                 750

Val Gly Ser Gln Asp His Val Thr Ala Ser Phe Pro Phe Glu Lys Asn
        755                 760                 765

Cys Glu Gly Asn Leu Gly Val Ser Phe Asn Phe Ser Gly Leu Gln Val
    770                 775                 780

Leu Glu Val Gly Ser Ser Pro Glu Leu Thr Val Thr Val Thr Val Trp
785                 790                 795                 800

Asn Glu Gly Glu Asp Ser Tyr Gly Thr Leu Ile Lys Phe Tyr Tyr Pro
                805                 810                 815

Ala Glu Leu Ser Tyr Arg Arg Val Thr Arg Ala Gln Gln Pro His Pro
            820                 825                 830

Tyr Pro Leu Arg Leu Ala Cys Glu Ala Glu Pro Thr Gly Gln Glu Ser
        835                 840                 845

Leu Arg Ser Ser Ser Cys Ser Ile Asn His Pro Ile Phe Arg Glu Gly
    850                 855                 860

Ala Lys Ala Thr Phe Met Ile Thr Phe Asp Val Ser Tyr Lys Ala Phe
865                 870                 875                 880

Leu Gly Asp Arg Leu Leu Leu Arg Ala Ser Ala Ser Ser Glu Asn Asn
                885                 890                 895

Lys Pro Glu Thr Ser Lys Thr Ala Phe Gln Leu Glu Leu Pro Val Lys
            900                 905                 910

Tyr Thr Val Tyr Thr Val Ile Ser Arg Gln Glu Asp Ser Thr Lys His
        915                 920                 925

Phe Asn Phe Ser Ser Ser His Gly Glu Arg Gln Lys Glu Ala Glu His
    930                 935                 940

Arg Tyr Arg Val Asn Asn Leu Ser Pro Leu Thr Leu Ala Ile Ser Val
945                 950                 955                 960

Asn Phe Trp Val Pro Ile Leu Leu Asn Gly Val Ala Val Trp Asp Val
                965                 970                 975

Thr Leu Arg Ser Pro Ala Gln Gly Val Ser Cys Val Ser Gln Arg Glu
            980                 985                 990

Pro Pro Gln His Ser Asp Leu Leu Thr Gln Ile Gln Gly Arg Ser Val
        995                 1000                1005

Leu Asp Cys Ala Ile Ala Asp Cys Leu His Leu Arg Cys Asp Ile Pro
    1010                1015                1020

Ser Leu Gly Thr Leu Asp Glu Leu Asp Phe Ile Leu Lys Gly Asn Leu
1025                1030                1035                1040
```

```
Ser Phe Gly Trp Ile Ser Gln Thr Leu Gln Lys Lys Val Leu Leu Leu
                1045                1050                1055

Ser Glu Ala Glu Ile Thr Phe Asn Thr Ser Val Tyr Ser Gln Leu Pro
            1060                1065                1070

Gly Gln Glu Ala Phe Leu Arg Ala Gln Val Ser Thr Met Leu Glu Glu
        1075                1080                1085

Tyr Val Val Tyr Glu Pro Val Phe Leu Met Val Phe Ser Val Gly
    1090                1095                1100

Gly Leu Leu Leu Ala Leu Ile Thr Val Ala Leu Tyr Lys Leu Gly
1105                1110                1115                1120

Phe Phe Lys Arg Gln Tyr Lys Glu Met Leu Asp Leu Pro Ser Ala Asp
                1125                1130                1135

Pro Asp Pro Ala Gly Gln Ala Asp Ser Asn His Glu Thr Pro Pro His
                1140                1145                1150

Leu Thr Ser
        1155
```

```
<210> SEQ ID NO 47
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 47
agttacggat ccggcaccat gaccttcggc actgtgatcc tcctgtgtg            49

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 48
gctggacgat ggcatccac                                              19

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 49
gtagagttac ggatccggca ccat                                        24

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 50
gcagccagct tcggacagac                                             20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: primer
```

```
<400> SEQUENCE: 51
ccatgtccac agaacagaga g                                              21

<210> SEQ ID NO 52
<211> LENGTH: 3803
<212> TYPE: DNA
<213> ORGANISM: Mus musculus
<220> FEATURE:
<221> NAME/KEY: CDS
<222> LOCATION: (1)..(3483)
<223> OTHER INFORMATION: Description of Artificial Sequence: primer
<221> NAME/KEY: misc_feature
<222> LOCATION: 3803
<223> OTHER INFORMATION: n = A or T or G or C

<400> SEQUENCE: 52 atg gtc cgt gga gtt gtg atc ctc ctg tgt ggc tgg gcc ctg gct tcc      48
Met Val Arg Gly Val Val Ile Leu Leu Cys Gly Trp Ala Leu Ala Ser
 1               5                  10                  15 tgt cat ggg tct aac ctg gat gtg gag aag ccc gtc gtg ttc aaa gag      96
Cys His Gly Ser Asn Leu Asp Val Glu Lys Pro Val Val Phe Lys Glu
             20                  25                  30 gat gca gcc agc ttc gga cag act gtg gtg cag ttt ggt gga tct cga     144
Asp Ala Ala Ser Phe Gly Gln Thr Val Val Gln Phe Gly Gly Ser Arg
         35                  40                  45 ctc gtg gtg gga gcc cct ctg gag gcg gtg gca gtc aac caa aca gga     192
Leu Val Val Gly Ala Pro Leu Glu Ala Val Ala Val Asn Gln Thr Gly
     50                  55                  60 cag tcg tct gac tgt ccg cct gcc act ggc gtg tgc cag ccc atc tta     240
Gln Ser Ser Asp Cys Pro Pro Ala Thr Gly Val Cys Gln Pro Ile Leu
 65                  70                  75                  80 ctg cac att ccc cta gag gca gtg aac atg tcc ctg ggc ctg tct ctg     288
Leu His Ile Pro Leu Glu Ala Val Asn Met Ser Leu Gly Leu Ser Leu
                 85                  90                  95 gtg gct gac acc aat aac tcc cag ttg ctg gct tgt ggt cca act gca     336
Val Ala Asp Thr Asn Asn Ser Gln Leu Leu Ala Cys Gly Pro Thr Ala
            100                 105                 110 cag aga gct tgt gca aag aac atg tat gca aaa ggt tcc tgc ctc ctt     384
Gln Arg Ala Cys Ala Lys Asn Met Tyr Ala Lys Gly Ser Cys Leu Leu
        115                 120                 125 ctg ggc tcc agc ttg cag ttc atc cag gca atc cct gct acc atg cca     432
Leu Gly Ser Ser Leu Gln Phe Ile Gln Ala Ile Pro Ala Thr Met Pro
    130                 135                 140 gag tgt cca gga caa gag atg gac att gct ttc ctg att gat ggc tcc     480
Glu Cys Pro Gly Gln Glu Met Asp Ile Ala Phe Leu Ile Asp Gly Ser
145                 150                 155                 160 ggc agc att gat caa agt gac ttt acc cag atg aag gac ttc gtc aaa     528
Gly Ser Ile Asp Gln Ser Asp Phe Thr Gln Met Lys Asp Phe Val Lys
                165                 170                 175 gct ttg atg ggc cag ttg gcg agc acc agc acc tcg ttc tcc ctg atg     576
Ala Leu Met Gly Gln Leu Ala Ser Thr Ser Thr Ser Phe Ser Leu Met
            180                 185                 190 caa tac tca aac atc ctg aag act cat ttt acc ttc acg gaa ttc aag     624
Gln Tyr Ser Asn Ile Leu Lys Thr His Phe Thr Phe Thr Glu Phe Lys
        195                 200                 205 agc agc ctg agc cct cag agc ctg gtg gat gcc atc gtc cag ctc caa     672
Ser Ser Leu Ser Pro Gln Ser Leu Val Asp Ala Ile Val Gln Leu Gln
    210                 215                 220 ggc ctg acg tac aca gcc tcg ggc atc cag aaa gtg gtg aaa gag cta     720
Gly Leu Thr Tyr Thr Ala Ser Gly Ile Gln Lys Val Val Lys Glu Leu
225                 230                 235                 240
```

-continued

| | | |
|---|---|---|
| ttt cat agc aag aat ggg gcc cga aaa agt gcc aag aag ata cta att<br>Phe His Ser Lys Asn Gly Ala Arg Lys Ser Ala Lys Lys Ile Leu Ile<br>245 250 255 | 768 | |
| gtc atc aca gat ggg cag aaa ttc aga gac ccc ctg gag tat aga cat<br>Val Ile Thr Asp Gly Gln Lys Phe Arg Asp Pro Leu Glu Tyr Arg His<br>260 265 270 | 816 | |
| gtc atc cct gaa gca gag aaa gct ggg atc att cgc tat gct ata ggg<br>Val Ile Pro Glu Ala Glu Lys Ala Gly Ile Ile Arg Tyr Ala Ile Gly<br>275 280 285 | 864 | |
| gtg gga gat gcc ttc cgg gaa ccc act gcc cta cag gag ctg aac acc<br>Val Gly Asp Ala Phe Arg Glu Pro Thr Ala Leu Gln Glu Leu Asn Thr<br>290 295 300 | 912 | |
| att ggc tca gct ccc tcg cag gac cac gtg ttc aag gtg ggc aat ttt<br>Ile Gly Ser Ala Pro Ser Gln Asp His Val Phe Lys Val Gly Asn Phe<br>305 310 315 320 | 960 | |
| gta gca ctt cgc agc atc cag cgg caa att cag gag aaa atc ttt gcc<br>Val Ala Leu Arg Ser Ile Gln Arg Gln Ile Gln Glu Lys Ile Phe Ala<br>325 330 335 | 1008 | |
| att gaa gga acc gaa tca agg tca agt agt tcc ttt cag cac gag atg<br>Ile Glu Gly Thr Glu Ser Arg Ser Ser Ser Ser Phe Gln His Glu Met<br>340 345 350 | 1056 | |
| tca caa gaa ggt ttc agc tca gct ctc tca atg gat gga cca gtt ctg<br>Ser Gln Glu Gly Phe Ser Ser Ala Leu Ser Met Asp Gly Pro Val Leu<br>355 360 365 | 1104 | |
| ggg gct gtg gga ggc ttc agc tgg tct gga ggt gcc ttc ttg tac ccc<br>Gly Ala Val Gly Gly Phe Ser Trp Ser Gly Gly Ala Phe Leu Tyr Pro<br>370 375 380 | 1152 | |
| tca aat atg aga tcc acc ttc atc aac atg tct cag gag aac gag gat<br>Ser Asn Met Arg Ser Thr Phe Ile Asn Met Ser Gln Glu Asn Glu Asp<br>385 390 395 400 | 1200 | |
| atg agg gac gct tac ctg ggt tac tcc acc gca ctg gcc ttt tgg aag<br>Met Arg Asp Ala Tyr Leu Gly Tyr Ser Thr Ala Leu Ala Phe Trp Lys<br>405 410 415 | 1248 | |
| ggg gtc cac agc ctg atc ctg ggg gcc cct cgc cac cag cac acg ggg<br>Gly Val His Ser Leu Ile Leu Gly Ala Pro Arg His Gln His Thr Gly<br>420 425 430 | 1296 | |
| aag gtt gtc atc ttt acc cag gaa tcc agg cac tgg agg ccc aag tct<br>Lys Val Val Ile Phe Thr Gln Glu Ser Arg His Trp Arg Pro Lys Ser<br>435 440 445 | 1344 | |
| gaa gtc aga ggg aca cag atc ggc tcc tac ttt ggg gca tct ctc tgt<br>Glu Val Arg Gly Thr Gln Ile Gly Ser Tyr Phe Gly Ala Ser Leu Cys<br>450 455 460 | 1392 | |
| tct gtg gac atg gat aga gat ggc agc act gac ctg gtc ctg att gga<br>Ser Val Asp Met Asp Arg Asp Gly Ser Thr Asp Leu Val Leu Ile Gly<br>465 470 475 480 | 1440 | |
| gtc ccc cat tac tat gag cac acc cga ggg ggg cag gtg tcg gtg tgc<br>Val Pro His Tyr Tyr Glu His Thr Arg Gly Gly Gln Val Ser Val Cys<br>485 490 495 | 1488 | |
| ccc atg cct ggt gtg agg agc agg tgg cat tgt ggg acc acc ctc cat<br>Pro Met Pro Gly Val Arg Ser Arg Trp His Cys Gly Thr Thr Leu His<br>500 505 510 | 1536 | |
| ggg gag cag ggc cat cct tgg ggc cgc ttt ggg gcg gct ctg aca gtg<br>Gly Glu Gln Gly His Pro Trp Gly Arg Phe Gly Ala Ala Leu Thr Val<br>515 520 525 | 1584 | |
| cta ggg gac gtg aat ggg gac agt ctg gcg gat gtg gct att ggt gca<br>Leu Gly Asp Val Asn Gly Asp Ser Leu Ala Asp Val Ala Ile Gly Ala<br>530 535 540 | 1632 | |
| ccc gga gag gag gag aac aga ggt gct gtc tac ata ttt cat gga gcc<br>Pro Gly Glu Glu Glu Asn Arg Gly Ala Val Tyr Ile Phe His Gly Ala | 1680 | |

```
545                 550                 555                 560
tcg aga cag gac atc gct ccc tcg cct agc cag cgg gtc act ggc tcc    1728
Ser Arg Gln Asp Ile Ala Pro Ser Pro Ser Gln Arg Val Thr Gly Ser
                565                 570                 575 cag ctc ttc ctg agg ctc caa tat ttt ggg cag tca tta agt ggg ggt    1776
Gln Leu Phe Leu Arg Leu Gln Tyr Phe Gly Gln Ser Leu Ser Gly Gly
            580                 585                 590 cag gac ctt aca cag gat ggc ctg gtg gac ctg gcc gtg gga gcc cag    1824
Gln Asp Leu Thr Gln Asp Gly Leu Val Asp Leu Ala Val Gly Ala Gln
            595                 600                 605 ggg cac gtg ctg ctg ctt agg agt ctg cct ttg ctg aaa gtg ggg atc    1872
Gly His Val Leu Leu Leu Arg Ser Leu Pro Leu Leu Lys Val Gly Ile
            610                 615                 620 tcc att aga ttt gcc ccc tca gag gtg gca aag act gtg tac cag tgc    1920
Ser Ile Arg Phe Ala Pro Ser Glu Val Ala Lys Thr Val Tyr Gln Cys
625                 630                 635                 640 tgg gga agg act ccc act gtc ctc gaa gct gga gag gcc acc gtc tgt    1968
Trp Gly Arg Thr Pro Thr Val Leu Glu Ala Gly Glu Ala Thr Val Cys
                645                 650                 655 ctc act gtc cgc aaa ggt tca cct gac ctg tta ggt gat gtc caa agc    2016
Leu Thr Val Arg Lys Gly Ser Pro Asp Leu Leu Gly Asp Val Gln Ser
            660                 665                 670 tct gtc agg tat gat ctg gcg ttg gat ccg ggc cgt ctg att tct cgt    2064
Ser Val Arg Tyr Asp Leu Ala Leu Asp Pro Gly Arg Leu Ile Ser Arg
            675                 680                 685 gcc att ttt gat gag acg aag aac tgc act ttg acc cga agg aag act    2112
Ala Ile Phe Asp Glu Thr Lys Asn Cys Thr Leu Thr Arg Arg Lys Thr
            690                 695                 700 ctg ggg ctt ggt gat cac tgc gaa aca atg aag ctg ctt ttg cca gac    2160
Leu Gly Leu Gly Asp His Cys Glu Thr Met Lys Leu Leu Leu Pro Asp
705                 710                 715                 720 tgt gtg gag gat gca gtg acc cct atc atc ctg cgc ctt aac tta tcc    2208
Cys Val Glu Asp Ala Val Thr Pro Ile Ile Leu Arg Leu Asn Leu Ser
                725                 730                 735 ctg gca ggg gac tct gct cca tcc agg aac ctt cgt cct gtg ctg gct    2256
Leu Ala Gly Asp Ser Ala Pro Ser Arg Asn Leu Arg Pro Val Leu Ala
            740                 745                 750 gtg ggc tca caa gac cat gta aca gct tct ttc ccg ttt gag aag aac    2304
Val Gly Ser Gln Asp His Val Thr Ala Ser Phe Pro Phe Glu Lys Asn
            755                 760                 765 tgt aag cag gag ctc ctg tgt gag ggg aac ctg ggc gtc agc ttc aac    2352
Cys Lys Gln Glu Leu Leu Cys Glu Gly Asn Leu Gly Val Ser Phe Asn
            770                 775                 780 ttc tca ggc ctg cag gtc ttg gag gta gga agc tcc cca gag ctc act    2400
Phe Ser Gly Leu Gln Val Leu Glu Val Gly Ser Ser Pro Glu Leu Thr
785                 790                 795                 800 gtg aca gta aca gtt tgg aat gag ggt gag gac agc tat gga acc tta    2448
Val Thr Val Thr Val Trp Asn Glu Gly Glu Asp Ser Tyr Gly Thr Leu
                805                 810                 815 atc aag ttc tac tac cca gca gag cta tct tac cga cgg gtg aca aga    2496
Ile Lys Phe Tyr Tyr Pro Ala Glu Leu Ser Tyr Arg Arg Val Thr Arg
            820                 825                 830 gcc cag caa cct cat ccg tac cca cta cgc ctg gca tgt gag gct gag    2544
Ala Gln Gln Pro His Pro Tyr Pro Leu Arg Leu Ala Cys Glu Ala Glu
            835                 840                 845 ccc acg ggc cag gag agc ctg agg agc agc agt tgt agc atc aat cac    2592
Pro Thr Gly Gln Glu Ser Leu Arg Ser Ser Ser Cys Ser Ile Asn His
            850                 855                 860 ccc atc ttc cga gaa ggt gcc aag gcc acc ttc atg atc aca ttt gat    2640
```

```
                                                       -continued

Pro Ile Phe Arg Glu Gly Ala Lys Ala Thr Phe Met Ile Thr Phe Asp
865                 870                  875                 880 gtc tcc tac aag gcc ttc ctg gga gac agg ttg ctt ctg agg gcc agc        2688
Val Ser Tyr Lys Ala Phe Leu Gly Asp Arg Leu Leu Leu Arg Ala Ser
                885                 890                 895 gca agc agt gag aat aat aag cct gaa acc agc aag act gcc ttc cag        2736
Ala Ser Ser Glu Asn Asn Lys Pro Glu Thr Ser Lys Thr Ala Phe Gln
            900                 905                 910 ctg gag ctt ccg gtg aag tac acg gtc tat acc gtg atc agt agg cag        2784
Leu Glu Leu Pro Val Lys Tyr Thr Val Tyr Thr Val Ile Ser Arg Gln
        915                 920                 925 gaa gat tct acc aag cat ttc aac ttc tca tct tcc cac ggg gag aga        2832
Glu Asp Ser Thr Lys His Phe Asn Phe Ser Ser Ser His Gly Glu Arg
    930                 935                 940 cag aaa gag gcc gaa cat cga tat cgt gtg aat aac ctg agt cca ttg        2880
Gln Lys Glu Ala Glu His Arg Tyr Arg Val Asn Asn Leu Ser Pro Leu
945                 950                 955                 960 acg ctg gcc atc agc gtt aac ttc tgg gtc ccc atc ctt ctg aat ggt        2928
Thr Leu Ala Ile Ser Val Asn Phe Trp Val Pro Ile Leu Leu Asn Gly
                965                 970                 975 gtg gcc gtg tgg gat gtg act ctg agg agc cca gca cag ggt gtc tcc        2976
Val Ala Val Trp Asp Val Thr Leu Arg Ser Pro Ala Gln Gly Val Ser
            980                 985                 990 tgt gtg tca cag agg gaa cct cct caa cat tcc gac ctt ctg acc cag        3024
Cys Val Ser Gln Arg Glu Pro Pro Gln His Ser Asp Leu Leu Thr Gln
        995                 1000                1005 atc caa gga cgc tct gtg ctg gac tgc gcc atc gcc gac tgc ctg cac        3072
Ile Gln Gly Arg Ser Val Leu Asp Cys Ala Ile Ala Asp Cys Leu His
    1010                1015                1020 ctc cgc tgt gac atc ccc tcc ttg ggc acc ctg gat gag ctt gac ttc        3120
Leu Arg Cys Asp Ile Pro Ser Leu Gly Thr Leu Asp Glu Leu Asp Phe
1025                1030                1035                1040 att ctg aag ggc aac ctc agc ttc ggc tgg atc agt cag aca ttg cag        3168
Ile Leu Lys Gly Asn Leu Ser Phe Gly Trp Ile Ser Gln Thr Leu Gln
                1045                1050                1055 aaa aag gtg ttg ctc ctg agt gag gct gaa atc aca ttc aac aca tct        3216
Lys Lys Val Leu Leu Leu Ser Glu Ala Glu Ile Thr Phe Asn Thr Ser
            1060                1065                1070 gtg tat tcc cag ctg ccg gga cag gag gca ttt ctg aga gcc cag gtg        3264
Val Tyr Ser Gln Leu Pro Gly Gln Glu Ala Phe Leu Arg Ala Gln Val
        1075                1080                1085 tca acg atg cta gaa gaa tac gtg gtc tat gag ccc gtc ttc ctc atg        3312
Ser Thr Met Leu Glu Glu Tyr Val Val Tyr Glu Pro Val Phe Leu Met
    1090                1095                1100 gtg ttc agc tca gtg gga ggt ctg ctg tta ctg gct ctc atc act gtg        3360
Val Phe Ser Ser Val Gly Gly Leu Leu Leu Leu Ala Leu Ile Thr Val
1105                1110                1115                1120 gcg ctg tac aag ctt ggc ttc ttc aaa cgt cag tat aaa gag atg ctg        3408
Ala Leu Tyr Lys Leu Gly Phe Phe Lys Arg Gln Tyr Lys Glu Met Leu
                1125                1130                1135 gat cta cca tct gca gat cct gac cca gcc ggc cag gca gat tcc aac        3456
Asp Leu Pro Ser Ala Asp Pro Asp Pro Ala Gly Gln Ala Asp Ser Asn
            1140                1145                1150 cat gag act cct cca cat ctc acg tcc taggaatcta ctttcctgta             3503
His Glu Thr Pro Pro His Leu Thr Ser
        1155                1160 tatctccaca attacgagat tggttttgct tttgcctatg aatctactgg catgggaaca    3563
agttctcttc agctctgggc tagcctggga aacttcccag aaatgatgcc ctacctcctg    3623
```

```
agctgggaga ttttatggt ttgcccatgt gtcagatttc agtgctgatc cacttttttt    3683
gcaagagcag gaatggggtc agcataaatt tacatatgga taagaactaa cacaagactg    3743
agtaatatgc tcaatattca atgtattgct tgtataaatt tttaaaaaat aaaatgaaan    3803
```

<210> SEQ ID NO 53
<211> LENGTH: 1161
<212> TYPE: PRT
<213> ORGANISM: Mus musculus

<400> SEQUENCE: 53

```
Met Val Arg Gly Val Val Ile Leu Leu Cys Gly Trp Ala Leu Ala Ser
 1               5                  10                  15

Cys His Gly Ser Asn Leu Asp Val Glu Lys Pro Val Val Phe Lys Glu
                20                  25                  30

Asp Ala Ala Ser Phe Gly Gln Thr Val Val Gln Phe Gly Gly Ser Arg
            35                  40                  45

Leu Val Val Gly Ala Pro Leu Glu Ala Val Ala Val Asn Gln Thr Gly
        50                  55                  60

Gln Ser Ser Asp Cys Pro Pro Ala Thr Gly Val Cys Gln Pro Ile Leu
    65                  70                  75                  80

Leu His Ile Pro Leu Glu Ala Val Asn Met Ser Leu Gly Leu Ser Leu
                85                  90                  95

Val Ala Asp Thr Asn Asn Ser Gln Leu Leu Ala Cys Gly Pro Thr Ala
               100                 105                 110

Gln Arg Ala Cys Ala Lys Asn Met Tyr Ala Lys Gly Ser Cys Leu Leu
           115                 120                 125

Leu Gly Ser Ser Leu Gln Phe Ile Gln Ala Ile Pro Ala Thr Met Pro
       130                 135                 140

Glu Cys Pro Gly Gln Glu Met Asp Ile Ala Phe Leu Ile Asp Gly Ser
145                 150                 155                 160

Gly Ser Ile Asp Gln Ser Asp Phe Thr Gln Met Lys Asp Phe Val Lys
               165                 170                 175

Ala Leu Met Gly Gln Leu Ala Ser Thr Ser Thr Ser Phe Ser Leu Met
           180                 185                 190

Gln Tyr Ser Asn Ile Leu Lys Thr His Phe Thr Phe Thr Glu Phe Lys
       195                 200                 205

Ser Ser Leu Ser Pro Gln Ser Leu Val Asp Ala Ile Val Gln Leu Gln
   210                 215                 220

Gly Leu Thr Tyr Thr Ala Ser Gly Ile Gln Lys Val Val Lys Glu Leu
225                 230                 235                 240

Phe His Ser Lys Asn Gly Ala Arg Lys Ser Ala Lys Lys Ile Leu Ile
               245                 250                 255

Val Ile Thr Asp Gly Gln Lys Phe Arg Asp Pro Leu Glu Tyr Arg His
           260                 265                 270

Val Ile Pro Glu Ala Glu Lys Ala Gly Ile Ile Arg Tyr Ala Ile Gly
       275                 280                 285

Val Gly Asp Ala Phe Arg Glu Pro Thr Ala Leu Gln Glu Leu Asn Thr
   290                 295                 300

Ile Gly Ser Ala Pro Ser Gln Asp His Val Phe Lys Val Gly Asn Phe
305                 310                 315                 320

Val Ala Leu Arg Ser Ile Gln Arg Gln Ile Gln Glu Lys Ile Phe Ala
               325                 330                 335

Ile Glu Gly Thr Glu Ser Arg Ser Ser Ser Phe Gln His Glu Met
           340                 345                 350
```

-continued

```
Ser Gln Glu Gly Phe Ser Ser Ala Leu Ser Met Asp Gly Pro Val Leu
        355                 360                 365
Gly Ala Val Gly Gly Phe Ser Trp Ser Gly Ala Phe Leu Tyr Pro
    370                 375                 380
Ser Asn Met Arg Ser Thr Phe Ile Asn Met Ser Gln Glu Asn Glu Asp
385                 390                 395                 400
Met Arg Asp Ala Tyr Leu Gly Tyr Ser Thr Ala Leu Ala Phe Trp Lys
                405                 410                 415
Gly Val His Ser Leu Ile Leu Gly Ala Pro Arg His Gln His Thr Gly
            420                 425                 430
Lys Val Val Ile Phe Thr Gln Glu Ser Arg His Trp Arg Pro Lys Ser
        435                 440                 445
Glu Val Arg Gly Thr Gln Ile Gly Ser Tyr Phe Gly Ala Ser Leu Cys
    450                 455                 460
Ser Val Asp Met Asp Arg Asp Gly Ser Thr Asp Leu Val Leu Ile Gly
465                 470                 475                 480
Val Pro His Tyr Tyr Glu His Thr Arg Gly Gly Gln Val Ser Val Cys
                485                 490                 495
Pro Met Pro Gly Val Arg Ser Arg Trp His Cys Gly Thr Thr Leu His
            500                 505                 510
Gly Glu Gln Gly His Pro Trp Gly Arg Phe Gly Ala Ala Leu Thr Val
        515                 520                 525
Leu Gly Asp Val Asn Gly Asp Ser Leu Ala Asp Val Ala Ile Gly Ala
    530                 535                 540
Pro Gly Glu Glu Glu Asn Arg Gly Ala Val Tyr Ile Phe His Gly Ala
545                 550                 555                 560
Ser Arg Gln Asp Ile Ala Pro Ser Pro Ser Gln Arg Val Thr Gly Ser
                565                 570                 575
Gln Leu Phe Leu Arg Leu Gln Tyr Phe Gly Gln Ser Leu Ser Gly Gly
        580                 585                 590
Gln Asp Leu Thr Gln Asp Gly Leu Val Asp Leu Ala Val Gly Ala Gln
    595                 600                 605
Gly His Val Leu Leu Leu Arg Ser Leu Pro Leu Leu Lys Val Gly Ile
610                 615                 620
Ser Ile Arg Phe Ala Pro Ser Glu Val Ala Lys Thr Val Tyr Gln Cys
625                 630                 635                 640
Trp Gly Arg Thr Pro Thr Val Leu Glu Ala Gly Glu Ala Thr Val Cys
                645                 650                 655
Leu Thr Val Arg Lys Gly Ser Pro Asp Leu Leu Gly Asp Val Gln Ser
            660                 665                 670
Ser Val Arg Tyr Asp Leu Ala Leu Asp Pro Gly Arg Leu Ile Ser Arg
        675                 680                 685
Ala Ile Phe Asp Glu Thr Lys Asn Cys Thr Leu Thr Arg Arg Lys Thr
    690                 695                 700
Leu Gly Leu Gly Asp His Cys Glu Thr Met Lys Leu Leu Leu Pro Asp
705                 710                 715                 720
Cys Val Glu Asp Ala Val Thr Pro Ile Ile Leu Arg Leu Asn Leu Ser
                725                 730                 735
Leu Ala Gly Asp Ser Ala Pro Ser Arg Asn Leu Arg Pro Val Leu Ala
            740                 745                 750
Val Gly Ser Gln Asp His Val Thr Ala Ser Phe Pro Phe Glu Lys Asn
        755                 760                 765
```

-continued

```
Cys Lys Gln Glu Leu Leu Cys Glu Gly Asn Leu Gly Val Ser Phe Asn
        770                 775                 780

Phe Ser Gly Leu Gln Val Leu Glu Val Gly Ser Ser Pro Glu Leu Thr
785                 790                 795                 800

Val Thr Val Thr Val Trp Asn Glu Gly Glu Asp Ser Tyr Gly Thr Leu
                805                 810                 815

Ile Lys Phe Tyr Tyr Pro Ala Glu Leu Ser Tyr Arg Arg Val Thr Arg
            820                 825                 830

Ala Gln Gln Pro His Pro Tyr Pro Leu Arg Leu Ala Cys Glu Ala Glu
        835                 840                 845

Pro Thr Gly Gln Glu Ser Leu Arg Ser Ser Ser Cys Ser Ile Asn His
    850                 855                 860

Pro Ile Phe Arg Glu Gly Ala Lys Ala Thr Phe Met Ile Thr Phe Asp
865                 870                 875                 880

Val Ser Tyr Lys Ala Phe Leu Gly Asp Arg Leu Leu Leu Arg Ala Ser
                885                 890                 895

Ala Ser Ser Glu Asn Asn Lys Pro Glu Thr Ser Lys Thr Ala Phe Gln
            900                 905                 910

Leu Glu Leu Pro Val Lys Tyr Thr Val Tyr Thr Val Ile Ser Arg Gln
        915                 920                 925

Glu Asp Ser Thr Lys His Phe Asn Phe Ser Ser Ser His Gly Glu Arg
    930                 935                 940

Gln Lys Glu Ala Glu His Arg Tyr Arg Val Asn Asn Leu Ser Pro Leu
945                 950                 955                 960

Thr Leu Ala Ile Ser Val Asn Phe Trp Val Pro Ile Leu Leu Asn Gly
                965                 970                 975

Val Ala Val Trp Asp Val Thr Leu Arg Ser Pro Ala Gln Gly Val Ser
            980                 985                 990

Cys Val Ser Gln Arg Glu Pro Pro Gln His Ser Asp Leu Leu Thr Gln
        995                 1000                1005

Ile Gln Gly Arg Ser Val Leu Asp Cys Ala Ile Ala Asp Cys Leu His
    1010                1015                1020

Leu Arg Cys Asp Ile Pro Ser Leu Gly Thr Leu Asp Glu Leu Asp Phe
1025                1030                1035                1040

Ile Leu Lys Gly Asn Leu Ser Phe Gly Trp Ile Ser Gln Thr Leu Gln
                1045                1050                1055

Lys Lys Val Leu Leu Leu Ser Glu Ala Glu Ile Thr Phe Asn Thr Ser
            1060                1065                1070

Val Tyr Ser Gln Leu Pro Gly Gln Glu Ala Phe Leu Arg Ala Gln Val
        1075                1080                1085

Ser Thr Met Leu Glu Glu Tyr Val Val Tyr Glu Pro Val Phe Leu Met
    1090                1095                1100

Val Phe Ser Ser Val Gly Gly Leu Leu Leu Leu Ala Leu Ile Thr Val
1105                1110                1115                1120

Ala Leu Tyr Lys Leu Gly Phe Phe Lys Arg Gln Tyr Lys Glu Met Leu
                1125                1130                1135

Asp Leu Pro Ser Ala Asp Pro Asp Pro Ala Gly Gln Ala Asp Ser Asn
            1140                1145                1150

His Glu Thr Pro Pro His Leu Thr Ser
        1155                1160

<210> SEQ ID NO 54
<211> LENGTH: 3597
<212> TYPE: DNA
```

```
<213> ORGANISM: Rattus rattus
<220> FEATURE:
<221> NAME/KEY: CDS
<222> LOCATION: (40)..(3522)
<223> OTHER INFORMATION: Description of Artificial Sequence: primer
<221> NAME/KEY: misc_feature
<222> LOCATION: 474
<223> OTHER INFORMATION: Xaa = any or unknown amino acid
<221> NAME/KEY: misc_feature
<222> LOCATION: 1128
<223> OTHER INFORMATION: Xaa = any or unknown amino acid

<400> SEQUENCE: 54
agctttacag ctctctactt ctcagtgcac tgctcagtg atg gcc ggt gga gtt        54
                                            Met Ala Gly Gly Val
                                             1               5 gtg atc ctc ctg tgt ggc tgg gtc ctg gct tcc tgt cat ggg tct aac      102
Val Ile Leu Leu Cys Gly Trp Val Leu Ala Ser Cys His Gly Ser Asn
             10                  15                  20 ctg gat gtg gag gaa ccc atc gtg ttc aga gag gat gca gcc agc ttt      150
Leu Asp Val Glu Glu Pro Ile Val Phe Arg Glu Asp Ala Ala Ser Phe
         25                  30                  35 gga cag act gtg gtg cag ttt ggt gga tct cga ctc gtg gtg gga gcc      198
Gly Gln Thr Val Val Gln Phe Gly Gly Ser Arg Leu Val Val Gly Ala
     40                  45                  50 cct ctg gag gcg gtg gca gtc aac caa aca gga cgg ttg tat gac tgt      246
Pro Leu Glu Ala Val Ala Val Asn Gln Thr Gly Arg Leu Tyr Asp Cys
 55                  60                  65 gca cct gcc act ggc atg tgc cag ccc atc gta ctg cgc agt ccc cta      294
Ala Pro Ala Thr Gly Met Cys Gln Pro Ile Val Leu Arg Ser Pro Leu
 70                  75                  80                  85 gag gca gtg aac atg tcc ctg ggc ctg tct ctg gtg act gcc acc aat      342
Glu Ala Val Asn Met Ser Leu Gly Leu Ser Leu Val Thr Ala Thr Asn
                 90                  95                 100 aac gcc cag ttg ctg gct tgt ggt cca act gca cag aga gct tgt gtg      390
Asn Ala Gln Leu Leu Ala Cys Gly Pro Thr Ala Gln Arg Ala Cys Val
            105                 110                 115 aag aac atg tat gcg aaa ggt tcc tgc ctc ctt ctc ggc tcc agc ttg      438
Lys Asn Met Tyr Ala Lys Gly Ser Cys Leu Leu Leu Gly Ser Ser Leu
        120                 125                 130 cag ttc atc cag gca gtc cct gcc tcc atg cca gag tgt cca aga caa      486
Gln Phe Ile Gln Ala Val Pro Ala Ser Met Pro Glu Cys Pro Arg Gln
    135                 140                 145 gag atg gac att gct ttc ctg att gat ggt tct ggc agc att aac caa      534
Glu Met Asp Ile Ala Phe Leu Ile Asp Gly Ser Gly Ser Ile Asn Gln
150                 155                 160                 165 agg gac ttt gcc cag atg aag gac ttt gtc aaa gct ttg atg gga gag      582
Arg Asp Phe Ala Gln Met Lys Asp Phe Val Lys Ala Leu Met Gly Glu
                170                 175                 180 ttt gcg agc acc agc acc ttg ttc tcc ctg atg caa tac tcg aac atc      630
Phe Ala Ser Thr Ser Thr Leu Phe Ser Leu Met Gln Tyr Ser Asn Ile
            185                 190                 195 ctg aag acc cat ttt acc ttc act gaa ttc aag aac atc ctg gac cct      678
Leu Lys Thr His Phe Thr Phe Thr Glu Phe Lys Asn Ile Leu Asp Pro
        200                 205                 210 cag agc ctg gtg gat ccc att gtc cag ctg caa ggc ctg acc tac aca      726
Gln Ser Leu Val Asp Pro Ile Val Gln Leu Gln Gly Leu Thr Tyr Thr
    215                 220                 225 gcc aca ggc atc cgg aca gtg atg gaa gag cta ttt cat agc aag aat      774
Ala Thr Gly Ile Arg Thr Val Met Glu Glu Leu Phe His Ser Lys Asn
230                 235                 240                 245 ggg tcc cgt aaa agt gcc aag aag atc ctc ctt gtc atc aca gat ggg      822
```

```
                                                              -continued

Gly Ser Arg Lys Ser Ala Lys Lys Ile Leu Leu Val Ile Thr Asp Gly
            250                 255                 260 cag aaa tac aga gac ccc ctg gag tat agt gat gtc att ccc gcc gca        870
Gln Lys Tyr Arg Asp Pro Leu Glu Tyr Ser Asp Val Ile Pro Ala Ala
                265                 270                 275 gac aaa gct ggc atc att cgt tat gct att ggg gtg gga gat gcc ttc        918
Asp Lys Ala Gly Ile Ile Arg Tyr Ala Ile Gly Val Gly Asp Ala Phe
            280                 285                 290 cag gag ccc act gcc ctg aag gag ctg aac acc att ggc tca gct ccc        966
Gln Glu Pro Thr Ala Leu Lys Glu Leu Asn Thr Ile Gly Ser Ala Pro
    295                 300                 305 cca cag gac cac gtg ttc aag gta ggc aac ttt gca gca ctt cgc agc       1014
Pro Gln Asp His Val Phe Lys Val Gly Asn Phe Ala Ala Leu Arg Ser
310                 315                 320                 325 atc cag agg caa ctt cag gag aaa atc ttc gcc att gag gga act caa       1062
Ile Gln Arg Gln Leu Gln Glu Lys Ile Phe Ala Ile Glu Gly Thr Gln
                330                 335                 340 tca agg tca agt agt tcc ttt cag cac gag atg tca caa gaa ggt ttc       1110
Ser Arg Ser Ser Ser Ser Phe Gln His Glu Met Ser Gln Glu Gly Phe
            345                 350                 355 agt tca gct ctc aca tcg gat gga ccc gtt ctg ggg gcc gtg gga agc       1158
Ser Ser Ala Leu Thr Ser Asp Gly Pro Val Leu Gly Ala Val Gly Ser
        360                 365                 370 ttc agc tgg tcc gga ggt gcc ttc tta tat ccc cca aat acg aga ccc       1206
Phe Ser Trp Ser Gly Gly Ala Phe Leu Tyr Pro Pro Asn Thr Arg Pro
    375                 380                 385 acc ttt atc aac atg tct cag gag aat gtg gac atg aga gac tcc tac       1254
Thr Phe Ile Asn Met Ser Gln Glu Asn Val Asp Met Arg Asp Ser Tyr
390                 395                 400                 405 ctg ggt tac tcc acc gca gtg gcc ttt tgg aag ggg gtt cac agc ctg       1302
Leu Gly Tyr Ser Thr Ala Val Ala Phe Trp Lys Gly Val His Ser Leu
                410                 415                 420 atc ctg ggg gcc ccg cgt cac cag cac acg ggg aag gtt gtc atc ttt       1350
Ile Leu Gly Ala Pro Arg His Gln His Thr Gly Lys Val Val Ile Phe
            425                 430                 435 acc cag gaa gcc agg cat tgg agg ccc aag tct gaa gtc aga ggg aca       1398
Thr Gln Glu Ala Arg His Trp Arg Pro Lys Ser Glu Val Arg Gly Thr
        440                 445                 450 cag atc ggc tcc tac ttc ggg gcc tct ctc tgt tct gtg gac gtg gat       1446
Gln Ile Gly Ser Tyr Phe Gly Ala Ser Leu Cys Ser Val Asp Val Asp
455                 460                 465 aga gat ggc agc acy gac ctg gtc ctg atc gga gcc ccc cat tac tat       1494
Arg Asp Gly Ser Xaa Asp Leu Val Leu Ile Gly Ala Pro His Tyr Tyr
470                 475                 480                 485 gag cag acc cga ggg ggg cag gtc tca gtg ttc ccc gtg ccc ggt gtg       1542
Glu Gln Thr Arg Gly Gly Gln Val Ser Val Phe Pro Val Pro Gly Val
                490                 495                 500 agg ggc agg tgg cag tgt gag gcc acc ctc cac ggg gag cag ggc cat       1590
Arg Gly Arg Trp Gln Cys Glu Ala Thr Leu His Gly Glu Gln Gly His
            505                 510                 515 cct tgg ggc cgc ttt ggg gtg gct ctg aca gtg ctg ggg gac gta aac       1638
Pro Trp Gly Arg Phe Gly Val Ala Leu Thr Val Leu Gly Asp Val Asn
        520                 525                 530 ggg gac aat ctg gca gac gtg gct att ggt gcc cct gga gag gag gag       1686
Gly Asp Asn Leu Ala Asp Val Ala Ile Gly Ala Pro Gly Glu Glu Glu
    535                 540                 545 agc aga ggt gct gtc tac ata ttt cat gga gcc tcg aga ctg gag atc       1734
Ser Arg Gly Ala Val Tyr Ile Phe His Gly Ala Ser Arg Leu Glu Ile
550                 555                 560                 565
```

```
atg ccc tca ccc agc cag cgg gtc act ggc tcc cag ctc tcc ctg aga      1782
Met Pro Ser Pro Ser Gln Arg Val Thr Gly Ser Gln Leu Ser Leu Arg
            570                 575                 580 ctg cag tat ttt ggg cag tca ttg agt ggg ggt cag gac ctt aca cag      1830
Leu Gln Tyr Phe Gly Gln Ser Leu Ser Gly Gly Gln Asp Leu Thr Gln
                585                 590                 595 gat ggc ctg gtg gac ctg gcc gtg gga gcc cag ggg cac gta ctg ctg      1878
Asp Gly Leu Val Asp Leu Ala Val Gly Ala Gln Gly His Val Leu Leu
        600                 605                 610 ctc agg agt ctg cct ctg ctg aaa gtg gag ctc tcc ata aga ttc gcc      1926
Leu Arg Ser Leu Pro Leu Leu Lys Val Glu Leu Ser Ile Arg Phe Ala
    615                 620                 625 ccc atg gag gtg gca aag gct gtg tac cag tgc tgg gaa agg act ccc      1974
Pro Met Glu Val Ala Lys Ala Val Tyr Gln Cys Trp Glu Arg Thr Pro
630                 635                 640                 645 act gtc ctc gaa gct gga gag gcc act gtc tgt ctc act gtc cac aaa      2022
Thr Val Leu Glu Ala Gly Glu Ala Thr Val Cys Leu Thr Val His Lys
                650                 655                 660 ggc tca cct gac ctg tta ggt aat gtc caa ggc tct gtc agg tat gat      2070
Gly Ser Pro Asp Leu Leu Gly Asn Val Gln Gly Ser Val Arg Tyr Asp
        665                 670                 675 ctg gcg tta gat ccg ggc cgc ctg att tct cgt gcc att ttt gat gag      2118
Leu Ala Leu Asp Pro Gly Arg Leu Ile Ser Arg Ala Ile Phe Asp Glu
    680                 685                 690 act aag aac tgc act ttg acg gga agg aag act ctg ggg ctt ggt gat      2166
Thr Lys Asn Cys Thr Leu Thr Gly Arg Lys Thr Leu Gly Leu Gly Asp
695                 700                 705 cac tgc gaa aca gtg aag ctg ctt ttg ccg gac tgt gtg gaa gat gca      2214
His Cys Glu Thr Val Lys Leu Leu Leu Pro Asp Cys Val Glu Asp Ala
710                 715                 720                 725 gtg agc cct atc atc ctg cgc ctc aac ttt tcc ctg gtg aga gac tct      2262
Val Ser Pro Ile Ile Leu Arg Leu Asn Phe Ser Leu Val Arg Asp Ser
                730                 735                 740 gct tca ccc agg aac ctg cat cct gtg ctg gct gtg ggc tca caa gac      2310
Ala Ser Pro Arg Asn Leu His Pro Val Leu Ala Val Gly Ser Gln Asp
        745                 750                 755 cac ata act gct tct ctg ccg ttt gag aag aac tgt aag caa gaa ctc      2358
His Ile Thr Ala Ser Leu Pro Phe Glu Lys Asn Cys Lys Gln Glu Leu
    760                 765                 770 ctg tgt gag ggg gac ctg ggc atc agc ttt aac ttc tca ggc ctg cag      2406
Leu Cys Glu Gly Asp Leu Gly Ile Ser Phe Asn Phe Ser Gly Leu Gln
775                 780                 785 gtc ttg gtg gtg gga ggc tcc cca gag ctc act gtg aca gtc act gtg      2454
Val Leu Val Val Gly Gly Ser Pro Glu Leu Thr Val Thr Val Thr Val
790                 795                 800                 805 tgg aat gag ggt gag gac agc tat gga act tta gtc aag ttc tac tac      2502
Trp Asn Glu Gly Glu Asp Ser Tyr Gly Thr Leu Val Lys Phe Tyr Tyr
                810                 815                 820 cca gca ggg cta tct tac cga cgg gta aca ggg act cag caa cct cat      2550
Pro Ala Gly Leu Ser Tyr Arg Arg Val Thr Gly Thr Gln Gln Pro His
        825                 830                 835 cag tac cca cta cgc ttg gcc tgt gag gct gag ccc gct gcc cag gag      2598
Gln Tyr Pro Leu Arg Leu Ala Cys Glu Ala Glu Pro Ala Ala Gln Glu
    840                 845                 850 gac ctg agg agc agc agc tgt agc att aat cac ccc atc ttc cga gaa      2646
Asp Leu Arg Ser Ser Ser Cys Ser Ile Asn His Pro Ile Phe Arg Glu
855                 860                 865 ggt gca aag acc acc ttc atg atc aca ttc gat gtc tcc tac aag gcc      2694
Gly Ala Lys Thr Thr Phe Met Ile Thr Phe Asp Val Ser Tyr Lys Ala
870                 875                 880                 885
```

| | | |
|---|---|---|
| ttc cta gga gac agg ttg ctt ctg agg gcc aaa gcc agc agt gag aat<br>Phe Leu Gly Asp Arg Leu Leu Leu Arg Ala Lys Ala Ser Ser Glu Asn<br>890                            895                            900 | 2742 |
| aat aag cct gat acc aac aag act gcc ttc cag ctg gag ctc cca gtg<br>Asn Lys Pro Asp Thr Asn Lys Thr Ala Phe Gln Leu Glu Leu Pro Val<br>    905                        910                         915 | 2790 |
| aag tac acc gtc tat acc ctg atc agt agg caa gaa gat tcc acc aac<br>Lys Tyr Thr Val Tyr Thr Leu Ile Ser Arg Gln Glu Asp Ser Thr Asn<br>        920                      925                    930 | 2838 |
| cat gtc aac ttt tca tct tcc cac ggg ggg aga agg caa gaa gcc gca<br>His Val Asn Phe Ser Ser Ser His Gly Gly Arg Arg Gln Glu Ala Ala<br>935                            940                            945 | 2886 |
| cat cgc tat cgt gtg aat aac ctg agt cca ctg aag ctg gcc gtc aga<br>His Arg Tyr Arg Val Asn Asn Leu Ser Pro Leu Lys Leu Ala Val Arg<br>950                            955                            960                         965 | 2934 |
| gtt aac ttc tgg gtc cct gtc ctt ctg aac ggt gtg gct gtg tgg gac<br>Val Asn Phe Trp Val Pro Val Leu Leu Asn Gly Val Ala Val Trp Asp<br>                970                            975                            980 | 2982 |
| gtg act ctg agc agc cca gca cag ggt gtc tcc tgc gtg tcc cag atg<br>Val Thr Leu Ser Ser Pro Ala Gln Gly Val Ser Cys Val Ser Gln Met<br>985                            990                              995 | 3030 |
| aaa cct cct cag aat ccc gac ttt ctg acc cag att cag aga cgt tct<br>Lys Pro Pro Gln Asn Pro Asp Phe Leu Thr Gln Ile Gln Arg Arg Ser<br>    1000                      1005                      1010 | 3078 |
| gtg ctg gac tgc tcc att gct gac tgc ctg cac ttc cgc tgt gac atc<br>Val Leu Asp Cys Ser Ile Ala Asp Cys Leu His Phe Arg Cys Asp Ile<br>1015                      1020                      1025 | 3126 |
| ccc tcc ttg gac atc cag gat gaa ctt gac ttc att ctg agg ggc aac<br>Pro Ser Leu Asp Ile Gln Asp Glu Leu Asp Phe Ile Leu Arg Gly Asn<br>1030                      1035                      1040                      1045 | 3174 |
| ctc agc ttc ggc tgg gtc agt cag aca ttg cag gaa aag gtg ttg ctt<br>Leu Ser Phe Gly Trp Val Ser Gln Thr Leu Gln Glu Lys Val Leu Leu<br>                1050                      1055                      1060 | 3222 |
| gtg agt gag gct gaa atc act ttc gac aca tct gtg tac tcc cag ctg<br>Val Ser Glu Ala Glu Ile Thr Phe Asp Thr Ser Val Tyr Ser Gln Leu<br>1065                      1070                      1075 | 3270 |
| cca gga cag gag gca ttt ctg aga gcc cag gtg gag aca acg tta gaa<br>Pro Gly Gln Glu Ala Phe Leu Arg Ala Gln Val Glu Thr Thr Leu Glu<br>1080                      1085                      1090 | 3318 |
| gaa tac gtg gtc tat gag ccc atc ttc ctc gtg gcg ggc agc tcg gtg<br>Glu Tyr Val Val Tyr Glu Pro Ile Phe Leu Val Ala Gly Ser Ser Val<br>1095                      1100                      1105 | 3366 |
| gga ggt ctg ctg tta ctg gct ctc atc aca gtg gta ctg tac aag ctt<br>Gly Gly Leu Leu Leu Leu Ala Leu Ile Thr Val Val Leu Tyr Lys Leu<br>1110                      1115                      1120                      1125 | 3414 |
| ggc ttc tyc aaa cgt cag tac aaa gaa atg ctg gac ggc aag gct gca<br>Gly Phe Xaa Lys Arg Gln Tyr Lys Glu Met Leu Asp Gly Lys Ala Ala<br>                1130                      1135                      1140 | 3462 |
| gat cct gtc aca gcc ggc cag gca gat ttc ggc tgt gag act cct cca<br>Asp Pro Val Thr Ala Gly Gln Ala Asp Phe Gly Cys Glu Thr Pro Pro<br>                      1145                      1150                      1155 | 3510 |
| tat ctc gtg agc taggaatcca ctctcctgcc tatctctgca atgaagattg<br>Tyr Leu Val Ser<br>        1160 | 3562 |
| gtcctgccta tgagtctact ggcatgggaa cgagt | 3597 |

<210> SEQ ID NO 55
<211> LENGTH: 1161
<212> TYPE: PRT

```
<213> ORGANISM: Rattus rattus
<220> FEATURE:
<221> NAME/KEY: misc_feature
<222> LOCATION: 474
<223> OTHER INFORMATION: Xaa = any or unknown amino acid
<221> NAME/KEY: misc_feature
<222> LOCATION: 1128
<223> OTHER INFORMATION: Xaa = any or unknown amino acid

<400> SEQUENCE: 55
```

```
Met Ala Gly Gly Val Val Ile Leu Leu Cys Gly Trp Val Leu Ala Ser
 1               5                  10                  15

Cys His Gly Ser Asn Leu Asp Val Glu Glu Pro Ile Val Phe Arg Glu
             20                  25                  30

Asp Ala Ala Ser Phe Gly Gln Thr Val Val Gln Phe Gly Gly Ser Arg
         35                  40                  45

Leu Val Val Gly Ala Pro Leu Glu Ala Val Ala Val Asn Gln Thr Gly
     50                  55                  60

Arg Leu Tyr Asp Cys Ala Pro Ala Thr Gly Met Cys Gln Pro Ile Val
 65                  70                  75                  80

Leu Arg Ser Pro Leu Glu Ala Val Asn Met Ser Leu Gly Leu Ser Leu
                 85                  90                  95

Val Thr Ala Thr Asn Asn Ala Gln Leu Leu Ala Cys Gly Pro Thr Ala
            100                 105                 110

Gln Arg Ala Cys Val Lys Asn Met Tyr Ala Lys Gly Ser Cys Leu Leu
        115                 120                 125

Leu Gly Ser Ser Leu Gln Phe Ile Gln Ala Val Pro Ala Ser Met Pro
    130                 135                 140

Glu Cys Pro Arg Gln Glu Met Asp Ile Ala Phe Leu Ile Asp Gly Ser
145                 150                 155                 160

Gly Ser Ile Asn Gln Arg Asp Phe Ala Gln Met Lys Asp Phe Val Lys
                165                 170                 175

Ala Leu Met Gly Glu Phe Ala Ser Thr Ser Thr Leu Phe Ser Leu Met
            180                 185                 190

Gln Tyr Ser Asn Ile Leu Lys Thr His Phe Thr Phe Thr Glu Phe Lys
        195                 200                 205

Asn Ile Leu Asp Pro Gln Ser Leu Val Asp Pro Ile Val Gln Leu Gln
    210                 215                 220

Gly Leu Thr Tyr Thr Ala Thr Gly Ile Arg Thr Val Met Glu Glu Leu
225                 230                 235                 240

Phe His Ser Lys Asn Gly Ser Arg Lys Ser Ala Lys Lys Ile Leu Leu
                245                 250                 255

Val Ile Thr Asp Gly Gln Lys Tyr Arg Asp Pro Leu Glu Tyr Ser Asp
            260                 265                 270

Val Ile Pro Ala Ala Asp Lys Ala Gly Ile Ile Arg Tyr Ala Ile Gly
        275                 280                 285

Val Gly Asp Ala Phe Gln Glu Pro Thr Ala Leu Lys Glu Leu Asn Thr
    290                 295                 300

Ile Gly Ser Ala Pro Pro Gln Asp His Val Phe Lys Val Gly Asn Phe
305                 310                 315                 320

Ala Ala Leu Arg Ser Ile Gln Arg Gln Leu Gln Glu Lys Ile Phe Ala
                325                 330                 335

Ile Glu Gly Thr Gln Ser Arg Ser Ser Ser Phe Gln His Glu Met
            340                 345                 350

Ser Gln Glu Gly Phe Ser Ser Ala Leu Thr Ser Asp Gly Pro Val Leu
        355                 360                 365
```

-continued

```
Gly Ala Val Gly Ser Phe Ser Trp Ser Gly Ala Phe Leu Tyr Pro
    370                 375                 380
Pro Asn Thr Arg Pro Thr Phe Ile Asn Met Ser Gln Glu Asn Val Asp
385                 390                 395                 400
Met Arg Asp Ser Tyr Leu Gly Tyr Ser Thr Ala Val Ala Phe Trp Lys
                405                 410                 415
Gly Val His Ser Leu Ile Leu Gly Ala Pro Arg His Gln His Thr Gly
                420                 425                 430
Lys Val Val Ile Phe Thr Gln Glu Ala Arg His Trp Arg Pro Lys Ser
                435                 440                 445
Glu Val Arg Gly Thr Gln Ile Gly Ser Tyr Phe Gly Ala Ser Leu Cys
    450                 455                 460
Ser Val Asp Val Asp Arg Asp Gly Ser Xaa Asp Leu Val Leu Ile Gly
465                 470                 475                 480
Ala Pro His Tyr Tyr Glu Gln Thr Arg Gly Gly Gln Val Ser Val Phe
                485                 490                 495
Pro Val Pro Gly Val Arg Gly Arg Trp Gln Cys Glu Ala Thr Leu His
                500                 505                 510
Gly Glu Gln Gly His Pro Trp Gly Arg Phe Gly Val Ala Leu Thr Val
    515                 520                 525
Leu Gly Asp Val Asn Gly Asp Asn Leu Ala Asp Val Ala Ile Gly Ala
    530                 535                 540
Pro Gly Glu Glu Glu Ser Arg Gly Ala Val Tyr Ile Phe His Gly Ala
545                 550                 555                 560
Ser Arg Leu Glu Ile Met Pro Ser Pro Ser Gln Arg Val Thr Gly Ser
                565                 570                 575
Gln Leu Ser Leu Arg Leu Gln Tyr Phe Gly Gln Ser Leu Ser Gly Gly
                580                 585                 590
Gln Asp Leu Thr Gln Asp Gly Leu Val Asp Leu Ala Val Gly Ala Gln
                595                 600                 605
Gly His Val Leu Leu Leu Arg Ser Leu Pro Leu Leu Lys Val Glu Leu
    610                 615                 620
Ser Ile Arg Phe Ala Pro Met Glu Val Ala Lys Ala Val Tyr Gln Cys
625                 630                 635                 640
Trp Glu Arg Thr Pro Thr Val Leu Glu Ala Gly Glu Ala Thr Val Cys
                645                 650                 655
Leu Thr Val His Lys Gly Ser Pro Asp Leu Leu Gly Asn Val Gln Gly
                660                 665                 670
Ser Val Arg Tyr Asp Leu Ala Leu Asp Pro Gly Arg Leu Ile Ser Arg
                675                 680                 685
Ala Ile Phe Asp Glu Thr Lys Asn Cys Thr Leu Thr Gly Arg Lys Thr
    690                 695                 700
Leu Gly Leu Gly Asp His Cys Glu Thr Val Lys Leu Leu Leu Pro Asp
705                 710                 715                 720
Cys Val Glu Asp Ala Val Ser Pro Ile Ile Leu Arg Leu Asn Phe Ser
                725                 730                 735
Leu Val Arg Asp Ser Ala Ser Pro Arg Asn Leu His Pro Val Leu Ala
                740                 745                 750
Val Gly Ser Gln Asp His Ile Thr Ala Ser Leu Pro Phe Glu Lys Asn
                755                 760                 765
Cys Lys Gln Glu Leu Leu Cys Glu Gly Asp Leu Gly Ile Ser Phe Asn
770                 775                 780
```

-continued

```
Phe Ser Gly Leu Gln Val Leu Val Gly Gly Ser Pro Glu Leu Thr
785                 790                 795                 800

Val Thr Val Thr Val Trp Asn Glu Gly Glu Asp Ser Tyr Gly Thr Leu
                805                 810                 815

Val Lys Phe Tyr Tyr Pro Ala Gly Leu Ser Tyr Arg Arg Val Thr Gly
            820                 825                 830

Thr Gln Gln Pro His Gln Tyr Pro Leu Arg Leu Ala Cys Glu Ala Glu
        835                 840                 845

Pro Ala Ala Gln Glu Asp Leu Arg Ser Ser Cys Ser Ile Asn His
850                 855                 860

Pro Ile Phe Arg Glu Gly Ala Lys Thr Thr Phe Met Ile Thr Phe Asp
865                 870                 875                 880

Val Ser Tyr Lys Ala Phe Leu Gly Asp Arg Leu Leu Arg Ala Lys
            885                 890                 895

Ala Ser Ser Glu Asn Asn Lys Pro Asp Thr Asn Lys Thr Ala Phe Gln
        900                 905                 910

Leu Glu Leu Pro Val Lys Tyr Thr Val Tyr Thr Leu Ile Ser Arg Gln
            915                 920                 925

Glu Asp Ser Thr Asn His Val Asn Phe Ser Ser His Gly Gly Arg
930                 935                 940

Arg Gln Glu Ala Ala His Arg Tyr Arg Val Asn Asn Leu Ser Pro Leu
945                 950                 955                 960

Lys Leu Ala Val Arg Val Asn Phe Trp Val Pro Val Leu Leu Asn Gly
            965                 970                 975

Val Ala Val Trp Asp Val Thr Leu Ser Ser Pro Ala Gln Gly Val Ser
            980                 985                 990

Cys Val Ser Gln Met Lys Pro Pro Gln Asn Pro Asp Phe Leu Thr Gln
        995                 1000                1005

Ile Gln Arg Arg Ser Val Leu Asp Cys Ser Ile Ala Asp Cys Leu His
    1010                1015                1020

Phe Arg Cys Asp Ile Pro Ser Leu Asp Ile Gln Asp Glu Leu Asp Phe
1025                1030                1035                1040

Ile Leu Arg Gly Asn Leu Ser Phe Gly Trp Val Ser Gln Thr Leu Gln
                1045                1050                1055

Glu Lys Val Leu Leu Val Ser Glu Ala Glu Ile Thr Phe Asp Thr Ser
            1060                1065                1070

Val Tyr Ser Gln Leu Pro Gly Gln Glu Ala Phe Leu Arg Ala Gln Val
        1075                1080                1085

Glu Thr Thr Leu Glu Glu Tyr Val Val Tyr Glu Pro Ile Phe Leu Val
    1090                1095                1100

Ala Gly Ser Ser Val Gly Gly Leu Leu Leu Ala Leu Ile Thr Val
1105                1110                1115                1120

Val Leu Tyr Lys Leu Gly Phe Xaa Lys Arg Gln Tyr Lys Glu Met Leu
            1125                1130                1135

Asp Gly Lys Ala Ala Asp Pro Val Thr Ala Gly Gln Ala Asp Phe Gly
            1140                1145                1150

Cys Glu Thr Pro Pro Tyr Leu Val Ser
        1155                1160
```

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: primer

```
<400> SEQUENCE: 56
cctgtcatgg gtctaacctg                                              20

<210> SEQ ID NO 57
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 57
aggttagacc catgacagg                                               19

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 58
ggccttgcag ctggacaatg                                              20

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 59
ccaaagctgg ctgcatcctc tc                                           22

<210> SEQ ID NO 60
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 60
ccgcctgcca ctggcgtgtg c                                            21

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 61
cccagatgaa ggacttcgtc aa                                           22

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 62
gctgggatca ttcgctatgc                                              20

<210> SEQ ID NO 63
```

```
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 63
caatggatgg accagttctg g                                              21

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 64
cagatcggct cctactttgg                                                20

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 65
catggagcct cgagacagg                                                 19

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 66
ccactgtcct cgaagctgga g                                              21

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 67
cttcgtcctg tgctggctgt gggctc                                         26

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 68
cgcctggcat gtgaggctga g                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 69
```

```
ccgtgatcag taggcaggaa g                                              21

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 70
gtcacagagg gaacctcc                                                  18

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 71
gctcctgagt gaggctgaaa tca                                            23

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 72
gagatgctgg atctaccatc tgc                                            23

<210> SEQ ID NO 73
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 73
ctgagctggg agatttttat gg                                             22

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 74
gtggatcagc actgaaatct g                                              21

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 75
cgtttgaaga agccaagctt g                                              21

<210> SEQ ID NO 76
<211> LENGTH: 20
<212> TYPE: DNA
```

<213> ORGANISM: Artificial Sequence
<220> FEATURE:
<223> OTHER INFORMATION: Description of Artificial Sequence: primer

<400> SEQUENCE: 76
cacagcggag gtgcaggcag                                              20

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 77
ctcactgctt gcgctggc                                                18

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 78
cggtaagata gctctgctgg                                              20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 79
gagcccacag ccagcacagg                                              20

<210> SEQ ID NO 80
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 80
gatccaacgc cagatcatac c                                            21

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 81
cacggccagg tccaccaggc                                              20

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 82
cacgtcccct agcactgtca g                                            21

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 83
ttgacgaagt ccttcatctg gg                                       22

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 84
gaactgcaag ctggagccca g                                        21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 85
ctggatgctg cgaagtgcta c                                        21

<210> SEQ ID NO 86
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 86
gccttggagc tggacgatgg c                                        21

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 87
gtaagatctc cagagtgtcc aagacaagag atg                           33

<210> SEQ ID NO 88
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 88
cttctcgagt gtgagagctg aactgaaacc ttc                           33

<210> SEQ ID NO 89
<211> LENGTH: 32
<212> TYPE: DNA
<213> ORGANISM: Artificial Sequence
<220> FEATURE:

```
-continued

<223> OTHER INFORMATION: Description of Artificial Sequence: primer

<400> SEQUENCE: 89
cgctgtgacg tcagagttga gtccaaatat gg                                32

<210> SEQ ID NO 90
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 90
ggtgacacta tagaataggg c                                            21

<210> SEQ ID NO 91
<211> LENGTH: 18
<212> TYPE: DNA
<213> ORGANISM: Mus musculus

<400> SEQUENCE: 91
aagcaggagc tcctgtgt                                                18

<210> SEQ ID NO 92
<211> LENGTH: 852
<212> TYPE: DNA
<213> ORGANISM: rabbit
<220> FEATURE:
<221> NAME/KEY: CDS
<222> LOCATION: (61)..(852)

<400> SEQUENCE: 92
tgatctccct ccaggccact gttccctctc cacttcccct caccgctgca ctgctcagag    60 atg gcc ctt ggg gct gtg gtc ctc ctt ggg gtc ctg gct tct tac cac   108
Met Ala Leu Gly Ala Val Val Leu Leu Gly Val Leu Ala Ser Tyr His
 1               5                  10                  15 gga ttc aac ttg gac gtg atg agc ggt gat ctt cca gga aga cgc agc   156
Gly Phe Asn Leu Asp Val Met Ser Gly Asp Leu Pro Gly Arg Arg Ser
             20                  25                  30 ggg ctt cgg gca gag cgt gat gca gtt tgg gga tct cga ctc gtg gtg   204
Gly Leu Arg Ala Glu Arg Asp Ala Val Trp Gly Ser Arg Leu Val Val
         35                  40                  45 gga gcc ccc ctg gcg gtg gtg tcg gcc aac cac aca gga cgg ctg tac   252
Gly Ala Pro Leu Ala Val Val Ser Ala Asn His Thr Gly Arg Leu Tyr
     50                  55                  60 gag tgt gcg cct gcc tcc ggc acc tgc acg ccc att ttc cca ttc atg   300
Glu Cys Ala Pro Ala Ser Gly Thr Cys Thr Pro Ile Phe Pro Phe Met
 65                  70                  75                  80 ccc ccc gaa gcc gtg aac atg tcc ctg ggc ctg tcc ctg gca gcc tcc   348
Pro Pro Glu Ala Val Asn Met Ser Leu Gly Leu Ser Leu Ala Ala Ser
                 85                  90                  95 ccc aac cat tcc cag ctg ctg gct tgt ggc ccg acc gtg cat aga gcc   396
Pro Asn His Ser Gln Leu Leu Ala Cys Gly Pro Thr Val His Arg Ala
            100                 105                 110 tgc ggg gag gac gtg tac gcc cag ggt ttc tgt gtg ctg ctg gat gcc   444
Cys Gly Glu Asp Val Tyr Ala Gln Gly Phe Cys Val Leu Leu Asp Ala
        115                 120                 125 cac gca cag ccc atc ggg act gtg cca gct gcc ctg ccc gag tgc cca   492
His Ala Gln Pro Ile Gly Thr Val Pro Ala Ala Leu Pro Glu Cys Pro
    130                 135                 140 gat caa gag atg gac att gtc ttc ctg att gac ggc tct ggc agc att   540
Asp Gln Glu Met Asp Ile Val Phe Leu Ile Asp Gly Ser Gly Ser Ile
```

```
145                 150                 155                 160
agc tca aat gac ttc cgc aag atg aag gac ttt gtc aga gct gtg atg    588
Ser Ser Asn Asp Phe Arg Lys Met Lys Asp Phe Val Arg Ala Val Met
            165                 170                 175 gac cag ttc aag gac acc aac acc cag ttc tcg ctg atg cag tac tcc    636
Asp Gln Phe Lys Asp Thr Asn Thr Gln Phe Ser Leu Met Gln Tyr Ser
            180                 185                 190 aat gtg ctg gtg aca cat ttc acc ttc agc agc ttc cgg aac agc tcc    684
Asn Val Leu Val Thr His Phe Thr Phe Ser Ser Phe Arg Asn Ser Ser
            195                 200                 205 aat cct cag ggc cta gtg gag ccc att gtg cag ctg aca ggc ctc acg    732
Asn Pro Gln Gly Leu Val Glu Pro Ile Val Gln Leu Thr Gly Leu Thr
    210                 215                 220 ttc acg gcc aca ggg atc ctg aaa gtg gtg aca gag ctg ttt caa acc    780
Phe Thr Ala Thr Gly Ile Leu Lys Val Val Thr Glu Leu Phe Gln Thr
225                 230                 235                 240 aag aac ggg gcc cgc gaa agt gcc aag aag atc ctc atc gtc atc aca    828
Lys Asn Gly Ala Arg Glu Ser Ala Lys Lys Ile Leu Ile Val Ile Thr
            245                 250                 255 gat ggg cag aag tac aaa gcg gca                                    852
Asp Gly Gln Lys Tyr Lys Ala Ala
            260

<210> SEQ ID NO 93
<211> LENGTH: 264
<212> TYPE: PRT
<213> ORGANISM: rabbit

<400> SEQUENCE: 93

Met Ala Leu Gly Ala Val Val Leu Leu Gly Val Leu Ala Ser Tyr His
1               5                   10                  15

Gly Phe Asn Leu Asp Val Met Ser Gly Asp Leu Pro Gly Arg Arg Ser
            20                  25                  30

Gly Leu Arg Ala Glu Arg Asp Ala Val Trp Gly Ser Arg Leu Val Val
        35                  40                  45

Gly Ala Pro Leu Ala Val Val Ser Ala Asn His Thr Gly Arg Leu Tyr
    50                  55                  60

Glu Cys Ala Pro Ala Ser Gly Thr Cys Thr Pro Ile Phe Pro Phe Met
65                  70                  75                  80

Pro Pro Glu Ala Val Asn Met Ser Leu Gly Leu Ser Leu Ala Ala Ser
                85                  90                  95

Pro Asn His Ser Gln Leu Leu Ala Cys Gly Pro Thr Val His Arg Ala
            100                 105                 110

Cys Gly Glu Asp Val Tyr Ala Gln Gly Phe Cys Val Leu Leu Asp Ala
        115                 120                 125

His Ala Gln Pro Ile Gly Thr Val Pro Ala Ala Leu Pro Glu Cys Pro
    130                 135                 140

Asp Gln Glu Met Asp Ile Val Phe Leu Ile Asp Gly Ser Gly Ser Ile
145                 150                 155                 160

Ser Ser Asn Asp Phe Arg Lys Met Lys Asp Phe Val Arg Ala Val Met
                165                 170                 175

Asp Gln Phe Lys Asp Thr Asn Thr Gln Phe Ser Leu Met Gln Tyr Ser
            180                 185                 190

Asn Val Leu Val Thr His Phe Thr Phe Ser Ser Phe Arg Asn Ser Ser
        195                 200                 205

Asn Pro Gln Gly Leu Val Glu Pro Ile Val Gln Leu Thr Gly Leu Thr
    210                 215                 220
```

```
Phe Thr Ala Thr Gly Ile Leu Lys Val Val Thr Glu Leu Phe Gln Thr
225                 230                 235                 240

Lys Asn Gly Ala Arg Glu Ser Ala Lys Lys Ile Leu Ile Val Ile Thr
            245                 250                 255

Asp Gly Gln Lys Tyr Lys Ala Ala
            260
```

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: primer

<400> SEQUENCE: 94

| ctggtctgga ggtgccttcc tg | 22 |
|---|---|

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 95

| cctgagcagg agcacctggc c | 21 |
|---|---|

<210> SEQ ID NO 96
<211> LENGTH: 2499
<212> TYPE: DNA
<213> ORGANISM: Homo sapiens

<400> SEQUENCE: 96

| atgaccttcg gcactgtgct tcttctgagt gtcctggctt cttatcatgg attcaacctg | 60 |
|---|---|
| gatgtggagg agcctacgat cttccaggag gatgcaggcg gctttgggca gagcgtggtg | 120 |
| cagttcggtg gatctcgact cgtggtggga gcacccctgg aggtggtggc ggccaaccag | 180 |
| acgggacggc tgtatgactg cgcagctgcc accggcatgt gccagcccat cccgctgcac | 240 |
| atccgccctg aggccgtgaa catgtccttg ggcctgaccc tggcagcctc caccaacggc | 300 |
| tcccggctcc tggcctgtgg cccgacccctg cacagagtct gtgggagaa ctcatactca | 360 |
| aagggttcct gcctcctgct gggctcgcgc tgggagatca tccagacagt ccccgacgcc | 420 |
| acgccagagt gtccacatca agagatggac atcgtcttcc tgattgacgg ctctggaagc | 480 |
| attgaccaaa atgactttaa ccagatgaag ggctttgtcc aagctgtcat gggccagttt | 540 |
| gagggcactg acaccctgtt tgcactgatg cagtactcaa acctcctgaa gatccacttc | 600 |
| accttcaccc aattccggac cagcccgagc cagcagagcc tggtggatcc catcgtccaa | 660 |
| ctgaaaggcc tgacgttcac ggccacgggc atcctgacag tggtgacaca gctatttcat | 720 |
| cataagaatg ggcccgaaa aagtgccaag aagatcctca ttgtcatcac agatgggcag | 780 |
| aagtacaaag accccctgga atacagtgat gtcatccccc aggcagagaa ggctggcatc | 840 |
| atccgctacg ctatcggggt gggacacgct ttccagggac ccactgccag caggagctg | 900 |
| aataccatca gctcagcgcc tccgcaggac cacgtgttca agtggacaa ctttgcagcc | 960 |
| cttggcagca tccagaagca gctgcaggag aagatctatg cagttgaggg aacccagtcc | 1020 |
| agggcaagca gctccttcca gcacgagatg tcccaagaag gcttcagcac agccctcaca | 1080 |
| atggatggcc tcttcctggg ggctgtgggg agctttagct ggtctggagg tgccttcctg | 1140 |

```
tatcccccaa atatgagccc caccttcatc aacatgtctc aggagaatgt ggacatgagg    1200
gactcttacc tgggttactc caccgagcta gccctgtgga aggggtaca gaacctggtc    1260 ctgggggccc cccgctacca gcataccggg aaggctgtca tcttcaccca ggtgtccagg    1320
caatggagga agaaggccga agtcacaggg acgcagatcg gctcctactt cggggcctcc    1380
ctctgctccg tggatgtgga cagcgatggc agcaccgacc tgatcctcat tggggccccc    1440
cattactatg agcagacccg aggggccag gtgtccgtgt gtcccttgcc taggggagg    1500 gtgcagtggc agtgtgacgc tgttctccgt ggtgagcagg gccacccctg gggccgcttt    1560
ggggcagccc tgacagtgtt ggggatgtg aatgaggaca agctgataga cgtggccatt    1620
ggggccccgg gagagcagga gaaccggggt gctgtctacc tgtttcacgg agcctcagaa    1680
tccggcatca gcccctccca cagccagcgg attgccagct cccagctctc ccccaggctg    1740
cagtattttg gcaggcgct gagtgggggt caggacctca cccaggatgg actgatggac    1800
ctggccgtgg gggccgggg ccaggtgctc ctgctcagga gtctgccggt gctgaaagtg    1860
ggggtggcca tgagattcag ccctgtggag gtggccaagg ctgtgtaccg gtgctgggaa    1920
gagaagccca gtgccctgga agctggggac gccaccgtct gtctcaccat ccagaaaagc    1980 tcactgacc agctaggtga catccaaagc tctgtcaggt ttgatctggc actgacccca    2040
ggtcgtctga cttctcgtgc cattttcaat gaaaccaaga ccccacttt gactcgaaga    2100 aaaaccctgg gactggggat tcactgtgaa accctgaagc tgcttttgcc agtgaggact    2160
ttgggttctg ggaaggggga gagaggagga gcccaaggct ggcctggagc accccgttc    2220 tctgctgagc gaggtgggaa gggttaggat gttgggctg gagagaggga cattagggca    2280
ggagaacctg gctccacggc ttggagggag cactgtcagg gcagtgggga gtggatgcag    2340
tggaggagga cttgtggtgg agcgtagaga ggacagcagg ttcttgaaag cctgttctct    2400
ctcaggattg tgtggaggat gtggtgagcc ccatcattct gcacctcaac ttctcactgg    2460
tgagagagcc catccctcc ccccagaacc tgcgtcctg                           2499
```

<210> SEQ ID NO 97
<211> LENGTH: 3956
<212> TYPE: DNA
<213> ORGANISM: Homo sapiens

<400> SEQUENCE: 97

```
tttaactgca ccaactttaa aatacgctat tggagctgga attaccgcgg ctgctggcac     60
cagacttgcc ctccaatgga tcctcgttaa aggatttaaa gtggactcat tccaattaca    120
gggcctcgaa agagtcctgt attgttattt ttcgtcacta cctccccggg tcgggagtgg    180
gtaatttgcg cgcctgctgc cttccttgga tgtggtagcc gtttctcagg ctccctctcc    240
ggaatcgaac cctgattccc cgtcacccgt ggtcaccatg gtaggcacgt gcagttcggt    300
ggatctcgac tcgtggtggg agcacccctg gaggtggtgg cggccaacca gacgggacgg    360
ctgtatgact gcgcagctgc caccggcatg tgccagccca tccgctgca catccgcccct   420 gaggccgtga acatgtcctt gggcctgacc ctggcagcct ccaccaacgg ctcccggctc    480
ctggcctgtg gccgaccct gcacagagtc tgtggggaga actcatactc aaagggttcc    540
tgcctcctgc tgggctcgcg ctgggagatc atccagacag tccccgacgc cacgccagag    600
tgtccacatc aagagatgga catcgtcttc ctgattgacg gctctggaag cattgaccaa    660
aatgacttta accagatgaa gggctttgtc caagctgtca tgggccagtt tgagggcact    720
```

```
gacaccctgt tgcactgat gcagtactca aacctcctga agatccactt cacctcacc      780
caattccgga ccagcccgag ccagcagagc ctggtggatc ccatcgtcca actgaaaggc    840
ctgacgttca cggccacggg catcctgaca gtggtgacac agctatttca tcataagaat   900
ggggcccgaa aaagtgccaa gaagatcctc attgtcatca cagatgggca gaagtacaaa   960
gacccctgg aatacagtga tgtcatcccc caggcagaga aggctggcat catccgctac    1020
gctatcgggg tgggacacgc tttccaggga cccactgcca ggcaggagct gaataccatc   1080
agctcagcgc tccgcaggga ccacgtgttc aaggtggaca ctttgcagc ccttggcagc    1140
atccagaagc agctgcagga gaagatctat gcagttgagg gaacccagtc cagggcaagc   1200
agctccttcc agcacgagat gtcccaagaa ggcttcagca cagccctcac aatggatggc   1260
ctcttcctgg gggctgtggg gagctttagc tggtctggag gtgccttcct gtatccccca   1320
aatatgagcc ccaccttcat caacatgtct caggagaatg tggacatgag ggactcttac   1380
ctgggttact ccaccgagct agccctgtgg aagggggtac agaacctggt cctgggggcc   1440
ccccgctacc agcataccgg gaaggctgtc atcttcaccc aggtgtccag gcaatggagg   1500
aagaaggccg aagtcacagg gacgcagatc ggctcctact tcggggcctc cctctgctcc   1560
gtggatgtgg acagcgatgg cagcaccgac ctgatcctca ttggggcccc ccattactat   1620
gagcagaccc gaggggcca ggtgtccgtg tgtcccttgc ctaggggag ggtgcagtgg     1680
cagtgtgacg ctgttctccg tggtgagcag ggccacccct ggggccgctt tggggcagcc   1740
ctgacagtgt tggggatgt gaatgaggac aagctgatag acgtggccat ggggccccg    1800
ggagagcagg agaaccgggg tgctgtctac ctgtttcacg gagcctcaga atccggcatc   1860
agcccctccc acagccagcg gattgccagc tcccagctct cccccaggct gcagtatttt   1920
gggcaggcgc tgagtggggg tcaggacctc acccaggatg gactgatgga cctggccgtg   1980
ggggccggg gccaggtgct cctgctcagg agtctgccgg tgctgaaagt gggggtggcc    2040
atgagattca gccctgtgga ggtggccaag gctgtgtacc ggtgctggga agagaagccc   2100
agtgccctgg aagctgggga cgccaccgtc tgtctcacca tccagaaaag ctcactggac   2160
cagctaggtg acatccaaag ctctgtcagg tttgatctgg cactggaccc aggtcgtctg   2220
acttctcgtg ccatttcaa tgaaaccaag aaccccactt tgactcgaag aaaaaccctg    2280
ggactgggga ttcactgtga aaccctgaag ctgcttttgc cagattgtgt ggaggatgtg   2340
gtgagcccca tcattctgca cctcaacttc tcactggtga gagagcccat cccctccccc   2400
cagaacctgc gtcctgtgct ggccgtgggc tcacaagacc tcttcactgc ttctctcccc   2460
ttcgagaaga actgtgggca agatggcctc tgtgaagggg acctgggtgt cacccctcagc   2520
ttctcaggcc tgcagaccct gaccgtgggg agctccctgg agctcaacgt gattgtgact   2580
gtgtggaacg caggtgagga ttcctacgga accgtggtca gcctctacta tccagcaggg   2640
ctgtcgcacc gacgggtgtc aggagcccag aagcagcccc atcagagtgc cctgcgcctg   2700
gcatgtgaga cagtgcccac tgaggatgag ggcctaagaa gcagccgctg cagtgtcaac   2760
caccccatct tccatgaggg ctctaacggc accttcatag tcacattcga tgtctcctac   2820
aaggccaccc tgggagacag gatgcttatg agggccagtg caagcagtga gaacaataag   2880
gcttcaagca gcaaggccac cttccagctg gagctcccgg tgaagtatgc agtctacacc   2940
atgatcagca ggcaggaaga atccaccaag tacttcaact tgcaacctc cgatgagaag   3000
aaatgaaag aggctgagca tcgataccgt gtgaataacc tcagccagcg agatctggcc   3060
atcagcatta acttctgggt tcctgtcctg ctgaacgggg tggctgtgtg ggatgtggtc   3120
```

-continued

```
atggaggccc catctcagag tctcccctgt gtttcagaga gaaaacctcc ccagcattct      3180
gacttcctga cccagatttc aagaagtccc atgctggact gctccattgc tgactgcctg      3240
cagttccgct gtgacgtccc ctccttcagc gtccaggagg agctggattt caccctgaag      3300
ggcaatctca gtttcggctg gtccgcgag acattgcaga agaaggtgtt ggtcgtgagt       3360
gtggctgaaa ttacgttcga cacatccgtg tactcccagc ttccaggaca ggaggcattt      3420
atgagagctc agatggagat ggtgctagaa gaagacgagg tctacaatgc cattcccatc      3480
atcatgggca gctctgtggg ggctctgcta ctgctggcgc tcatcacagc cacactgtac      3540
aagcttggct tcttcaaacg ccactacaag gaaatgctgg aggacaagcc tgaagacact      3600
gccacattca gtggggacga tttcagctgt gtggccccaa atgtgccttt gtcctaataa      3660
tccactttcc tgtttatctc taccactgtg ggctggactt gcttgcaacc ataaatcaac      3720
ttacatggaa acaacttctg catagatctg cactggccta agcaacctac caggtgctaa      3780
gcaccttctc ggagagatag agattgtcaa tgttttttaca tatctgtcca tcttttttcag    3840 caatgaccca cttttttacag aagcaggcat ggtgccagca taaattttca tatgcttaag     3900
aattgtcaca tgaaaaaaaa aaaaaaaaa aaaaaaaaa aaaaaaaaa ctttag              3956
```

<210> SEQ ID NO 98
<211> LENGTH: 3785
<212> TYPE: DNA
<213> ORGANISM: Homo sapiens
<220> FEATURE:
<221> NAME/KEY: CDS
<222> LOCATION: (1)..(3483)

<400> SEQUENCE: 98

```
atg acc ttc ggc act gtg ctt ctt ctg agt gtc ctg gct tct tat cat        48
Met Thr Phe Gly Thr Val Leu Leu Leu Ser Val Leu Ala Ser Tyr His
 1               5                   10                  15 gga ttc aac ctg gat gtg gag gag cct acg atc ttc cag gag gat gca        96
Gly Phe Asn Leu Asp Val Glu Glu Pro Thr Ile Phe Gln Glu Asp Ala
                20                  25                  30 ggc ggc ttt ggg cag agc gtg gtg cag ttc ggt gga tct cga ctc gtg       144
Gly Gly Phe Gly Gln Ser Val Val Gln Phe Gly Gly Ser Arg Leu Val
         35                  40                  45 gtg gga gca ccc ctg gag gtg gtg gcg gcc aac cag acg gga cgg ctg       192
Val Gly Ala Pro Leu Glu Val Val Ala Ala Asn Gln Thr Gly Arg Leu
     50                  55                  60 tat gac tgc gca gct gcc acc ggc atg tgc cag ccc atc ccg ctg cac       240
Tyr Asp Cys Ala Ala Ala Thr Gly Met Cys Gln Pro Ile Pro Leu His
 65                  70                  75                  80 atc cgc cct gag gcc gtg aac atg tcc ttg ggc ctg acc ctg gca gcc       288
Ile Arg Pro Glu Ala Val Asn Met Ser Leu Gly Leu Thr Leu Ala Ala
                 85                  90                  95 tcc acc aac ggc tcc cgg ctc ctg gcc tgt ggc ccg acc ctg cac aga       336
Ser Thr Asn Gly Ser Arg Leu Leu Ala Cys Gly Pro Thr Leu His Arg
                100                 105                 110 gtc tgt ggg gag aac tca tac tca aag ggt tcc tgc ctc ctg ctg ggc       384
Val Cys Gly Glu Asn Ser Tyr Ser Lys Gly Ser Cys Leu Leu Leu Gly
         115                 120                 125 tcg cgc tgg gag atc atc cag aca gtc ccc gac gcc acg cca gag tgt       432
Ser Arg Trp Glu Ile Ile Gln Thr Val Pro Asp Ala Thr Pro Glu Cys
     130                 135                 140 cca cat caa gag atg gac atc gtc ttc ctg att gac ggc tct gga agc       480
Pro His Gln Glu Met Asp Ile Val Phe Leu Ile Asp Gly Ser Gly Ser
145                 150                 155                 160
```

```
att gac caa aat gac ttt aac cag atg aag ggc ttt gtc caa gct gtc    528
Ile Asp Gln Asn Asp Phe Asn Gln Met Lys Gly Phe Val Gln Ala Val
            165                 170                 175 atg ggc cag ttt gag ggc act gac acc ctg ttt gca ctg atg cag tac    576
Met Gly Gln Phe Glu Gly Thr Asp Thr Leu Phe Ala Leu Met Gln Tyr
        180                 185                 190 tca aac ctc ctg aag atc cac ttc acc ttc acc caa ttc cgg acc agc    624
Ser Asn Leu Leu Lys Ile His Phe Thr Phe Thr Gln Phe Arg Thr Ser
    195                 200                 205 ccg agc cag cag agc ctg gtg gat ccc atc gtc caa ctg aaa ggc ctg    672
Pro Ser Gln Gln Ser Leu Val Asp Pro Ile Val Gln Leu Lys Gly Leu
210                 215                 220 acg ttc acg gcc acg ggc atc ctg aca gtg gtg aca cag cta ttt cat    720
Thr Phe Thr Ala Thr Gly Ile Leu Thr Val Val Thr Gln Leu Phe His
225                 230                 235                 240 cat aag aat ggg gcc cga aaa agt gcc aag aag atc ctc att gtc atc    768
His Lys Asn Gly Ala Arg Lys Ser Ala Lys Lys Ile Leu Ile Val Ile
            245                 250                 255 aca gat ggg cag aag tac aaa gac ccc ctg gaa tac agt gat gtc atc    816
Thr Asp Gly Gln Lys Tyr Lys Asp Pro Leu Glu Tyr Ser Asp Val Ile
        260                 265                 270 ccc cag gca gag aag gct ggc atc atc cgc tac gct atc ggg gtg gga    864
Pro Gln Ala Glu Lys Ala Gly Ile Ile Arg Tyr Ala Ile Gly Val Gly
    275                 280                 285 cac gct ttc cag gga ccc act gcc agg cag gag ctg aat acc atc agc    912
His Ala Phe Gln Gly Pro Thr Ala Arg Gln Glu Leu Asn Thr Ile Ser
290                 295                 300 tca gcg cct ccg cag gac cac gtg ttc aag gtg gac aac ttt gca gcc    960
Ser Ala Pro Pro Gln Asp His Val Phe Lys Val Asp Asn Phe Ala Ala
305                 310                 315                 320 ctt ggc agc atc cag aag cag ctg cag gag aag atc tat gca gtt gag   1008
Leu Gly Ser Ile Gln Lys Gln Leu Gln Glu Lys Ile Tyr Ala Val Glu
            325                 330                 335 gga acc cag tcc agg gca agc agc tcc ttc cag cac gag atg tcc caa   1056
Gly Thr Gln Ser Arg Ala Ser Ser Ser Phe Gln His Glu Met Ser Gln
        340                 345                 350 gaa ggc ttc agc aca gcc ctc aca atg gat ggc ctc ttc ctg ggg gct   1104
Glu Gly Phe Ser Thr Ala Leu Thr Met Asp Gly Leu Phe Leu Gly Ala
    355                 360                 365 gtg ggg agc ttt agc tgg tct gga ggt gcc ttc ctg tat ccc cca aat   1152
Val Gly Ser Phe Ser Trp Ser Gly Gly Ala Phe Leu Tyr Pro Pro Asn
370                 375                 380 atg agc ccc acc ttc atc aac atg tct cag gag aat gtg gac atg agg   1200
Met Ser Pro Thr Phe Ile Asn Met Ser Gln Glu Asn Val Asp Met Arg
385                 390                 395                 400 gac tct tac ctg ggt tac tcc acc gag cta gcc ctg tgg aag ggg gta   1248
Asp Ser Tyr Leu Gly Tyr Ser Thr Glu Leu Ala Leu Trp Lys Gly Val
            405                 410                 415 cag aac ctg gtc ctg ggg gcc ccc cgc tac cag cat acc ggg aag gct   1296
Gln Asn Leu Val Leu Gly Ala Pro Arg Tyr Gln His Thr Gly Lys Ala
        420                 425                 430 gtc atc ttc acc cag gtg tcc agg caa tgg agg aag aag gcc gaa gtc   1344
Val Ile Phe Thr Gln Val Ser Arg Gln Trp Arg Lys Lys Ala Glu Val
    435                 440                 445 aca ggg acg cag atc ggc tcc tac ttc ggg gcc tcc ctc tgc tcc gtg   1392
Thr Gly Thr Gln Ile Gly Ser Tyr Phe Gly Ala Ser Leu Cys Ser Val
450                 455                 460 gat gtg gac agc gat ggc agc acc gac ctg atc ctc att ggg gcc ccc   1440
Asp Val Asp Ser Asp Gly Ser Thr Asp Leu Ile Leu Ile Gly Ala Pro
```

```
465                 470                 475                 480
cat tac tat gag cag acc cga ggg ggc cag gtg tcc gtg tgt ccc ttg    1488
His Tyr Tyr Glu Gln Thr Arg Gly Gly Gln Val Ser Val Cys Pro Leu
                    485                 490                 495 cct agg ggg agg gtg cag tgg cag tgt gac gct gtt ctc cgt ggt gag    1536
Pro Arg Gly Arg Val Gln Trp Gln Cys Asp Ala Val Leu Arg Gly Glu
                500                 505                 510 cag ggc cac ccc tgg ggc cgc ttt ggg gca gcc ctg aca gtg ttg ggg    1584
Gln Gly His Pro Trp Gly Arg Phe Gly Ala Ala Leu Thr Val Leu Gly
            515                 520                 525 gat gtg aat gag gac aag ctg ata gac gtg gcc att ggg gcc ccg gga    1632
Asp Val Asn Glu Asp Lys Leu Ile Asp Val Ala Ile Gly Ala Pro Gly
        530                 535                 540 gag cag gag aac cgg ggt gct gtc tac ctg ttt cac gga gcc tca gaa    1680
Glu Gln Glu Asn Arg Gly Ala Val Tyr Leu Phe His Gly Ala Ser Glu
545                 550                 555                 560 tcc ggc atc agc ccc tcc cac agc cag cgg att gcc agc tcc cag ctc    1728
Ser Gly Ile Ser Pro Ser His Ser Gln Arg Ile Ala Ser Ser Gln Leu
                565                 570                 575 tcc ccc agg ctg cag tat ttt ggg cag gcg ctg agt ggg ggt cag gac    1776
Ser Pro Arg Leu Gln Tyr Phe Gly Gln Ala Leu Ser Gly Gly Gln Asp
            580                 585                 590 ctc acc cag gat gga ctg atg gac ctg gcc gtg ggg gcc cgg ggc cag    1824
Leu Thr Gln Asp Gly Leu Met Asp Leu Ala Val Gly Ala Arg Gly Gln
        595                 600                 605 gtg ctc ctg ctc agg agt ctg ccg gtg ctg aaa gtg ggg gtg gcc atg    1872
Val Leu Leu Leu Arg Ser Leu Pro Val Leu Lys Val Gly Val Ala Met
    610                 615                 620 aga ttc agc cct gtg gag gtg gcc aag gct gtg tac cgg tgc tgg gaa    1920
Arg Phe Ser Pro Val Glu Val Ala Lys Ala Val Tyr Arg Cys Trp Glu
625                 630                 635                 640 gag aag ccc agt gcc ctg gaa gct ggg gac gcc acc gtc tgt ctc acc    1968
Glu Lys Pro Ser Ala Leu Glu Ala Gly Asp Ala Thr Val Cys Leu Thr
                645                 650                 655 atc cag aaa agc tca ctg gac cag cta ggt gac atc caa agc tct gtc    2016
Ile Gln Lys Ser Ser Leu Asp Gln Leu Gly Asp Ile Gln Ser Ser Val
            660                 665                 670 agg ttt gat ctg gca ctg gac cca ggt cgt ctg act tct cgt gcc att    2064
Arg Phe Asp Leu Ala Leu Asp Pro Gly Arg Leu Thr Ser Arg Ala Ile
        675                 680                 685 ttc aat gaa acc aag aac ccc act ttg act cga aga aaa acc ctg gga    2112
Phe Asn Glu Thr Lys Asn Pro Thr Leu Thr Arg Arg Lys Thr Leu Gly
    690                 695                 700 ctg ggg att cac tgt gaa acc ctg aag ctg ctt ttg cca gat tgt gtg    2160
Leu Gly Ile His Cys Glu Thr Leu Lys Leu Leu Leu Pro Asp Cys Val
705                 710                 715                 720 gag gat gtg gtg agc ccc atc att ctg cac ctc aac ttc tca ctg gtg    2208
Glu Asp Val Val Ser Pro Ile Ile Leu His Leu Asn Phe Ser Leu Val
                725                 730                 735 aga gag ccc atc ccc tcc ccc cag aac ctg cgt cct gtg ctg gcc gtg    2256
Arg Glu Pro Ile Pro Ser Pro Gln Asn Leu Arg Pro Val Leu Ala Val
            740                 745                 750 ggc tca caa gac ctc ttc act gct tct ctc ccc ttc gag aag aac tgt    2304
Gly Ser Gln Asp Leu Phe Thr Ala Ser Leu Pro Phe Glu Lys Asn Cys
        755                 760                 765 ggg caa gat ggc ctc tgt gaa ggg gac ctg ggt gtc acc ctc agc ttc    2352
Gly Gln Asp Gly Leu Cys Glu Gly Asp Leu Gly Val Thr Leu Ser Phe
    770                 775                 780 tca ggc ctg cag acc ctg acc gtg ggg agc tcc ctg gag ctc aac gtg    2400
```

-continued

```
Ser Gly Leu Gln Thr Leu Thr Val Gly Ser Ser Leu Glu Leu Asn Val
785                 790                 795                 800 att gtg act gtg tgg aac gca ggt gag gat tcc tac gga acc gtg gtc         2448
Ile Val Thr Val Trp Asn Ala Gly Glu Asp Ser Tyr Gly Thr Val Val
                805                 810                 815 agc ctc tac tat cca gca ggg ctg tcg cac cga cgg gtg tca gga gcc         2496
Ser Leu Tyr Tyr Pro Ala Gly Leu Ser His Arg Arg Val Ser Gly Ala
            820                 825                 830 cag aag cag ccc cat cag agt gcc ctg cgc ctg gca tgt gag aca gtg         2544
Gln Lys Gln Pro His Gln Ser Ala Leu Arg Leu Ala Cys Glu Thr Val
        835                 840                 845 ccc act gag gat gag ggc cta aga agc agc cgc tgc agt gtc aac cac         2592
Pro Thr Glu Asp Glu Gly Leu Arg Ser Ser Arg Cys Ser Val Asn His
850                 855                 860 ccc atc ttc cat gag ggc tct aac ggc acc ttc ata gtc aca ttc gat         2640
Pro Ile Phe His Glu Gly Ser Asn Gly Thr Phe Ile Val Thr Phe Asp
865                 870                 875                 880 gtc tcc tac aag gcc acc ctg gga gac agg atg ctt atg agg gcc agt         2688
Val Ser Tyr Lys Ala Thr Leu Gly Asp Arg Met Leu Met Arg Ala Ser
                885                 890                 895 gca agc agt gag aac aat aag gct tca agc agc aag gcc acc ttc cag         2736
Ala Ser Ser Glu Asn Asn Lys Ala Ser Ser Ser Lys Ala Thr Phe Gln
            900                 905                 910 ctg gag ctc ccg gtg aag tat gca gtc tac acc atg atc agc agg cag         2784
Leu Glu Leu Pro Val Lys Tyr Ala Val Tyr Thr Met Ile Ser Arg Gln
        915                 920                 925 gaa gaa tcc acc aag tac ttc aac ttt gca acc tcc gat gag aag aaa         2832
Glu Glu Ser Thr Lys Tyr Phe Asn Phe Ala Thr Ser Asp Glu Lys Lys
    930                 935                 940 atg aaa gag gct gag cat cga tac cgt gtg aat aac ctc agc cag cga         2880
Met Lys Glu Ala Glu His Arg Tyr Arg Val Asn Asn Leu Ser Gln Arg
945                 950                 955                 960 gat ctg gcc atc agc att aac ttc tgg gtt cct gtc ctg ctg aac ggg         2928
Asp Leu Ala Ile Ser Ile Asn Phe Trp Val Pro Val Leu Leu Asn Gly
                965                 970                 975 gtg gct gtg tgg gat gtg gtc atg gag gcc cca tct cag agt ctc ccc         2976
Val Ala Val Trp Asp Val Val Met Glu Ala Pro Ser Gln Ser Leu Pro
            980                 985                 990 tgt gtt tca gag aga aaa cct ccc cag cat tct gac ttc ctg acc cag         3024
Cys Val Ser Glu Arg Lys Pro Pro Gln His Ser Asp Phe Leu Thr Gln
        995                 1000                1005 att tca aga agt ccc atg ctg gac tgc tcc att gct gac tgc ctg cag         3072
Ile Ser Arg Ser Pro Met Leu Asp Cys Ser Ile Ala Asp Cys Leu Gln
    1010                1015                1020 ttc cgc tgt gac gtc ccc tcc ttc agc gtc cag gag gag ctg gat ttc         3120
Phe Arg Cys Asp Val Pro Ser Phe Ser Val Gln Glu Glu Leu Asp Phe
1025                1030                1035                1040 acc ctg aag ggc aat ctc agt ttc ggc tgg gtc cgc gag aca ttg cag         3168
Thr Leu Lys Gly Asn Leu Ser Phe Gly Trp Val Arg Glu Thr Leu Gln
                1045                1050                1055 aag aag gtg ttg gtc gtg agt gtg gct gaa att acg ttc gac aca tcc         3216
Lys Lys Val Leu Val Val Ser Val Ala Glu Ile Thr Phe Asp Thr Ser
            1060                1065                1070 gtg tac tcc cag ctt cca gga cag gag gca ttt atg aga gct cag atg         3264
Val Tyr Ser Gln Leu Pro Gly Gln Glu Ala Phe Met Arg Ala Gln Met
        1075                1080                1085 gag atg gtg cta gaa gaa gac gag gtc tac aat gcc att ccc atc atc         3312
Glu Met Val Leu Glu Glu Asp Glu Val Tyr Asn Ala Ile Pro Ile Ile
    1090                1095                1100
```

```
atg ggc agc tct gtg ggg gct ctg cta ctg ctg gcg ctc atc aca gcc    3360
Met Gly Ser Ser Val Gly Ala Leu Leu Leu Leu Ala Leu Ile Thr Ala
1105            1110                1115                1120 aca ctg tac aag ctt ggc ttc ttc aaa cgc cac tac aag gaa atg ctg    3408
Thr Leu Tyr Lys Leu Gly Phe Phe Lys Arg His Tyr Lys Glu Met Leu
        1125                1130                1135 gag gac aag cct gaa gac act gcc aca ttc agt ggg gac gat ttc agc    3456
Glu Asp Lys Pro Glu Asp Thr Ala Thr Phe Ser Gly Asp Asp Phe Ser
            1140                1145                1150 tgt gtg gcc cca aat gtg cct ttg tcc taataatcca ctttcctgtt          3503
Cys Val Ala Pro Asn Val Pro Leu Ser
        1155                1160 tatctctacc actgtgggct ggacttgctt gcaaccataa atcaacttac atggaaacaa  3563
cttctgcata gatctgcact ggcctaagca acctaccagg tgctaagcac cttctcggag  3623
agatagagat tgtcaatgtt tttacatatc tgtccatctt tttcagcaat gacccacttt  3683
ttacagaagc aggcatggtg ccagcataaa ttttcatatg cttaagaatt gtcacatgaa  3743
aaaaaaaaaa aaaaaaaaaa aaaaaaaaaa aaaaaactttt ag                    3785

<210> SEQ ID NO 99
<211> LENGTH: 1161
<212> TYPE: PRT
<213> ORGANISM: Homo sapiens

<400> SEQUENCE: 99

Met Thr Phe Gly Thr Val Leu Leu Leu Ser Val Leu Ala Ser Tyr His
  1               5                  10                  15

Gly Phe Asn Leu Asp Val Glu Glu Pro Thr Ile Phe Gln Glu Asp Ala
                 20                  25                  30

Gly Gly Phe Gly Gln Ser Val Val Gln Phe Gly Gly Ser Arg Leu Val
             35                  40                  45

Val Gly Ala Pro Leu Glu Val Val Ala Ala Asn Gln Thr Gly Arg Leu
         50                  55                  60

Tyr Asp Cys Ala Ala Ala Thr Gly Met Cys Gln Pro Ile Pro Leu His
 65                  70                  75                  80

Ile Arg Pro Glu Ala Val Asn Met Ser Leu Gly Leu Thr Leu Ala Ala
                 85                  90                  95

Ser Thr Asn Gly Ser Arg Leu Leu Ala Cys Gly Pro Thr Leu His Arg
            100                 105                 110

Val Cys Gly Glu Asn Ser Tyr Ser Lys Gly Ser Cys Leu Leu Leu Gly
        115                 120                 125

Ser Arg Trp Glu Ile Ile Gln Thr Val Pro Asp Ala Thr Pro Glu Cys
    130                 135                 140

Pro His Gln Glu Met Asp Ile Val Phe Leu Ile Asp Gly Ser Gly Ser
145                 150                 155                 160

Ile Asp Gln Asn Asp Phe Asn Gln Met Lys Gly Phe Val Gln Ala Val
                165                 170                 175

Met Gly Gln Phe Glu Gly Thr Asp Thr Leu Phe Ala Leu Met Gln Tyr
            180                 185                 190

Ser Asn Leu Leu Lys Ile His Phe Thr Phe Thr Gln Phe Arg Thr Ser
        195                 200                 205

Pro Ser Gln Gln Ser Leu Val Asp Pro Ile Val Gln Leu Lys Gly Leu
    210                 215                 220

Thr Phe Thr Ala Thr Gly Ile Leu Thr Val Val Thr Gln Leu Phe His
225                 230                 235                 240
```

-continued

```
His Lys Asn Gly Ala Arg Lys Ser Ala Lys Lys Ile Leu Ile Val Ile
            245                 250                 255

Thr Asp Gly Gln Lys Tyr Lys Asp Pro Leu Glu Tyr Ser Asp Val Ile
            260                 265                 270

Pro Gln Ala Glu Lys Ala Gly Ile Ile Arg Tyr Ala Ile Gly Val Gly
            275                 280                 285

His Ala Phe Gln Gly Pro Thr Ala Arg Gln Glu Leu Asn Thr Ile Ser
    290                 295                 300

Ser Ala Pro Pro Gln Asp His Val Phe Lys Val Asp Asn Phe Ala Ala
305                 310                 315                 320

Leu Gly Ser Ile Gln Lys Gln Leu Gln Glu Lys Ile Tyr Ala Val Glu
                325                 330                 335

Gly Thr Gln Ser Arg Ala Ser Ser Phe Gln His Glu Met Ser Gln
            340                 345                 350

Glu Gly Phe Ser Thr Ala Leu Thr Met Asp Gly Leu Phe Leu Gly Ala
            355                 360                 365

Val Gly Ser Phe Ser Trp Ser Gly Gly Ala Phe Leu Tyr Pro Pro Asn
    370                 375                 380

Met Ser Pro Thr Phe Ile Asn Met Ser Gln Glu Asn Val Asp Met Arg
385                 390                 395                 400

Asp Ser Tyr Leu Gly Tyr Ser Thr Glu Leu Ala Leu Trp Lys Gly Val
                405                 410                 415

Gln Asn Leu Val Leu Gly Ala Pro Arg Tyr Gln His Thr Gly Lys Ala
            420                 425                 430

Val Ile Phe Thr Gln Val Ser Arg Gln Trp Arg Lys Lys Ala Glu Val
    435                 440                 445

Thr Gly Thr Gln Ile Gly Ser Tyr Phe Gly Ala Ser Leu Cys Ser Val
    450                 455                 460

Asp Val Asp Ser Asp Gly Ser Thr Asp Leu Ile Leu Ile Gly Ala Pro
465                 470                 475                 480

His Tyr Tyr Glu Gln Thr Arg Gly Gly Gln Val Ser Val Cys Pro Leu
                485                 490                 495

Pro Arg Gly Arg Val Gln Trp Gln Cys Asp Ala Val Leu Arg Gly Glu
            500                 505                 510

Gln Gly His Pro Trp Gly Arg Phe Gly Ala Ala Leu Thr Val Leu Gly
            515                 520                 525

Asp Val Asn Glu Asp Lys Leu Ile Asp Val Ala Ile Gly Ala Pro Gly
    530                 535                 540

Glu Gln Glu Asn Arg Gly Ala Val Tyr Leu Phe His Gly Ala Ser Glu
545                 550                 555                 560

Ser Gly Ile Ser Pro Ser His Ser Gln Arg Ile Ala Ser Ser Gln Leu
                565                 570                 575

Ser Pro Arg Leu Gln Tyr Phe Gly Gln Ala Leu Ser Gly Gly Gln Asp
            580                 585                 590

Leu Thr Gln Asp Gly Leu Met Asp Leu Ala Val Gly Ala Arg Gly Gln
    595                 600                 605

Val Leu Leu Leu Arg Ser Leu Pro Val Leu Lys Val Gly Val Ala Met
    610                 615                 620

Arg Phe Ser Pro Val Glu Val Ala Lys Ala Val Tyr Arg Cys Trp Glu
625                 630                 635                 640

Glu Lys Pro Ser Ala Leu Glu Ala Gly Asp Ala Thr Val Cys Leu Thr
                645                 650                 655

Ile Gln Lys Ser Ser Leu Asp Gln Leu Gly Asp Ile Gln Ser Ser Val
```

```
                    660                 665                 670
            Arg Phe Asp Leu Ala Leu Asp Pro Gly Arg Leu Thr Ser Arg Ala Ile
                    675                 680                 685

Phe Asn Glu Thr Lys Asn Pro Thr Leu Thr Arg Arg Lys Thr Leu Gly
                    690                 695                 700

Leu Gly Ile His Cys Glu Thr Leu Lys Leu Leu Leu Pro Asp Cys Val
            705                 710                 715                 720

Glu Asp Val Val Ser Pro Ile Ile Leu His Leu Asn Phe Ser Leu Val
                            725                 730                 735

Arg Glu Pro Ile Pro Ser Pro Gln Asn Leu Arg Pro Val Leu Ala Val
                            740                 745                 750

Gly Ser Gln Asp Leu Phe Thr Ala Ser Leu Pro Phe Glu Lys Asn Cys
                    755                 760                 765

Gly Gln Asp Gly Leu Cys Glu Gly Asp Leu Gly Val Thr Leu Ser Phe
            770                 775                 780

Ser Gly Leu Gln Thr Leu Thr Val Gly Ser Ser Leu Glu Leu Asn Val
            785                 790                 795                 800

Ile Val Thr Val Trp Asn Ala Gly Glu Asp Ser Tyr Gly Thr Val Val
                            805                 810                 815

Ser Leu Tyr Tyr Pro Ala Gly Leu Ser His Arg Arg Val Ser Gly Ala
                            820                 825                 830

Gln Lys Gln Pro His Gln Ser Ala Leu Arg Leu Ala Cys Glu Thr Val
                    835                 840                 845

Pro Thr Glu Asp Glu Gly Leu Arg Ser Ser Arg Cys Ser Val Asn His
                    850                 855                 860

Pro Ile Phe His Glu Gly Ser Asn Gly Thr Phe Ile Val Thr Phe Asp
            865                 870                 875                 880

Val Ser Tyr Lys Ala Thr Leu Gly Asp Arg Met Leu Met Arg Ala Ser
                            885                 890                 895

Ala Ser Ser Glu Asn Asn Lys Ala Ser Ser Lys Ala Thr Phe Gln
                            900                 905                 910

Leu Glu Leu Pro Val Lys Tyr Ala Val Tyr Thr Met Ile Ser Arg Gln
                    915                 920                 925

Glu Glu Ser Thr Lys Tyr Phe Asn Phe Ala Thr Ser Asp Glu Lys Lys
                    930                 935                 940

Met Lys Glu Ala Glu His Arg Tyr Arg Val Asn Asn Leu Ser Gln Arg
            945                 950                 955                 960

Asp Leu Ala Ile Ser Ile Asn Phe Trp Val Pro Val Leu Leu Asn Gly
                            965                 970                 975

Val Ala Val Trp Asp Val Val Met Glu Ala Pro Ser Gln Ser Leu Pro
                            980                 985                 990

Cys Val Ser Glu Arg Lys Pro Pro Gln His Ser Asp Phe Leu Thr Gln
                    995                 1000                1005

Ile Ser Arg Ser Pro Met Leu Asp Cys Ser Ile Ala Asp Cys Leu Gln
                1010                1015                1020

Phe Arg Cys Asp Val Pro Ser Phe Ser Val Gln Glu Glu Leu Asp Phe
            1025                1030                1035                1040

Thr Leu Lys Gly Asn Leu Ser Phe Gly Trp Val Arg Glu Thr Leu Gln
                        1045                1050                1055

Lys Lys Val Leu Val Val Ser Val Ala Glu Ile Thr Phe Asp Thr Ser
                        1060                1065                1070

Val Tyr Ser Gln Leu Pro Gly Gln Glu Ala Phe Met Arg Ala Gln Met
                    1075                1080                1085
```

```
Glu Met Val Leu Glu Glu Asp Glu Val Tyr Asn Ala Ile Pro Ile Ile
    1090                1095                1100
Met Gly Ser Ser Val Gly Ala Leu Leu Leu Ala Leu Ile Thr Ala
1105                1110                1115                1120
Thr Leu Tyr Lys Leu Gly Phe Phe Lys Arg His Tyr Lys Glu Met Leu
            1125                1130                1135
Glu Asp Lys Pro Glu Asp Thr Ala Thr Phe Ser Gly Asp Asp Phe Ser
            1140                1145                1150
Cys Val Ala Pro Asn Val Pro Leu Ser
        1155                1160

<210> SEQ ID NO 100
<211> LENGTH: 1318
<212> TYPE: DNA
<213> ORGANISM: rabbit
<220> FEATURE:
<221> NAME/KEY: CDS
<222> LOCATION: (17)..(1255)

<400> SEQUENCE: 100
```

| | | |
|---|---|---|
| aattcggcac gagctt ggg gct gtg gtc ctc ctt ggg gtc ctg gct tct tac<br>                     Gly Ala Val Val Leu Leu Gly Val Leu Ala Ser Tyr<br>                      1               5              10 | 52 |
| cac gga ttc aac ttg gac gtg gat gag ccg gtg atc ttc cag gaa gac<br>His Gly Phe Asn Leu Asp Val Asp Glu Pro Val Ile Phe Gln Glu Asp<br>       15               20              25 | 100 |
| gca gcg ggc ttc ggg cag agc gtg atg cag ttt gga gga tct cga ctc<br>Ala Ala Gly Phe Gly Gln Ser Val Met Gln Phe Gly Gly Ser Arg Leu<br>   30               35              40 | 148 |
| gtg gtg gga gcc ccc ctg gcg gtg gtg tcg gcc aac cac aca gga cgg<br>Val Val Gly Ala Pro Leu Ala Val Val Ser Ala Asn His Thr Gly Arg<br>45               50              55              60 | 196 |
| ctg tac gag tgt gcg cct gcc tcc ggc acc tgc acg ccc att ttc cca<br>Leu Tyr Glu Cys Ala Pro Ala Ser Gly Thr Cys Thr Pro Ile Phe Pro<br>         65               70              75 | 244 |
| ttc atg ccc ccc gaa gcc gtg aac atg tcc ctg ggc ctg tcc ctg gca<br>Phe Met Pro Pro Glu Ala Val Asn Met Ser Leu Gly Leu Ser Leu Ala<br>            80              85              90 | 292 |
| gcc tcc ccc aac cat tcc cag ctg ctg gct tgt ggc ccg acc gtg cat<br>Ala Ser Pro Asn His Ser Gln Leu Leu Ala Cys Gly Pro Thr Val His<br>               95             100            105 | 340 |
| aga gcc tgc ggg gag gac gtg tac gcc cag ggt ttc tgt gtg ctg ctg<br>Arg Ala Cys Gly Glu Asp Val Tyr Ala Gln Gly Phe Cys Val Leu Leu<br>       110             115            120 | 388 |
| gat gcc cac gca cag ccc atc ggg act gtg cca gct gcc ctg ccc gag<br>Asp Ala His Ala Gln Pro Ile Gly Thr Val Pro Ala Ala Leu Pro Glu<br>125              130              135            140 | 436 |
| tgc cca gat caa gag atg gac att gtc ttc ctg att gac ggc tct ggc<br>Cys Pro Asp Gln Glu Met Asp Ile Val Phe Leu Ile Asp Gly Ser Gly<br>               145            150            155 | 484 |
| agc att agc tca aat gac ttc cgc aag atg aag gac ttt gtc aga gct<br>Ser Ile Ser Ser Asn Asp Phe Arg Lys Met Lys Asp Phe Val Arg Ala<br>         160             165            170 | 532 |
| gtg atg gac cag ttc aag gac acc aac acc cag ttc tcg ctg atg cag<br>Val Met Asp Gln Phe Lys Asp Thr Asn Thr Gln Phe Ser Leu Met Gln<br>175              180              185 | 580 |
| tac tcc aat gtg ctg gtg aca cat ttc acc ttc agc agc ttc cgg aac<br>Tyr Ser Asn Val Leu Val Thr His Phe Thr Phe Ser Ser Phe Arg Asn<br>       190             195            200 | 628 |

```
agc tcc aat cct cag ggc cta gtg gag ccc att gtg cag ctc aca ggc      676
Ser Ser Asn Pro Gln Gly Leu Val Glu Pro Ile Val Gln Leu Thr Gly
205                 210                 215                 220 ctc acg ttc acg gcc aca ggg atc ctg aaa gtg gtg aca gag ctg ttt      724
Leu Thr Phe Thr Ala Thr Gly Ile Leu Lys Val Val Thr Glu Leu Phe
                225                 230                 235 caa acc aag aac ggg gcc cgc gaa agt gcc aag aag atc ctc atc gtc      772
Gln Thr Lys Asn Gly Ala Arg Glu Ser Ala Lys Lys Ile Leu Ile Val
            240                 245                 250 atc aca gat ggg cag aag tac aaa gac ccc ctg cac tac agt gct gtc      820
Ile Thr Asp Gly Gln Lys Tyr Lys Asp Pro Leu His Tyr Ser Ala Val
        255                 260                 265 atc cca cag gca gag cag gcg ggc atc atc cgc tac gcc atc ggg gtg      868
Ile Pro Gln Ala Glu Gln Ala Gly Ile Ile Arg Tyr Ala Ile Gly Val
    270                 275                 280 ggg gac gcg ttc cag aaa ccc aca gcc agg cag gag ctg gac acc atc      916
Gly Asp Ala Phe Gln Lys Pro Thr Ala Arg Gln Glu Leu Asp Thr Ile
285                 290                 295                 300 gcc tcc gag ccg ccc gac gcc cac gtg ttc cag gtg gac aat ttc tca      964
Ala Ser Glu Pro Pro Asp Ala His Val Phe Gln Val Asp Asn Phe Ser
                305                 310                 315 gca ctc agc agc atc caa aag cag ctg tat gac agg atc ttt gcc gtc     1012
Ala Leu Ser Ser Ile Gln Lys Gln Leu Tyr Asp Arg Ile Phe Ala Val
            320                 325                 330 gag gga acc ctg tca tcg gca agc acc tcc ttc cag cat gag atg tcc     1060
Glu Gly Thr Leu Ser Ser Ala Ser Thr Ser Phe Gln His Glu Met Ser
        335                 340                 345 caa gag ggc ttc agc tca ctt ctc acc acg gaa gga ccg gtg ctg ggg     1108
Gln Glu Gly Phe Ser Ser Leu Leu Thr Thr Glu Gly Pro Val Leu Gly
    350                 355                 360 gct gtg ggc agc ttc gat tgg tcc ggg ggt gct ttc ctg tac ccc ccc     1156
Ala Val Gly Ser Phe Asp Trp Ser Gly Gly Ala Phe Leu Tyr Pro Pro
365                 370                 375                 380 ggc ggg agc ccc acc ttc atc aac atg tct cag cag aac gtg gac atg     1204
Gly Gly Ser Pro Thr Phe Ile Asn Met Ser Gln Gln Asn Val Asp Met
                385                 390                 395 agg gac tcc tac ctg ggt gag gaa ggg gtg ggg gtg ggg aca ggt ggg     1252
Arg Asp Ser Tyr Leu Gly Glu Glu Gly Val Gly Val Gly Thr Gly Gly
            400                 405                 410 agc tgaggcttgg ggtggggtgg ggctgggctg ggaggggagg gaagaggagg          1305
Ser ggagaggcaa aga                                                      1318

<210> SEQ ID NO 101
<211> LENGTH: 413
<212> TYPE: PRT
<213> ORGANISM: rabbit

<400> SEQUENCE: 101

Gly Ala Val Val Leu Leu Gly Val Leu Ala Ser Tyr His Gly Phe Asn
1               5                   10                  15

Leu Asp Val Asp Glu Pro Val Ile Phe Gln Glu Asp Ala Ala Gly Phe
                20                  25                  30

Gly Gln Ser Val Met Gln Phe Gly Gly Ser Arg Leu Val Val Gly Ala
            35                  40                  45

Pro Leu Ala Val Val Ser Ala Asn His Thr Gly Arg Leu Tyr Glu Cys
        50                  55                  60

Ala Pro Ala Ser Gly Thr Cys Thr Pro Ile Phe Pro Phe Met Pro Pro
65                  70                  75                  80
```

```
Glu Ala Val Asn Met Ser Leu Gly Leu Ser Leu Ala Ser Pro Asn
                85                  90                  95

His Ser Gln Leu Leu Ala Cys Gly Pro Thr Val His Arg Ala Cys Gly
            100                 105                 110

Glu Asp Val Tyr Ala Gln Gly Phe Cys Val Leu Leu Asp Ala His Ala
            115                 120                 125

Gln Pro Ile Gly Thr Val Pro Ala Ala Leu Pro Glu Cys Pro Asp Gln
            130                 135                 140

Glu Met Asp Ile Val Phe Leu Ile Asp Gly Ser Gly Ser Ile Ser Ser
145                 150                 155                 160

Asn Asp Phe Arg Lys Met Lys Asp Phe Val Arg Ala Val Met Asp Gln
                165                 170                 175

Phe Lys Asp Thr Asn Thr Gln Phe Ser Leu Met Gln Tyr Ser Asn Val
            180                 185                 190

Leu Val Thr His Phe Thr Phe Ser Ser Phe Arg Asn Ser Ser Asn Pro
            195                 200                 205

Gln Gly Leu Val Glu Pro Ile Val Gln Leu Thr Gly Leu Thr Phe Thr
            210                 215                 220

Ala Thr Gly Ile Leu Lys Val Thr Glu Leu Phe Gln Thr Lys Asn
225                 230                 235                 240

Gly Ala Arg Glu Ser Ala Lys Lys Ile Leu Ile Val Ile Thr Asp Gly
                245                 250                 255

Gln Lys Tyr Lys Asp Pro Leu His Tyr Ser Ala Val Ile Pro Gln Ala
            260                 265                 270

Glu Gln Ala Gly Ile Ile Arg Tyr Ala Ile Gly Val Gly Asp Ala Phe
            275                 280                 285

Gln Lys Pro Thr Ala Arg Gln Glu Leu Asp Thr Ile Ala Ser Glu Pro
            290                 295                 300

Pro Asp Ala His Val Phe Gln Val Asp Asn Phe Ser Ala Leu Ser Ser
305                 310                 315                 320

Ile Gln Lys Gln Leu Tyr Asp Arg Ile Phe Ala Val Glu Gly Thr Leu
            325                 330                 335

Ser Ser Ala Ser Thr Ser Phe Gln His Glu Met Ser Gln Glu Gly Phe
            340                 345                 350

Ser Ser Leu Leu Thr Thr Glu Gly Pro Val Leu Gly Ala Val Gly Ser
            355                 360                 365

Phe Asp Trp Ser Gly Gly Ala Phe Leu Tyr Pro Pro Gly Gly Ser Pro
            370                 375                 380

Thr Phe Ile Asn Met Ser Gln Gln Asn Val Asp Met Arg Asp Ser Tyr
385                 390                 395                 400

Leu Gly Glu Glu Gly Val Gly Val Gly Thr Gly Gly Ser
                405                 410

<210> SEQ ID NO 102
<211> LENGTH: 1484
<212> TYPE: DNA
<213> ORGANISM: rabbit
<220> FEATURE:
<221> NAME/KEY: CDS
<222> LOCATION: (1)..(1482)

<400> SEQUENCE: 102 gat gtc cag agc tcc atc agc tat gat ctg gca ctg gac cca ggc cgc      48
Asp Val Gln Ser Ser Ile Ser Tyr Asp Leu Ala Leu Asp Pro Gly Arg
 1               5                  10                  15
```

-continued

| | |
|---|---|
| ctg gtc tct cgg gcc att ttt caa gag acc cag aac cag act tta act<br>Leu Val Ser Arg Ala Ile Phe Gln Glu Thr Gln Asn Gln Thr Leu Thr<br>            20                  25                    30 | 96 |
| cga agg aag acc ctg ggg ctg ggg cgt cac tgt gaa acc atg agg cta<br>Arg Arg Lys Thr Leu Gly Leu Gly Arg His Cys Glu Thr Met Arg Leu<br>        35                    40                    45 | 144 |
| ctt ttg cca gac tgc gta gag gac gtg gtg aac ccc atc gtc ctg cac<br>Leu Leu Pro Asp Cys Val Glu Asp Val Val Asn Pro Ile Val Leu His<br>50                    55                    60 | 192 |
| ctc aac ttc tcc ctg gag gga cag cca atc ctc tca tcc cag aat ctg<br>Leu Asn Phe Ser Leu Glu Gly Gln Pro Ile Leu Ser Ser Gln Asn Leu<br>65                    70                    75                  80 | 240 |
| cgc cct gtg ctg gcc acg ggc tcg cag gac cac ttc att gcc tcc ctc<br>Arg Pro Val Leu Ala Thr Gly Ser Gln Asp His Phe Ile Ala Ser Leu<br>            85                    90                    95 | 288 |
| ccc ttt gag aag aac tgc gga caa gat cgc ctg tgt gag ggg gac ctg<br>Pro Phe Glu Lys Asn Cys Gly Gln Asp Arg Leu Cys Glu Gly Asp Leu<br>                100                  105                  110 | 336 |
| agc atc agc ttc aac ttc tcg ggc ttg aat acc ctg ctg gtg ggg ctc<br>Ser Ile Ser Phe Asn Phe Ser Gly Leu Asn Thr Leu Leu Val Gly Leu<br>                115                  120                  125 | 384 |
| tcc ctg gag ctc aca gtg aca gtg acc gtg cgg aat gag ggc gag gac<br>Ser Leu Glu Leu Thr Val Thr Val Thr Val Arg Asn Glu Gly Glu Asp<br>130                    135                  140 | 432 |
| tcc tat ggg acc gcc atc acc ctc tac tac cca gca ggg cta tcc tac<br>Ser Tyr Gly Thr Ala Ile Thr Leu Tyr Tyr Pro Ala Gly Leu Ser Tyr<br>145                    150                  155                  160 | 480 |
| agg cgg gtg tcg ggc cag aca caa ccc tgg cag cgc ccc ctg cac ctc<br>Arg Arg Val Ser Gly Gln Thr Gln Pro Trp Gln Arg Pro Leu His Leu<br>                165                  170                  175 | 528 |
| gca tgt gag gct gta cct acc gag agc gag ggc ttg agg agt acc agc<br>Ala Cys Glu Ala Val Pro Thr Glu Ser Glu Gly Leu Arg Ser Thr Ser<br>                  180                  185                  190 | 576 |
| tgc agc gtc aac cac ccc atc ttc caa ggg ggt gct cag ggc act ttc<br>Cys Ser Val Asn His Pro Ile Phe Gln Gly Gly Ala Gln Gly Thr Phe<br>                195                  200                  205 | 624 |
| gta gtc aag ttc gat gtc tcc tcc aag gcc agc ctg ggt gac agg ttg<br>Val Val Lys Phe Asp Val Ser Ser Lys Ala Ser Leu Gly Asp Arg Leu<br>210                    215                  220 | 672 |
| ctc atg ggg gcc agt gcc agc agt gag aat aat aag cct gcg agc aac<br>Leu Met Gly Ala Ser Ala Ser Ser Glu Asn Asn Lys Pro Ala Ser Asn<br>225                    230                  235                  240 | 720 |
| aag acc tcc ttt gag ctg gaa ctg cca gtg aaa tac gct gtc tac atg<br>Lys Thr Ser Phe Glu Leu Glu Leu Pro Val Lys Tyr Ala Val Tyr Met<br>                245                  250                  255 | 768 |
| atg atc aca agg cac gaa ggc tcc acc agg ttc ttc aac ttt tcc act<br>Met Ile Thr Arg His Glu Gly Ser Thr Arg Phe Phe Asn Phe Ser Thr<br>                260                  265                  270 | 816 |
| tcc gct gag aag agc agc aaa gag gcc gag cac cgc tat cgg gtg aac<br>Ser Ala Glu Lys Ser Ser Lys Glu Ala Glu His Arg Tyr Arg Val Asn<br>                275                  280                  285 | 864 |
| aac ctg agt ctg cga gat gtg gcc gtc agc gtg gac ttc tgg gcc ccc<br>Asn Leu Ser Leu Arg Asp Val Ala Val Ser Val Asp Phe Trp Ala Pro<br>            290                  295                  300 | 912 |
| gtg cag ctg aac gga gca gct gtg tgg gac gtg gcg gtg gag gcc cct<br>Val Gln Leu Asn Gly Ala Ala Val Trp Asp Val Ala Val Glu Ala Pro<br>305                    310                  315                  320 | 960 |
| gcc cag agc ctg ccc tgt gcg cgg gag agg gaa cct ccg agg acc tct<br>Ala Gln Ser Leu Pro Cys Ala Arg Glu Arg Glu Pro Pro Arg Thr Ser<br>                325                  330                  335 | 1008 |

```
gac ctg agc cgg gtc ccg ggg agt ccc gtg ctg gac tgc agc gtt gcg      1056
Asp Leu Ser Arg Val Pro Gly Ser Pro Val Leu Asp Cys Ser Val Ala
            340                 345                 350 cac tgc ctg agg ttc cgc tgc cac atc ccc tcc ttc agc gcc aag gag      1104
His Cys Leu Arg Phe Arg Cys His Ile Pro Ser Phe Ser Ala Lys Glu
        355                 360                 365 gag ctc cac ttc acc ctg aag ggc aac ctc agc ttc gcc tgg gtc agc      1152
Glu Leu His Phe Thr Leu Lys Gly Asn Leu Ser Phe Ala Trp Val Ser
    370                 375                 380 cag atg ctg caa aag aag gtg tcg gtg gtg agt gtg gcc gag atc acc      1200
Gln Met Leu Gln Lys Lys Val Ser Val Val Ser Val Ala Glu Ile Thr
385                 390                 395                 400 ttc aac agg gcc gtg tac tcc caa gtt ccg ggc gag gag ccc ttt atg      1248
Phe Asn Arg Ala Val Tyr Ser Gln Val Pro Gly Glu Glu Pro Phe Met
                405                 410                 415 aga gcc cag gtg gag acg gtg ctg gag gag tat gag gag cac gac ccc      1296
Arg Ala Gln Val Glu Thr Val Leu Glu Glu Tyr Glu Glu His Asp Pro
            420                 425                 430 gtc ccc ctg gtg gtg ggc agc tgt gtg ggc ggc ctg ctg ctg ctg gct      1344
Val Pro Leu Val Val Gly Ser Cys Val Gly Gly Leu Leu Leu Leu Ala
        435                 440                 445 ctc atc tca gcc acc ctg tac aag ctt ggc ttc ttc aag cgc cgg tac      1392
Leu Ile Ser Ala Thr Leu Tyr Lys Leu Gly Phe Phe Lys Arg Arg Tyr
    450                 455                 460 aag gag atg ctg ggc gag aaa ccg gga gac gcg gcc acc ttc ccc ggg      1440
Lys Glu Met Leu Gly Glu Lys Pro Gly Asp Ala Ala Thr Phe Pro Gly
465                 470                 475                 480 gag gac gcc agc tgc ggg gct tca gat ttg cct ttg tcc cag tg           1484
Glu Asp Ala Ser Cys Gly Ala Ser Asp Leu Pro Leu Ser Gln
                485                 490

<210> SEQ ID NO 103
<211> LENGTH: 494
<212> TYPE: PRT
<213> ORGANISM: rabbit

<400> SEQUENCE: 103

Asp Val Gln Ser Ser Ile Ser Tyr Asp Leu Ala Leu Asp Pro Gly Arg
  1               5                  10                  15

Leu Val Ser Arg Ala Ile Phe Gln Glu Thr Gln Asn Gln Thr Leu Thr
                 20                  25                  30

Arg Arg Lys Thr Leu Gly Leu Gly Arg His Cys Glu Thr Met Arg Leu
             35                  40                  45

Leu Leu Pro Asp Cys Val Glu Asp Val Val Asn Pro Ile Val Leu His
         50                  55                  60

Leu Asn Phe Ser Leu Glu Gly Gln Pro Ile Leu Ser Ser Gln Asn Leu
 65                  70                  75                  80

Arg Pro Val Leu Ala Thr Gly Ser Gln Asp His Phe Ile Ala Ser Leu
                 85                  90                  95

Pro Phe Glu Lys Asn Cys Gly Gln Asp Arg Leu Cys Glu Gly Asp Leu
            100                 105                 110

Ser Ile Ser Phe Asn Phe Ser Gly Leu Asn Thr Leu Leu Val Gly Leu
        115                 120                 125

Ser Leu Glu Leu Thr Val Thr Val Thr Val Arg Asn Glu Gly Glu Asp
    130                 135                 140

Ser Tyr Gly Thr Ala Ile Thr Leu Tyr Tyr Pro Ala Gly Leu Ser Tyr
145                 150                 155                 160
```

```
Arg Arg Val Ser Gly Gln Thr Gln Pro Trp Gln Arg Pro Leu His Leu
                165                 170                 175

Ala Cys Glu Ala Val Pro Thr Glu Ser Glu Gly Leu Arg Ser Thr Ser
            180                 185                 190

Cys Ser Val Asn His Pro Ile Phe Gln Gly Gly Ala Gln Gly Thr Phe
        195                 200                 205

Val Val Lys Phe Asp Val Ser Ser Lys Ala Ser Leu Gly Asp Arg Leu
    210                 215                 220

Leu Met Gly Ala Ser Ala Ser Glu Asn Asn Lys Pro Ala Ser Asn
225                 230                 235                 240

Lys Thr Ser Phe Glu Leu Glu Leu Pro Val Lys Tyr Ala Val Tyr Met
                245                 250                 255

Met Ile Thr Arg His Glu Gly Ser Thr Arg Phe Phe Asn Phe Ser Thr
            260                 265                 270

Ser Ala Glu Lys Ser Ser Lys Glu Ala Glu His Arg Tyr Arg Val Asn
        275                 280                 285

Asn Leu Ser Leu Arg Asp Val Ala Val Ser Val Asp Phe Trp Ala Pro
    290                 295                 300

Val Gln Leu Asn Gly Ala Ala Val Trp Asp Val Ala Val Glu Ala Pro
305                 310                 315                 320

Ala Gln Ser Leu Pro Cys Ala Arg Glu Arg Glu Pro Pro Arg Thr Ser
                325                 330                 335

Asp Leu Ser Arg Val Pro Gly Ser Pro Val Leu Asp Cys Ser Val Ala
            340                 345                 350

His Cys Leu Arg Phe Arg Cys His Ile Pro Ser Phe Ser Ala Lys Glu
        355                 360                 365

Glu Leu His Phe Thr Leu Lys Gly Asn Leu Ser Phe Ala Trp Val Ser
    370                 375                 380

Gln Met Leu Gln Lys Lys Val Ser Val Val Ser Val Ala Glu Ile Thr
385                 390                 395                 400

Phe Asn Arg Ala Val Tyr Ser Gln Val Pro Gly Glu Glu Pro Phe Met
                405                 410                 415

Arg Ala Gln Val Glu Thr Val Leu Glu Glu Tyr Glu Glu His Asp Pro
            420                 425                 430

Val Pro Leu Val Val Gly Ser Cys Val Gly Gly Leu Leu Leu Leu Ala
        435                 440                 445

Leu Ile Ser Ala Thr Leu Tyr Lys Leu Gly Phe Phe Lys Arg Arg Tyr
    450                 455                 460

Lys Glu Met Leu Gly Glu Lys Pro Gly Asp Ala Ala Thr Phe Pro Gly
465                 470                 475                 480

Glu Asp Ala Ser Cys Gly Ala Ser Asp Leu Pro Leu Ser Gln
                485                 490
```

<210> SEQ ID NO 104
<211> LENGTH: 26
<212> TYPE: DNA
<213> ORGANISM: Artificial Sequence
<220> FEATURE:
<223> OTHER INFORMATION: Description of Artificial Sequence: primer

<400> SEQUENCE: 104
tgtccaggac aagagatgga cattgc                                    26

<210> SEQ ID NO 105
<211> LENGTH: 24
<212> TYPE: DNA

```
<213> ORGANISM: Artificial Sequence
<220> FEATURE:
<223> OTHER INFORMATION: Description of Artificial Sequence: primer

<400> SEQUENCE: 105
gagctatttc atagcaagaa tggg                                            24

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: primer

<400> SEQUENCE: 106
tatagcatag cgaatgatcc                                                 20

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 107
atggtccgtg gagttgtgat c                                               21

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 108
tcgagatcca ccaaactgca c                                               21

<210> SEQ ID NO 109
<211> LENGTH: 14
<212> TYPE: PRT
<213> ORGANISM: monkey

<400> SEQUENCE: 109

Asn Leu Asp Val Glu Glu Pro Thr Ile Phe Gln Glu Asp Ala
 1               5                  10

<210> SEQ ID NO 110
<211> LENGTH: 14
<212> TYPE: PRT
<213> ORGANISM: monkey
<220> FEATURE:
<221> NAME/KEY: misc_feature
<222> LOCATION: 11
<223> OTHER INFORMATION: Xaa = any or unknown amino acid

<400> SEQUENCE: 110

Asn Leu Asp Val Glu Glu Pro Thr Ile Phe Xaa Glu Asp Ala
 1               5                  10

<210> SEQ ID NO 111
<211> LENGTH: 15
<212> TYPE: PRT
<213> ORGANISM: monkey

<400> SEQUENCE: 111

Phe Asn Leu Asp Val Glu Glu Pro Thr Ile Phe Gln Glu Asp Ala
```

-continued

```
<210> SEQ ID NO 112
<211> LENGTH: 17
<212> TYPE: PRT
<213> ORGANISM: Homo sapiens

<400> SEQUENCE: 112

Phe Asn Leu Asp Val Glu Glu Pro Thr Ile Phe Gln Glu Asp Ala Gly
 1               5                  10                  15

Gly

<210> SEQ ID NO 113
<211> LENGTH: 16
<212> TYPE: PRT
<213> ORGANISM: Homo sapiens

<400> SEQUENCE: 113

Phe Asn Leu Asp Thr Glu Glu Leu Thr Ala Phe Val Asp Ser Ala Gly
 1               5                  10                  15

<210> SEQ ID NO 114
<211> LENGTH: 17
<212> TYPE: PRT
<213> ORGANISM: Homo sapiens

<400> SEQUENCE: 114

Phe Asn Leu Asp Thr Glu Asn Ala Met Thr Phe Gln Glu Asn Ala Arg
 1               5                  10                  15

Gly
```